(12) United States Patent
Ward et al.

(10) Patent No.: US 7,557,361 B2
(45) Date of Patent: *Jul. 7, 2009

(54) ION SOURCES, SYSTEMS AND METHODS

(75) Inventors: Billy W. Ward, Merrimac, MA (US); John A. Notte, IV, Gloucester, MA (US); Louis S. Farkas, III, Durham, NH (US); Randall G. Percival, Raymond, NH (US); Raymond Hill, Rowley, MA (US)

(73) Assignee: ALIS Corporation, Peabody, MA (US)

( * ) Notice: Subject to any disclaimer, the term of this patent is extended or adjusted under 35 U.S.C. 154(b) by 329 days.

This patent is subject to a terminal disclaimer.

(21) Appl. No.: 11/600,874

(22) Filed: Nov. 15, 2006

(65) Prior Publication Data
US 2007/0210251 A1 Sep. 13, 2007

Related U.S. Application Data

(63) Continuation-in-part of application No. 10/966,243, filed on Oct. 15, 2004, now Pat. No. 7,368,727, and a continuation-in-part of application No. 11/147,102, filed on Jun. 7, 2005, now Pat. No. 7,321,118, and a continuation-in-part of application No. 11/146,741, filed on Jun. 7, 2005, now Pat. No. 7,414,243, and a continuation-in-part of application No. 11/385,136, filed on Mar. 20, 2006, now abandoned, and a continuation-in-part of application No. 11/385,215, filed on Mar. 20, 2006.

(60) Provisional application No. 60/799,203, filed on May 9, 2006, provisional application No. 60/795,806, filed on Apr. 28, 2006, provisional application No. 60/784,500, filed on Mar. 20, 2006, provisional application No. 60/784,331, filed on Mar. 20, 2006, provisional application No. 60/784,388, filed on Mar. 20, 2006, provisional application No. 60/784,390, filed on Mar. 20, 2006, provisional application No. 60/741,956, filed on Dec. 2, 2005, provisional application No. 60/511,726, filed on Oct. 16, 2003.

(51) Int. Cl.
H01J 49/10 (2006.01)
H01J 27/26 (2006.01)
H01J 27/02 (2006.01)

(52) U.S. Cl. .................... 250/423 F; 250/423 R; 250/424; 250/426; 250/492.21; 250/492.2

(58) Field of Classification Search ............. 250/423 F, 250/423 R, 424, 426, 492.21, 492.2
See application file for complete search history.

(56) References Cited

U.S. PATENT DOCUMENTS 2,893,624 A 7/1959 Fricke (Continued)

FOREIGN PATENT DOCUMENTS

DE 196 04 272 8/1996

(Continued)

OTHER PUBLICATIONS

Bernatskii and Pavlov, "Field Desorption of a Potassium-Gold Film on Tungsten," Physics of the Solid State, 46(8):1538-1541, 2004.

(Continued)

Primary Examiner—Nikita Wells
(74) Attorney, Agent, or Firm—Fish & Richardson P.C.

(57) ABSTRACT

Ion sources, systems and methods are disclosed.

110 Claims, 56 Drawing Sheets

U.S. PATENT DOCUMENTS

| | | |
|---|---|---|
| 3,121,155 A | 2/1964 | Berry |
| 3,602,710 A | 8/1971 | Mueller |
| 3,868,507 A | 2/1975 | Panitz |
| 4,044,255 A | 8/1977 | Krisch et al. |
| 4,139,773 A | 2/1979 | Swanson |
| 4,236,073 A | 11/1980 | Martin |
| 4,255,661 A | 3/1981 | Liebl |
| 4,352,985 A | 10/1982 | Martin |
| 4,451,737 A | 5/1984 | Isakozawa |
| 4,467,240 A | 8/1984 | Futamoto et al. |
| 4,633,084 A | 12/1986 | Gruen et al. |
| 4,638,209 A | 1/1987 | Asamaki et al. |
| 4,639,307 A | 1/1987 | Goodrich |
| 4,649,316 A | 3/1987 | Cleaver et al. |
| 4,721,878 A | 1/1988 | Hagiwara et al. |
| 4,774,414 A | 9/1988 | Umemura et al. |
| 4,785,177 A | 11/1988 | Besocke |
| 4,874,947 A | 10/1989 | Ward et al. |
| 4,954,711 A | 9/1990 | Fink et al. |
| 4,983,540 A | 1/1991 | Yamaguchi et al. |
| 4,985,634 A | 1/1991 | Stengl et al. |
| 5,034,612 A | 7/1991 | Ward et al. |
| 5,059,785 A | 10/1991 | Doyle et al. |
| 5,063,294 A | 11/1991 | Kawata et al. |
| 5,083,033 A | 1/1992 | Komano et al. |
| 5,151,594 A | 9/1992 | McClelland |
| 5,188,705 A | 2/1993 | Swanson et al. |
| 5,324,950 A | 6/1994 | Otaka et al. |
| 5,414,261 A | 5/1995 | Ellisman et al. |
| 5,574,280 A | 11/1996 | Fujii et al. |
| 5,750,990 A | 5/1998 | Mizuno et al. |
| 5,783,830 A | 7/1998 | Hirose et al. |
| 5,976,390 A | 11/1999 | Muramatsu |
| 5,986,270 A | 11/1999 | Bormans et al. |
| 6,028,953 A | 2/2000 | Nakamura et al. |
| 6,042,738 A | 3/2000 | Casey et al. |
| 6,211,527 B1 | 4/2001 | Chandler |
| 6,268,608 B1 | 7/2001 | Chandler |
| 6,354,438 B1 | 3/2002 | Lee et al. |
| 6,395,347 B1 | 5/2002 | Adachi et al. |
| 6,414,307 B1 | 7/2002 | Gerlach et al. |
| 6,504,151 B1 | 1/2003 | Mitchell et al. |
| 6,538,254 B1 | 3/2003 | Tomimatsu et al. |
| 6,579,665 B2 | 6/2003 | Lee et al. |
| 6,581,023 B1 | 6/2003 | Kim |
| 6,700,122 B2 | 3/2004 | Matsui et al. |
| 6,753,535 B2 | 6/2004 | Rose |
| 6,791,084 B2 | 9/2004 | Shimoma et al. |
| 6,822,245 B2 | 11/2004 | Muto et al. |
| 6,875,981 B2 | 4/2005 | Nishikawa |
| 7,084,399 B2 | 8/2006 | Muto et al. |
| 7,119,333 B2 | 10/2006 | Herschbein et al. |
| 7,230,244 B2 | 6/2007 | Trotz et al. |
| 7,321,118 B2 | 1/2008 | Ward |
| 7,368,727 B2 | 5/2008 | Ward |
| 7,414,243 B2 | 8/2008 | Ward |
| 2002/0134949 A1 | 9/2002 | Gerlach et al. |
| 2002/0144892 A1 | 10/2002 | Lee et al. |
| 2002/0170675 A1 | 11/2002 | Libby et al. |
| 2003/0047691 A1 | 3/2003 | Musil et al. |
| 2003/0062487 A1 | 4/2003 | Hiroi et al. |
| 2003/0174879 A1 | 9/2003 | Chen |
| 2004/0031936 A1 | 2/2004 | Oi et al. |
| 2004/0121069 A1 | 6/2004 | Ferranti et al. |
| 2005/0045821 A1 | 3/2005 | Noji et al. |
| 2006/0060777 A1 | 3/2006 | Motoi et al. |
| 2006/0097166 A1 | 5/2006 | Ishitani et al. |
| 2006/0197017 A1 | 9/2006 | Motoi et al. |
| 2006/0284091 A1 | 12/2006 | Ward |
| 2006/0284092 A1 | 12/2006 | Ward |
| 2007/0025907 A1 | 2/2007 | Rezeq et al. |
| 2007/0051900 A1 | 3/2007 | Ward |
| 2007/0138388 A1* | 6/2007 | Ward et al. ............ 250/288 |
| 2007/0158555 A1 | 7/2007 | Ward et al. |
| 2007/0158556 A1* | 7/2007 | Ward et al. ............ 250/309 |
| 2007/0158557 A1 | 7/2007 | Ward et al. |
| 2007/0158558 A1 | 7/2007 | Ward et al. |
| 2007/0158580 A1 | 7/2007 | Ward et al. |
| 2007/0158581 A1* | 7/2007 | Ward et al. ............ 250/426 |
| 2007/0158582 A1 | 7/2007 | Ward et al. |
| 2007/0187621 A1 | 8/2007 | Ward et al. |
| 2007/0194226 A1 | 8/2007 | Ward et al. |
| 2007/0194251 A1 | 8/2007 | Ward et al. |
| 2007/0205375 A1 | 9/2007 | Ward et al. |
| 2007/0210250 A1 | 9/2007 | Ward et al. |
| 2007/0215802 A1 | 9/2007 | Ward et al. |
| 2007/0221843 A1 | 9/2007 | Ward et al. |
| 2007/0227883 A1 | 10/2007 | Ward et al. |
| 2007/0228287 A1 | 10/2007 | Ward et al. |
| 2008/0067408 A1* | 3/2008 | Winkler ............ 250/423 F |
| 2008/0217555 A1* | 9/2008 | Ward et al. ............ 250/423 F |

FOREIGN PATENT DOCUMENTS

| | | |
|---|---|---|
| DE | 197 15 226 A | 10/1998 |
| DE | 197 44 126 A | 4/1999 |
| EP | 0 317 952 | 5/1989 |
| EP | 0 427 532 | 5/1991 |
| EP | 0 477 992 A2 | 4/1992 |
| EP | 1 491 654 | 12/2004 |
| EP | 1 655 265 | 5/2006 |
| EP | 2 031 633 | 3/2009 |
| FR | 2244257 A | 4/1975 |
| GB | 1 604 898 | 12/1981 |
| JP | 55-126949 | 10/1980 |
| JP | 5209844 | 12/1983 |
| JP | 62 051134 | 3/1987 |
| JP | 63 040241 A | 2/1988 |
| JP | 63 045740 | 2/1988 |
| JP | 63 200434 | 8/1988 |
| JP | 1-130450 | 5/1989 |
| JP | 02 087440 | 3/1990 |
| JP | 03-214554 | 9/1991 |
| JP | 04 341734 | 11/1992 |
| JP | 04 341743 | 11/1992 |
| JP | 5275050 | 10/1993 |
| JP | 05-297146 | 11/1993 |
| JP | 07045230 | 2/1995 |
| JP | 2789610 | 8/1995 |
| JP | 07-272652 | 10/1995 |
| JP | 2001 176440 | 6/2001 |
| JP | 02 025488 | 1/2002 |
| JP | 2003 302579 A | 10/2003 |
| WO | 98/47172 | 10/1998 |
| WO | 2001/04611 | 1/2001 |
| WO | WO 2004/015496 | 2/2004 |
| WO | 2004/068538 | 8/2004 |
| WO | 2006/133241 | 12/2006 |

OTHER PUBLICATIONS

Boerret et al., "Long time current stability of a gas filed ion source with a supertip," J. Phys. D. Appl. Phys. 21(12):1835-1837, 1988.

Giannuzzi and Stevie, *Introduction to Focused Ion Beams—Instrumentation, Theory, Techniques and Practice*, Nov. 2004, Springer, XP002442742, Chapter 3, see especially p. 56, second section.

Giannuzzi and Stevie, *Introduction to Focused Ion Beams—Instrumentation, Theory, Techniques and Practice*, Nov. 2004, Springer, XP002462691, Chapter 5—Device Edits and Modifications.

Golubev et al., "Field Emission Study of the Growth of Close-Packed and Stepped Surfaces of a Tungsten Single Crystal," J. Crystal Growth 52:48-52, 1981.

Hiroshima et al., "A focused He+ ion beam with a high angular current density," Jpn. J. Appl Phys., 31(1)(12B):4492-4495, 1992.

Kuo et al., "Noble Metal/W(111) Single-Atom Tips and Their Field Electron and Ion Emission Characteristics," Jpn. J. App. Phy., 45(11):8972-8983, 2006.

Kubena et al., "A low magnification focused ion beam system with 8 nm spot size," J. Vac. Sci. Technol., 9(6):3079-3083, 1991.

Liu and Orloff, "Analytical model of a gas phase filed ionization source," J. Vac. Sci. Technol. B 23(6):2816-2820, 2005.

Melngailis, "Focused ion beam Lithography", Nuclear Instr. And Methods in Phys. Res. B80(81):1271-1280, 1993.

Pavlov, "Atomically Sharp <111> Trihedral Angle of a Tungsten Tip," Physics of a Solid State, 49(8):1579-1582, 2007.

Pavlov, "Field-Desorption Microscopy Study of the Deformation of a Tungsten Tip Subjected to Thermal Treatment in an Electric Field," Physics of the Solid State, 47(11):2180-2185, 2005.

Pavlov, "Field Desorption Microscopy of the <111> Trihedral Angle of a Reconstructed Tungsten Tip," Technical Physics, 51(9):1210-1214, 2006.

Pavlov, "Observation of the Drawing out of Needles by Electric Fields," A translation of JETP Pis'ma v Redaktsiyu of the Academy of Sciences of the USSR, 17(5):177-179, 1973.

Pavlov, "Variations in Shapes of Outgrowths on a Tungsten Tip during Growth in an Electric Field," Physics of a Solid State, 48(5):969-972, 2006.

Sakai et al., "Contrast mechanisms in scanning ion microscope imaging for metals," App. Phys. Letters, AIP, vol. 73, No. 5, pp. 611-613, Aug. 3, 1998.

Sakata et al., "Helium field ion source for application in a 100 keV focused ion beam system," J. Vac. Sci. Technol. B 10(6):2842-2845, 1992.

Sendecki and Barwinski, "A scanning field emission microscope," Meas. Sci. Technol., 6(3):306-309, (1995).

Shrednik et al., "Growth of Tips in the Directions Normal to Close-Packed Faces by Heating in the Presence of an Electric Field," Phys. Stat. Sol. (a), 23(1):373-381, 1974.

Unger et al., "Probe hole field electron/field ion microscopy and energy spectroscopy of ultrasharp [111]-oriented tungsten tips," Applied Surface Science 87(88):45-52, 1995.

Vlasov et al., "High-temperature filed evaporation of thermofield microscopic protuberances," Sov. Tech. Phys. Lett. 12(5):224-225, 1986.

Ward et al., "Focused Ion Beam Induced Optical Emission Spectroscopy," J. Vac. Sci. Technol. 6(6):2100-2103, 1988.

Nova 600 Nanolab Product Data, Fei Company Product Data, 2003, XP007903648.

Fink, H.-W., "Mono-atomic tips for scanning tunneling microscopy", IBM J. Res. Develop. 30: 460-465 (1986).

Fink, H.-W., "Point Source for Ions and Electrons", Physica Scripta 38: 260-263 (1988).

Binh, V.T., "In situ fabrication and regeneration of microtips for scanning tunneling microscopy", J. Microscopy 152(2): 355-361 (1988).

Stocker, W. et al., "Low-energy electron and ion projection microscopy", Ultramicroscopy 31: 379-384 (1989).

Bell, A.E. et al., "High-field ion sources", Rev. Sci. Instrum. 61(1): 363-365 (1990).

Schmid, H. et al., "Combined electron and ion projection microscopy", Appl. Surf. Sci. 67: 436-443 (1993).

Muller, H.U. et al., "Emission properties of electron point sources", Ultramicroscopy 50: 57-64 (1993).

Horch, S. et al., "Field emission from atomic size sources", J. Appl. Phys. 74(6): 3652-3657 (1993).

Fink, H.-W. et al., "Electron and Ion Microscopy Without Lenses", Nanostructures and Quantum Effects (Springer-Verlag, 1994), pp. 17-27.

Edinger, K. et al., "Development of a high brightness gas field ion source", J. Vac. Sci. Technol. B 15(6): 2365-2368 (1997).

Horiuchi, K. et al., "Emission characteristics and stability of a helium field ion source", J. Vac. Sci. Technol. B. 6(3): 937-940 (1988).

Melngailis, J., "Focused ion beam technology and applications", J. Vac. Sci. Technol. B 5(2): 469-495 (1987).

Fu, T.-Y. et al., "Method of creating a Pd-covered single-atom sharp W pyramidal tip: Mechanism and energetics of its formation", Phys. Rev. B 64: 113401-1-4 (2001).

Lucier, A.-S., "Preparation and Characterization of Tungsten Tips Suitable for Molecular Electronics Studies", excerpts from MSc Thesis, McGill University, 2004.

Fotino, M., "Tip sharpening by normal and reverse electrochemical etching", Rev. Sci. Instrum. 64(1): 159-167 (1993).

Wengelnik, H. et al., "Oxygen-induced sharpening process of W(111) tips for scanning tunneling microsope use," J. Vac. Sci. Technol. A 8(1): 438-440 (1990).

Rezeq, M. et al., "Sharpening of a Field of Ion Microscope (FIM) Tungsten Tip by the Controlled Interation of Nitrogen with the Tip Surface Atoms," Abastract from APS March Meeting (2004).

McGuinness, P.E., "Seeing at Atomic Resolution is Believing: Welcome the Helium Ion Microscope", Scanning 27(6): 323 (2005).

Notte, J. et al., "Sample Interaction and Contrast Mechanisms of the Helium Ion Microscope" (Scanning Conference, Apr. 2006).

Notte, J.A. et al., "An Introduction to Helium Ion Microscopy and its Nanotechnology Applications" (NanoScience and Technology Institute, May 2006).

Ward, B.W. et al., "The Helium Ion Microscope: A New Tool for Nanoscale Microscopy and Metrology" (Electron, Ion, and Photon Beam Nanotechnology Conference, May 2006).

Morgan, J. et al., "An Introduction to the Helium Ion Microscope" (Microscopy Today, Jul. 2006).

Hill, R. et al., "The ALIS He Ion Source and its Application to High Resolution Microscopy" (Seventh International Conference on Charged Particle Optics, Jul. 2006).

Notte, J. et al., "An Introduction to Helium Ion Microscopy" (Microscopy and Micro-Analysis, Jul. 2006).

"An Introduction to the Helium Ion Microscope" (Materials Research Society Meeting, Nov. 2006).

J. Melngailis, "Ion Sources for Nanofabrication & High Resolution Lithography," IEEE Proceedings of the 2001 Particle Accelerator Conference, Chicago, Illinoise, (2002).

K. Jousten et al. "Growth & Current Charities of a Stable field Ion Emitter," Ultramicroscope 26, pp. 301-312 (1988).

Qing Ji, "Maskless, Resistless Ion Beam Lithography Process," Ph.D. Dissertation, Department of Electrical Engineering and Computer Sciences, UCAL Berkeley (2003).

Escovitz et al., "Scanning Transmission Ion Microscope with a Field Ion Source," Feb. 24, 1975, Proceedings of the National Academy of the Sciences, vol. 72, No. 5, Published May 1975, pp. 1826-1828.

Russell P.E. et al., "Chemically and geometrically enhanced focused ion beam micromachining," Journal of Vacuum Science and Tehcnology B, vol. 16, No. 4, Jul./Aug. 1998, 2494-2498.

Schmid et al., "In-line holography using low-energy electrons and photons: Applications for manipulation on a nanometer scale," Journal of Vacuum Science & Technology B: Microelectronics and Nanometer Structures, Nov. 1995, vol. 13, Issue 6, pp. 2428-2431.

Fink et al., "Atomic Resolution in Lensless Low-energy Electron Holography," Phys. Rev. Lett. 67, Issue 12-16 Sep. 1991, pp. 1543-1546.

Brune et al., "Surface migration of "hot" adatoms in the course of dissociative chemisorption of oxygen on Al(111)," Phys. Rev. Lett. 68, Issue 5-3 Feb. 1992, pp. 624-626.

Fink et al., "Lattice Steps and Adatom Binding on Tungsten (211)," Surf. Sci., vol. 143, No. 1, pp. 125-144, Jul. 1984.

Schmid et al., "Mechanical and electronic manipulation of nanometer-sized wires," Nanotechnology, vol. 5, pp. 26-32, 1994.

Fink et al., "Coherent point source electron beams," Journal of Vacuum Science & Technology B: Microelectronics and Nanometer Structures, Nov. 1990, vol. 8, Issue 6, pp. 1323-1324.

Purcell et al., "Characterization of atomic-size metal ion sources," Journal of Vacuum Science & Technology B: Microelectronics and Nanometer Structures, Jan. 2001, vol. 19, Issue 1, pp. 79-86.

Thompson et al., "Towards a commercial gas field ion source," Proceedings of SPIE, vol. 2437.

Wilbertz et al., "Recent Progress in gas field ion source technology," Proceeding of SPIE, vol. 2194.

Mutsaers, "Nuclear Microprobe Design," Nuclear Instruments & Methods in Physics Research, Section—B: Beam Interactions with Materials and Atoms, Elsevier, Amsterdam, NL, vol. 113, No. 1, Jun. 1996, pp. 323-329.

Jaksic et al., "New Developments in IBIC for the Study of Change Transport Properties of Radiation Detector Materials," Nuclear Intruments & Methods in Physics Research, Section—B: Beam Interactions with Materials and Atoms, Elsevier, Amsterdam, NL, vol. 158, No. 1-4, Sep. 2, 1999, pp. 458-463.

Butz et al., "From Micro- to Nanoprobes: Auspices and Horizons," Nuclear Intruments & Methods in Physics Research, Section—B: Beam Interactions with Materials and Atoms, Elsevier, Amsterdam, NL, vol. 113, No. 1, Jun. 1996, pp. 317-322.

Tondare V. N., "Quest for high brightness, monochromatic noble gas ion sources," J.Vac.Sci.Technol., A 23, 1498 (2005).

Grivet et al., "Ion Microscopy: History and Actual Trends," Ann NY Acad Sci, 1978 NY Acad of Sci, vol. 306, Feb. 23, 1977, pp. 158-182.

Magnan, "The Proton Microscope," Nucleonics, vol. 4, No. 4, Apr. 1949, pp. 52-66.

Chanson et al., "Sur les premieres images obtenues avec un microscope protonique," Comptes Rendus Hebdomadaires des Seances de l'Academie des Sciences France, vol. 233, Dec. 3, 1951, pp. 1436-1438.

Knoll et al., "Das Elektronenmikroskop" Zeitshrift fur Physik Germany, vol. 78, No. 5-6, Oct. 4, 1932, pp. 318-339.

Breese et al., "Ion optical study of a transmission ion microscopy," Muclear instruments & Methods in Physics Research, Section—B: Beam Interactions with Materials and Atoms, Elsevier, Amsterdam, NL, vol. 158, No. 1-4, Sep. 2, 1999, pp. 236-240.

Valdiviez et al., "The mechanical design of a proton microscope for radiography at 800 MeV,"Institute of Electrical and Electronics Engineers: Proceedings of the 2003 Particle Accelerator Conference. PAC 2003. Portland, OR, May 12-16, 2003, Particle Accelerator Conference, New York, NY: IEEE, US. vol. 1 of 5, May 12, 2003.

Breguet and Clavel, "Stick and Slip Actuators: design, control, performances and applications," Micromechatronics and Human Science, Proceedings of the 1998 International Symposium, 89-95, 1998.

Fu et al., "Microfabrication of microlens array by focused ion beam technology," Microelectronic Engineering, 54(3-4):211-221, 2000.

Liu and Wang, "A self-moving precision positioning stage utilizing impact force of spring-mounted piezoelectric actuator," Sensors and Actuators, 102(1-2):83-92, 2002.

Nomura et al., "Application of Electromagnetic Actuator using Rubber Film to Three-Degrees-of-Freedom Precision Stage," Advanced Intelligent Mechatronics (AIM 2003), 101-106, 2003.

Orloff et al., "High Resolution Focused Ion Beams: FIB and its Applications," Review of Scientific Instruments, 136-145, 2003.

Orloff et al., "Fundamental limits to imaging resolution for focused ion beams," J. Vacuum Science & Tech., 14(6):3759-3763, 1996.

Versteyhe et al., "A rigid and accurate piezo-stepper based on smooth learning hybrid force-position controlled clamping," Proceedings of the 1998 IEEE International Conference on Robotics & Automation, 4:3059-3064, 1998.

Bunday et al., "Determination of optimal parameters for CD-SEM measurement of line-edge roughness," Metrology, Inspection, and Process Control for Microlithography XVIII, Proceedings of SPIE—The International Society for Optical Engineering, vol. 5375, pp. 515-533, May 24, 2004.

Hong-Shi et al., "Preparation and characterization of single-atom tips," Nano Letters, vol. 4, No. 12, pp. 2379-2382, Dec. 2004.

Itakura et al., "Focusing Column For Helium Field Ion Source," Microelectric Engineering, Elsevier Publishers BV., Amsterdam, NL, vol. 3, No. 1-4, pp. 153-160, Sep. 23, 1985.

Itakura et al., "Microprobe of Helium Ions," Journal of Vacuum Science and Technology: Part B, AVS / AIP, Melville, New York, NY, vol. 9, No. 5, pp. 2596-2601, Sep. 1, 1991.

Kalbitzer et al., "High-brightness source for ion and electron beams (invited)," Review of Scientific Instruments, American Institute of Physics, vol. 69, No. 2, pp. 1026-1031, Feb. 2, 1998.

Kalbitzer et al., "Ion beam modification for submicron technology," Nuclear Instruments & Methods in Physics Research, Section—B: Beam Interations With Materials and Atoms, Elsevier, Amsterdam, NL, vol. 113, No. 1, pp. 154-160, Jun. 1996.

Kalbitzer et al., "Multipurpose nanobeam source with supertip emitter," Journal of Vacuum Science & Technology B: Microelectronics Processing and Phenomena, American Vacuum Society, vol. 16, No. 4, pp. 2455-2461, Jul. 1998.

Kalbitzer, "Bright ion beams for the nuclear microprobe," Nuclear Instruments & Methods In Physics Research, Section—B: Beam Interactions With Materials And Atoms, Elsevier, Amsterdam, NL., vol. 158, No. 1-4, pp. 53-60, Sep. 2, 1999.

Kim et al., "Effects of low-energy (1-1.5 kV) nitrogen-ion bombardment on sharply pointed tips: Sputtering, implantation, and metal-nitride formation," Journal of Applied Physics, American Institute of Physics, vol. 81, No. 2, p. 944, Jan. 15, 1997.

Levi-Setti, "High Resolution Scanning Ion Probes: Application to Physics and Biology," Nuclear Instruments and Methods, North-Holland, vol. 168, No. 1-3, pp. 139-149, Jun. 25, 1979.

Levi-Setti, "Proton Scanning Microscopy: Feasiblity and Promise," Scanning Electron Microscopy. Proceedings of The Annual Scanning Electron Microscope Symposium, Chicago, IL., pp. 125-134, Apr. 11, 1974.

Liu et al., "A Study of Optical Properties of Gas Phase Field Ionization Sources," Advances in Imagin and Electron Physics, Elsevier Academic Press, vol. 138, pp. 147-175, Oct. 2005.

Orloff et al., "A Scanning Ion Microscope with A Field Ionization Source," Scanning Electron Microscopy. Proceedings of The Annual Scanning Electron Microscope Symposium, Chicago, IL, No. 10, pp. 57-62, Mar. 1977.

Orloff et al., "High-Resolution Focused Ion Beams: FIB and its Applications," Kluwer Academic / Plenum Publishers, New York, Chapter 6.8, (2003).

Orloff, "High-Resolution Focused Ion Beams," Review of Scientific Instruments, AIP, vol. 64, No. 5, pp. 1106-1107, May 1, 1993.

Stevie et al., "Focused Ion Beam Gases for Deposition and Enhanced Etch," Chapter 3 of Introduction to Focused Ion Beam—Instrumentation, Theory, Techniques and Practice, Edited by Giannuzi et al., Published by Springer, pp. 53-72, (2005).

Tondare et al., "The concept of a high-brightness, miniaturized gas field ion source," Vacuum Microelectronics Conference, 2003. Technical Digest of the 16th International IEEE, pp. 307-308, Jul. 7, 2003.

Wolf et al., "Design and performance of a scanning probe-hole field emission microscope," Surface Science, vol. 246, No. 1-3, pp. 420-427, Apr. 1991.

Doyle et al., "A new approach to nuclear microscopy: the ion-electron emission microscope," Nuclear Instruments & Methods in Physics Research B 158 (1999) pp. 6-17.

Hanson et al., "H2 and rare gas field ion source with high angular current," J Vacuum Science and Technology, 16(6) Nov./Dec. 1979, pp. 1875-1878.

Tomaru et al., "Thermal lensing in an cryogenic sapphire substrates," Class. Quantum Grav. 19 (2002), pp. 2045-2049.

Marquardt et al., "Cryogenic Material Properties Database," 11th International Cryocooler Conference, Jun. 20-22, 2000, Keystone, CO.

* cited by examiner

FIG. 35A
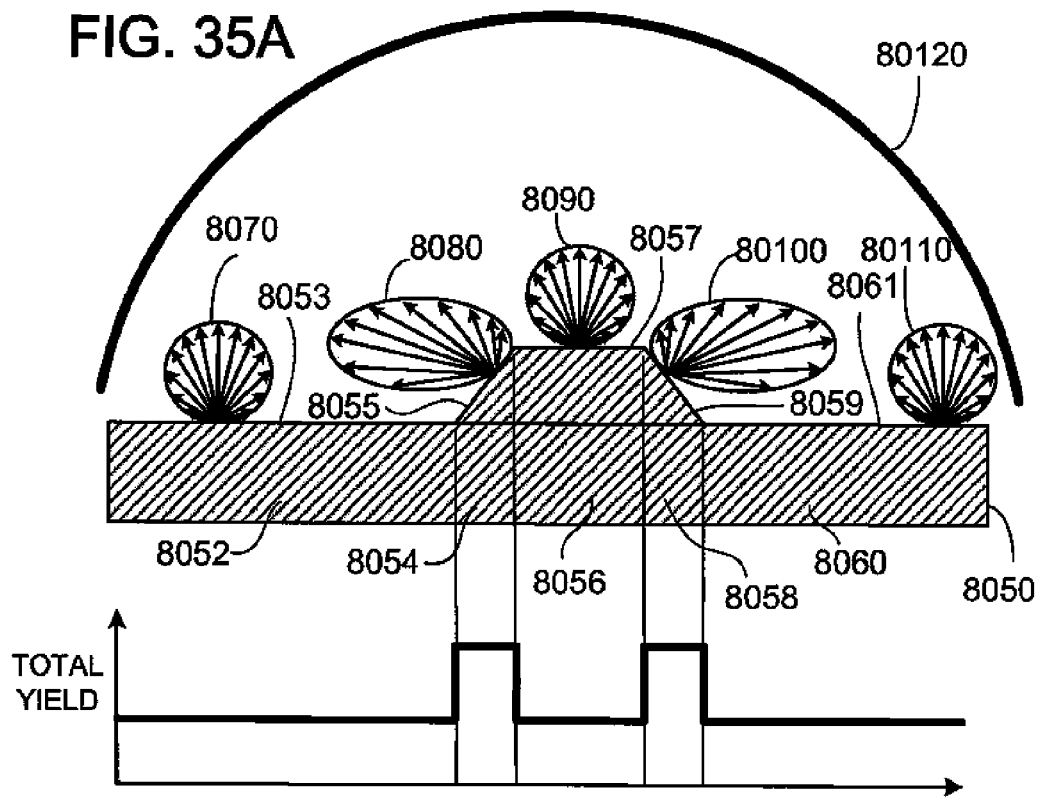
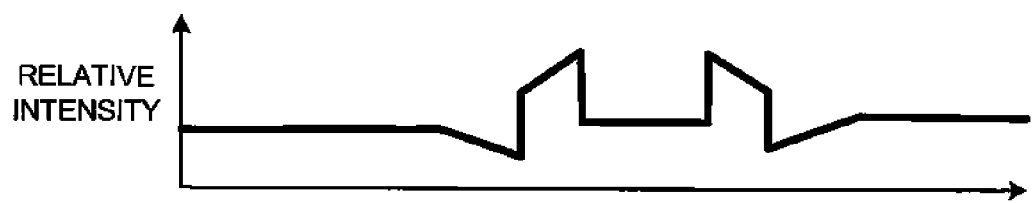
FIG. 35B
FIG. 35C

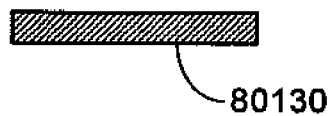
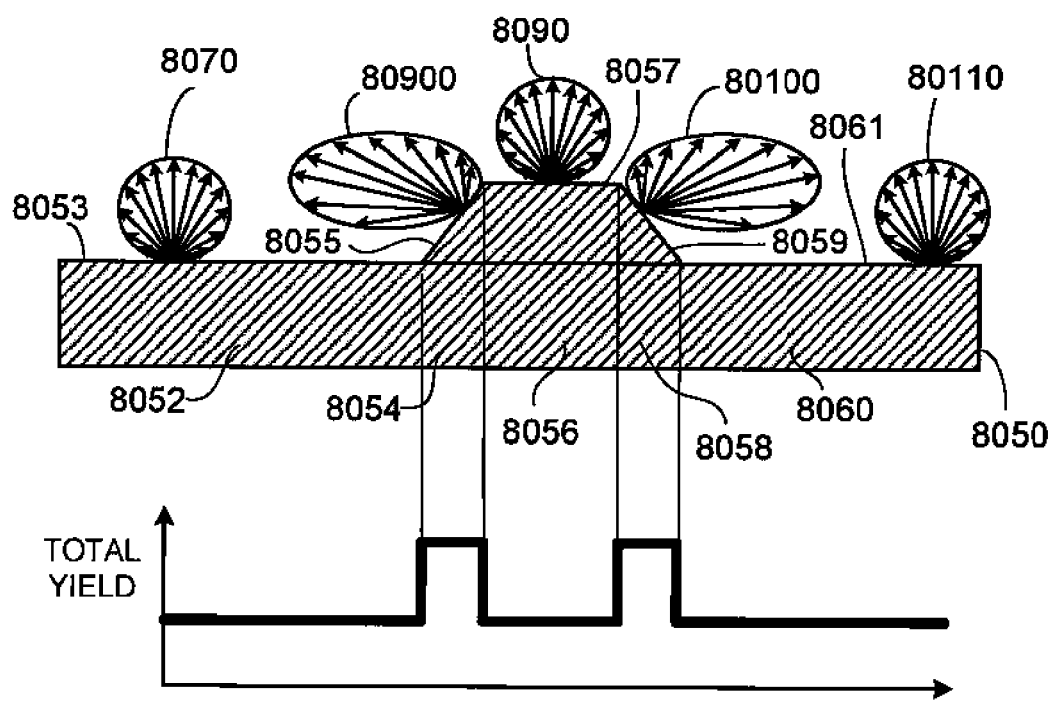
FIG. 35D
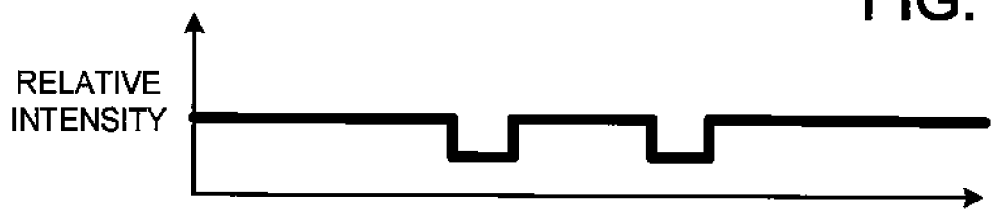
FIG. 35E
FIG. 35F

FIG. 35G
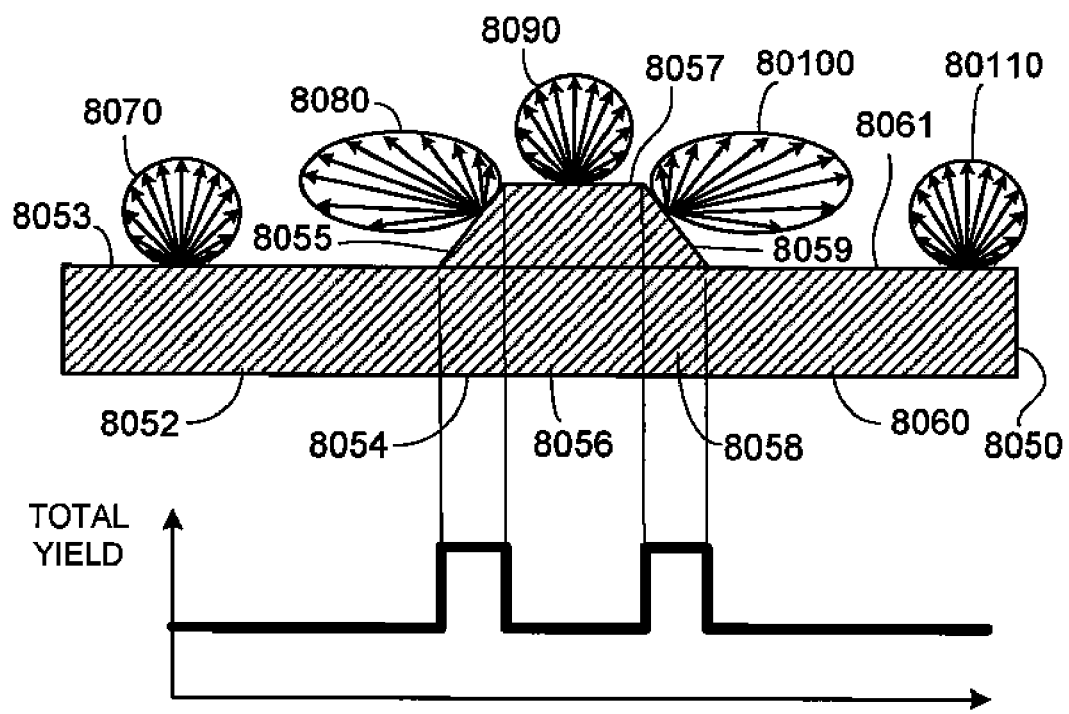
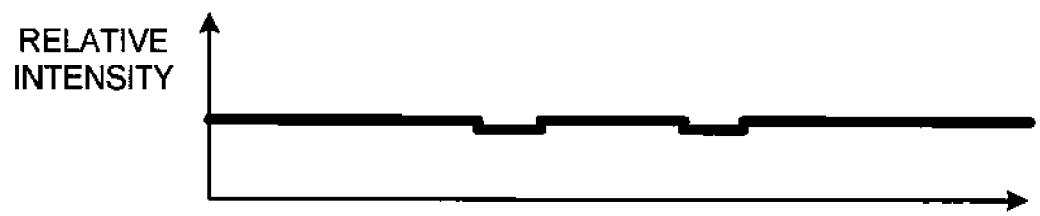
FIG. 35H
FIG. 35I

ION SOURCES, SYSTEMS AND METHODS

CROSS-REFERENCE TO RELATED APPLICATIONS

This application is a continuation-in-part of, and claims priority under 35 U.S.C. §120 to, U.S. application Ser. No. 10/966,243, filed Oct. 15, 2004 now U.S. Pat. No. 7,368,727, which claims priority under 35 U.S.C. §119(e)(1) to U.S. Provisional Application Ser. No. 60/511,726, filed Oct. 16, 2003. This application is also a continuation-in-part of, and claims priority under 35 U.S.C. §120 to, U.S. application Ser. No. 11/147,102, filed Jun. 7, 2005 now U.S. Pat. No. 7,321,118. This application is also a continuation-in-part of, and claims priority under 35 U.S.C. §120 to, U.S. application Ser. No. 11/146,741, filed Jun. 7, 2005 now U.S. Pat. No. 7,414,243. This application is also a continuation-in-part of, and claims priority under 35 U.S.C. §120 to, U.S. application Ser. No. 11/385,136, filed Mar. 20, 2006 now abandoned.

This application is also a continuation-in-part of, and claims priority under 35 U.S.C. §120 to, U.S. application Ser. No. 11/385,215, filed Mar. 20, 2006.

This application claims priority under 35 U.S.C. §119(e)(1) to: U.S. Patent Application Ser. No. 60/741,956, filed Dec. 2, 2005; U.S. Patent Application Ser. No. 60/784,390, filed Mar. 20, 2006; U.S. Patent Application Ser. No. 60/784,388, filed Mar. 20, 2006; U.S. Patent Application Ser. No. 60/784,331, filed Mar. 20, 2006; U.S. Patent Application Ser. No. 60/784,500, filed Mar. 20, 2006; U.S. Patent Application Ser. No. 60/795,806, filed Apr. 28, 2006; and U.S. Patent Application Ser. No. 60/799,203, filed May 9, 2006.

Each of these applications is incorporated herein by reference.

TECHNICAL FIELD

The disclosure relates to ion sources, systems and methods.

BACKGROUND

Ions can be formed using, for example, a liquid metal ion source or a gas field ion source. In some instances, ions formed by an ion source can be used to determine certain properties of a sample that is exposed to the ions, or to modify the sample. In other instances, ions formed by an ion source can be used to determine certain characteristics of the ion source itself.

SUMMARY

In one aspect, the invention features a system that includes a gas field ion source capable of interacting with a gas to generate an ion beam having a spot size with a dimension of 10 nm or less at a surface of a sample.

In another aspect, the invention features a system that includes an ion source capable of interacting with a gas to generate an ion beam having a spot size with a dimension of three nm or less at a surface of a sample.

In a further aspect, the invention features a system that includes a gas field ion source capable of interacting with a gas to generate an ion beam having a brightness of $1\times10^9$ $A/cm^2 sr$ or more at a surface of a sample.

In an additional aspect, the invention features a system that includes a gas field ion source capable of interacting with a gas to generate an ion beam having a reduced brightness of $5\times10^8$ $A/m^2 srV$ or more at a surface of a sample.

In one aspect, the invention features a system that includes a gas field ion source capable of interacting with a gas to generate an ion beam having an etendue of $5\times10^{-21}$ $cm^2 sr$ or less.

In another aspect, the invention features a system that includes a gas field ion source capable of interacting with a gas to generate an ion beam having a reduced etendue of $1\times10^{-16}$ $cm^2 srV$ or less.

In a further aspect, the invention features a system that includes a gas field ion source including an electrically conductive tip. The gas field ion source is capable of interacting with a gas to generate an ion beam for a time period of one week or more without removing the electrically conductive tip from the system.

In an additional aspect, the invention features a system that includes a gas field ion source capable of interacting with a gas to generate an ion beam for a time period of one week or more with a total interruption time of 10 hours or less.

In one aspect, the invention features an ion microscope capable of producing an image of a sample. The sample is different from the ion microscope, and the image of the sample has a resolution of three nm or less.

In another aspect, the invention features gas field ion microscope capable of producing an image of a sample. The sample is different from the ion microscope, and the image of the sample having a resolution of 10 nm or less.

In a further aspect, the invention features a gas field ion microscope having a quality factor of 0.25 or more.

In an additional aspect, the invention features an ion microscope having a damage test value of 25 nm or less.

In one aspect, the invention features an ion microscope that includes an ion source with an electrically conductive tip having a terminal shelf with 20 atoms or less.

In another aspect, the invention features a system that includes a gas field ion source with an electrically conductive tip with an average full cone angle of from 15° to 45°.

In a further aspect, the invention features a system that includes a gas field ion source including an electrically conductive tip with an average radius of curvature of 200 nm or less.

In an additional aspect, the invention features a system that includes a gas field ion source having an electrically conductive tip with a terminal shelf having one or more atoms. The system is configured so that, during use of the system, the one or more atoms interact with a gas to generate an ion beam, and 70% or more of the ions in the ion beam that reach a surface of a sample are generated via an interaction of the gas with only one atom of the one or more atoms.

In one aspect, the invention features a system that includes a gas field ion source with an electrically conductive tip capable of interacting with a gas to generate an ion beam. The system also includes ion optics configured so that during use at least a portion of the ion beam passes through the ion optics. The system further includes a moving mechanism coupled to the gas field ion source so that the moving mechanism can translate the electrically conductive tip, tilt the electrically conductive tip or both.

In another aspect, the invention features a system that includes an ion source capable of interacting with a gas to generate an ion beam that can interact with a sample to cause multiple different types of particles to leave the sample. The system also includes at least one detector configured to detect at least two different types of particles of the multiple different types of particles. The multiple different types of particles are selected from secondary electrons, Auger electrons, secondary ions, secondary neutral particles, primary neutral particles, scattered ions and photons.

In a further aspect, the invention features a system that includes a gas field ion source capable of interacting with a gas to generate an ion beam that can interact with a sample to cause particles to leave the sample. The particles are selected from Auger electrons, secondary ions, secondary neutral particles, primary neutral particles, scattered ions and photons. The system also includes at least one detector configured so that, during use, the at least one detector detects at least some of the particles to determine information about the sample.

In an additional aspect, the invention features a system that includes a gas field ion source capable of interacting with a gas to generate an ion beam that can interact with a sample to cause particles to leave the sample. The system also includes at least one detector configured so that, during use, the at least one detector can detect at least some of the particles. For a given detected particle, the at least one detector produces a signal based on an energy of the given detected particle.

In one aspect, the invention features a system that includes a gas field ion source capable of interacting with a gas to generate an ion beam that can interact with a sample to cause particles to leave the sample. The system also includes at least one detector configured so that, during use, the at least one detector can detect at least some of the particles. For a given detected particle, the at least one detector produces a signal based on an angle of a trajectory of the given detected particle.

In another aspect, the invention features a system that includes a gas field ion source capable of interacting with a gas to generate an ion beam that can interact with a sample to cause scattered ions to leave the sample. The system also includes at least one detector configured so that, during use, the at least one detector can detect at least some of the scattered ions. The system further includes an electronic processor electrically connected to the at least one detector so that, during use, the electronic processor can process information based on the detected scattered ions to determine information about the sample.

In a further aspect, the invention features a system that includes a gas field ion source capable of interacting with a gas to generate an ion beam that can interact with a sample to cause primary neutral particles to leave the sample. The system also includes at least one detector configured so that, during use, the at least one detector can detect at least some of the primary neutral particles. The system further includes an electronic processor electrically connected to the at least one detector so that, during use, the electronic processor can process information based on the detected primary neutral particles to determine information about the sample.

In one aspect, the invention features a system that includes a gas field ion source capable of interacting with a gas to generate an ion beam that can interact with a sample to cause photons to leave the sample. The system also includes at least one detector configured so that, during use, the at least one detector can detect at least some of the photons. The system further includes an electronic processor electrically connected to the at least one detector so that, during use, the electronic processor can process information based on the detected photons to determine information about the sample.

In another aspect, the invention features a system that includes a gas field ion source capable of interacting with a gas to generate an ion beam that can interact with a sample to cause secondary ions to leave the sample. The system also includes at least one detector configured so that, during use, the at least one detector can detect at least some of the secondary ions. The system further includes an electronic processor electrically connected to the at least one detector so that, during use, the electronic processor can process information based on the detected secondary ions to determine information about the sample.

In a further aspect, the invention features a system that includes a gas field ion source capable of interacting with a gas to generate an ion beam that can interact with a sample to cause secondary neutral particles to leave the sample. The system also includes at least one detector configured so that, during use, the at least one detector can detect at least some of the secondary neutral particles. The system further includes an electronic processor electrically connected to the at least one detector so that, during use, the electronic processor can process information based on the detected secondary neutral particles to determine information about the sample.

In an additional aspect, the invention features a system that includes a gas field ion source capable of interacting with a gas to generate an ion beam that can interact with a sample to cause Auger electrons to leave the sample. The system also includes at least one detector configured so that, during use, the at least one detector can detect at least some of the Auger electrons. The system further includes an electronic processor electrically connected to the at least one detector so that, during use, the electronic processor can process information based on the detected Auger electrons to determine information about the sample.

In one aspect, the invention features a system that includes a gas field ion source capable of interacting with a gas to generate an ion beam that can interact with a sample to cause ions to leave the sample. The system also includes at least one detector configured so that, during use, the at least one detector can detect the ions. The interaction of the ion beam with the sample may cause secondary electrons to leave the sample, and, when the interaction of the ion beam with the sample causes secondary electrons to leave the sample, the at least one detector can detect at least some of the ions without detecting the secondary electrons.

In another aspect, the invention features a system that includes a gas field ion source capable of interacting with a gas to generate an ion beam that can interact with a sample to cause neutral particles to leave the sample. The system also includes at least one detector configured so that, during use, the at least one detector can detect the neutral particles. The interaction of the ion beam with the sample may cause secondary electrons to leave the sample, and, when the interaction of the ion beam with the sample causes secondary electrons to leave the sample, the at least one detector can detect at least some of the neutral particles without detecting the secondary electrons.

In a further aspect, the invention features a system that includes a gas field ion source capable of interacting with a gas to generate an ion beam that can interact with a sample to cause photons to leave the sample. The system also includes at least one detector configured so that, during use, the at least one detector can detect the photons. The interaction of the ion beam with the sample may cause secondary electrons to leave the sample, and, when the interaction of the ion beam with the sample causes secondary electrons to leave the sample, the at least one detector can detect at least some of the photons without detecting the secondary electrons.

In one aspect, the invention features a system that includes a gas field ion source capable of interacting with a gas to generate an ion beam having a spot size with a dimension of 10 nm or less on a surface of a sample. The system also includes ion optics configured to direct the ion beam toward the surface of the sample, the ion optics having at least one adjustable setting. When the adjustable setting of the ion optics are at a first setting, the ion beam interacts with a first location of the sample. When the adjustable setting of the ion optics are at a second setting, the ion beam interacts with a second location of the sample. The first setting of the ion optics is different from the second setting of the ion optics, and the first location of the sample is different from the second location of the sample.

In another aspect, the invention features a system that includes a gas field ion source capable of interacting with a gas to generate an ion beam that is directed toward a sample. The system also includes a charged particle source configured so that, during use, the charged particle source provides a beam of charged particles that is directed toward the sample. The gas field ion source is different from the charged particle source.

In a further aspect, the invention features a method that includes interacting an ion beam with a sample to cause multiple different types of particles to leave the sample, and detecting at least two different types of particles of the multiple different types of particles. The multiple different types of particles are selected from secondary electrons, Auger electrons, secondary ions, secondary neutral particles, primary neutral particles, scattered ions and photons.

In an additional aspect, the invention features a method that includes generating an ion beam by interacting a gas with a gas field ion source, and interacting the ion beam with a sample to cause particles to leave the sample. The particles are selected from Auger electrons, secondary ions, secondary neutral particles, primary neutral particles, scattered ions and photons. The method also includes detecting at least some of the particles to determine information about the sample.

In one aspect, the invention features a method that includes generating an ion beam by interacting a gas with a gas field ion source, and interacting the ion beam with a sample to cause particles to leave the sample. The method also includes producing a signal from a detector based on an energy of a particle detected by the detector.

In another aspect, the invention features a method that includes generating an ion beam by interacting a gas with a gas field ion source, and interacting the ion beam with a sample to cause particles to leave the sample. The method also includes producing a signal from a detector based on an angle of a trajectory of a particle detected by the detector.

In a further aspect, the invention features a method that includes generating an ion beam by interacting a gas with a gas field ion source, and interacting the ion beam with a sample to cause scattered ions to leave the sample. The method also includes detecting at least some of the scattered ions, and determining information about the sample based on the detected scattered ions.

In an additional aspect, the invention features a method that includes generating an ion beam by interacting a gas with a gas field ion source, and interacting the ion beam with a sample to cause primary neutral particles to leave the sample. The method also includes detecting at least some of the primary neutral particles, and determining information about the sample based on the detected primary neutral particles.

In one aspect, the invention features a method that includes generating an ion beam by interacting a gas with a gas field ion source, and interacting the ion beam with a sample to cause photons to leave the sample. The method also includes detecting at least some of the photons, and determining information about the sample based on the detected photons.

In another aspect, the invention features a method that includes generating an ion beam by interacting a gas with a gas field ion source, and interacting the ion beam with a sample to cause secondary ions to leave the sample. The method also includes detecting at least some of the secondary ions.

In a further aspect, the invention features a method that includes generating an ion beam by interacting a gas with a gas field ion source, and interacting the ion beam with a sample to cause secondary neutral particles to leave the sample. The method also includes detecting at least some of the secondary neutral particles or particles derived from the secondary neutral particles.

In an additional aspect, the invention features a method that includes generating an ion beam by interacting a gas with a gas field ion source, and interacting the ion beam with a sample to cause Auger electrons to leave the sample. The method also includes detecting at least some of the Auger electrons.

In one aspect, the invention features a method that includes forming a gas field ion source, and, after forming the gas field ion source, disposing the ion source into a chamber to provide a gas field ion system.

In another aspect, forming an ion source having an emission axis, and, after forming the ion source, aligning the emission axis of the ion source with an entry axis of an ion optics system.

In a further aspect, the invention features a method that includes generating an ion beam by interacting a gas with a gas field ion source, the ion beam having a spot size with a dimension of 10 nm or less on a surface of a sample, and moving the ion beam from a first location on the surface of the sample to a second location on the surface of the sample, the first location being different from the second location.

In an additional aspect, the invention features a method that includes generating an ion beam by interacting a gas with a gas field ion source, and contacting a sample with the ion beam. The method also includes contacting the sample with a charged particle beam from a charged particle source.

In one aspect, the invention features a method that includes generating an ion beam by interacting a gas with a gas field ion source, and interacting the ion beam with a sample to cause particles to leave the sample. The method also includes detecting at least some of the particles, and determining crystalline information about the sample based on the detected particles.

In another aspect, the invention features a method that includes generating an ion beam by interacting a gas with a gas field ion source, and inducing a voltage on a portion of the sample. The method also includes detecting particles to determine voltage contrast information about the sample.

In a further aspect, the invention features a method that includes generating an ion beam by interacting a gas with a gas field ion source, and interacting the ion beam with a sample to cause particles to leave the sample. The sample including at least a first material and a second material. The method also includes distinguishing the first and second materials based on the particles.

In an additional aspect, the invention features a method that includes generating an ion beam by interacting a gas with a gas field ion source, and interacting the ion beam with an activating gas to promote a chemical reaction at a surface of a sample.

In one aspect, the invention features a method that includes generating an ion beam by interacting a gas with a gas field ion source, and using the ion beam to determine sub-surface information about a semiconductor article. The method also includes editing the semiconductor article based on the sub-surface information.

In another aspect, the invention features a method that includes generating an ion beam by interacting a gas with a gas field ion source, and using the ion beam to determine information about a semiconductor article. The ion beam has a spot size of 10 nm or less at a surface of the semiconductor article. The method also includes editing the semiconductor article based on the information.

In a further aspect, the invention features a method that includes generating an ion beam by interacting a gas with a gas field ion source, and using the ion beam to determine information about a lithography mask. The ion beam has a spot size of 10 nm or less at a surface of the semiconductor article. The method also includes repairing the lithography mask based on the information.

In an additional aspect, the invention features a method that includes using an ion beam to pattern a resist on a sample. The ion beam has a spot size of 10 nm or less at the sample.

In one aspect, the invention features a method that includes generating an ion beam by interacting a gas with a gas field ion source, and interacting the ion beam with a sample including a feature. The ion beam has a spot size of 50 nm or less on a surface of a sample. The method also includes determining the size of the feature.

In another aspect, the invention features a method that includes generating an ion beam by interacting a gas with a gas field ion source, and interacting the ion beam with a sample to cause particles to the leave the sample. The sample has multiple stacked layers including first and second layers. The method also includes detecting the particles to determine whether the second layer is registered with the first layer.

In a further aspect, the invention features a method that includes exposing a sample to a focused ion beam, and generating a second ion beam by interacting a gas with a gas field ion source. The method also includes exposing the sample to the second ion beam.

In an additional aspect, the invention features a method that includes forming an electrically conductive tip of a gas field ion source when the gas field ion source is present within an ion microscope.

In one aspect, the invention features a system that includes an ion source. The system is capable of imaging the ion source in a first mode, and the system is capable of using the ion source to collect an image of a sample in a second mode. The sample is different from the ion source.

In another aspect, the invention features a sample manipulator that includes a housing, a disk supported by the housing, a member supported by the disk, the member having legs and a surface configured to support a sample, and a device. The device contacts the member to move the sample in a first mode, and the device is not in contact with the member in a second mode.

In an additional aspect, the invention features a system that includes a gas field ion source and a sample manipulator. The sample manipulator includes a housing, a disk supported by the housing, a member supported by the disk, the member having legs and a surface configured to support a sample, and a device. The device contacts the member to move the sample in a first mode, and the device is not in contact with the member in a second mode.

In one aspect, the invention features a method that includes generating a first beam containing ions by interacting a gas with a gas field ion source, and removing non-singly charged chemical species from the first beam to form a second beam containing singly-charged ions.

In an additional aspect, the invention features a system that includes a gas field ion source capable of interacting with a gas to generate a beam comprising chemical species including charged chemical species. The system also includes at least one biased electrode configured to cause beam paths of chemical species in the beam to diverge based on the charge of the chemical species.

In another aspect, the invention features a method that includes generating ions by interacting a gas with a gas field ion source, and sputtering a sample with the ions.

In a further aspect, the invention features a method that includes generating an ion beam by interacting a gas with a gas field ion source, and generating an electron beam using a system different from the gas field ion source. The method also includes using both the ion beam and the electron beam to investigate a sample.

In another aspect, the invention features a system that includes a scanning electron microscope capable of providing an electron beam. The system also includes a gas field ion source capable of interacting with a gas to generate an ion beam. The scanning electron microscope and the gas field ion microscope are positioned so that, during use, both the electron beam and the ion beam can be used to investigate a sample.

In an additional aspect, the invention features a method that includes generating a first ion beam by interacting a gas with a gas field ion source. The first ion beam has a first current. The method also includes using the first ion beam having the first current to prepare the gas field ion source for investigating a sample. The method further includes generating a second ion beam by interacting a gas with the gas field ion source. The second ion beam has a second current. In addition, the method includes using the second ion beam to investigate the sample.

Embodiments may include one or more of the following advantages.

In some embodiments, an ion source (e.g., a gas field ion source) can provide a relatively small spot size on the surface of a sample. An ion microscope (e.g., a gas field ion microscope) using such an ion source can, for example, obtain an image of a sample with relatively high resolution.

In certain embodiments, an ion source (e.g., a gas field ion source) can have a relatively high brightness and/or a relatively high reduced brightness. An ion microscope (e.g., a gas field ion microscope) using such an ion source can, for example, take a good quality image of a sample in a relatively short period of time, which can, in turn, increase the speed with which large numbers of samples can be imaged.

In some embodiments, an ion source (e.g., a gas field ion source) can have a relatively high brightness for a given ion current (e.g., a relatively low etendue). An ion microscope (e.g., a gas field ion microscope) using such an ion source can, for example, take a good quality image of a sample with relatively little damage to the sample.

In certain embodiments, a gas field ion microscope can have a relatively high reliability. Thus, for example, the gas field ion source can be used for an extended period of time without replacing the gas field ion source, which can, for example, increase the speed with which large numbers of samples can be imaged, reduce the down time associated with imaging a large number of samples, and/or reduce the cost associated with imaging a large number of samples.

In some embodiments, an ion microscope (e.g., a gas field ion microscope) is configured so that vibrations are substantially decoupled from the ion source. This can enhance the ability of the ion microscope to achieve one or more of the advantages noted above.

In certain embodiments, an ion microscope (e.g., a gas field ion microscope) can be operated at relatively high temperature while still providing one or more of the above-mentioned advantages. For example, liquid nitrogen can be used as the coolant for the ion microscope. This can reduce the cost and/or complexity associated with using certain other coolants, such as liquid helium. This can also reduce potential problems associated with certain mechanical systems used with liquid helium coolant that can create substantial vibrations.

Other features and advantages of the invention will be apparent from the description, drawings, and claims.

DESCRIPTION OF DRAWINGS

FIGS. 35A, 35D and 35G are schematic diagrams showing respective embodiments of helium ion scattering patterns from a surface using different detectors to detect the scattered helium ions.

FIGS. 35B, 35E and 35H are plots of the total scattered helium ion yield for the systems shows in FIGS. 35A, 35D and 35G, respectively.

FIGS. 35C, 35F and 35I are plots of the relative abundance of scattered helium ions detected by the detectors in FIGS. 35A, 35D and 35G, respectively.

Like reference symbols in the various drawings indicate like elements.

DETAILED DESCRIPTION

General Introduction

Ions can be produced and used for sample imaging and other applications in microscope systems. Microscope systems that use a gas field ion source to generate ions that can be used in sample analysis (e.g., imaging) are referred to as gas field ion microscopes. A gas field ion source is a device that includes an electrically conductive tip (typically having an apex with 10 or fewer atoms) that can be used to ionize neutral gas species to generate ions (e.g., in the form of an ion beam) by bringing the neutral gas species into the vicinity of the electrically conductive tip (e.g., within a distance of about four to five angstroms) while applying a high positive potential (e.g., one kV or more relative to the extractor (see discussion below)) to the apex of the electrically conductive tip.

Figure 1:
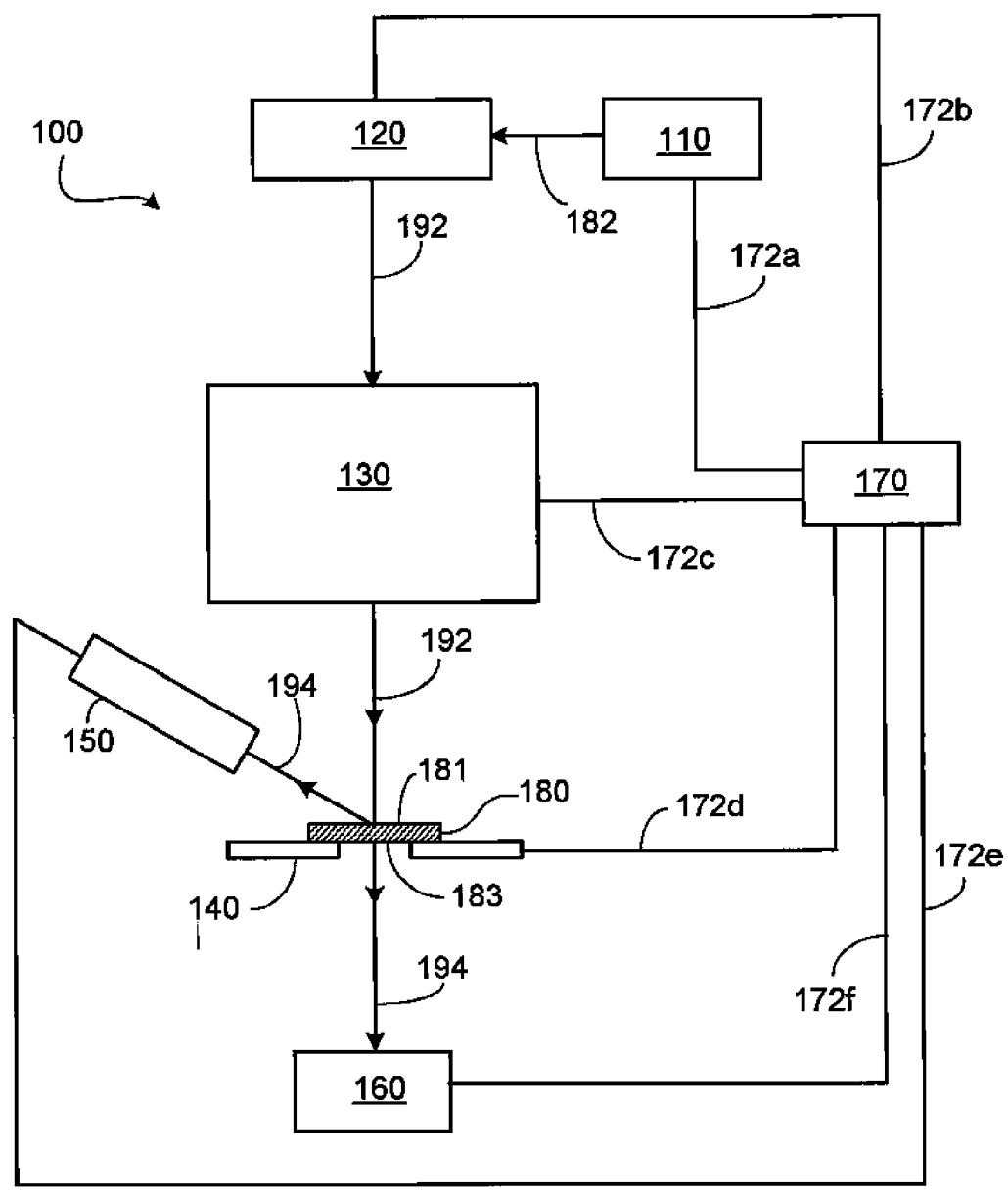
FIG. 1 is a schematic diagram of an ion microscope system.

FIG. 1 shows a schematic diagram of a gas field ion microscope system 100 that includes a gas source 110, a gas field ion source 120, ion optics 130, a sample manipulator 140, a front-side detector 150, a back-side detector 160, and an electronic control system 170 (e.g., an electronic processor, such as a computer) electrically connected to various components of system 100 via communication lines 172a-172f. A sample 180 is positioned in/on sample manipulator 140 between ion optics 130 and detectors 150, 160. During use, an ion beam 192 is directed through ion optics 130 to a surface 181 of sample 180, and particles 194 resulting from the interaction of ion beam 192 with sample 180 are measured by detectors 150 and/or 160.

In general, it is desirable to reduce the presence of certain undesirable chemical species in system 100 by evacuating the system. Typically, different components of system 100 are maintained at different background pressures. For example, gas field ion source 120 can be maintained at a pressure of approximately $10^{-10}$ Torr. When gas is introduced into gas field ion source 120, the background pressure rises to approximately $10^{-5}$ Torr. Ion optics 130 are maintained at a background pressure of approximately $10^{-8}$ Torr prior to the introduction of gas into gas field ion source 120. When gas is introduced, the background pressure in ion optics 130 typically increase to approximately $10^{-7}$ Torr. Sample 180 is positioned within a chamber that is typically maintained at a background pressure of approximately $10^{-6}$ Torr. This pressure does not vary significantly due to the presence or absence of gas in gas field ion source 120.

Figure 2:
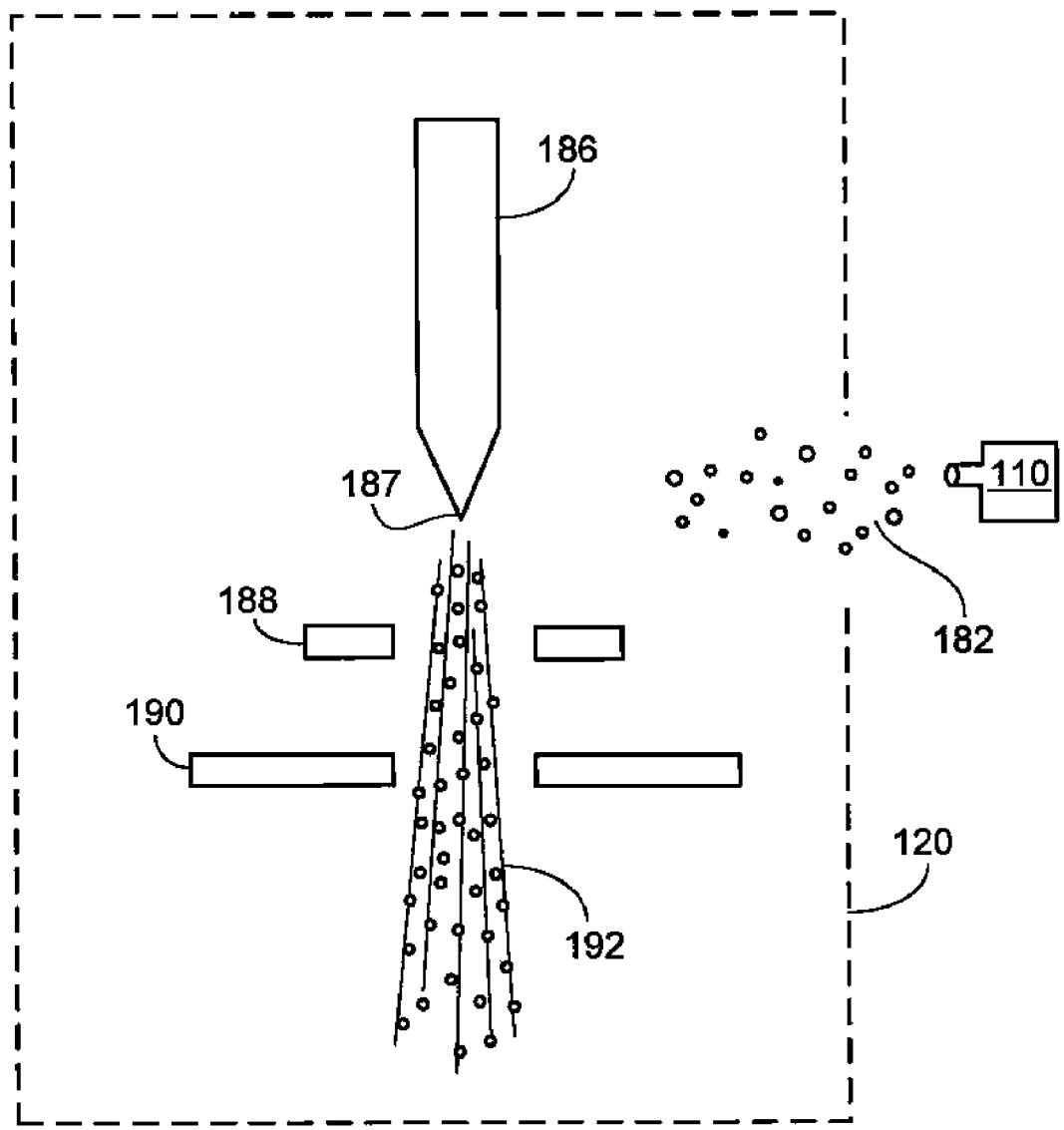
FIG. 2 is a schematic diagram of a gas field ion source.

As shown in FIG. 2, gas source 110 is configured to supply one or more gases 182 to gas field ion source 120. As described in more detail below, gas source 110 can be configured to supply the gas(es) at a variety of purities, flow rates, pressures, and temperatures. In general, at least one of the gases supplied by gas source 110 is a noble gas (helium (He), neon (Ne), argon (Ar), krypton (Kr), xenon (Xe)), and ions of the noble gas are desirably the primary constituent in ion beam 192. In general, as measured at surface 181 of sample 180, the current of ions in ion beam 192 increases monotonically as the pressure of the noble gas in system 100 increases. In certain embodiments, this relationship can be described by a power law where, for a certain range of noble gas pressures, the current increases generally in proportion to gas pressure. During operation, the pressure of the noble gas is typically $10^{-2}$ Torr or less (e.g., $10^{-3}$ Torr or less, $10^{-4}$ Torr or less), and/or $10^{-7}$ Torr or more (e.g., $10^{-6}$ Torr or more, $10^{-5}$ Torr or more) adjacent the tip apex (see discussion below). In general, it is desirable to use relatively high purity gases (e.g., to reduce the presence of undesirable chemical species in the system). As an example, when He is used, the He can be at least 99.99% pure (e.g., 99.995% pure, 99.999% pure, 99.9995% pure, 99.9999% pure). Similarly, when other noble gases are used (Ne gas, Ar gas, Kr gas, Xe gas), the purity of the gases is desirably high purity commercial grade.

Optionally, gas source 110 can supply one or more gases in addition to the noble gas(es). As discussed in more detail below, an example of such a gas is nitrogen. Typically, while the additional gas(es) can be present at levels above the level of impurities in the noble gas(es), the additional gas(es) still constitute minority components of the overall gas mixture introduced by gas source 110. As an example, in embodiments in which He gas and Ne gas are introduced by gas source 110 into gas field ion source 120, the overall gas mixture can include 20% or less (e.g., 15% or less, 12% or less) Ne, and/or 1% or more (e.g., 3% or more, 8% or more) Ne. For example, in embodiments in which He gas and Ne gas are introduced by gas source 110, the overall gas mixture can include from 5% to 15% (e.g., from 8% to 12%, from 9% to 11%) Ne. As another example, in embodiments in which He gas and nitrogen gas are introduced by gas source 110, the overall gas mixture can include 1% or less (e.g., 0.5% or less, 0.1% or less) nitrogen, and/or 0.01% or more (e.g., 0.05% or more) nitrogen. For example, in embodiments in which He gas and nitrogen gas are introduced by gas source 110, the overall gas mixture can include from 0.01% to 1% (e.g., from 0.05% to 0.5%, from 0.08 to 0.12%) nitrogen. In some embodiments, the additional gas(es) are mixed with the noble gas(es) before entering system 100 (e.g., via the use of a gas manifold that mixes the gases and then delivers the mixture into system 100 through a single inlet). In certain embodiments, the additional gas(es) are not mixed with the noble gas(es) before entering system 100 (e.g., a separate inlet is used for inputting each gas into system 100, but the separate inlets are sufficiently close that the gases become mixed before interacting with any of the elements in gas field ion source 120).

Gas field ion source 120 is configured to receive the one or more gases 182 from gas source 110 and to produce gas ions from gas(es) 182. Gas field ion source 120 includes an electrically conductive tip 186 with a tip apex 187, an extractor 190 and optionally a suppressor 188. Typically, the distance from tip apex 187 to surface 181 of sample 180 (not shown in FIG. 2) is five cm or more (e.g., 10 cm or more, 15 cm or more, 20 cm or more, 25 cm or more), and/or 100 cm or less (e.g., 80 cm or less, 60 cm or less, 50 cm or less). For example, in some embodiments, the distance from tip apex 187 to surface 181 of sample 180 is from five cm to 100 cm (e.g., from 25 cm to 75 cm, from 40 cm to 60 cm, from 45 cm to 55 cm).

Electrically conductive tip 186 can be formed of various materials. In some embodiments, tip 186 is formed of a metal (e.g., tungsten (W), tantalum (Ta), iridium (Ir), rhenium (Rh), niobium (Nb), platinum (Pt), molybdenum (Mo)). In certain embodiments, electrically conductive tip 186 can be formed of an alloy. In some embodiments, electrically conductive tip 186 can be formed of a different material (e.g., carbon (C)).

During use, tip 186 is biased positively (e.g., approximately 20 kV) with respect to extractor 190, extractor 190 is negatively or positively biased (e.g., from $-20$ kV to $+50$ kV) with respect to an external ground, and optional suppressor 188 is biased positively or negatively (e.g., from $-5$ kV to $+5$ kV) with respect to tip 186. Because tip 186 is formed of an electrically conductive material, the electric field of tip 186 at tip apex 187 points outward from the surface of tip apex 187. Due to the shape of tip 186, the electric field is strongest in the vicinity of tip apex 187. The strength of the electric field of tip 186 can be adjusted, for example, by changing the positive voltage applied to tip 186. With this configuration, un-ionized gas atoms 182 supplied by gas source 110 are ionized and become positively-charged ions in the vicinity of tip apex 187. The positively-charged ions are simultaneously repelled by positively charged tip 186 and attracted by negatively charged extractor 190 such that the positively-charged ions are directed from tip 186 into ion optics 130 as ion beam 192. Suppressor 188 assists in controlling the overall electric field between tip 186 and extractor 190 and, therefore, the trajectories of the positively-charged ions from tip 186 to ion optics 130. In general, the overall electric field between tip 186 and extractor 190 can be adjusted to control the rate at which positively-charged ions are produced at tip apex 187, and the efficiency with which the positively-charged ions are transported from tip 186 to ion optics 130.

As an example, without wishing to be bound by theory, it is believed that He ions can be produced as follows. Gas field ion source 120 is configured so that the electric field of tip 186 in the vicinity of tip apex 187 exceeds the ionization field of the un-ionized He gas atoms 182, and tip 186 is maintained at a relatively low temperature. When the un-ionized He gas atoms 182 are in close proximity to tip apex 187, the He atoms can be polarized by the electric field of the tip, producing a weakly attractive force between He atoms 182 and tip apex 187. As a result, He atoms 182 may contact tip apex 187 and remain bound (e.g., physisorbed) thereto for some time. In the vicinity of tip apex 187, the electric field is high enough to ionize He atoms 182 adsorbed onto tip apex 187, generating positively charged He ions (e.g., in the form of an ion beam).

Figure 3:
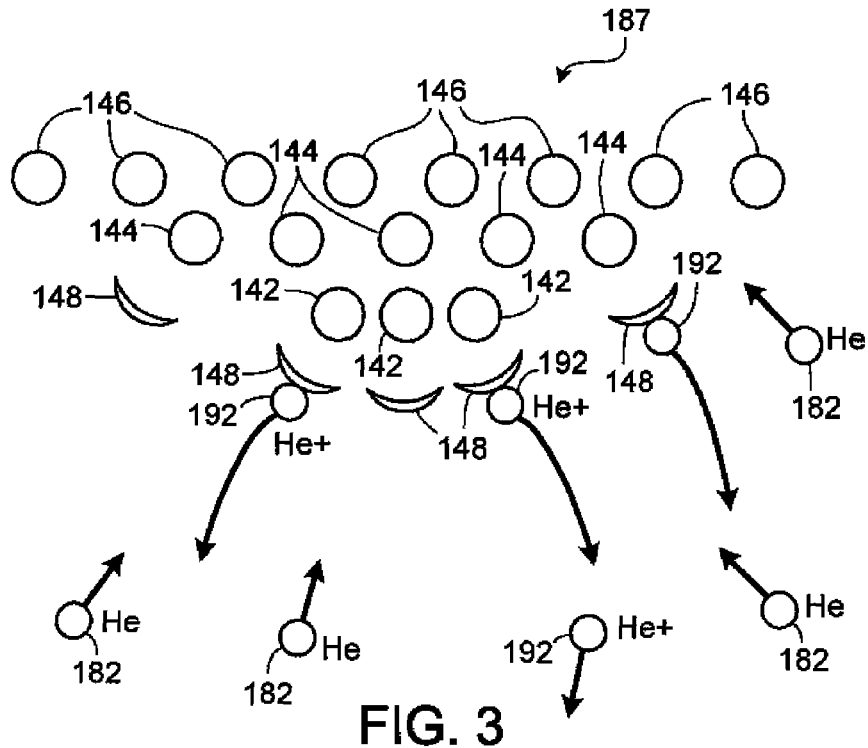
FIG. 3 is a schematic representation of an enlarged side view of an embodiment of a tip apex.

FIG. 3 is a schematic representation of tip apex 187 (formed of W(111), see discussion below). Tip apex 187 includes layers of atoms arranged to form atomic shelves. A terminal atomic shelf is formed by atoms 142. A second atomic shelf is formed by atoms 144, and a third atomic shelf is formed by atoms 146. Neutral gas atoms 182 delivered by gas source 110 are present in the vicinity of tip apex 187. Atoms 182 become polarized due to the electric field of tip apex 187, and experience a relatively weak attractive force that causes atoms 182 to move towards tip apex 187, as indicated by the arrows on atoms 182.

Depending upon the strength of the tip's electric field, each atoms in the atomic shelves near tip apex 187 can have a corresponding ionization disk 148. An ionization disk 148 is a region of space in which a neutral He atom, venturing thereinto, has a high probability of undergoing ionization. Typically, ionization of a neutral He atom occurs via electron tunneling from the neutral He atom to a tip apex atom. Ionization disks 148 therefore represent spatial regions in which He ions are generated, and from which the He ions emerge.

The sizes of the ionization disks 148 for particular tip apex atoms are dependent upon the shape of tip apex 187 and the electrical potential applied to tip apex 187. In general, ionization of He atoms can occur in spatial regions adjacent to tip apex 187 where the local electric field exceeds the ionization potential of He atoms. For a large electric potential applied to tip apex 187, therefore, many tip atoms will have ionization disks. In addition, the local electric field in the vicinity of tip apex 187 depends upon the shape of tip apex 187. For a relatively sharp tip apex, the local electric field in the vicinity of tip apex 187 will be relatively high. For a relatively blunt tip apex, the local electric field, even in the vicinity of tip apex 187, will be smaller.

Ionization disks 148 corresponding to individual atoms of tip apex 187 are spatially separated from one another in FIG. 3. In some embodiments, if the electric field of tip apex 187 is sufficiently large, ionization disks from more than one atom (e.g., atoms 142) can overlap spatially, creating a larger ionization disk that spans a region of space proximal to multiple tip apex atoms. By reducing the electric field at tip apex 187, the volume of space occupied by ionization disks 148 can be reduced, and the geometry depicted in FIG. 3 can be realized where a few tip apex atoms each have their own individual, spatially separated ionization disks. Because, in many instances, the shape of tip apex 187 is not easily altered during use of ion source 120, the electric field in the vicinity of tip apex 187 is typically controlled by adjusting the electrical potential applied to tip apex 187.

By further reducing the potential applied to tip apex 187, some of the ionization disks in FIG. 3 can be eliminated. For example, tip apex 187 is not as sharp in the vicinity of second atomic shelf atoms 144, and by reducing the potential applied to tip apex 187, the electric field of tip apex 187 in the vicinity of atoms 144 can be reduced so that He atom ionization does not occur with high probability in these regions. As a result, ionization disks corresponding to atoms 144 are no longer present. However, the electric field of tip apex 187 in the vicinity of terminal shelf atoms 142 can still be high enough to cause He atom ionization, and so ionization disks 148 corresponding to atoms 142 remain. By carefully controlling the electrical potential applied to tip apex 187, ion source 120 can operate so that the only ionization disks present correspond to terminal shelf atoms 142, and the ionization disks corresponding to the terminal shelf atoms are spatially separated from one another. As a result, a He atom that is ionized in the vicinity of tip apex 187 is produced via ionization in the vicinity of a particular terminal shelf atom.

Neutral He atoms 182 have a higher probability of undergoing ionization the longer they remain within ionization disks 148. The polarization of He atoms which is induced by the electric field of tip apex 187, and which causes polarized He atoms to move toward tip apex 187, further ensures that the polarized He atoms remain bound to tip apex 187, increasing the amount of time that the He atoms 182 remain within ionization disks 148, and increasing the probability of ionization of the polarized He atoms over time.

Polarized He atoms can also move from one position to another along the surface of tip apex 187. Because the attractive force between a polarized He atom and tip apex 187 depends on the local strength of the electric field of tip apex 187 at the position of the polarized He atom, the motion of polarized He atoms tends to transport the atoms toward the end of tip apex 187 of tip 186 (e.g., toward terminal shelf 142) where the local electric field is highest. This transport mechanism of polarized He atoms, in combination with control over the electrical potential applied to tip 186 (e.g., to ensure that discrete ionization disks corresponding to only terminal shelf atoms 142 are present), can be used to operate ion source 120 such that a He ion beam 192 is produced by gas field ionization source 120, where individual He ions in the ion beam are generated via the interaction of He gas with one of the terminal shelf atoms 142. Ion beam 192 therefore includes a plurality of He ions from each of the terminal shelf atoms 142, where each He ion can be attributed to ionization at one of the terminal shelf atoms 142.

As discussed above, in general, the size and shape of ionization disks 148 can be modified by changing the electrical potential applied to tip apex 187, and adjacent ionization disks 148 can be made to overlap with a suitably large applied potential, or maintained spatially distinct from one another by a suitably small applied potential. Typically, ionization disks 148 are spaced from tip atoms 142, 144, and 146 by a distance of approximately 0.4 nm. Individual ionization disks corresponding to tip atoms typically have a thickness of approximately 0.02 nm, measured in a direction along a line joining a given disk and its corresponding atom. Ionization disks 148 typically have a diameter, measured in a direction normal to the line joining a given disk and its corresponding atom, of approximately the diameter of the corresponding atom.

Figure 4:
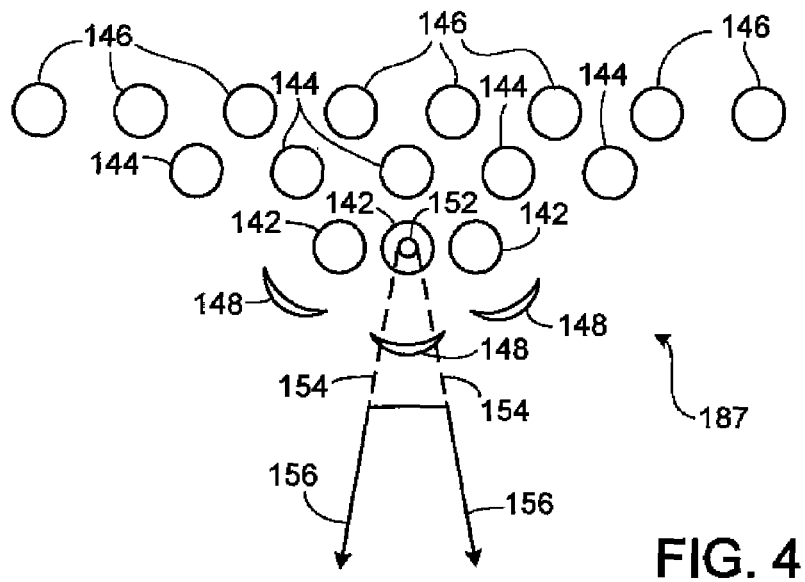
FIG. 4 is a schematic representation of an enlarged side view of the tip of FIG. 3.

FIG. 4 shows an operating configuration of tip apex 187 where the electrical potential applied to tip 186 produces three ionization disks 148, each of which corresponds to one of three terminal atomic shelf atoms 142. Once He ions are produced in the vicinity of tip apex 187, they are rapidly accelerated away from the tip due to the large positive tip potential. He ions are accelerated away from tip apex 187 along a plurality of trajectories. Two such trajectories 156 are shown in FIG. 4. As depicted in FIG. 4, trajectories 156 correspond to the left- and right-hand limits of the full width at half maximum (FWHM) trajectory distribution for the middle terminal shelf atom. As such, if trajectories 156 are extrapolated backwards (e.g., along lines 154) to the position of the middle terminal shelf atom, they define a virtual source 152 for the middle terminal shelf atom. The diameter of virtual source 152 is typically smaller than the diameter of the middle terminal shelf atom, and may be much smaller than the diameter of the middle terminal shelf atom (e.g., by a factor of 2 or more, a factor of 3 or more, a factor of 5 or more, a factor of 10 or more). Similar considerations apply to the other terminal shelf atoms, and each terminal shelf atom has a corresponding virtual source size.

The small virtual source size for terminal shelf atoms can provide a number of advantages. For example, the small virtual source size of ion beam 192 and the relatively small thickness of the ionization disk 148 from which ions in ion beam 192 arise can assist in ensuring that ion beam 192 has a relatively high brightness and a relatively narrow ion energy distribution.

Without wishing to be bound by theory, it is believed that using a tip temperature that is too low can negatively impact current stability and/or increase undesirable effects from increased impurity adsorption on the tip. In general, the temperature of tip 186 is 5 K or more (e.g., 10 K or more, 25 K or more, 50 K or more 75 K or more), and/or 100 K or less (e.g., 90 K or less, 80 K or less). For example, the temperature of tip 186 can be from 5 K to 100 K (e.g., from 25 K to 90 K, from 50 K to 90 K, from 75 K to 80 K). The temperature of tip 186 can be attained by thermal coupling with a coolant, such as, for example, liquid helium or liquid nitrogen. Alternatively or additionally, tip 186 can be thermally cooled using a cryogenic refrigerator.

It is believed that, if the temperature of tip 186 is too low, the rate at which adsorbed He atoms are transported by moving to atoms 142 in the terminal atomic shelf of tip apex 187 is reduced so that not enough He atoms per unit time reach atoms 142 where they can be ionized. As a result, when the emission pattern of tip 186 is observed (e.g., by using field ion microscope (FIM) techniques, or by scanning FIM (SFIM) techniques), the abundance of ions from individual terminal shelf atoms alternates from relatively high abundance to relatively low abundance (commonly referred to as blinking). This can occur, for example, when there are no He atoms available for ionization in the vicinity of the terminal shelf atom at certain times. As the temperature of tip 186 is increased, the transport rate of He atoms toward the terminal shelf of atoms of tip apex 187 increases, and the observation of this alternating high/low abundance from terminal shelf atoms 142 is reduced or eliminated.

It is also believed that, if the temperature of tip 186 is too high, polarized He atoms will have too much kinetic energy to remain bound to tip 186 for sufficiently long periods of time to ensure efficient ionization of He atoms in the vicinity of terminal shelf atoms 142. This can also result in disappearance of the emission pattern from individual terminal shelf atoms as observed using FIM and/or SFIM imaging techniques. As a result, to ensure that the He ionization process at each of the terminal shelf atoms 142 produces stable ion currents from each of the terminal shelf atoms 142, the temperature of tip 186 is carefully controlled to mitigate against both undesirable high- and low-temperature effects.

In general, ion optics 130 are configured to direct ion beam 192 onto surface 181 of sample 180. As described in more detail below, ion optics 130 can, for example, focus, collimate, deflect, accelerate, and/or decelerate ions in beam 192. Ion optics 130 can also allow only a portion of the ions in ion beam 192 to pass through ion optics 130. Generally, ion optics 130 include a variety of electrostatic and other ion optical elements that are configured as desired. By manipulating the electric field strengths of one or more components (e.g., electrostatic deflectors) in ion optics 130, He ion beam 192 can be scanned across surface 181 of sample 180. For example, ion optics 130 can include two deflectors that deflect ion beam 192 in two orthogonal directions. The deflectors can have varying electric field strengths such that ion beam 192 is rastered across a region of surface 181.

When ion beam 192 impinges on sample 180, a variety of different types of particles 194 can be produced. These particles include, for example, secondary electrons, Auger electrons, secondary ions, secondary neutral particles, primary neutral particles, scattered ions and photons (e.g., X-ray photons, IR photons, visible photons, UV photons). Detectors 150 and 160 are positioned and configured to each measure one or more different types of particles resulting from the interaction between He ion beam 192 and sample 180. As shown in FIG. 1, detector 150 is positioned to detect particles 194 that originate primarily from surface 181 of sample 180, and detector 160 is positioned to detect particles 194 that emerge primarily from surface 183 of sample 180 (e.g., transmitted particles). As described in more detail below, in general, any number and configuration of detectors can be used in the microscope systems disclosed herein. In some embodiments, multiple detectors are used, and some of the multiple detectors are configured to measure different types of particles. In certain embodiments, the detectors are configured to provide different information about the same type of particle (e.g., energy of a particle, angular distribution of a given particle, total abundance of a given particle). Optionally, combinations of such detector arrangements can be used.

In general, the information measured by the detectors is used to determine information about sample 180. Exemplary information about sample 180 includes topographical information about surface 181, material constituent information (of surface 181 and/or of a sub-surface region of sample 180), crystalline orientation information of sample 180, voltage contrast information about (and therefore electrical properties of) surface 181, voltage contrast information about a sub-surface region of sample 180, optical properties of sample 180, and/or magnetic properties of sample 180. Typically, this information is determined by obtaining one or more images of sample 180. By rastering ion beam 192 across surface 181, pixel-by-pixel information about sample 180 can be obtained in discrete steps. Detectors 150 and/or 160 can be configured to detect one or more different types of particles 194 at each pixel. Typically, a pixel is a square, although in some embodiments, pixels can have different shapes (e.g., rectangular). A pixel size, which corresponds to a length of a side of the pixel, can be, for example, from 100 pm to two μm (e.g., from one nm to one μm). In some embodiments, the location of adjacent pixels can be determined to within at least 200 pm (e.g., to within at least 100 pm, to within at least 75 pm, to within at least 50 pm). Thus, the operator of the system can determine the location of the center of the beam spot to within at least 200 pm (e.g., to within at least 100 pm, to within at least 75 pm, to within at least 50 pm). In certain embodiments, the field of view (FOV) of sample 180 is 200 nm or more (e.g., 500 nm or more, 1 μm or more, 50 μm or more, 100 μm or more, 500 μm or more, 1 mm or more, 1.5 mm or more), and/or 25 mm or less (15 mm or less, 10 mm or less, five mm or less). The field of view refers to the area of a sample surface that is imaged by the ion microscope.

The operation of microscope system 100 is typically controlled via electronic control system 170. For example, electronic control system 170 can be configured to control the gas(es) supplied by gas source 110, the temperature of tip 186, the electrical potential of tip 186, the electrical potential of extractor 190, the electrical potential of suppressor 188, the settings of the components of ion optics 130, the position of sample manipulator 140, and/or the location and settings of detectors 150 and 160. Optionally, one or more of these parameters may be manually controlled (e.g., via a user interface integral with electronic control system 170). Additionally or alternatively, electronic control system 170 can be used (e.g., via an electronic processor, such as a computer) to analyze the information collected by detectors 150 and 160 and to provide information about sample 180 (e.g., topography information, material constituent information, crystalline information, voltage contrast information, optical property information, magnetic information), which can optionally be in the form of an image, a graph, a table, a spreadsheet, or the like. Typically, electronic control system 170 includes a user interface that features a display or other kind of output device, an input device, and a storage medium.

Helium Ion Microscope Systems

A. Overview

Figure 5:
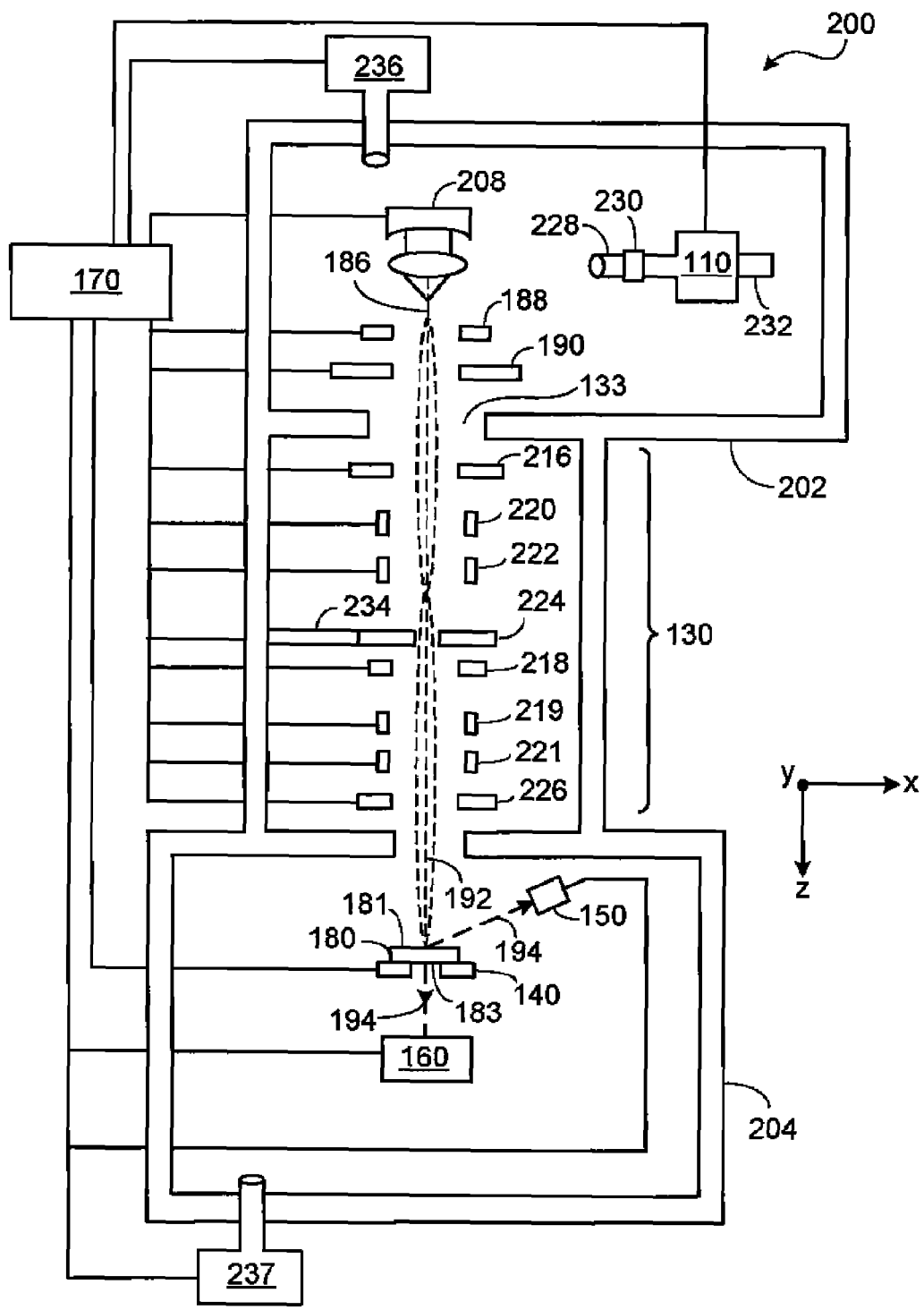
FIG. 5 is a schematic diagram of a helium ion microscope system.

FIG. 5 shows a schematic diagram of a He ion microscope system 200. Microscope system 200 includes a first vacuum housing 202 enclosing a He ion source and ion optics 130, and a second vacuum housing 204 enclosing sample 180 and detectors 150 and 160. Gas source 110 delivers He gas to microscope system 200 through a delivery tube 228. A flow regulator 230 controls the flow rate of He gas through delivery tube 228, and a temperature controller 232 controls the temperature of He gas in gas source 110. The He ion source includes a tip 186 affixed to a tip manipulator 208. The He ion source also includes an extractor 190 and a suppressor 188 that are configured to direct He ions from tip 186 into ion optics 130. Ion optics 130 include a first lens 216, alignment deflectors 220 and 222, an aperture 224, an astigmatism corrector 218, scanning deflectors 219 and 221, and a second lens 226. Aperture 224 is positioned in an aperture mount 234. Sample 180 is mounted in/on a sample manipulator 140 within second vacuum housing 204. Detectors 150 and 160, also positioned within second vacuum housing 204, are configured to detect particles 194 from sample 180. Gas source 110, tip manipulator 208, extractor 190, suppressor 188, first lens 216, alignment deflectors 220 and 222, aperture mount 234, astigmatism corrector 218, scanning deflectors 219 and 221, sample manipulator 140, and/or detectors 150 and/or 160 are typically controlled by electronic control system 170. Optionally, electronic control system 170 also controls vacuum pumps 236 and 237, which are configured to provide reduced-pressure environments inside vacuum housings 202 and 204, and within ion optics 130.

B. Ion Source

Figure 6:
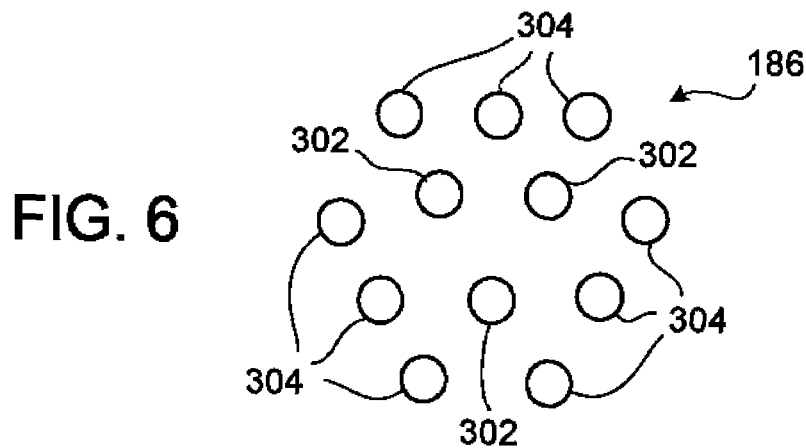
FIG. 6 is a schematic representation of an enlarged top view of an embodiment of a W(111) tip.
Figure 7:
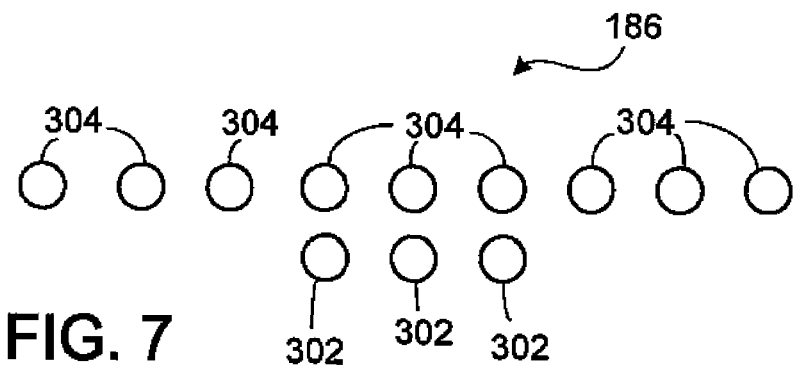
FIG. 7 is a schematic representation of an enlarged side view of the W(111) tip of FIG. 6.

As noted above, in general, tip 186 can be formed of any appropriate electrically conductive material. In certain embodiments, tip 186 can be formed of a single crystal material, such as a single crystal metal. Typically, a particular single crystal orientation of the terminal shelf of atoms of tip apex 187 is aligned with a longitudinal axis of tip 186 to within 3° or less (e.g., within 2° or less, within 1° or less). In some embodiments, apex 187 of tip 186 can terminate in an atomic shelf having a certain number of atoms (e.g., 20 atoms or less, 15 atoms or less, 10 atoms or less, nine atoms or less, six atoms or less, three atoms or less). For example, apex 187 of tip 186 can be formed of W(111) and can have a terminal shelf with three atoms (a trimer). FIGS. 6 and 7 show schematic representations of enlarged top and side views, respectively, of the two atomic shelves of a W tip 186 that are nearest to the apex of tip. The terminal shelf, which includes three W atoms 302 arranged in a trimer, corresponds to a (111) surface of W. Without wishing to be bound by theory, it is believed that this trimer surface is advantageous (in terms of its ease of formation, re-formation and stability) because the surface energy of the W(111) crystal face favorably supports a terminal shelf formed by three W atoms arranged in an equilateral triangle to form a trimer. The trimer atoms 302 are supported by a second shelf of W atoms 304.

In some embodiments, tip 186 can have a terminal shelf that includes fewer than three atoms or more than three atoms. For example, a W(111) tip can have a terminal shelf that includes two atoms, or a terminal shelf that includes only one atom. Alternatively, a W(111) tip can have a terminal shelf that includes four or more atoms (e.g., five or more atoms, six or more atoms, seven or more atoms, eight or more atoms, nine or more atoms, ten or more atoms, more than ten atoms).

Alternatively, or in addition, tips that correspond to other W crystalline orientations (e.g., W(112), W(110) or W(100)) can be used, and such tips can have terminal shelves that include one or more atoms (e.g., two or more atoms, three or more atoms, four or more atoms, five or more atoms, six or more atoms, seven or more atoms, eight or more atoms, nine or more atoms, ten or more atoms, more than ten atoms).

In some embodiments, tips formed from a material other than single crystal W can be used in the ion source (e.g., a single crystal of a metal, such as a single crystal of one of the metals noted above), and such tips can have terminal shelves that include one or more atoms (e.g., two or more atoms, three or more atoms, four or more atoms, five or more atoms, six or more atoms, seven or more atoms, eight or more atoms, nine or more atoms, ten or more atoms, more than ten atoms).

Figure 8:
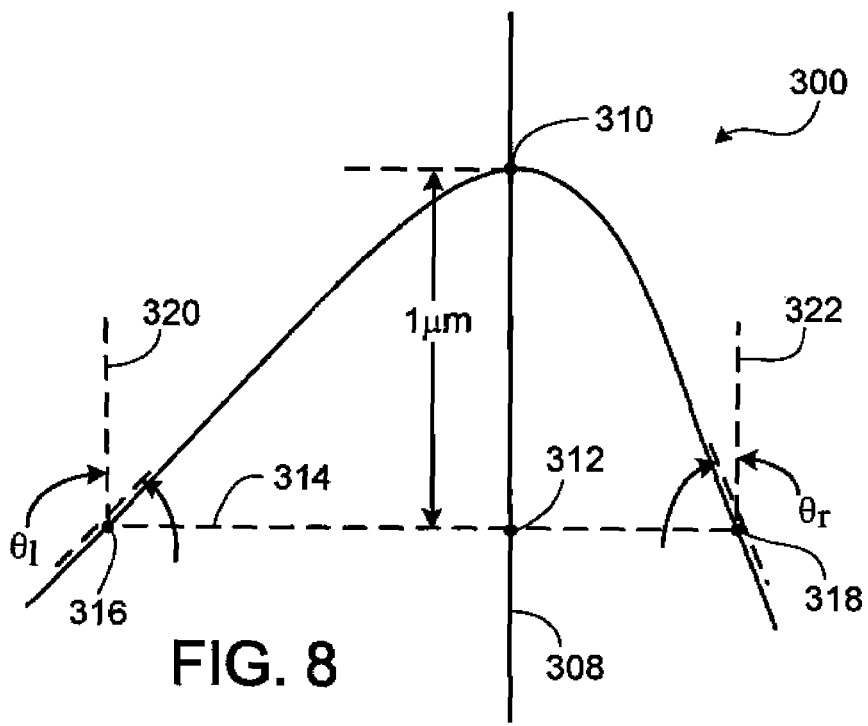
FIG. 8 is a side view of a tip showing a cone angle measurement.

As described below, the shape of tip apex 187 can have an impact on the quality of the ion beam, which can have an impact on the performance of microscope system 200. For example, when viewed from the side, tip apex 187 can be symmetrically formed about its longitudinal axis, or it can be asymmetrically formed about its longitudinal axis. In certain embodiments, from one or more side views, tip apex 187 may be symmetrically formed about its longitudinal axis, and, from one or more different side views, tip apex 187 may be asymmetrically formed about its longitudinal axis. FIG. 8 shows a side view of an exemplary tip 300 (at much smaller magnification than in FIGS. 6 and 7) that is asymmetrically formed with respect to its longitudinal axis 308. From a given side view, the degree to which tip 300 is asymmetrically formed along longitudinal axis 308 can be quantified using parameters such as, for example, an average full cone angle and an average cone direction. These parameters are determined as follows.

An image of tip 300 is obtained using a scanning electron microscope (SEM). FIG. 8 is a schematic representation of such an image. Tip 300 includes an apex point 310 and a second point 312, both located on longitudinal axis 308, with point 312 spaced one μm from apex point 310 along longitudinal axis 308. An imaginary line 314 extends perpendicular to axis 308 and through point 312 in the plane of FIG. 8. Line 314 intersects the profile of tip 300 at points 316 and 318. The left cone angle $\theta_l$ is the angle between the tangent to the profile of tip 300 at point 316 and line 320 (an imaginary line through point 316 and extending parallel to axis 308). Similarly, the right cone angle $\theta_r$ is the angle between the tangent to the profile of tip 300 at point 318 and line 322 (an imaginary line through point 318 and extending parallel to axis 308). The full cone angle of tip 300 is the sum of the magnitudes of $\theta_l$ and $\theta_r$. For example, for a given side view in an embodiment in which the magnitude of $\theta_l$ is 21.3° and the magnitude of $\theta_r$ is 11.6°, the full cone angle for the profile of tip 300 for that side view 32.9°. Because tip 300 can appear symmetric in one side view and asymmetric in a different side view, it is generally desirable to determine an average full cone angle for tip 300. The average full cone angle is determined by measuring the full cone angle for eight different side views of tip 300 (each corresponding to a successive rotation of tip 300 by 45° about axis 308 with respect to the previous side view of tip 300), and then calculating the average of the eight full cone angles thus determined, resulting in the average full cone angle. Without wishing to be bound by theory, it is believed that if the average full cone angle is too small, arcing may occur during use of the tip (e.g., when tip 300 is used to produce ion beam 192), and generation of He ions via the interaction He atoms with tip atoms other than those on the terminal shelf of the tip may occur due to large electric fields in the vicinity of tip 300. It is also believed that, if the average full cone angle is too large, the ability to reproducibly re-build tip 300 can be reduced, and electric fields in the vicinity of tip 300 may be too low to reliably ionize He atoms and produce a stable He ion current. In some embodiments, the average full cone angle of tip 300 can be 45° or less (e.g., 42° or less, 40° or less, 35° or less, 32° or less, 31° or less), and/or the average full cone angle can be 15° or more (e.g., 20° or more, 23° or more, 25° or more, 28° or more, 29° or more). For example, the average full cone angle of tip 300 can be from 27° to 33° (e.g., from 28° to 32°, from 29° to 31°, 30°). In certain embodiments, the standard deviation of the eight full cone angle measurements is 40% or less (e.g., 30% or less, 20% or less, 10% or less) of the average full cone angle.

The cone direction is half of the absolute value of the difference between the magnitudes of $\theta_l$ and $\theta_r$. Thus, for example, for a given side view in an embodiment in which the magnitude of $\theta_l$ is 21.3° and the magnitude of $\theta_r$ is 11.6°, the cone direction is 0.5*|21.3°−11.6°|, or 4.9°. For the same reasons discussed above with respect to the average full cone angle, it can be desirable to determine the average cone direction of a tip. The average cone direction is determined by measuring the cone direction for eight different side views of tip 300 (each corresponding to a successive rotation of tip 300 about axis 308 by 45° with respect to the previous view), and then calculating the average of the eight cone direction measurements, resulting in the average cone direction. In some embodiments, the average cone direction of tip 300 can be 10° or less (e.g., 9° or less, 8° or less, 7° or less, 6° or less, 5° or less), and/or the average cone direction of tip 300 can be 0° or more (e.g., 1° or more, 2° or more, 3° or more, 4° or more). In certain embodiments, the average cone direction of tip 300 is from 0° to 10° (e.g., from 1° to 10°, from 3° to 10°, from 6° to 10°, from 2° to 8°, from 4° to 6°).

Figure 9:
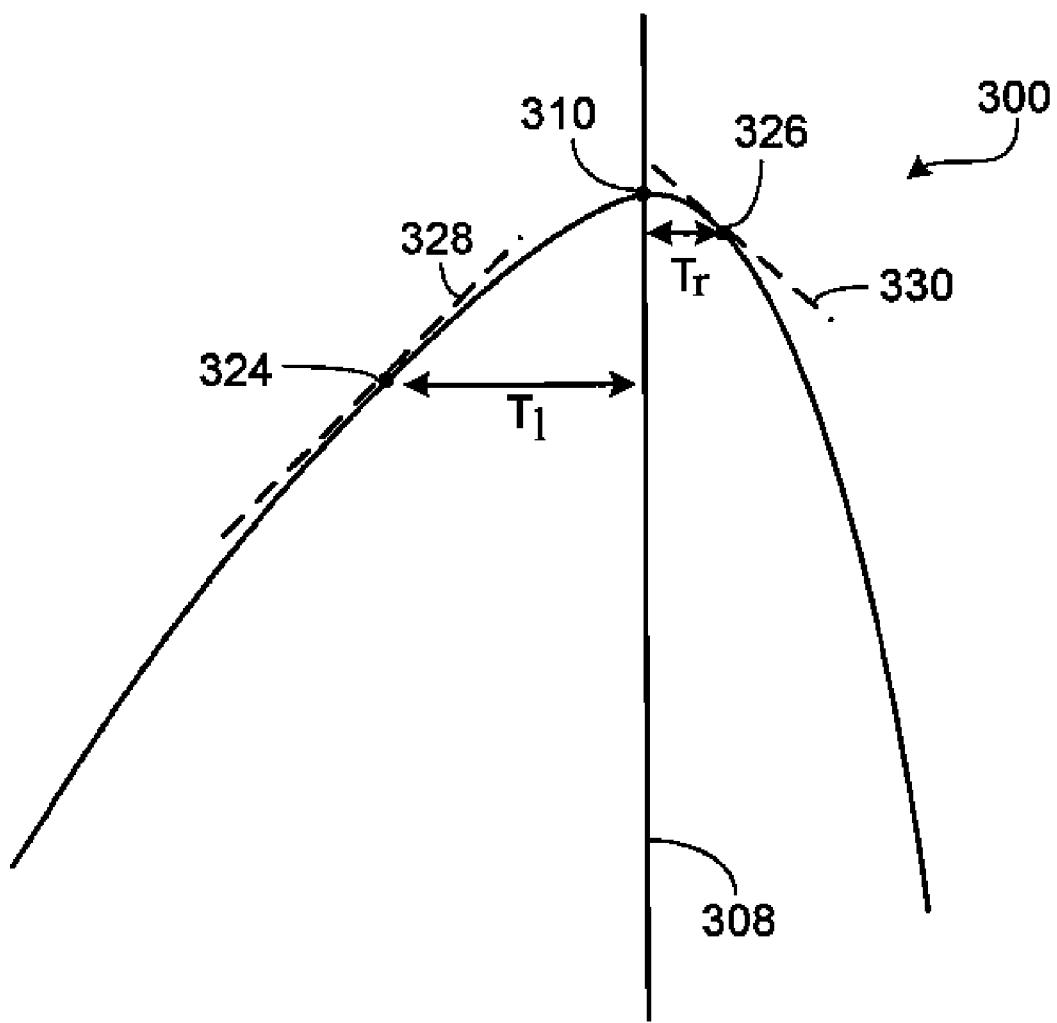
FIG. 9 is a side view of a tip showing a radius of curvature measurement.

Tip 300 can also be characterized by its radius of curvature, which can be determined as follows. FIG. 9 shows a schematic side view of tip 300. In practice, this side view is obtained using a SEM. On either side of longitudinal axis 308, the slope of the profile of tip 300 is measured. Points 324 and 326 are points on the surface of tip 300 nearest to apex 310 where the slope of the profile of tip 300 (indicated by tangent lines 328 and 330, respectively) has a value of 1 and −1, respectively (e.g., 45° lines of inclination). The distance, measured perpendicular to axis 308 and in the plane of FIG. 9, between point 324 and axis 308 is the left tangent distance, $T_l$, of tip 300. The distance, measured perpendicular to axis 308 and in the plane of FIG. 9, between point 326 and axis 308 is the right tangent distance, $T_r$, of tip 300. The left radius, $R_l$, is calculated as $R_l = \sqrt{2} \cdot T_l$, and the right radius, $R_r$, is calculated as $R_r = \sqrt{2} \cdot T_r$. The radius of curvature, R, of tip 300 is calculated as an average of $R_l$ and $R_r$. Thus, for example, in an embodiment where $T_l$ is 120 nm and $T_r$ is 43 nm, $R_l$ is 169 nm, $R_r$ is 61 nm, and R is 115 nm. For the same reasons as discussed above with respect to average full cone angle and average cone direction, it can be desirable to determine the average radius of curvature of a tip. The average radius of curvature is determined by measuring the radius of curvature for eight different side views of tip 300 (each corresponding to a successive rotation of tip 300 about axis 308 by 45° with respect to the previous side view), and then calculating the average of the eight radii of curvature, resulting in the average radius of curvature. Without wishing to be bound by theory, it is believed that if the average radius of curvature is too small, arcing may occur during tip use and/or ionization of He gas may occur in the vicinity of tip atoms other than those on the tip's terminal atomic shelf. If the average radius of curvature is too large, the ability to reproducibly re-build the tip can be reduced, and the rate of ionization of He atoms in the vicinity of tip 300 may be reduced due to lower field strengths in the vicinity of tip 300. In some embodiments, the average radius of curvature of tip 300 is 200 nm or less (e.g., 180 nm or less, 170 nm or less, 160 nm or less, 150 nm or less, 140 nm or less, 130 nm or less), and/or the average radius of curvature of tip 300 is 40 nm or more (e.g., 50 nm or more, 60 nm or more, 70 nm or more, 80 nm or more, 90 nm or more, 100 nm or more, 110 nm or more). For example, in some embodiments, the average radius of curvature of tip 300 is from 40 nm to 200 nm (e.g., from 50 nm to 190 nm, from 60 nm to 180 nm, from 70 nm to 170 nm, from 80 nm to 160 nm). In certain embodiments, the standard deviation of the eight radius of curvature measurements is 40% or less (e.g., 30% or less, 20% or less, 10% or less) of the average radius of curvature.

Figure 10:
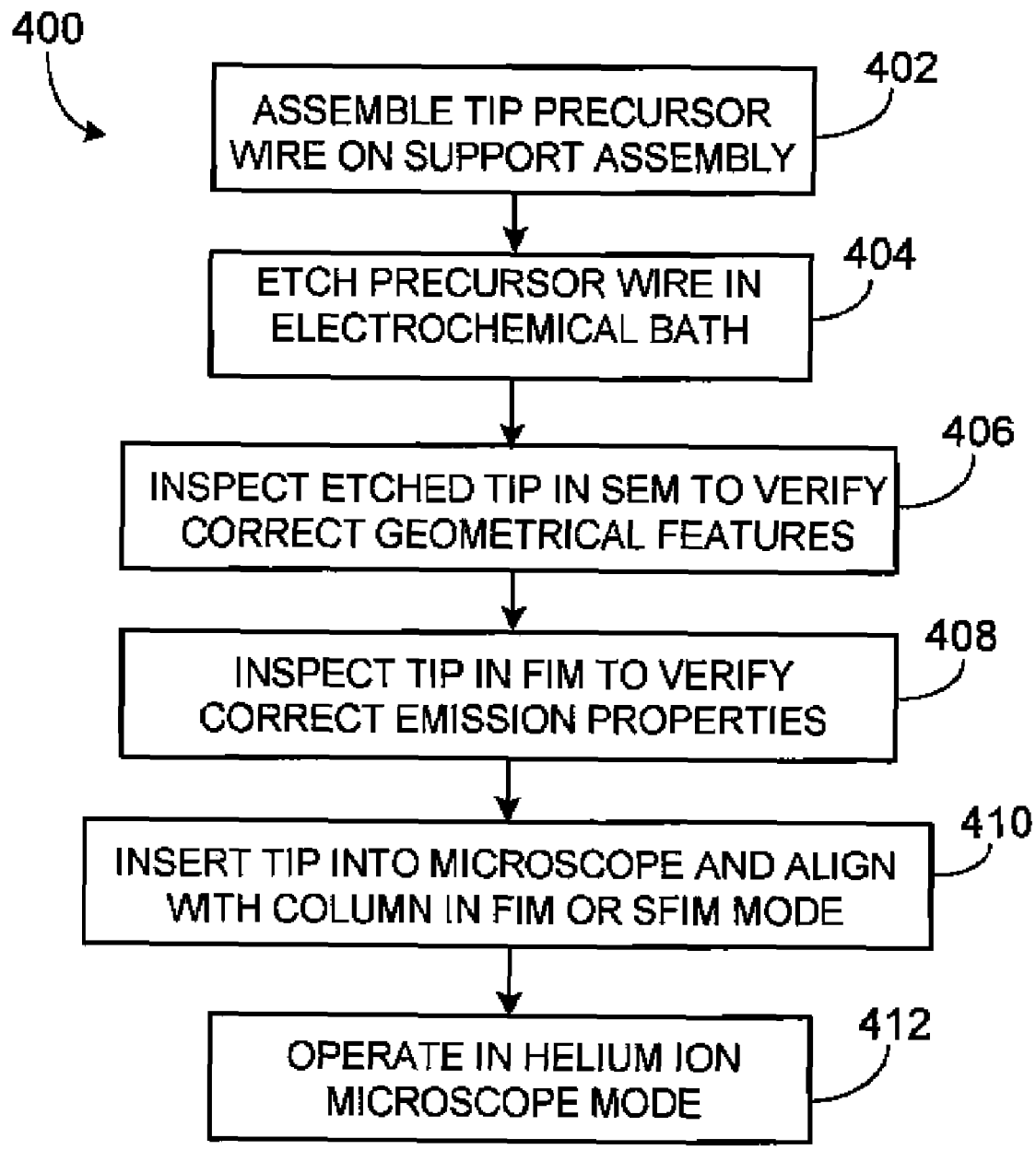
FIG. 10 is a flow chart showing an embodiment of a method of making a tip.

FIG. 10 is a flow chart for a process 400 of making a W(111) tip having a terminal atomic shelf that is a trimer. In a first step 402, a single crystal W(111) precursor wire is attached to a support assembly. Typically, the W(111) precursor wire has a diameter of 3 mm or less (e.g., 2 mm or less, 1 mm or less), and/or 0.2 mm or more (e.g., 0.3 mm or more, 0.5 mm or more). In some embodiments, the W(111) precursor wire has a diameter of from 0.2 mm to 0.5 mm (e.g., from 0.3 mm to 0.4 mm, 0.25 mm). Suitable precursor wires can be obtained, for example, from FEI Beam Technology (Hillsboro, Oreg.).

More generally, in some embodiments, the tip precursor can be in a form that is different from a wire. For example, the tip precursor can be formed of an electrically conductive material that has a protrusion that terminates in a crystalline structure. The terminus of the protrusion can be a single crystal structure, for example, and can be formed of W(111), or formed of another material in a similar or different crystal orientation.

Figure 11A:
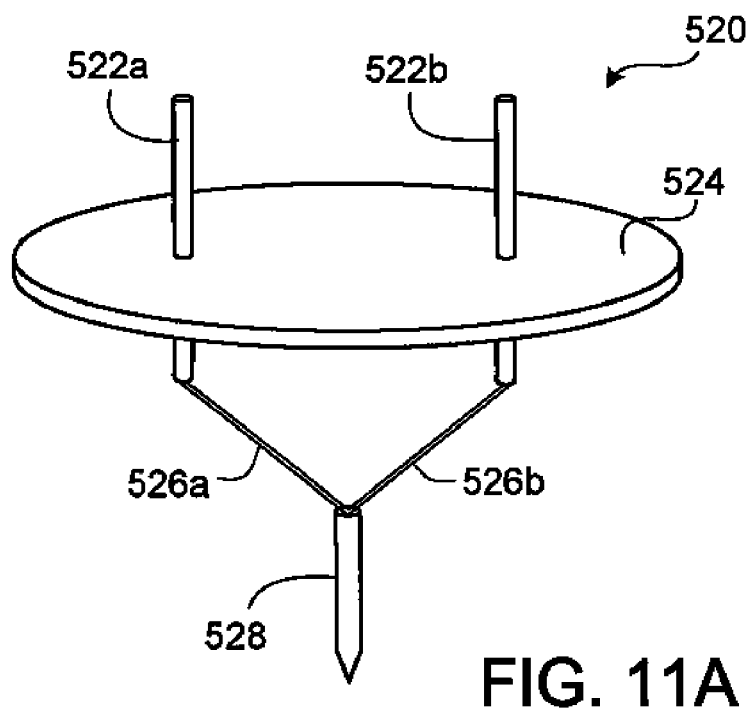
FIG. 11A is a perspective view of an embodiment of a support assembly for a tip.
Figure 11B:
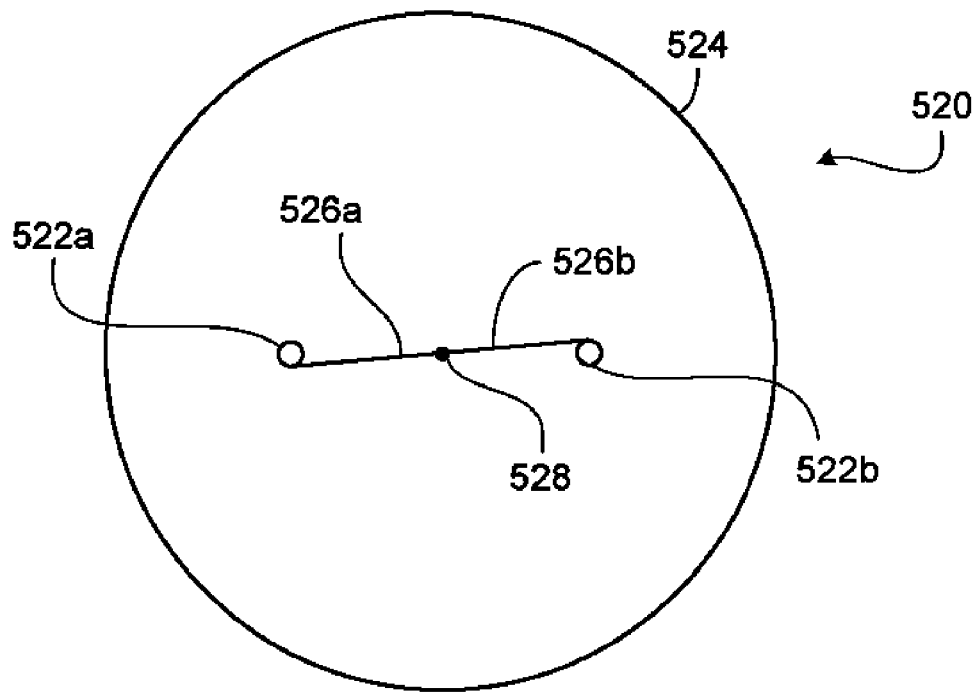
FIG. 11B is a bottom view of the support assembly of FIG. 11A.

FIGS. 11A and 11B show perspective and bottom views, respectively, of an embodiment of a support assembly 520. Support assembly 520 includes support posts 522a and 522b connected to a support base 524. Posts 522a and 522b are connected to heater wires 526a and 526b, and a length of a W(111) precursor wire 528 is connected to heater wires 526a and 526b (e.g., via welding). Posts 522a and 522b can be connected to auxiliary devices such as, for example, electric current sources (e.g., power supplies) to permit control of the temperature of W(111) precursor wire 528.

Base 524 provides mechanical support for assembly 520 and is generally formed of one or more materials that can withstand temperature cycling, and that act as electrical insulators. For example, in some embodiments, base 524 is formed from electrically insulating materials such as glass and/or rigid polymers and/or ceramic.

Posts 522a and 522b are generally formed of one or more electrically conducting materials. Typically, the material used to form posts 522a and 522b is chosen so that posts 522a and 522b and base 524 have a similar coefficient of thermal expansion, and so that posts 522a and 522b remain fixed in position relative to base 524 during temperature cycling of precursor wire 528. In some embodiments, posts 522a and 522b are formed from an alloy that includes iron, nickel and cobalt. An example of a commercially available material from which posts 522a and 522b can be formed is KOVAR™.

In general, heater wires 526a and 526b are formed from one or more materials that have higher electrical resistivity than precursor wire 528. For example, in some embodiments, heater wires 526a and 526b can be formed from materials such as a tungsten-rhenium alloy. As explained below, heater wires 526a and 526b generate heat when electric current (e.g., from an external power supply) is passed through the wires, and the heat can be used to increase and/or control the temperature of precursor wire 528 during various tip processing steps. In general, the diameter and materials of heater wires 526a and 526b are selected to ensure that suitable control over the temperature of precursor wire 528 can be achieved during fabrication processes. In some embodiments, heater wires 526a and 526b have diameters of from 100 μm to 750 μm, for example.

The geometrical properties of base 524, posts 522a and 522b, and heater wires 526a and 526b can generally be selected as desired. For example, in some embodiments, a distance between posts 522a and 522b can be from 1 mm to 10 mm.

Optionally, more than two posts (e.g., three posts, four posts, five posts, six posts) can be attached to base 524, with each post being connected to precursor wire 528 through a corresponding heater wire. Providing additional posts may increase the stability of assembly 520 and/or reduce susceptibility of assembly 520 to mechanical vibrations.

Figure 12:
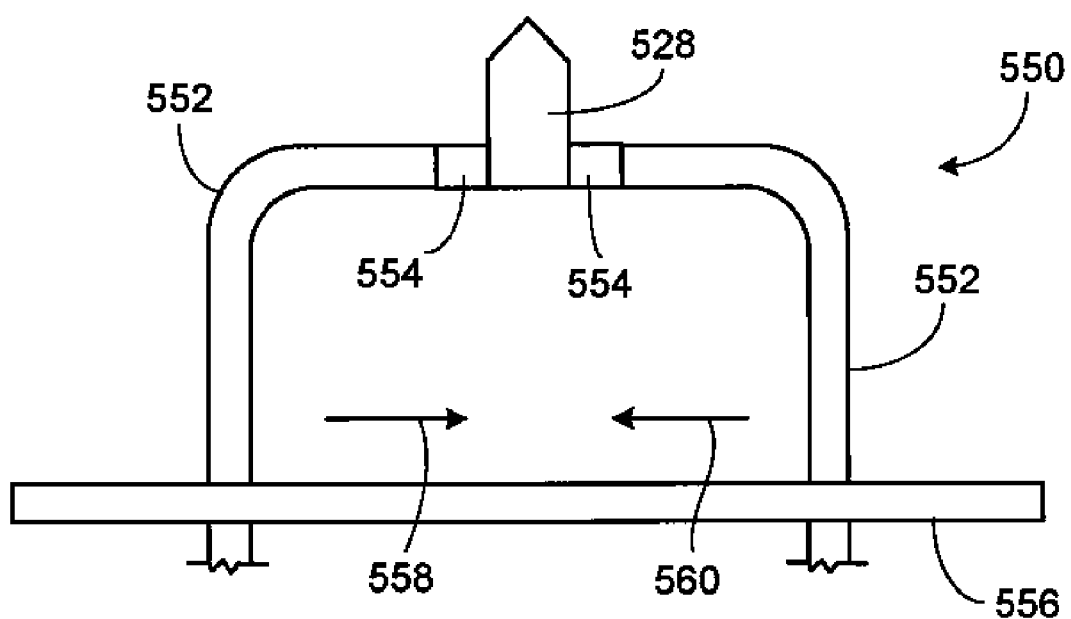
FIG. 12 is a side view of an embodiment of a support assembly that includes a Vogel mount to support a tip.

In some embodiments, precursor wire 528 can be held in position by a support assembly that applies a compressive force to the wire. For example, FIG. 12 shows an exemplary support assembly 550 including a Vogel mount to secure precursor wire 528. Suitable Vogel mounts are available commercially from AP Tech (McMinnville, Oreg.), for example. Support assembly 550 includes a support base 556 and mounting arms 552 attached to base 556. To secure precursor wire 528, arms 552 are pried apart and spacers (e.g., formed of pyrolytic carbon) 554 are inserted into the space between the arms. Precursor wire 528 is then inserted into the opening between spacers 554, and then mounting arms 552 are released. Due to the resiliency of arms 552, the arms apply a compressive force to spacers 554 and precursor wire 528 in directions indicated by arrows 558 and 560, thereby securing precursor wire 528 against spacers 554. Static frictional forces between wire 528, spacers 554, and arms 552 discourage relative movement of these components, ensuring that wire 528 remains fixed in position in support assembly 550. Typically, wire 528 extends above arms 552 a distance of between 1 mm and 5 mm, for example.

Base 556 can be formed from materials similar to those which can be used to form base 524 (e.g., glass and/or rigid polymers and/or ceramic). The material of base 556 is typically an electrically insulating material that can withstand temperature cycling.

Mounting arms 552 can be formed from one or more electrically conducting materials. The materials used to form arms 552 can also be chosen so that base 556 and arms 552 have a similar coefficient of thermal expansion, and so that arms 552 remain fixed in position relative to base 556 during temperature cycling of precursor wire 528. In some embodiments, arms 552 are formed from an alloy that includes iron, nickel, and cobalt. Suitable commercially available materials for forming arms 552 include KOVAR™.

Spacers 554 are formed from a material such as pyrolytic carbon. Suitable pyrolytic carbon spacers are available from, for example, AP Tech (McMinnville, Oreg.). Pyrolytic carbon spacers typically are formed of a series of flat carbon sheets stacked atop one another to create a laminar structure. In general, the resistivity of pyrolytic carbon varies according to direction, with the resistivity of the carbon in a direction perpendicular to the sheets (e.g., in a direction approximately normal to the planes of the stacked sheets) being higher than the resistivity along a direction in a plane parallel to the planes of the sheets. During mounting, spacers 554 are oriented so that the higher resistivity direction of spacers 554 is approximately parallel to the direction of compressive force applied by arms 552 (e.g., approximately parallel to arrows 558 and 560). When current is introduced into arms 552, spacers 554 generate heat due to their high resistivity. Accordingly, spacers 554 can serve as heating elements for adjusting the temperature of precursor wire 528.

Referring again to FIG. 10, in a second step 404, precursor wire 528 is etched in an electrochemical bath to shape the tip of wire 528. In general, step 404 includes multiple sub-steps.

The first sub-step in the etching process can optionally be a cleaning step to remove surface contaminants from wire 528. This etching process can involve disposing wire 528 in an electrochemical etch solution and exposing wire 528 to an alternating current (AC) voltage. For example, the solution can be a 1N solution of sodium hydroxide (NaOH), and an AC voltage of 1 V can be used. Subsequently, the entire support assembly (e.g., support assembly 520 or 550) can be cleaned (e.g., ultrasonically cleaned in water) to remove certain remaining contaminants.

The next sub-step in step 404 is to optionally apply a resist material to a portion of wire 528. Typically, the resist material is applied over a length of approximately 0.5 mm of wire 528, starting from the apex of wire 528. Application of the resist material can be achieved, for example, by placing a drop of resist solution onto a clean surface and dipping wire 528 into the resist several times, allowing the resist to dry slightly between applications. The applied resist limits the amount of precursor wire 528 that is etched during subsequent processing steps. Because formation of a subsequent tip on a precursor wire 528 often follows removal of a previous tip by etching, use of the resist material permits a larger number of tips to be formed on a given precursor wire before the wire is discarded. A variety of different resist materials can be applied to precursor wire 528. An exemplary resist material is cosmetic nail polish. In some embodiments, more than one resist material may be used. Use of a resist material is optional to the tip formation process, however, and in some embodiments, resist material may not be applied to precursor wire 528 before undertaking subsequent steps in the fabrication process.

The next sub-step in step 404 is to electrochemically etch precursor wire 528. A variety of electrochemical etching procedures can be used. In some embodiments, the following electrochemical etching procedure is used. The support assembly is placed in an etching fixture that includes a translation apparatus for translating the support assembly, a dish, and an electrode (e.g., a stainless steel electrode) that extends into the dish. An etching solution is placed in the dish such that the solution is in contact with the electrode. The support assembly is lowered toward the dish via the translation apparatus until the resist interface on wire 528 just contacts the etching solution. Wire 528 is then lowered an additional amount (e.g., 0.2 mm) into the etching solution.

The etching solution includes a constituent (e.g., NaOH) that chemically corrodes wire 528. In embodiments in which the etching solution contains NaOH, the concentration of NaOH in the etching solution can be selected to vary the corrosion rate of precursor wire 528 and the chemical environment of the solution. For example, in some embodiments, the concentration of NaOH can be 0.1 M or more (e.g., 0.2 M or more, 0.5 M or more, 0.6 M or more, 0.8 M or more, 1.0 M or more, 1.2 M or more, 1.4 M or more, 1.6 M or more, 2.0 M or more, 2.5 M or more, 3.0 M or more), and/or 10.0 M or less (e.g., 9.0 M or less, 8.0 M or less, 7.0 M or less, 6.5 M or less, 6.0 M or less, 5.5 M or less, 5.0 M or less, 4.5 M or less, 4.0 M or less). In some embodiments, the concentration of NaOH is from 0.5 M to 10.0 M (e.g., from 1.0 M to 9.0 M, from 1.5 M to 8.0 M, from 2.0 M to 7.0 M, from 2.0 M to 6.0 M, from 2.0 M to 3.0 M).

In certain embodiments, other corrosive agents can be added to the etching solution in place of, or in addition to, NaOH. Examples of such corrosive agents include KOH (including molten KOH), HCl, $H_3PO_4$, $H_2SO_4$, KCN, and/or molten $NaNO_3$. Corrosive agents in the etching solution may be selected based on their ability to corrode a precursor wire formed of a specific type of material. For example, an agent such as NaOH can be used to corrode wires formed of W. For wires formed of a different material such as Ir, other corrosive agents can be used in the etching solution.

In some embodiments, the etching solution can include a relatively small amount of surfactant. Without wishing to be bound by theory, it is believed that the surfactant can assist in promoting symmetric etching of precursor wire 528. Suitable surfactants for this purpose include materials such as Photo-Flo 200, available from Eastman Kodak (Rochester, N.Y.). In general the concentration of surfactant in the etching solution is 0.1 volume % or more (e.g., 0.2 volume % or more, 0.3 volume % or more, 0.4 volume % or more), and/or 2 volume % or less (e.g., 1 volume % or less, 0.8 volume % or less, 0.6 volume % or less).

In some embodiments, the etching process can also be performed with stirring of the etching solution. The rate at which the etching solution is stirred can be determined empirically based upon the results of the etching process.

After positioning precursor wire 528 in the etching solution, an external power supply is connected to both wire 528 and the electrode, and a potential is applied across wire 528 and the electrode to facilitate an electrochemical corrosion reaction of wire 528. In general, the voltage can be applied from either an AC source or a direct current (DC) source. The amplitude of the applied voltage can generally be selected as desired, based upon an empirical determination of an amplitude that produces a uniformly etched precursor wire 528. For example, in some embodiments, the amplitude of the applied potential is 3.0 V or more (e.g., 3.2 V or more, 3.5 V or more, 4.0 V or more, 5.0 V or more, 10 V or more, 15 V or more, 20 V or more), and/or 50 V or less (e.g., 40 V or less, 35 V or less, 30 V or less, 25 V or less). In some embodiments, the amplitude of the applied potential is between 3.0 V and 50 V (e.g., from 3.5 V to 40 V, from 4.0 V to 30 V, from 4.5 V to 20 V).

The duration of AC pulses applied to the etching solution can generally vary as desired to promote controlled etching of wire 528. For example, in some embodiments, pulses applied to the etching solution have a duration of 10 ms or more (e.g., 25 ms or more, 50 ms or more, 75 ms or more, 100 ms or more, 150 ms or more, 200 ms or more, 250 ms or more), and/or one second or less (e.g., 900 ms or less, 800 ms or less, 700 ms or less, 650 ms or less, 600 ms or less). In some embodiments, pulses applied to the etching solution have a duration of from 10 ms to one second (e.g., from 10 ms to 900 ms, from 10 ms to 800 ms, from 10 ms to 700 ms, from 10 ms to 600 ms).

In general, pulses of varying duration and/or amplitude can be applied to the etching solution to cause erosion of precursor wire 528 in the region of the wire that contacts the solution. Typically, during processing, a portion of the end of precursor wire 528 drops off into the etching solution, and the newly exposed, etched region of precursor wire 528 is processed further in subsequent steps. For example, a suitable etching regimen includes an initial application of approximately 100 AC pulses of amplitude 5 V, each pulse having a duration of approximately 580 ms. Thereafter, a series of approximately 60 pulses are applied, with each pulse having a duration of approximately 325 ms and an amplitude of 5 V. Then, pulses having a duration of 35 ms and an amplitude of 5 V are applied until a portion of the end of wire 528 drops off into the etching solution.

During application of electrical pulses to the etching solution, the immersion depth of precursor wire 528 can be adjusted. Typically, the etching process leads to formation of a narrow-diameter region of precursor wire 528. Adjusting the immersion depth of wire 528 can help ensure that the meniscus of the etching solution is positioned near a midpoint of the narrow-diameter region, which can enhance the probability of forming a relatively symmetric tip. As the drop-off point is approached (e.g., as the diameter in the narrow-diameter region becomes very small), adjustment of the immersion depth is performed to ensure that the end of precursor wire 528 is not snapped off. After drop-off of the end of precursor wire 528, the newly exposed tip of wire 528 is immersed very slightly in the etching solution and additional electrical pulses are applied. In some embodiments, two electrical pulses are applied. As an example, the first pulse can be from 1 V to 10 V (e.g., from 3 V to 7V, 5V) with a duration of from 20 ms to 50 ms (e.g., from 30 ms to 40 ms, 35 ms), and the second pulse can be from 1 V to 10 V (e.g., from 3 V to 7V, 5V) with a duration of from 10 ms to 25 ms (e.g., from 15 ms to 20 ms, 17 ms).

The support assembly is then removed from the etching fixture, rinsed (e.g., with distilled or deionized water) and dried (e.g., under a stream of dry nitrogen gas).

The next step 406 of process 400 is to examine the support assembly (and particularly, the etched tip of wire 528) to verify that the etched tip has suitable geometrical features. As discussed previously, for example, determination of geometrical features includes obtaining profile images of the etched tip and calculating various geometrical parameters from data obtained from the profile images. The inspection can be performed using a SEM, for example. Profile images of the tip of wire 528 can be obtained at very high magnification, such as a magnification of 65,000×, for example. The measured geometrical parameters can include average tip radius of curvature, average cone direction, and average full cone angle, for example. At this point, if the shape of the etched tip is unsuitable, it may be possible to re-shape the tip slightly by inserting the assembly back into the etching fixture and lowering the etched tip of wire 528 toward the dish until the tip just contacts the etching solution. A small number of electrical pulses (e.g., from one to three pulses of duration 35 ms and amplitude 5 V) can be used to re-shape the tip of wire 528. For example, if the average full cone angle of the tip of wire 528 is too small, a small number of short duration pulses can be used to increase the average full cone angle without substantially increasing the average radius of the etched tip. Following application of these additional electrical pulses, the tip can then be re-examined in the SEM to verify that it has been correctly re-shaped.

Subsequently, in step 408, the terminal shelf of the apex of the tip of etched wire 528 is formed into a trimer. This process generally involves imaging the tip (e.g., using FIM or SFIM) and shaping the tip (e.g., using field evaporation).

In some embodiments, step 408 includes installing the support assembly in a FIM and evacuating the FIM. The tip of wire 528 is cooled (e.g., to liquid nitrogen temperature), and He gas is supplied to the FIM (e.g., at a pressure of approximately $5\times10^{-6}$ Torr). A positive potential with respect to the extractor (e.g., 5 kV or more relative to the extractor) is applied to the tip of wire 528, and the He atoms interact with the apex of the tip of wire 528 to form He ions. The He ions are accelerated away from the positively charged apex of the tip of wire 528. A detector, such as a phosphor screen optically coupled to a two-dimensional imaging device such as a CCD camera, is positioned at a selected distance from the ion source, and oriented approximately perpendicular to the principal ion beam trajectory from the ion source. Impinging ions cause the phosphor screen to emit photons, which are detected by the CCD camera. Regions of the images that correspond to relatively larger numbers of detected ions will appear brighter than regions that correspond to relatively fewer numbers of detected ions. Ionization of He gas atoms occurs in the vicinity of individual ion source atoms at the apex of the tip of wire 528. As a result, images captured by the detector correspond to the emission pattern of the ion source. More particularly, bright spots in images obtained from the detector correspond to individual atoms at the ion source apex. Thus, the FIM image is an image of the apex of the tip of wire 528 that is atomically resolved. Based on the FIM image, the crystal structure, orientation, and specific arrangement of atoms at the ion source apex can be determined.

If the desired properties of the apex of the tip of wire 528 are not present, the tip can be shaped, using, for example, field evaporation. During field evaporation, with an image of the etched tip of wire 528 in focus on the FIM detector and with the background pressure of He gas still present in the FIM, the positive electrical potential on the tip is increased (e.g., 15 kV or more relative to the extractor) until the resulting field begins to remove W atoms (and contaminant atoms) from positions on the tip where the local electric field is highest. The rate at which atoms are removed is controlled to prevent groups of atoms from being removed simultaneously. In general, field evaporation continues with monitoring of the FIM emission pattern until it is verified that the surface of the etched tip is in the correct crystal orientation, and it is determined that there are no undesirable contaminants at the terminal shelf of the tip.

After field evaporation, it may be desirable to sharpen the tip. To sharpen the tip, the He gas is pumped out of the FIM chamber, and the bias on the tip of wire 528 is changed to being negative with respect to the common ground so that the apex of the tip of wire 528 emits electrons. A detector which generates photons in response to incident electrons, such as a phosphor-coated glass screen, is positioned to intercept electrons from the tip. The generated photons are detected by a suitable detector (e.g., a CCD device, a photomultiplier tube, a photodiode, or another type of photon detector) and used to monitor electron emission from the tip. In some embodiments, the detector can be directly coupled to the photon-generating device. In certain embodiments, the detector and photon-generating device are not directly coupled. For example, optical elements such as mirrors can be used to direct generated photons to the detector.

The voltage bias applied to the tip is adjusted until a desired electron current is measured (e.g., from 25 pA to 75 pA, from 40 pA to 60 pA, 50 pA). The tip is then heated to a desired temperature (e.g., from 1000 K to 1700 K, from 1300 K to 1600 K, 1500 K), and the tip is monitored visually to detect light emitted from the tip in response to the application of both voltage and heat. Light emission from the tip can be monitored, for example, using a mirror positioned to reflect light emitted by the tip toward a suitable photon detector (e.g., a CCD device, a photomultiplier tube, a photodiode, or another type of photon detector). Heat can be applied to the tip using a variety of devices such as a resistive heating device (e.g., a filament heater), a radiative heating device, an inductive heating device, or an electron beam. From 15 seconds to 45 seconds (e.g., from 25 seconds to 35 seconds, 30 seconds) after the first appearance of light from the tip, both the applied potential and the heating device are turned off, yielding wire 528 with a trimer as its terminal atomic shelf.

Optionally, a gas can be used to sharpen the tip. For example, oxygen can be introduced into the FIM chamber to promote sharpening of a rounded W tip surface. The sharpening gas (e.g., oxygen) is introduced after He has been removed from the FIM chamber, and the tip is heated in the presence of oxygen at a selected pressure for a period of time. For example, to sharpen a rounded W tip, He is first pumped out of the FIM chamber and then the tip is heated to a temperature of between 1300K and 1700 K (e.g., 1500 K). The tip is maintained at 1500 K for between one and five minutes. Next, oxygen can be introduced into the chamber at a pressure of approximately $10^{-5}$ Torr, while maintaining the temperature of the tip for approximately two minutes. With oxygen flow to the chamber continuing, the temperature of the tip is then reduced to between 700 K and 1200 K (e.g., 1000 K), and the tip is maintained at that temperature for approximately two minutes. Finally, the oxygen supply to the chamber is closed and oxygen is pumped out of the chamber until the oxygen pressure therein is less than $10^{-7}$ Torr. At the same time, the tip is cooled to its normal operating temperature (e.g., approximately 77 K in some embodiments) and He is re-introduced into the FIM chamber. When the tip is imaged in FIM mode, a W trimer atop the tip corresponding to a W(111) facet is observed. The W(111) wire having a terminal shelf that is a trimer can then be removed from the FIM and stored for future use.

Although the foregoing describes embodiments in which a FIM separate from system 200 is used to image/shape the wire tip apex, in some embodiments, system 200 can be used as the FIM. In such embodiments, the support assembly is installed within the ion source and system 200 is operated as a FIM, generally according to the procedure described in the preceding paragraphs. In some embodiments, when operating system 200 in FIM mode, the detector can be positioned either where sample 280 is normally positioned (i.e., sample 180 is not present in its normal position). In certain embodiments, when operating system 200 in FIM mode, a flat sample with a relatively high secondary electron yield can be positioned where sample 180 is normally positioned, and the secondary electrons generated by the interaction of the He ions with the flat sample are detected because the intensity of the secondary electrons detected will generally scale with the intensity of the He ions incident on the flat sample.

Optionally, system 200 can be operated in SFIM mode during the process of imaging/shaping the wire tip apex. In such embodiments, the process is as described in the preceding paragraphs, except that alignment deflectors 220 and 222 are used to raster the ion beam across the surface of aperture 224 to generate a field emission pattern of the apex of the wire tip. Portions of the ion beam which pass through aperture 224 can optionally be focused by second lens 226, or remain unfocused. In SFIM mode, an image of the wire tip is acquired pixel-by-pixel, and each measured pixel intensity corresponds to a portion of ion beam permitted to pass through aperture 224. The pixel intensities together can be used to represent the field emission pattern of the tip as an image or, more generally, as a plurality of electrical signals. The field emission pattern can then be used to assess various properties of the tip to determine its suitability for use in a gas field ion microscope. In SFIM mode, the detector can be located and of the type as described in the preceding paragraphs. Optionally, the detector can be a spatially integrating detector such as a photomultiplier tube or a photodiode.

The procedures described above can generally be used to sharpen a W tip for the first time, and can also be used for re-sharpening of a W tip within an ion microscope system. Such re-sharpening can be performed in system 200 even if the initial process for sharpening the W tip was performed in a FIM other than system 200. Re-sharpening can generally be performed in the same manner as the initial sharpening, or the re-sharpening techniques can be different from the original sharpening technique. In some embodiments, to assess whether re-sharpening is desirable, microscope system 200 can be configured to operate in FIM and/or SFIM mode, as described above. Based upon one or more images of the tip, the re-sharpening process can be initiated or postponed. In certain embodiments, other criteria can be used to determined when to initiate re-sharpening. For example, if the measured ion current from the tip falls below an established threshold value after a period of operation, re-sharpening can be initiated.

As a first step in re-sharpening, the tip can be field evaporated to remove atoms near the tip apex. For example, microscope system 200 can be configured to operate in FIM and/or SFIM mode, as discussed above, and the potential applied to the tip can be carefully adjusted to produce controlled field evaporation of tip atoms. During the field evaporation process, a field emission image of the tip can be obtained in FIM or SFIM mode by a detector (e.g., a phosphor-coupled photon detector, or a secondary electron detector configured to measured secondary electron emission from a flat sample) and monitored to determine when to halt the field evaporation process. As before, when the surface of the tip is in the correct crystal orientation and is clean, the tip can be re-sharpened.

He gas is pumped out of microscope system 200 until the background He pressure is less than approximately $10^{-7}$ Torr. In some embodiments, to initiate re-sharpening, a negative electrical potential is applied to the tip to operate microscope system 200 in electron mode, and the tip is sharpened via heating as described previously. In certain embodiments, a sharpening gas such as oxygen is introduced into microscope system 200, and the tip is heated in the presence of oxygen for a selected time, as described previously. Following the re-sharpening procedure, He gas is re-introduced into microscope system 200, and with the system configured to operated in FIM and/or SFIM mode, one or more images of the re-sharpened tip are captured to verify that the tip apex includes a trimer corresponding to a W(111) facet.

In some embodiments, certain re-sharpening steps can be performed automatically by hardware and/or software in electronic control system 170. For example, in certain embodiments, the sharpening procedure that is applied to a rounded tip can be performed in an automated manner. An example of a sharpening algorithm implemented by electronic control system 170 is as follows. First, control system 170 evacuates microscope system 200 by activating pumps 236 and/or 237 and cools the tip to liquid nitrogen temperature. When the background pressure of gas in microscope system 200 is less than an established threshold, the tip is heated by control system 170 to a temperature of 1500 K by applying a calibrated electrical current to the heater wires supporting the tip. After two minutes at 1500 K, control system 170 introduces oxygen gas into microscope system 200 by opening a valve on an oxygen gas source. The valve opening is adjusted to maintain an oxygen pressure of approximately $10^{-5}$ Torr in microscope system 200. After two additional minutes, the temperature of the tip is reduced to 1100 K by control system 170 by regulating the flow of liquid nitrogen coolant into the system. After two minutes at 1100 K, control system 170 shuts off the oxygen supply to the system and cools the tip to liquid nitrogen temperature. At this point, FIM and/or SFIM images of the tip (measured by an operator) can be used to manually verify the presence of a W(111) at the apex of the tip.

Without wishing to be bound by theory, it is believed that oxygen can promote formation of a trimer as the terminal atomic shelf of a tip. In certain embodiments, the pressure of oxygen gas in the FIM chamber can be $10^{-7}$ Torr or more (e.g., $10^{-6}$ Torr or more, $10^{-5}$ Torr or more, $10^{-4}$ Torr or more), and/or 1 Torr or less (e.g., $10^{-1}$ Torr or less, $10^{-2}$ Torr or less, $10^{-3}$ Torr or less). In certain embodiments, the pressure of oxygen gas in the FIM chamber can be from $10^{-8}$ Torr to $10^{-2}$ Torr (e.g., from $10^{-7}$ Torr to $10^{-3}$ Torr, from $10^{-6}$ Torr to $10^{-4}$ Torr). Other gases and materials can also be used to promote formation of a trimer as the terminal atomic shelf during tip sharpening. For example, materials such as palladium, platinum, gold, and/or iridium can be vapor deposited onto the surface of a rounded tip prior to re-sharpening. It is believed that these materials may promote more reliable trimer formation at the apex of the tip.

In some embodiments, sharpening of a W tip can be achieved by controlled heating of the tip without the application of a field or the intentional addition of oxygen. For example, a W tip can be sharpened by the following steps: 1) install tip in FIM chamber; 2) reduce pressure in FIM chamber; 3) heat tip to 1000K for five minutes; and cool (e.g., to liquid nitrogen temperature). Without wishing to be bound by theory, it is believed that trace amounts of oxygen present on the tip as oxides may assist in sharpening the tip using heat. In certain embodiments, an unsharpened tip can be exposed to a stream of oxygen, placed in a substantially oxygen-free environment, and sharpened by controlled heating. It is believed that this approach may produce W oxides on the surface of the tip, and oxygen liberated from the W oxides upon heating may assist the tip sharpening process.

In some embodiments, one or more additional gases may be present during tip sharpening. For example, in certain embodiments, nitrogen gas may be present. Without wishing to be bound by theory, it is believed that nitrogen gas may assist in etching the tip to provide a more rounded structure with a terminal atomic shelf that is a trimer; such a structure is believed to be more stable than a less-rounded, trimer-terminated tip. In general, the nitrogen gas is introduced simultaneously with the oxygen gas. In certain embodiments, the pressure of nitrogen gas in the FIM chamber can be $10^{-8}$ Torr or more (e.g., $10^{-7}$ Torr or more), and/or $10^{-5}$ Torr or less (e.g., $10^{-6}$ Torr). In certain embodiments, the pressure of nitrogen gas in the FIM chamber can be from $10^{-5}$ Torr to $10^{-8}$ Torr (e.g., from $10^{-6}$ Torr to $10^{-7}$ Torr).

Optionally, after forming the trimer and to assist in ensuring that the tip sharpening process is repeatable, the positive electrical potential applied to the sharpened tip is increased so that controlled field evaporation of the tip occurs. After field-evaporating the tip for a period of time, the tip apex reassumes a rounded shape. Typically, the rounded tip produces an emission pattern that is similar to the emission pattern of the tip after the initial field evaporation step. Then, the rounded tip is again sharpened in electron mode to produce a terminal atomic shelf that is a trimer (e.g., using the procedure described above). In some embodiments, to increase the sharpened tip lifetime and stability, one or more trimers can be removed from the sharpened tip using field evaporation techniques. For example, the top-most atomic layer on the sharpened tip, which is formed by a three-atom shelf, can be removed to reveal an atomic shelf underneath that includes more than three atoms. The newly exposed atomic shelf can be further field evaporated to produce a W atom trimer at its apex. This newly formed trimer, along with additional trimers formed during field evaporation, can be evaporated. This process leads to a layer-by-layer rounding of the tip in the vicinity of its apex. By rounding the tip, the electric field gradient near the tip apex is reduced, reducing the probability that tip atoms undergo field evaporation while microscope system 200 is operating, and increasing the stability and lifetime of the tip.

In step 410 of process 400, the apex 187 of tip 186 is aligned within system 200. With the support assembly installed in microscope system 200, microscope system 200 is evacuated using one or more vacuum pumps, and then heat is applied to tip 187 to remove, for example, oxides, condensates, and/or any other impurities that may have adhered to the tip surface. Typically, for example, tip 186 is heated to a temperature of 900 K or more (e.g., 1000 K or more, 1100 K or more) for a duration of 10 s or more (e.g., 30 s or more, 60 s or more). Heating may also assist in re-faceting tip 186, in the event that the tip shape is compromised by the presence of impurities.

With tip 186 glowing radiatively as a result of the applied heat, the tip is then roughly aligned with the longitudinal axis of ion optics 130 by observing light from tip 186 propagating along the longitudinal axis (e.g., by inserting a reflective element such as a mirror and directing a portion of the light to a detector such as a CCD camera). The position and/or orientation of tip 186 can be changed by adjusting tip manipulator 208 to direct the light from tip 186 through ion optics 130.

Following this rough alignment procedure, microscope system 200 is configured to operate in FIM or SFIM mode by reducing the background pressure in vacuum housings 202 and 204, cooling tip 186 (e.g., to approximately liquid nitrogen temperature), and introducing a stream of He gas atoms into a region in the vicinity of tip 186 via gas source 110. An image of the field emission pattern of He ions from tip 186 is measured by a suitably configured detector and based upon this image, tip manipulator 208 is used to align the field emission pattern with a longitudinal axis of ion optics 130, so that the field emission pattern of tip 186 is centered upon the longitudinal axis. A centering test can be performed by changing the electrical potential applied to first lens 216 while observing the induced modulation of the field emission pattern of tip 186. If the size of the field emission pattern observed by the detector changes due to the variation of the electrical potential applied to lens 216, but the position of the center of the pattern does not change, then tip 186 is aligned with a longitudinal axis of first lens 216. Conversely, if the center position of the field emission pattern of tip 186 changes in response to the variation of the potential applied to first lens 216, then tip 186 is not centered on the longitudinal axis of first lens 216. Adjustments of the orientation and position of tip 186 via tip manipulator 208 can be repeated iteratively until tip 186 is sufficiently well aligned with the longitudinal axis of first lens 216. Typically, this centering test is performed without aperture 224 in position.

A fine alignment procedure can then be performed to ensure that He ions generated via the interaction of He gas atoms with the three-atom shelf at apex 187 of tip 186 pass through aperture 224. The electrical potentials applied to deflectors 220 and 222 (see discussion below) are adjusted so that 70% or more (e.g., 75% or more, 80% or more, 85% or more, 90% or more, 95% or more, 97% or more, 99% or more) of the He ions in ion beam 192 that pass through aperture 224 are generated via the interaction of He gas atoms with only one of the three trimer atoms at the apex of tip 186. At the same time, the adjustment of the potentials applied to deflectors 220 and 222 ensures that aperture 224 prevents 50% or more (e.g., 60% or more, 70% or more, 80% or more, 90% or more, 95% or more, 98% or more) of the He ions in ion beam 192 generated by the interaction of He gas atoms with the other two trimer atoms from reaching surface 181 of sample 180. As a result of this fine alignment procedure, the He ion beam that passes through aperture 224 and exits ion optics 130 includes He atoms that were ionized primarily in the vicinity of only one of the three trimer atoms at the apex of tip 186.

Referring again to FIG. 10, with tip 186 aligned with the longitudinal axis of first lens 216, and the He ion beam aligned so that a portion of ion beam 192 passes through aperture 224, microscope system 200 can be operated in He ion mode in step 412 of process 400. In embodiments in which system 200 was used in FIM mode during tip sharpening, the FIM detectors and/or other FIM componentry is moved so that sample 180 can be positioned for exposure to ion beam 192. An electrical potential that is positive with respect to extractor 190 is applied to tip 186, and He gas is introduced into vacuum housing 202 via gas source 110. He ions generated via the interaction of He gas atoms with primarily one of the three trimer atoms at the apex of tip 186 are guided by ion optics 130 through aperture 224, and are directed to sample 180.

In some embodiments, the potential applied to tip 186 is 5 kV or more (e.g., 10 kV or more, 15 kV or more, 20 kV or more). In certain embodiments, the potential applied to tip 186 is 35 kV or less (e.g., 30 kV or less, 25 kV or less). For example, in some embodiments, the potential applied to tip 186 is from 5 kV to 35 kV (e.g., from 10 kV to 30 kV, from 15 kV to 25 kV).

In some embodiments, during operation of microscope system 200, the He gas pressure is $10^{-8}$ Torr or more (e.g., $10^{-7}$ Torr or more, $10^{-6}$ Torr or more, $10^{-5}$ Torr or more). In certain embodiments, the He gas pressure in microscope system 200 is $10^{-1}$ Torr or less (e.g., $10^{-2}$ Torr or less, $10^{-3}$ Torr or less, $10^{-4}$ Torr or less). For example, in some embodiments, the He gas pressure in microscope system 200 is from $10^{-7}$ Torr to $10^{-1}$ Torr (e.g., from $10^{-6}$ Torr to $10^{-2}$ Torr, from $10^{-5}$ Torr to $10^{-3}$ Torr).

To verify the integrity of tip 186, the field emission pattern from tip 186 can be periodically monitored by operating microscope system 200 in FIM or SFIM mode, as discussed above. If the trimer structure remains intact at tip apex 187, then tip 186 can continue to be used to provide ion beam 192 to microscope system 200. However, under certain circumstances, FIM or SFIM imaging of tip 186 may reveal that the trimer structure is no longer intact on tip apex 187. In this case, tip 186 can first be field evaporated to round the tip and remove the damaged trimer structure, and then re-sharpened in situ (e.g., without removing tip 186 from microscope system 200) using a process as described above.

Monitoring of the field emission pattern from tip 186 can be performed automatically based on criteria such as reduced performance (e.g., reduced ion current), observed imaging aberrations and/or errors, or other predetermined criteria. To capture a FIM image of tip 186, sample 180 can be removed from its position and a detector, such as a phosphor-coupled CCD detector, can be placed at the former location of sample 180. Alternatively, a flat sample with a relatively high secondary electron yield can be translated into position in place of sample 180, and a suitable detector can be positioned and configured to detect secondary electrons that leave the sample due to the interaction of the He ions with the sample. Aperture 224 can be removed (or a large diameter opening 225 can be selected) so that ions generated from the interaction of He gas atoms with tip 186 are not significantly obstructed. These operations can be performed in an automated fashion.

To capture a SFIM image of tip 186, a detector can be introduced as described for FIM imaging, and aperture 224 can be maintained in position. Alignment deflectors 220 and 222 can be used to raster the ion emission pattern of tip 186 across aperture 224 to acquire an image of tip 186 in pixel-by-pixel fashion. Acquisition of one or more images of tip 186 can be automated by electronic control system 170, which can control placement of apertures, movement of samples and detectors, and electrical potentials applied to tip 186 and to alignment deflectors 220 and 222.

Figure 13:
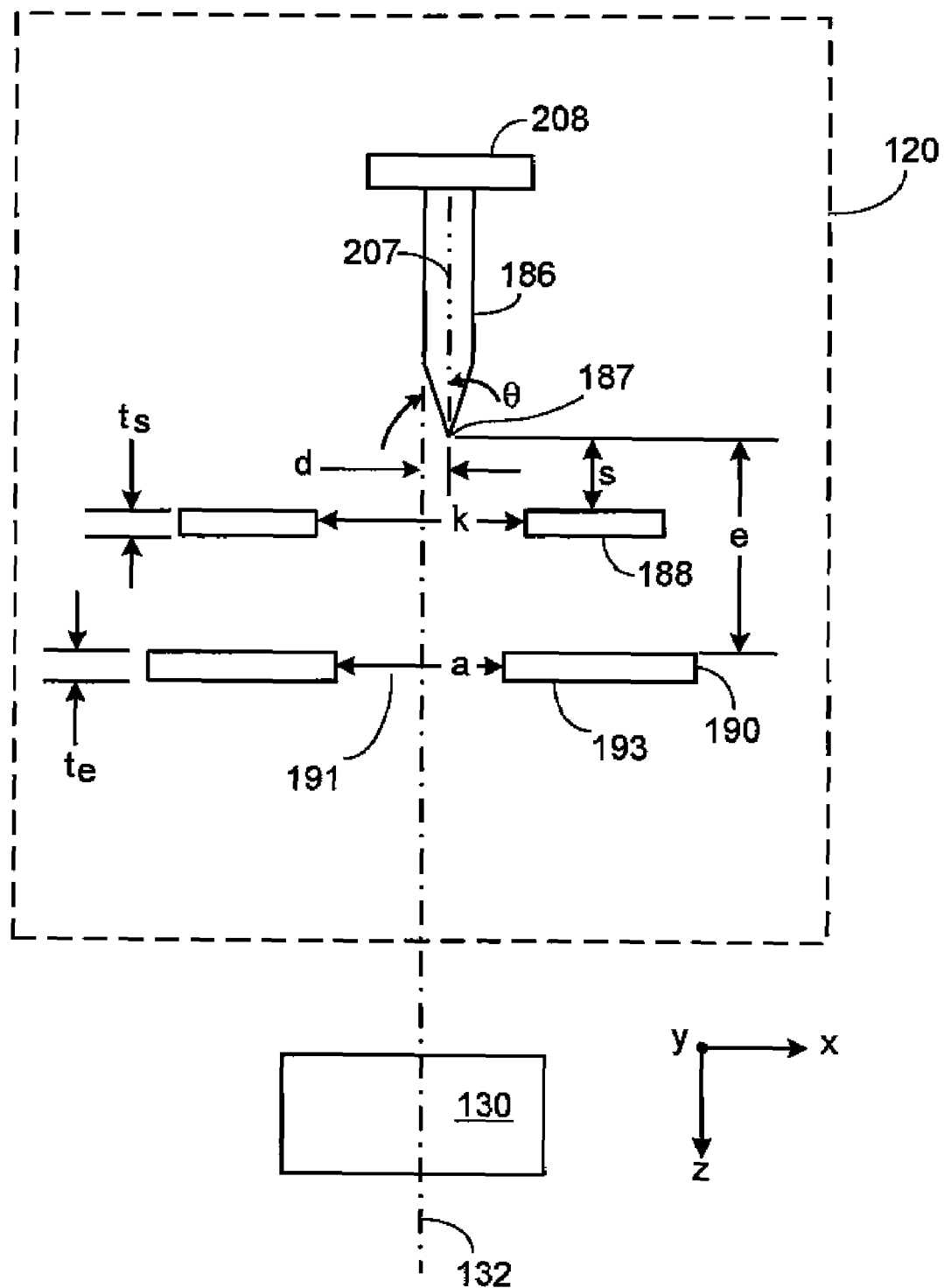
FIG. 13 is a schematic view of an embodiment of a gas field ion source and ion optics.

Referring to FIG. 13, the alignment procedure described above typically aligns a longitudinal axis 207 of tip 186 with a longitudinal axis 132 of ion optics 130 so that the distance d between axes 207 and 132 at apex 187 of tip 186 is less than 2 mm (e.g., less than 1 mm, less than 500 µm, less than 200

μm). In some embodiments, the angle between axes 207 and 132 at apex 187 of tip 186 is 2° or less (e.g., 1° or less, 0.5° or less, 0.2° or less).

Extractor 190 includes an opening 191. In general, the shape of extractor 190 and of opening 191 can be selected as desired. Typically, these features are chosen to ensure that He ions are efficiently and reliably directed into ion optics 130. For example, as shown in FIG. 13, extractor 190 has a thickness $t_e$ measured in the z direction, an opening 191 of width a measured in the x-direction, and is positioned a distance e measured in the z-direction from apex 187 of tip 186. In some embodiments, $t_e$ is 100 μm or more (e.g., 500 μm or more, 1 mm or more, 2 mm or more), and/or $t_e$ is 10 mm or less (e.g., 7 mm or less, 5 mm or less, 3 mm or less). In certain embodiments, the distance e between apex 187 of tip 186 and extractor 190 is 10 mm or less (e.g., 8 mm or less, 6 mm or less, 5 mm or less, 4 mm or less, 3 mm or less, 2 mm or less, 1 mm or less). In some embodiments, extractor 190 is positioned further in the +z direction than tip 186, as shown in FIG. 13. In certain embodiments, extractor 190 is positioned further in the −z direction than tip 186. In such embodiments, for example, tip 186 protrudes through extractor 190 and extends further along the z-axis in the +z direction than extractor 190. While extractor 190 is shown as having a particular configuration in FIG. 13, more generally, extractor 190 can be of any desired design. For example, in some embodiments, opening 191 can have curved sides of any desired shape.

Extractor 190 can generally be biased either positively or negatively with respect to tip 186. In some embodiments, the electrical potential applied to extractor 190 is −10 kV or more (e.g., −5 kV or more, 0 kV or more), and/or 20 kV or less (e.g., 15 kV or less, 10 kV or less) with respect to tip 186.

Optionally, suppressor 188 can also be present in the vicinity of tip 186. Suppressor 188 can be used, for example, to alter the electric field distribution in the vicinity of tip 186 by adjusting the potential applied to suppressor 188. Together with extractor 190, suppressor 188 can be used to control the trajectory of He ions produced at tip 186. Suppressor 188 has an opening of width k measured in the x-direction, a thickness $t_s$ measured in the z-direction, and is positioned at a distance s, measured in the z-direction, from the apex of tip 186. In some embodiments, k is three μm or more (e.g., four μm or more, five μm or more) and/or eight μm or less (e.g., seven μm or less, six μm or less). In certain embodiments, $t_s$ is 500 μm or more (e.g., 1 mm or more, 2 mm or more), and/or 15 mm or less (e.g., 10 mm or less, 8 mm or less, 6 mm or less, 5 mm or less, 4 mm or less). In some embodiments, s is 5 mm or less (e.g., 4 mm or less, 3 mm or less, 2 mm or less, 1 mm or less). In certain embodiments, as shown in FIG. 13, suppressor 188 is positioned further along in the +z-direction than tip 186. In some embodiments, tip 186 is positioned further along in the +z-direction than suppressor 188, so that tip 186 extends through suppressor 188 in the +z-direction.

In general, microscope system 200 can be configured so that after passing through extractor 190, the energy of the ions in ion beam 192 can be selected as desired. Typically, the average energy of the ions in ion beam 192 is 5 keV or more (e.g., 10 keV or more, 20 keV or more, 30 keV or more) and/or 100 keV or less (e.g., 90 keV or less, 80 keV less, 60 keV or less, 50 kV or less, 40 kV or less, 30 kV or less) after passing through entry opening 133 to ion optics 130. For example, in some embodiments, after passing through entry opening 133, the energy of the ions in ion beam 192 is from 5 keV to 100 keV (e.g., from 10 keV to 90 keV, from 20 keV to 80 keV). For example, in embodiments where it is desirable to detect ions that are transmitted through a sample, higher ion energies (e.g., 50 keV to 100 keV) may be used.

Further, in certain embodiments, the energy of the ions in ion beam 192 can be changed without changing the ion current. That is, the electrical potential applied to tip 186 can be adjusted to modify the average energy of ion beam 192 without substantially changing the ion beam current from ion beam 192.

C. Ion Optics

Figure 14:
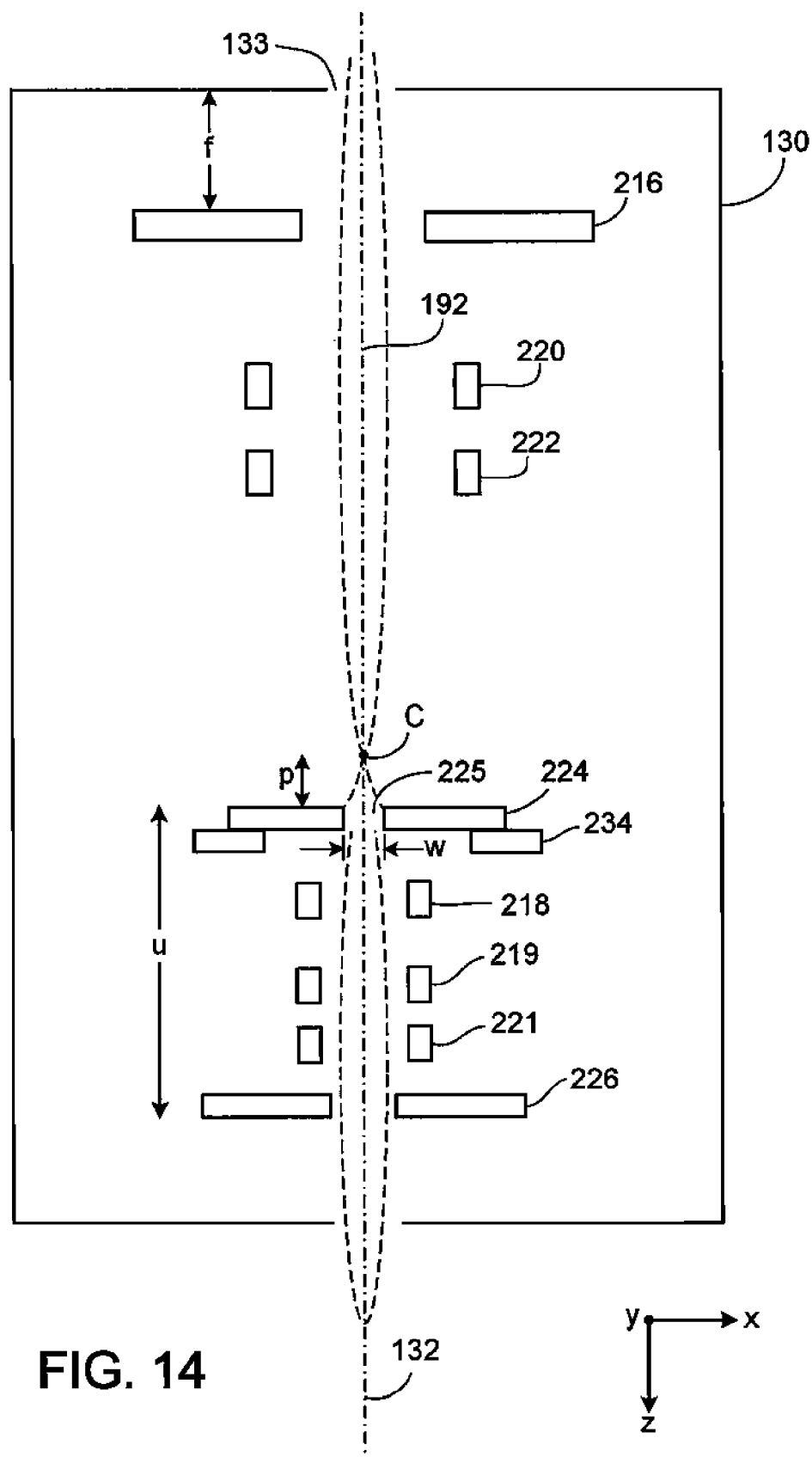
FIG. 14 is a schematic view of an embodiment of an ion optical system.

Referring to FIG. 14, ion beam 192 enters ion optics 130 via entry opening 133 from gas field ion source 120. Ion beam 192 passes first through first lens 216. The position and electrical potential of first lens 216 are generally selected to focus ion beam 192 to a cross-over point C, where point C is a distance p, measured in the z-direction, from aperture 224. In general, first lens 216 is positioned a distance f, measured in the z-direction, from entry opening 133. In some embodiments, the distance f is 5 mm or more (e.g., 10 mm or more, 15 mm or more), and/or 30 mm or less (e.g., 25 mm or less, 20 mm or less).

In general, first lens 216 can be biased positively or negatively with respect to tip 186. In some embodiments, the electrical potential applied to first lens 216 is −30 kV or more (e.g., −20 kV or more, −10 kV or more), and/or 40 kV or less (e.g., 30 kV or less, 20 kV or less, 15 kV or less, 10 kV or less) relative to tip 186.

In general, the distance p can be 1 mm or more (e.g., 5 mm or more, 10 mm or more), and/or 100 mm or less (e.g., 70 mm or less, 50 mm or less, 30 mm or less, 20 mm or less). Changing the position of point C can change the size of ion beam 192 in the x- and/or y-directions at the position of aperture 224, which can selectively control the fraction of ions in ion beam 192 that pass through aperture 224. Although shown in FIG. 14 as being positioned further in the −z-direction than aperture 224, cross-over point C can, in some embodiments, be positioned further in the +z-direction than aperture 224.

Alignment deflectors 220 and 222 are configured to direct a portion of ion beam 192 to pass through both aperture 224 and second lens 226. Various designs and/or components can be used to construct the deflectors. In some embodiments, for example, deflectors 220 and 222 can each be quadrupole electrodes, with the two quadrupole electrodes being arranged in series.

Deflectors 220 and 222 can each deflect He ion beam 192 in both x- and y-directions. The electrical potentials applied to the electrodes of deflectors 220 and 222 can be adjusted to ensure that a portion of ion beam 192 passes through both aperture 224 and second lens 226. In certain embodiments, the potentials applied to deflectors 220 and 222 are adjusted to achieve a particular alignment condition, and then the potentials remain static while microscope system 200 is in operation. Alignment of ion beam 192 through aperture 224 is assessed by observing ion beam 192 using a suitable detector configured, for example, to image aperture 224. Deflectors 220 and/or 222 can also be adjusted so that the portion of ion beam 192 that passes through aperture 224 is aligned with a longitudinal axis of second lens 226. To assess alignment of ion beam 192 through second lens 226, the electrical potential applied to second lens 226 can be varied (commonly referred to as wobbling) and the results observed on the imaging detector. If, as a result of the changing potential applied to second lens 226, the image of ion beam 192 changes in size but not in position, then ion beam 192 is aligned through second lens 226. If the position of the center of ion beam 192 changes as a result of the changing potential, then ion beam 192 is not aligned with second lens 226. In this case, the potentials applied to deflectors 222 and/or 220 can be further adjusted and the wobble test repeated, in iterative fashion, until alignment is achieved.

In general, electrical potentials applied to various electrode elements of alignment deflectors 220 and 222 can be selected as desired to produce deflection of ion beam 192 to a particular location relative to both aperture 224 and second lens 226. Each of the electrodes in deflectors 220 and 222 can be biased either positively or negatively with respect to a common external ground. In general, the electrical potential applied to any electrode can be 100 V or less (e.g., 75 V or less, 50 V or less) and/or 10 V or more (e.g., 25 V or more, 40 V or more) relative to a common external ground. During operation, for example, the electrical potential applied to any electrode in deflectors 220 and 222 can be from 10 V to 100 V (e.g., from 10 V to 75 V, from 10 V to 50 V) relative to a common external ground.

Aperture 224 is positioned relative to ion beam 192 to permit a fraction of the ions in ion beam 192 to pass therethrough. Typically, aperture 224 does not have an applied electrical potential. In some embodiments, the width w, measured in the x-direction, of opening 225 in aperture 224 is one µm or more (e.g., 2 µm or more, 5 µm or more, 10 µm or more, 15 µm or more, 20 µm or more, 25 µm or more, 30 µm or more), and/or 100 µm or less (e.g., 90 µm or less, 80 µm or less, 70 µm or less, 60 µm or less, 50 µm or less). For example, in certain embodiments, w is from one µm to 100 µm (e.g., from 5 µm to 90 µm, from 15 µm to 50 µm, from 20 µm to 50 µm). In some embodiments, the width of opening 225 in aperture 224 measured in the y direction is one µm or more (e.g., 2 µm or more, 5 µm or more, 10 µm or more, 15 µm or more, 20 µm or more, 25 µm or more, 30 µm or more), and/or 100 µm or less (e.g., 90 µm or less, 80 µm or less, 70 µm or less, 60 µm or less, 50 µm or less). For example, in certain embodiments, w is from one µm to 100 µm (e.g., from 5 µm to 90 µm, from 15 µm to 50 µm, from 20 µm to 50 µm).

Aperture 224 is positioned on aperture mount 234. Aperture mount 234 permits translation of aperture 224 in the x-y plane, according to control signals received from electronic control system 170. In some embodiments, aperture mount 234 can also permit translation of aperture 224 in the z direction along longitudinal axis 132 of ion optics 130. Further, in certain embodiments, aperture mount 234 can permit tilting of aperture 224 with respect to the x-y plane. Tilting aperture 224 can be used to align a longitudinal axis of aperture 224 with longitudinal axis 132 of ion optics 130.

Figure 15:
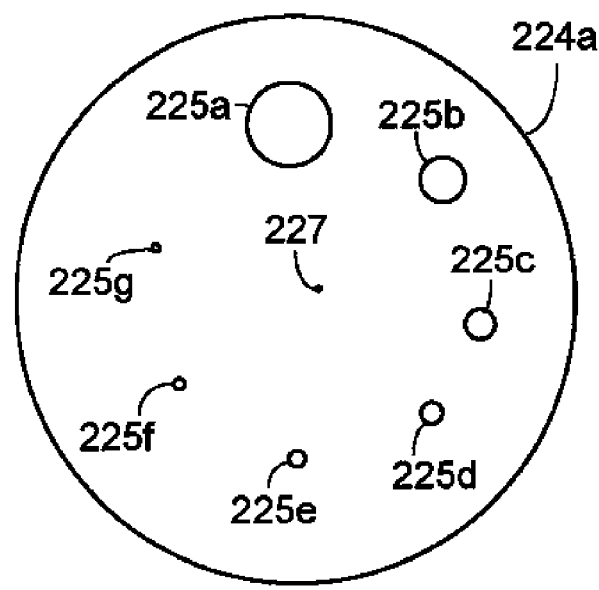
FIG. 15 is a top view of an embodiment of a multi-opening aperture.

In some embodiments, aperture 224 can include a plurality of openings having different widths w. For example, FIG. 15 is a top view (along the z-direction) of a disk-shaped aperture 224a that includes multiple openings 225a-225g. Aperture 224a is configured to rotate about a pivot point 227 that coincides with the center of aperture 224a. The centers of each of openings 225a-225g are positioned at the same distance from pivot point 227. An aperture opening of a particular size can therefore be selected by rotating aperture disk 224a such that a selected opening is positioned in the path of ion beam 192, and then translating aperture disk 224a, if desired, to ensure correct alignment of the opening with ion beam 192.

Figure 16:
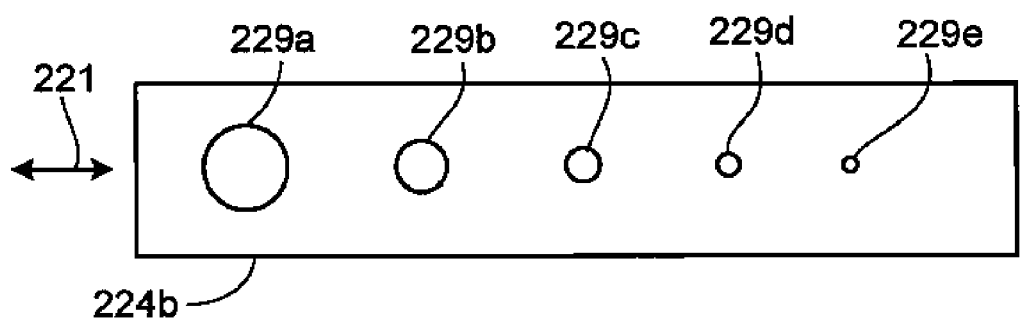
FIG. 16 is a top view of an embodiment of a multi-opening aperture.

FIG. 16 is a top view (along the z-direction) of a rod-shaped aperture 224b that includes multiple openings 229a-229e extending through aperture 224b. The aperture size can be chosen by selecting an opening in aperture 224b. This selection is performed by translating aperture 224b in a direction parallel to arrow 221 to align one of the openings 229a-229e with ion beam 192.

Typically, openings 225a-225g and 229a-229e have diameters that can be chosen as desired. For example, in some embodiments, the diameter of any of the openings can be five µm or more (e.g., 10 µm or more, 25 µm or more, 50 µm or more) and/or 200 µm or less (e.g., 150 µm or less, 100 µm or less). In certain embodiments, the diameters of openings 225a-225g and/or 229a-229e can be from five µm to 200 µm (e.g., five µm to 150 µm, five µm to 100 µm).

In some embodiments, devices other than an aperture can be used to permit only a portion of the ions in ion beam 192 to pass through ion optics 130 and impinge on the surface of sample 180. For example, two perpendicular slits can be positioned in series along the flight path of the ion beam.

Astigmatism corrector 218 is generally configured, via its shape, position along the path of ion beam 192, and applied electrical potential, to reduce or eliminate astigmatism in ion beam 192. Although various components can be used to construct astigmatism corrector 218, astigmatism corrector 218 is typically an octupole electrode positioned between aperture 224 and scanning deflectors 219 and 221. Typically, the eight electrodes of an octupolar astigmatism corrector are divided into two groups of four electrodes, with a first controller configured to adjust the voltages of four of the electrodes (e.g., the first group of four electrodes, positively biased with respect to tip 186) and a second controller that adjusts the voltages of the other four electrodes (e.g., the second group of four electrodes, negatively biased with respect to tip 186). Electrodes from the first and second electrode groups are arranged in alternating fashion to form the segments of the octupole, where adjacent segments have bias voltages of opposite signs. This arrangement of electrodes forms a cusp field which focuses ion beams propagating along a longitudinal axis of the octupole, and de-focuses off-axis ion beams.

In general, each of the electrodes of the octupole can be configured independently, and astigmatism corrector 218 therefore permits sensitive control over ion beam 192. In some embodiments, the electrical potential applied to any of the electrodes of astigmatism corrector 218, relative to the common external ground, can be −30 V or more (e.g., −20 V or more, −10 V or more, −5 V or more), and/or 30 V or less (e.g., 20 V or less, 10 V or less, 5V or less).

In addition to alignment deflectors 220 and 222, ion optics 130 include scanning deflectors 219 and 221. Scanning deflectors 219 and 221 are typically positioned between astigmatism corrector 218 and second lens 226, although in general, other arrangements of scanning deflectors 219 and 221 within ion optics 130 are also possible.

Scanning deflectors 219 and 221 are configured to scan ion beam 192 across a surface of sample 180. Deflector 219, for example, can be configured to deflect ion beam 192 in the x-direction, and deflector 221 can be configured to deflect ion beam 192 in the y-direction. The combined deflection produced by deflectors 219 and 221 can position ion beam 192 at a particular location on sample 180.

Typically, the electrical potentials applied to deflectors 219 and 221 are adjusted to produce a particular deflection of ion beam 192. The applied electrical potentials can be varied systematically to raster scan beam 192 over a portion of sample 180. For example, in some embodiments, the electrical potential applied to deflector 221 is increased in stepwise fashion at regular intervals to deflect ion beam 192 across sample 180 in discrete steps (e.g., row-by-row) in the y-direction. At the same time, the electrical potential applied to deflector 219 is increased in stepwise fashion to deflect ion beam 192 across sample 180 in discrete steps (e.g., column-by-column) in the x-direction. The rate at which the potential applied to deflector 221 is increased can be selected so that ion beam 192 is deflected in the y-direction to a new row once ion beam 192 has made a complete scan across all columns via the stepwise increases in the potential applied to deflector 219. For each row, the same stepwise pattern of incremental potential increases can be applied to deflector 219 to sweep ion beam 192 in discrete steps in the x-direction.

In general, scanning deflectors 219 and/or 221 can be formed from a plurality of electrodes. For example, in some embodiments, scanning deflectors 219 and/or 221 can each include a pair of parallel plate electrodes. The electrodes in deflector 219 can be oriented to deflect ion beam 192 in a direction orthogonal to the deflection of ion beam 192 produced by deflector 221.

In certain embodiments, scanning deflectors 219 and/or 221 can be of a more complex design. For example, scanning deflectors 219 and/or 221 can include quadrupolar electrodes and/or octupolar electrodes. These electrodes can each be configured to provide deflection of ion beam 192 in a single direction in the x-y plane, or in more than one direction in the x-y plane.

Each of the electrode elements in scanning deflectors 219 and 221 can be biased either positively or negatively with respect to the common external ground. In general, the voltage applied to each electrode can be −150 V or more (e.g., −100 V or more, −50 V or more, −20 V or more) and/or 150 V or less (e.g., 100 V or less, 50 V or less, 20 V or less). During operation, for example, the voltage applied to each electrode in deflectors 219 and 221 can be from −150 V to 150 V (e.g., from −100 V to 100 V, from −50 V to 50 V, from −20 V to 20 V).

In general, the position and electrical potential of second lens 226 are selected so that second lens 226 assists in focusing ion beam 192 onto surface 181 of sample 180. The electrical potential applied to second lens 226 can, in general, be either positive or negative with respect to the common external ground. In certain embodiments, the electrical potential applied to second lens 226 is −50 kV or more (e.g., −40 kV or more, −30 kV or more), and/or 40 kV or less (e.g., 30 kV or less, 20 kV or less) relative to the common external ground. Second lens 226 is spaced from aperture 224 by a distance u, measured in the z direction. In some embodiments, u is 5 cm or more (e.g., 10 cm or more, 15 cm or more), and/or 50 cm or less (e.g., 45 cm or less, 40 cm or less, 35 cm or less, 30 cm or less, 25 cm or less, 20 cm or less).

Second lens 226 is spaced from sample 180 by a distance h (commonly referred to as the working distance) measured along the z-axis. In some embodiments, h can be 2 mm or more (e.g., 5 mm or more, 10 mm or more, 15 mm or more 20 mm or more) and/or 200 mm or less (e.g., 175 mm or less, 150 mm or less, 125 mm or less, 100 mm or less, 75 mm or less, 65 mm or less, 55 mm or less, 45 mm or less). In certain embodiments, h is from 2 mm to 200 mm (e.g., from 5 mm to 175 mm, from 10 mm to 150 mm, from 15 mm to 125 mm, 20 mm to 100 mm). Typically, h can be adjusted by changing the electrical potential applied to second lens 226 to adjust the focal plane of lens 226, and translating sample 180 (via sample manipulator 140) into the new focal plane of lens 226. The relatively large distance h permitted by microscope system 200 provides a number of advantages. For example, uneven samples with surface protrusions can be investigated using microscope system. Further, samples can also be tilted at large angles with respect to the principal axis of ion beam 192. For example, in some embodiments, the angle between a normal to surface 181 of sample 180 and the principal axis of ion beam 192 is 5° or more (e.g., 10° or more, 20° or more, 30° or more, 40° or more, 50° or more, 60° or more) and/or 85° or less (e.g., 80° or less, 75° or less, 70° or less, 65° or less). In certain embodiments, the angle between the normal to surface 181 of sample 180 and the principal axis of ion beam 192 is from 5° to 85° (e.g., from 10° to 80°, from 20° to 70°, from 30° to 70°, from 40° to 60°). In addition, the relatively large distance h also permits a variety of detectors and other devices to be positioned in close proximity to the region of incidence of ion beam 192 on surface 181, and can allow for detection of particles leaving the sample over a relatively large range of solid angles. Typically, this permits detection of stronger signals and detection of multiple different types of signals (e.g., using different types of detectors).

In some embodiments, second lens 226 is shaped as a right-angled cone with a cone half-angle of 10° or more (e.g., 15° or more, 20° or more, 25° or more) and/or 50° or less (e.g., 45° or less, 40° or less, 35° or less). In certain embodiments, the cone half-angle of second lens 226 is from 10° to 50° (e.g., from 15° to 45°, from 20° to 40°). Relatively small cone half-angles for lens 226 provide a number of advantages, including a greater range of tilt angles of sample 180 with respect to ion beam 192, and a larger volume of free space in the vicinity of the incident beam spot on surface 181 in which detectors and other devices can be positioned.

As discussed above, typically, substantially only He ions generated via the interaction of He atoms with one of the trimer atoms at apex 187 of tip 186 pass through aperture 224. However, in some embodiments, components in ion optics 130 (e.g., first lens 216 and/or alignment deflectors 220, 222 and/or aperture 224) can be set so that a substantial fraction of He ions generated via the interaction of He atoms with two of the trimer atoms pass through aperture 224. This can be achieved, for example, by appropriate selection of the electrical potentials applied to first lens 216 and/or deflectors 220, 222, and/or by changing the size of aperture 224 (e.g., by selecting a different aperture opening on an aperture wheel or rod, as shown in FIGS. 15 and 16, respectively). In certain embodiments, components in ion optics 130 (e.g., first lens 216 and/or alignment deflectors 220, 222 and/or aperture 224) can be set so that a substantial fraction of He ions generated via the interaction of He gas atoms with all three of the trimer atoms pass through aperture 224. This can be achieved, for example, by appropriate selection of the electrical potentials applied to first lens 216 and/or deflectors 220, 222, and/or by changing the size of aperture 224 (e.g., by selecting a different aperture opening on an aperture wheel or rod, as shown in FIGS. 15 and 16, respectively).

Optionally, one or more additional electrodes (e.g., lenses, deflectors, and/or other elements) can be positioned along the path of ion beam 192 in ion optics 130. Additional electrodes can be positioned after second lens 226, for example, or can be introduced between existing elements. The additional elements can be biased either positively or negatively with respect to tip 186 to perform functions such as increasing or decreasing the energy of the ions in ion beam 192 within ion optics 130 and/or to change the trajectories of the ions. For example, one or more accelerating electrodes can be positioned in the vicinity of sample 180 to change the energy with which the ions in ion beam 192 are incident on sample 180.

As another example, ion optics 130 can include a negatively biased (relative to the common external ground) column liner tube to increase the energy of the ions in ion beam 192 at surface 181 of sample 180. The tube can be biased at −50 kV or more (e.g., −25 kV or more, −15 kV or more, −10 kV or more) and/or −1 kV or less (e.g., −3 kV or less, −5 kV or less) relative to the common external ground. In general, the tube can be located at any position along axis 132 of ion optics 130 such as, for example, between aperture 224 and second lens 226. Certain advantages can be realized by accelerating ions as they pass through ion optics 130 including, for example, a reduction of the interaction time between like-charged ions, which can help to reduce the divergence of ion beam 192.

In some embodiments, the energy of the ions in ion beam 192 at surface 181 of sample 180 can be increased or decreased by biasing sample 180 (e.g., positively, if a decrease in the energy of the ions in ion beam 192 is desired, or negatively, if an increase in the energy of the ions in ion beam 192 is desired). At larger angles of incidence of ion beam 192, the cylindrical asymmetry of the electric field produced by biased sample 180 can produce a prism-like effect, where low energy ions in ion beam 192 are deflected by a greater amount in the x- and y-directions than higher energy ions, resulting in an increase in spot size of ion beam 192 on surface 181 of sample 180 and potentially other undesirable consequences. In some embodiments, therefore, sample 180 is biased to alter the energy of ions in ion beam 192, and an angle between ion beam 192 and a normal to surface 181 is less than 6° (e.g., less than 5°, less than 4°, less than 3°, less than 1°).

While certain embodiments of ion optics have been described, other embodiments of ion optics can also be used. As an example, where a certain electrode type (e.g., octupole) has been described, one or more different electrode types (e.g., quadrupole) may be used to achieve the same effect. More generally, a variety of different ion optics systems can be used in microscope system 200. In some embodiments, for example, ion optics 130 include only a single lens in addition to deflectors, apertures, and other ion optical elements. In certain embodiments, ion optics 130 include first and second lenses with an aperture therebetween.

As another example, in some embodiments, the ion optics include a first lens, a second lens, an aperture between the first and second lenses, no electrodes, and the ion optics are designed so that the first lens can reduce the divergence of the ion beam (e.g., such that the ion beam is substantially aligned with the longitudinal axis of the ion optics system), the aperture can block a portion of the ion beam from passing therethrough, and the second lens can help focus the ion beam to a relatively small spot size on the surface of the sample. In such embodiments, the ions in the ion beam that reach the surface of the sample can be generated predominantly by the interaction of He atoms with only one atom of the trimer (as described above, for example). In some embodiments, approximately equal numbers of ions in the ion beam that reach the surface of the sample are generated via the interaction of He atoms with each of the three trimer atoms.

As an additional example, in certain embodiments, the ion optics include a first lens, a second lens, an aperture between the first and second lenses, no electrodes, and the ion optics are designed so that the first lens can focus the ion beam toward the center of the opening in the aperture, the aperture can allow the focused ion beam to diverge and pass therethrough, and the second lens can help focus the ion beam to a relatively small spot size on the surface of the sample. In such embodiments, the ion beam that reaches the surface of the sample can include approximately equal numbers of ions generated by the interaction of gas atoms with each of the three atoms in the trimer. If the apex of tip 186 includes more than three atoms (e.g., five or more atoms, seven or more atoms, nine or more atoms), the ion beam can include approximately equal numbers of ions generated via the interaction of gas atoms with each of the atoms at the apex of tip 186.

As a further example, in some embodiments, the ion optics include a first lens, a second lens, an aperture between the first and second lenses, no electrodes, and the ion optics are designed so that the first lens can reduce the divergence of the ion beam and direct the low divergence beam toward the aperture, the aperture can allow substantially all the ions in the ion beam to pass therethrough, and the second lens can help focus the ion beam to a relatively small spot size on the surface of the sample. In such embodiments, the ion beam that reaches the surface of the sample can include approximately equal numbers of ions generated via the interaction of gas atoms with each of the three atoms in the trimer. If the apex of tip 186 includes more than three atoms (e.g., five or more atoms, seven or more atoms, nine or more atoms), the ion beam can include approximately equal numbers of ions generated via the interaction of gas atoms with each of the atoms at the apex of tip 186.

As another example, in certain embodiments, the ion optics include a first lens, a second lens, an aperture between the first and second lenses, no electrodes, and the ion optics are designed so that the first lens can partially focus the ion beam toward the aperture, the aperture can block a portion of the ions in the ion beam from passing therethrough (but still allow a relatively large fraction of the ions in the ion beam to pass therethrough), and the second lens can help focus the ion beam to a relatively small spot size on the surface of the sample. In such embodiments, the ion beam that reaches the surface of the sample can include approximately equal numbers of ions generated via the interaction of gas atoms with each of the three atoms in the trimer. If the apex of tip 186 includes more than three atoms (e.g., five or more atoms, seven or more atoms, nine or more atoms), the ion beam can include approximately equal numbers of ions generated via the interaction of gas atoms with each of the atoms at the apex of tip 186.

D. Tip Tilt and Translation Mechanism

Figure 17:
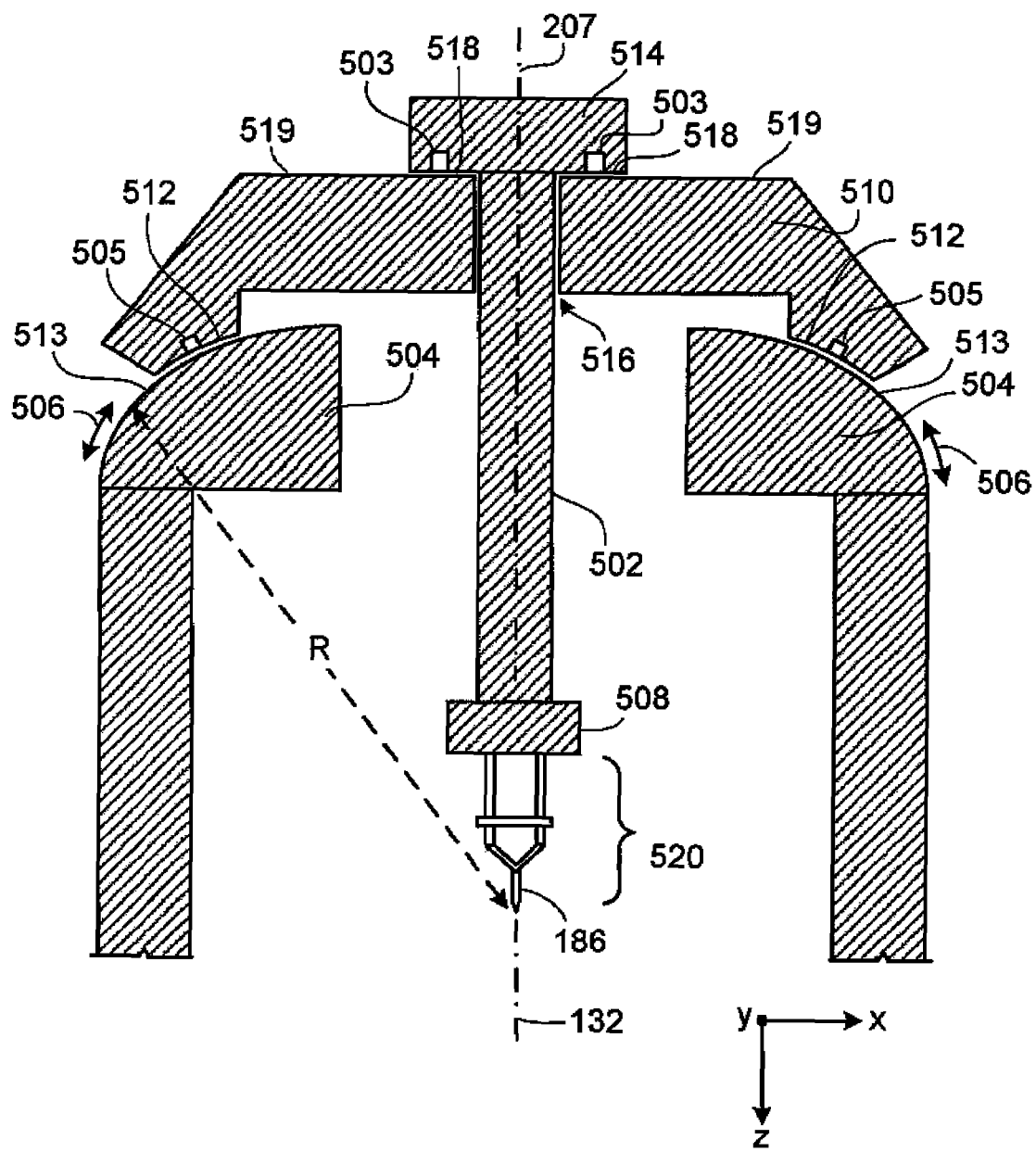
FIG. 17 is a cross-sectional view of an embodiment of a movement mechanism for a gas field ion microscope tip.

Tip manipulator 208 is configured to permit both translation of tip 186 in the x-y plane, and tilting of tip 186 with respect to axis 132 of ion optics 130. FIG. 17 is a cross-sectional view of a portion of microscope system 200 including tip 186, support assembly 520 and an embodiment of a tip manipulator. Tip manipulator 208 includes a shaft 502, a dome 504, a shoulder 510 and a translator 514. Translator 514 is connected to shaft 502, which is dimensioned to fit through an opening 516 in shoulder 510. Shaft 502 is further connected to base 508, which in turn is connected to assembly 520. Shoulder 510 is in a fixed position relative to dome 504 by static frictional forces between surfaces 512 and 513, and translator 514 is in a fixed position relative to shoulder 510 by static frictional forces between surfaces 518 and 519.

Tip manipulator 208 provides for translation of tip 186 in the x-y plane. To translate tip 206, a high pressure gas is introduced into inlet 503. The high pressure gas introduced into inlet 503 can be a gas such as room air, for example. Typically, the gas can be introduced at a pressure of 50 pounds per square inch (psi) or more (e.g., 75 psi or more, 100 psi or more, 125 psi or more). As a result of introducing the high pressure gas, a force is applied to translator 514 in the −z direction, away from shoulder 510. The applied force lessens (but does not reduce to zero) the frictional force between surfaces 518 and 519, and permits repositioning of translator 514 with respect to shoulder 510 by applying a lateral force in the x-y plane. Tip 186 is translated in the x-y plane when translator 514 is repositioned. When tip 186 is in its new position, the supply of high pressure gas is turned off and strong static frictional forces between surfaces 518 and 519 are re-established by evacuating the interior of tip manipulator 208 using one or more vacuum pumps. Tip 186 is rigidly fixed in position as a result of the re-established strong frictional forces.

Tip manipulator 208 also provides for tilting of tip 186 with respect to axis 132 of ion optics 130. To tilt tip 186, a high pressure gas is introduced into inlet 505. The high pressure gas introduced into inlet 505 can be a gas such as room air, for example. Typically, the gas can be introduced at a pressure of 50 pounds per square inch (psi) or more (e.g., 75 psi or more, 100 psi or more, 125 psi or more). As a result of introducing the high pressure gas, a force is applied to shoulder 510 in the −z direction, away from dome 504. The applied force lessens (but does not reduce to zero) the frictional force between surfaces 512 and 513. Shoulder 510 can then be re-positioned with respect to dome 504 by applying a lateral force to translate shoulder 510 in a direction indicated by arrows 506. Translation of shoulder 510 corresponds to relative movement along the curved surface of dome 504. As a result of this movement, the angle between axes 132 and 207 (which corresponds to the tilt angle of tip 186) changes. When adjustment of the tilt of tip 186 is complete, the supply of high pressure gas is turned off and strong static frictional forces between surfaces 512 and 513 are re-established by evacuating the interior of tip manipulator 208. Tip 186 is rigidly fixed in position as a result of the re-established strong frictional forces.

In some embodiments, as shown in FIG. 17, tip manipulator 208 is configured so that the center of the radius of curvature, R, of dome 504 coincides with the position of the apex of tip 186. As a result, when tip 186 is tilted to change the angle between axes 132 and 207, translation of tip 186 in the x-y plane does not occur. As a result, tip manipulator 208 can be used to align the trajectories of ions generated via the interaction of gas atoms with one of the tip atoms with the longitudinal axis of first lens 216 without causing translation of tip 186 with respect to the axis of first lens 216.

In certain embodiments, tip manipulator 208 can be configured to permit rotational motion about additional axes. For example, in the embodiment shown in FIG. 17, when high pressure gas is introduced into inlet 503 to reduce the frictional force between surfaces 518 and 519 and permit translation of translator 514 in the x-y plane, translator 514 can also be rotated about axis 207 by applying a suitable torque to translator 514. This rotation can be performed separately from, or in addition to, translation of tip 186 and tilt adjustment of tip 186.

E. Sample Stage

Referring again to FIG. 5, microscope system 200 includes a sample manipulator 140 for supporting and positioning sample 180. In response to control signals from electronic control system 170, sample manipulator 140 can translate sample 180 in each of the x-, y-, and z-directions. In some embodiments, sample manipulator 140 can also rotate sample 180 in the x-y plane in response to control signals. Further, in certain embodiments, sample manipulator 140 can tilt sample 180 out of the x-y plane in response to suitable control signals. Each of these degrees of freedom can be independently adjusted to achieve a suitable orientation of sample 180 with respect to ion beam 192.

As described in more detail below, in some embodiments, sample manipulator 140 can be biased, either positively or negatively with respect to the common external ground, by applying a relatively small electrical potential to manipulator 140. For example, in some embodiments, a positive potential bias of 5 V or more (e.g., 10 V or more, 20 V or more, 30 V or more, 40 V or more, 50 V or more) relative to the common external ground can be applied to manipulator 140 to assist in preventing positively charged He ions from adhering to surface 181 of sample 180. In certain embodiments, a negative potential bias of −200 V or more (e.g., −150 V or more, −100 V or more, −50 V or more, −40 V or more, −30 V or more, −20 V or more, −10 V or more, −5 V or more) relative to the common external ground can be applied to manipulator 140 to assist, for example, in accelerating secondary electrons (that leave surface 181 of sample 180 via the interaction of the ions with sample 180) away from the sample, ensuring that the secondary electrons can be detected by a suitably configured detector. In general, the potential applied to manipulator 140 can be chosen as desired according to the particular material under study, the He ion current, and exposure time of the sample.

F. Detectors

Detectors 150 and 160 are depicted schematically in FIG. 5, with detector 150 positioned to detect particles from surface 181 of sample 180 (the surface on which the ion beam impinges), and detector 160 positioned to detect particles from surface 183 of sample 180. In general, a wide variety of different detectors can be employed in microscope system 200 to detect different particles, and a microscope system 200 can typically include any desired number of detectors. The configuration of the various detector(s) can be selected in accordance with particles to be measured and the measurement conditions. In some embodiments, a spectrally resolved detector may be used. Such detectors are capable of detecting particles of different energy and/or wavelength, and resolving the particles based on the energy and/or wavelength of each detected particles. In certain embodiments, a spectrally resolved detector includes componentry capable of directing particles to different regions of the detector based on the energy and/or wavelength of the particle.

Certain exemplary detectors and arrangements of detectors are described below.

(i) Everhart-Thornley Detectors

Figure 18:
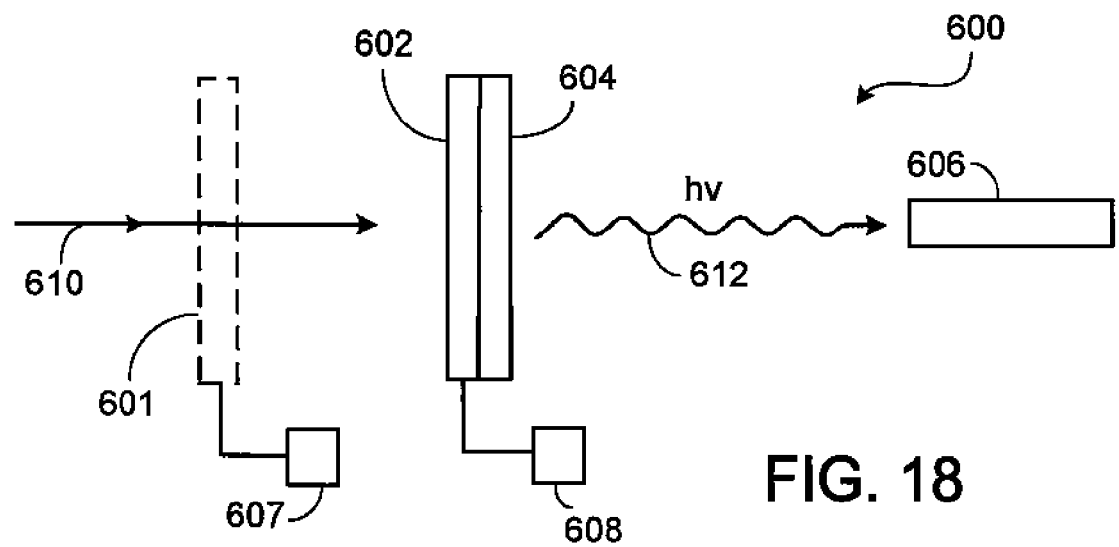
FIG. 18 is a schematic diagram of an Everhart-Thornley detector.

An Everhart-Thornley (ET) detector can be used to detect secondary electrons, ions, and/or neutral particles. FIG. 18 shows a schematic diagram of an ET detector 600 that includes a particle selector 601, a conversion material 602, a support 604, a photon detector 606, and voltage sources 607 and 608.

Particle selector 601 is formed of an electrically conductive material. In some embodiments, for example, particle selector 601 can be a metal grid or mesh with a metal fill-factor of less than approximately 30% (e.g., less than 25%, less than 20%, less than 10%, less than 5%). Because the grid is predominantly open space, particles impinging on the grid can pass through relatively unobstructed.

In certain embodiments, particle selector 601 is formed of a metal ring or tube. For example, particle selector 601 can be a ring or tube that is substantially cylindrical in shape, with an interior opening that permits particles to pass through the ring or tube. The ring or tube can be formed of a highly conductive metal such as copper or aluminum, for example.

More generally, particle selector 601 can be formed from any open electrode structure that includes a passage for particles to pass through. Particle selector 601 can be formed from one or more electrodes, and potentials applied to the one or more electrodes can generally be selected as desired according to the type of particles being measured.

Conversion material 602 is formed of a material that, upon interaction with a charged particle (e.g., an ion, an electron) can form a photon. Exemplary materials include phosphor materials and/or scintillator materials (e.g., crystalline materials, such as yttrium-aluminum-garnet (YAG) and yttrium-aluminum-phosphate (YAP). Support 604 is formed of a material that is relatively transparent to photons formed by conversion material 602.

During operation, voltage source 607 applies a voltage of relatively small magnitude (e.g., 500 V or less, such as from 100 V to 500 V) to particle selector 601 (formed of a conductive material), and voltage source 608 applies a voltage of relatively large magnitude (e.g., 5 kV or more, 10 kV or more) to conversion material 602. In embodiments in which the ET detector is used to measure electrons from sample 180 (e.g., secondary electrons), the sign of the voltage applied to particle selector 601 and conversion material 602 is positive with respect to sample 180. In embodiments in which the ET detector is used to measure ions from sample 180 (e.g., secondary ions, scattered ions), the sign of the voltage applied to particle selector 601 and conversion material 602 is negative with respect to sample 180. In certain embodiments, sample 180 can also be biased (with respect to the common external ground) to assist in delivering particles from sample 180 to detector 600. For example, when the ET detector is used to measure secondary electrons from sample 180, the sample can be negatively biased relative to the common external ground. Applying a negative potential bias to manipulator 140 may be particularly useful, for example, when detecting secondary electrons generated in a high aspect ratio (e.g., deep) hole or via in the sample. The negative potential bias relative to the common external ground can assist in accelerating electrons out of the hole or via and away from the sample, making detection of the electrons easier. In the absence of the negative bias, many of the secondary electrons might instead re-enter the sample at points along the hole or via walls, never escaping the hole or via to be detected.

Sample 180 can be positively biased, for example, when the ET detector is used to measure ions from the sample. The magnitude of the electrical potential applied to bias the sample can be 5 V or more (e.g., 10 V or more, 15 V or more, 20 V or more, 30 V or more, 50 V or more, 100 V or more).

Charged particles 610 (e.g., electrons or ions) from sample 180 are attracted to particle selector 601, pass through particle selector 601, and are accelerated toward conversion material 602. Charged particles 610 then collide with conversion material 602, generating photons 612. Photons 612 pass through support 604 and are detected by photon detector 606.

While operation of an ET detector has been described with respect to measuring charged particles, an ET detector can also be used to detect neutral particles because, in general, particles impinging on conversion material 602 do not have to be charged to generate photons 612. In particular, primary atoms from sample 180, impinging on conversion material 602, can generate photons 612 for detection by photon detector 606. Photon detector 606 can be, for example, a photomultiplier tube (PMT), a diode, a diode array, or a CCD camera.

An ET detector can be located at any position relative to sample 180 to detect neutral or charged particles. Typically, for example, an ET detector is positioned adjacent to second lens 226 of ion optics 130. Optionally, an ET detector can also be positioned such that it is tilted downward slightly towards sample 180 (e.g., in a similar configuration as that depicted for detector 150 in FIG. 5).

In certain embodiments, an ET detector can be positioned in the vicinity of surface 183 of sample 180. Such a configuration may be desirable, for example, when seeking to measure secondary electrons from sample 180 that emerge from surface 183 (e.g., after being transmitted through sample 180). In such embodiments, the ET detector can have a configuration that is similar to the configuration of detector 160 in FIG. 5.

(ii) Photon Detectors

To detect photons generated by the interaction of the ions with sample 180, a standard photon detector such as a PMT can be used. If the photon flux emanating from sample 180 is sufficiently large, less sensitive photon detectors such as diodes, diode arrays, and CCD cameras can be used.

In some embodiments, the photon detector can also include various optical elements that can be configured, for example, to isolate a particular optical signal of interest from among other optical signals. For example, in certain embodiments, the photon detector can include optical elements such as filters to select particular wavelength bands in the photon signal emerging from sample 180, which can provide material constituent information about sample 180. The filters can, for example, block photons of undesired wavelengths (e.g., by absorbing photons of undesired wavelengths, by reflecting photons of undesired wavelengths, by diverting photons of undesired wavelengths). In some embodiments, the optical elements can provide spectral resolution (e.g., to measure the spectrum of photons generated by sample 180) by dispersing different wavelengths spatially (e.g., diffractive elements such as one or more gratings, and/or refractive elements such as one or more prisms, and/or one or more spectrometer systems that provide wavelength-resolved detection of photons). In some embodiments, the photon detector can include polarization manipulating elements such as waveplates and/or polarizers. These polarization manipulating elements can be configured to permit photons having only a selected polarization state to reach the PMT, for example, allowing polarization-selective detection of the photon signal emerging from sample 180 (e.g., to assist in determining crystalline orientation information for sample 180). In certain embodiments, the photon detector can also include optical elements such as mirrors, lenses, beamsplitters, and other elements for re-directing and manipulating incident photons (e.g., to increase the solid angle of the photons that are detected).

In general, photon detectors can be positioned to detect photons at any desired angle and distance from sample 180. For example, in certain embodiments, a photon detector can be positioned to detect photons emerging from surface 181 (the surface of sample 180 upon which ion beam 192 is incident), or from surface 183 (the surface of sample 180 opposite to the surface upon which ion beam 192 is incident). Optionally, multiple photon detectors can be used and configured to detect photons from surfaces 181 (the surface on which the ion beam impinges), 183 (the surface on the opposite side from where the ion beam impinges) and/or other surfaces of sample 180.

For some samples, photons are scattered in particular directions according to selection rules for optical processes occurring in sample 180, and angle-resolved measurement of the photon yield from sample 180 can provide, for example, material constituent information about sample 180.

(iii) Microchannel Plate Detectors

In some embodiments, a microchannel plate detector can be used to amplify a flux of secondary electrons, neutral atoms, or ions from sample 180. Microchannel plates are typically formed from materials such as fused silica, and generally include a large number of small diameter channels arranged in the form of an array. Particles enter individual channels and collide with channel walls, generating free electrons. Typically, multiple free electrons are generated on each collision of a particle (neutral atom, ion, or electron) with a channel wall. As a result, a cascaded electron signal corresponding to an amplification of the input particle signal exits the microchannel plate.

Microchannel plate-based detectors (which can include one or more microchannel plates) can be configured to detect ions, secondary electrons, and/or neutral atoms from sample 180. Neutral particles and/or ions (e.g., secondary ions and atoms, scattered ions and primary atoms) formed from sample 180 typically leave surface 181 of sample 180 (the surface on which the ion beam impinges). Accordingly, microchannel plate-based detectors configured to measure neutrals and/or ions from sample 180 are generally located at positions similar to the position of detector 150 depicted in FIGS. 1 and 5. However, in certain embodiments, neutral particles and/or ions (e.g., transmitted ions) can be investigated. In such embodiments, a microchannel plate-based detector can be located at positions similar to the position of detector 160 in FIGS. 1 and 5. Secondary electrons can be detected either from surface 181 (the surface on which the ion beam impinges) and/or surface 183 of sample 180 (the surface on the opposite side from where the ion beam impinges), and microchannel plate-based detectors configured to detect secondary electrons from sample 180 are located at positions similar to detector 150 and/or detector 160 as depicted in FIGS. 1 and 5.

Microchannel plates amplify an incoming particle signal and convert the incoming signal to an outgoing electron signal. To visualize the outgoing electron signal, microchannel plate-based detectors can also include a conversion material, a screen, and a photon detector (see discussion above).

Figure 19:
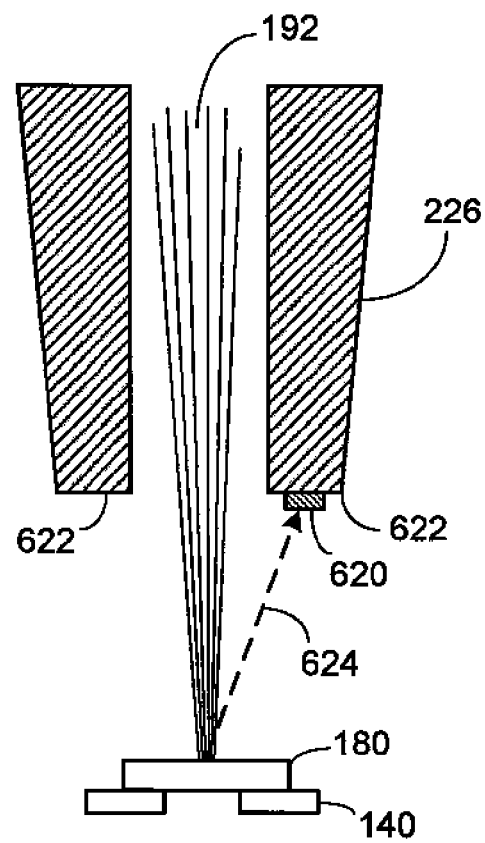
FIG. 19 is a cross-sectional view of a portion of a gas field ion microscope system including a microchannel plate detector.

In some embodiments, microchannel plates are affixed directly to elements of ion optics 130. FIG. 19 shows a cross-sectional view of a microchannel plate detector 620 mounted directly to second lens 226. Second lens 226 has a conical shape, with a flat lower surface 622. Detector 620 is mounted directly to surface 622. When sample 180 is exposed to ion beam 192, ions, secondary electrons, and/or neutral atoms from sample 180 (collectively indicated by arrow 624) can be detected by microchannel plate detector 620. Detector 620 registers a current that is proportional to the detected particle flux, which can be conveyed to electronic control system 170.

(iv) Conversion Plates

In some embodiments, a conversion plate can be used to detect ions (e.g., scattered ions, secondary ions) from sample 180 or neutral particles (e.g., primary neutral He atoms) from sample 180. Typically, a conversion plate can be formed from a thin foil material that, when struck by an incident ion or atom, has a high secondary electron yield. An example of such a material is platinum. The secondary electron yield produces an abundance of secondary electrons that are readily detected, for example, by an appropriate electron detector configured, for example, as detectors 150 and/or 160 (FIGS. 1 and 5).

(v) Channeltron Detectors

Channeltron detectors can also be used to detect particles such as electrons, ions and neutral atoms leaving sample 180. Channeltron detectors function by amplifying particle signals through multiple internal collisions in a manner similar to that described in connection with microchannel plate detectors. Measurement of relatively weak secondary electron, ion, or neutral atom fluxes from sample 180 is possible by measuring the amplified particle signals that are output by a channeltron detector (e.g., using electronic control system 170). When measuring secondary electrons from sample 180, a channeltron detector can be located in a position similar to that depicted for detector 150 and/or detector 160 in FIGS. 1 and 5. Typically, for the measurement of ions and/or neutral particles from sample 180, a channeltron detector is located in a position similar to the position of detector 150 and/or the position of detector 160 as depicted in FIGS. 1 and 5.

(vi) Phosphor Detectors

Phosphor-based detectors, which include a thin layer of a phosphor material deposited atop a transparent substrate, and a photon detector such as a CCD camera, a PMT, or one or more diodes, can be used to detect electrons, ions and/or neutral particles from sample 180. Particles strike the phosphor layer, inducing emission of photons from the phosphor which are detected by the photon detector. Phosphor-based detectors can be arranged in positions similar to those of detector 150 and/or detector 160 as depicted in FIGS. 1 and 5, depending upon the type of particle that is measured (see discussion above).

(vii) Solid State Detectors

Solid state detectors can be used to detect secondary electrons, ions, and/or neutral atoms from sample 180. A solid state detector can be constructed from a sensor formed of a material such as silicon, or a doped silicon material. When incident particles strike the sensor, electron-hole pairs are created in the sensor material, producing a current that can be detected by electronic control system 170. The number of electron-hole pairs generated by an incident particle, and therefore the corresponding magnitude of the current produced, depends in part upon the particle's energy. Thus, a solid state detector can be particularly useful for energy measurements of particles, which can be especially advantageous when detecting high energy particles (e.g., scattered He ions and neutral He atoms) from sample 180.

(viii) Scintillator Detectors

Similar to phosphor-based detectors, scintillator-based detectors include a scintillator material that generates photons in response to being struck by an incident particle (electron, ion, or neutral atom). Suitable scintillator materials include, for example, YAG and YAP. The photon yield in scintillator-based detectors depends on the energy of the incident particles. As a result, a scintillator detector can be particularly useful for energy measurements of particles, which can be especially advantageous when detecting high energy particles (e.g., scattered He ions and neutral He atoms) from sample 180.

(ix) Energy Detectors for Ions

A variety of different detectors and detection schemes can be implemented to measure energies of ions (e.g., scattered He ions) from sample 180. Electrostatic prism detectors, in which an electric and/or magnetic field is used to deflect incident ions, where the amount of deflection depends on the energy of the ions, can be used to spatially separate ions with different energies. Magnetic prism detectors may also be used to spatially separate ions based on the energy of the ions. Any of the suitable detectors discussed above (e.g., microchannel plates, channeltrons, and others) can then be used to detect the deflected ions.

Quadrupole detectors can also be used to analyze energies of ions from sample 180. In a quadrupole detector, a radio-frequency (RF) field within the quadrupole ensures that ions having a chosen mass and energy propagate along a straight, undeflected trajectory within the quadrupole. Ions with a different mass and/or energy propagate along a curved trajectory within the quadrupole. From the deflected position of ions within the quadrupole analyzer, energies of the ions can be determined.

In some embodiments, ion energy can be determined by placing a positively biased particle selector (e.g., a screen or mesh of electrically conductive material, or a cylindrical metal tube or ring) along the flight path of the ions and in front of the detector. The magnitude of the electrical potential applied to particle selector 601 can initially be very high (e.g., a value certain to prevent ions from sample 180 from passing therethrough), and the magnitude of the electrical potential can be reduced while using an appropriate detector (see discussion above) to detect the ions. The current of ions that reach the detector as a function of the magnitude of the potential bias on the particle selector can be used to determine information about the energy of the ions.

(x) Energy Detectors for Electrons

A variety of different detectors and detection schemes can be implemented to measure energies of electrons (e.g., secondary electrons) from sample 180. Prism detectors, in which an electric and/or magnetic field is used to deflect incident electrons, and where the amount of deflection depends on the energy of the electrons, can be used to spatially separate electrons with different energies. Any of the suitable detectors discussed above can then be used to detect the deflected electrons.

In some embodiments, electron energies can be determined by placing a negatively biased particle selector (e.g., a screen or mesh of electrically conductive material, or a cylindrical metal tube or ring) along the flight path of the electrons and in front of the detector. The magnitude of the electrical potential of the particle selector can initially be very high (e.g., a value certain to prevent the electrons from sample 180 from passing therethrough), and the magnitude of the electrical potential can be reduced while using an appropriate detector (see discussion above) to detect the electrons. The electron current that reaches the detector as a function of the magnitude of the applied electrical potential on the particle selector can be used to determine information about the energies of the electrons.

(xi) Time-of-Flight Detectors

The detectors disclosed above can also be configured to measure time-of-flight information for secondary electrons, ions, and neutral atoms. To perform time-of-flight detection, ion beam 192 is operated in pulsed mode. Ion beam 192 can be pulsed, for example, by rapidly changing the electrical potential applied to one or both of deflectors 220 and 222. By increasing these potentials, for example, ion beam 192 can be diverted from its usual path in ion optics 130 such that ion beam 192 is temporarily blocked by aperture 224. If the potentials of deflectors 220 and 222 are then returned to their normal values for a short time before being increased again, a pulse of He ions can be delivered to sample 180.

At the same time, detectors 150 and 160 can be synchronized to a clock signal from electronic control system 170 that is based upon the temporal variation in potentials applied to deflectors 220 and/or 222. As a result, the time interval between the launch of a He ion pulse and the detection of particles from sample 180 can be accurately measured. From known information about the time of propagation of the He ion pulse within ion optics 130, the time-of-flight of the detected particles between sample 180 and detectors 150 and/or 160 can be determined.

(xii) Angle-Dependent Measurements

In addition to measuring relative abundances and energies of particles from sample 180, angle-dependent scattering information can be obtained using the detectors disclosed above. Typically, to acquire angle-dependent information, a detector is affixed to a mount (e.g., a swivel mount) that permits movement of the detector throughout a range of solid angles about sample 180. At a given orientation with respect to sample 180 that corresponds to a particular solid angle, abundance and/or energy measurements of particles are recorded. The detector is sequentially re-positioned at different solid angles and the measurements are repeated to determine the angular dependence of the measured quantities. In some embodiments, a limiting aperture such as a pinhole can be placed in front of the detector in the path of the scattered particles to further restrict the range of angles over which measurement of particles from sample 180 occurs.

G. Operational Parameters

Figure 20A:
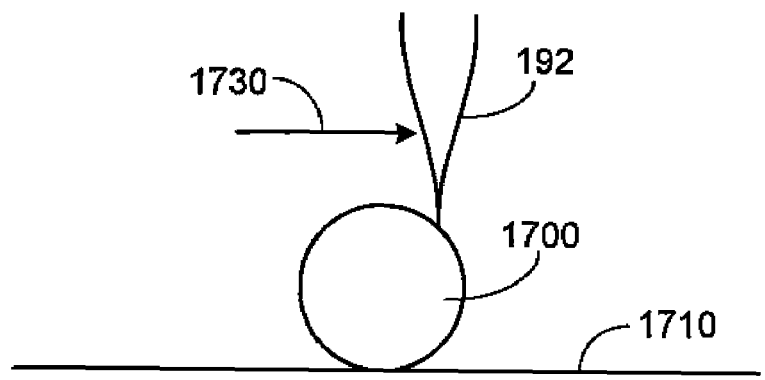
FIGS. 20A and 20B are side and top views of a gold island supported by a carbon surface.
Figure 20B:
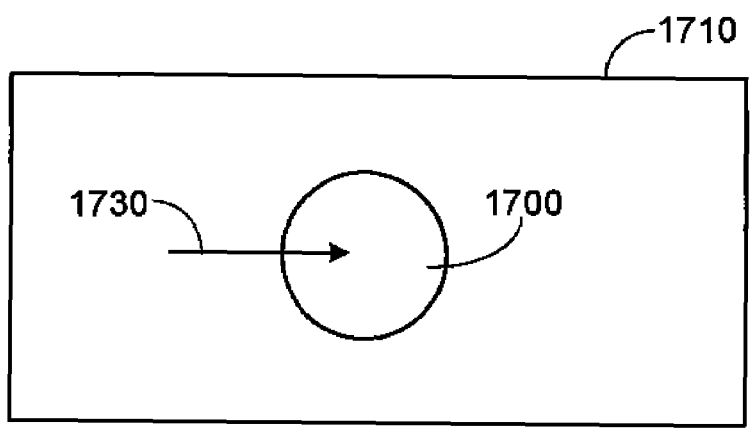
Figure 20C:
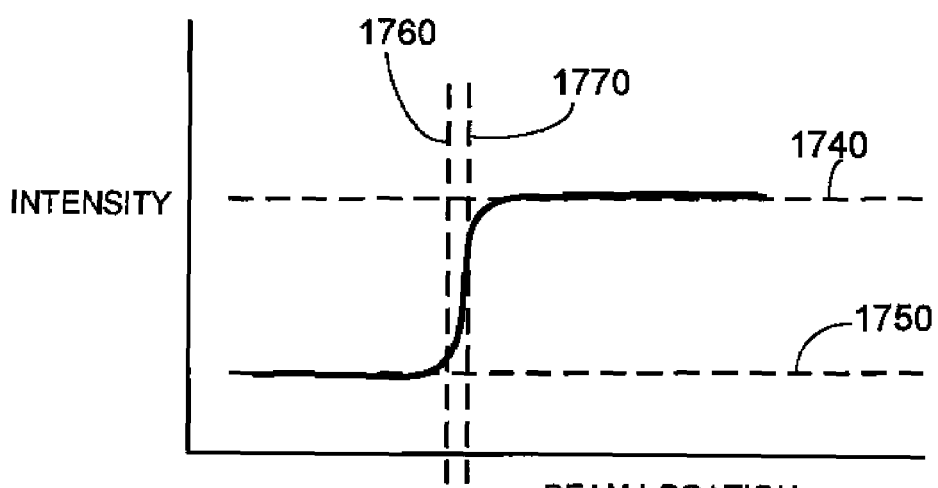
FIG. 20C is a plot of average measured secondary electron total abundance as a function of ion beam position for the sample of FIGS. 20A and 20B.

Ion beam 192 can have a relatively small spot size on surface 181 of sample 180. For example, in some embodiments, the spot size of ion beam 192 on surface 181 of sample 180 can have a dimension of 10 nm or less (e.g., nine nm or less, eight nm or less, seven nm or less, six nm or less, five nm or less, four nm or less, three nm or less, two nm or less, one nm or less). In certain embodiments, the spot size of ion beam 192 on surface 181 of sample 180 has a dimension of 0.05 nm or more (e.g., 0.1 nm or more, 0.2 nm or more, 0.25 nm or more, 0.5 nm or more, 0.75 nm or more, one nm or more, two nm or more, three nm or more). In some embodiments, the spot size of ion beam 192 on surface 181 has a dimension of from 0.05 nm to 10 nm (e.g., from 0.1 nm to 10 nm, 0.2 nm to 10 nm, 0.25 nm to 3 nm, 0.25 nm to one nm, 0.1 nm to 0.5 nm, 0.1 nm to 0.2 nm). As used herein, spot size is determined as follows with reference to FIGS. 20A-20C. An island 1700 formed of gold and having a dimension of from 50 nm to 2000 nm is disposed on a carbon surface 1710. The gold island is formed, for example, by vapor deposition of gold onto the carbon surface. Measurement samples that include gold islands deposited on carbon, suitable for the resolution measurements described herein, are available commercially from Structure Probe Inc. (West Chester, Pa.), for example. The ion microscope is operated such that it moves ion beam 192 linearly across a portion of the gold island, as well as the portions of the carbon surface on one side of the gold island (arrow 1730). The intensity of secondary electrons is measured as a function of the location of the ion beam (FIG. 20C). Asymptotic lines 1740 and 1750 are calculated (or drawn) corresponding to the average total abundance values for the carbon and gold, and vertical lines 1760 and 1770 are calculated (or drawn) corresponding to the locations where the total abundance is 25% and 75%, respectively, of the abundance difference between asymptotic lines 1740 and 1750. The spot size of ion microscope 200 is the distance between lines 1760 and 1770.

In general, the current of ion beam 192 at surface 181 of sample 180 is one nA or less (e.g., 100 pA or less, 50 pA or less), and/or 0.1 fA or more (e.g., one fA or more, 10 fA or more, 50 fA or more, 100 fA or more, one pA or more, 10 pA or more). For example, in some embodiments, the current of ion beam 192 at surface 181 of sample 180 is from 0.1 fA to one nA (e.g., from 10 fA to 100 pA, from 100 fA to 50 pA). In certain embodiments, it can be desirable to use a relatively low beam current when imaging a sample. For example, in some biological and/or pharmaceutical applications, it may be more important to use a low current to image in the sample (e.g., to reduce possible damage to the sample). In such embodiments, one current can be used to prepare the gas field ion microscope for use (e.g., a current of 10 fA or more), and a different current can be used to image the sample (e.g., a current of less than one fA, such as 0.1 fA).

Generally, ion beam 192 has an energy spread at surface 181 of sample 180 of five eV or less (e.g., four eV or less, three eV or less, two eV or less, one eV or less, 0.5 eV or less). In some embodiments, ion beam 192 has an energy spread at surface 181 of sample 180 of 0.1 eV or more (e.g., 0.2 eV or more, 0.3 eV or more, 0.4 eV or more). For example, ion beam 192 can have an energy spread at surface 181 of sample 180 of from 0.1 eV to five eV (e.g., from 0.1 eV to three eV, from 0.1 eV to one eV).

Ion beam 192 can have a relatively high brightness at surface 181 of sample 180. For example, ion beam 192 can have a brightness of $1 \times 10^9$ A/cm$^2$sr (e.g., $1 \times 10^{10}$ A/cm$^2$sr or more, $1 \times 10^{11}$ A/cm$^2$sr or more) at surface 181 of sample 180. In some embodiments, the brightness can be increased by increasing the gas pressure adjacent to tip 186 and/or decreasing the temperature of tip 186. As referred to herein, the brightness of an ion beam is measured as follows. The FWHM of the distribution of ion trajectories in ion beam 192—in a region of space between extractor 190 and first lens 216 where the net electric field is relatively small and the ion trajectories are nearly straight lines—is determined in both the x- and y-directions. A total of 100 ion trajectories that fall within the FWHM width in both the x- and y-directions are chosen at random from the distribution of ion trajectories in ion beam 192. Each of the 100 ion trajectories is nearly a straight line, and is projected back toward tip apex 187. The spatial extent of the trajectories at a particular point $Z_t$ along the z-axis is assessed by constructing, in a plane $Z_t$ parallel to the x-y plane and passing through point $z_t$, the smallest-diameter circle that encloses all of the points of intersection of the back-propagated trajectories with the plane $Z_t$. The diameter of the smallest-diameter circle is $d_s$. Typically, for points $z_t$ closer to tip apex 187, $d_s$ will be smaller and for points $z_t$ closer to sample 180, $d_s$ will be larger. At a particular point $z_t = z_0$, $d_s$ will be a minimum value $d_0$. That is, the spatial extent of the trajectories in a plane parallel to the x-y plane will be a minimum. The diameter $d_0$ of the minimum-diameter circle at point $z_0$ is referred to as the virtual source size of microscope system 200. Next, the divergence and beam current of ion beam 192 in the FWHM region of ion beam 192 between extractor 190 and first lens 216, as discussed above, are measured. Finally, brightness is calculated as beam current divided by the product of the virtual source size and the solid divergence angle of ion beam 192.

Ion beam 192 can have a relatively high reduced brightness at surface 181 of sample 180. For example, ion beam 192 can have a reduced brightness of $5 \times 10^8$ A/m$^2$srV or more (e.g., $1 \times 10^9$ A/cm$^2$srV or more, $1 \times 10^{10}$ A/cm$^2$srV or more) at surface 181 of sample 180. As referred to herein, the reduced brightness of an ion beam is the brightness of the ion beam divided by the average energy of the ions in the ion beam at the position where the beam current is measured Ion beam 192 can have a relatively low etendue at a distal end 193 of extractor 190. For example, ion beam 192 can have an etendue of $5 \times 10^{-21}$ cm$^2$sr or less (e.g., $1 \times 10^{-22}$ cm$^2$sr or less, $1 \times 10^{-23}$ cm$^2$sr or less, $1 \times 10^{-23}$ cm$^2$sr or less, $1 \times 10^{-24}$ cm$^2$sr or less) at distal end 193 of extractor 190. As referred to herein, the etendue of an ion beam is calculated as the mathematical product of the reciprocal of the brightness and the beam current.

Ion beam 192 can have a relatively low reduced etendue at a distal end 193 of extractor 190. For example, ion beam 192 can have a reduced etendue of $1 \times 10^{-16}$ cm$^2$sr or less (e.g., $1 \times 10^{-17}$ cm$^2$sr or less, $1 \times 10^{-18}$ cm$^2$sr or less, $1 \times 10^{-19}$ cm$^2$sr or less) at distal end 193 of extractor 190. Reduced etendue of an ion beam is the mathematical product of the etendue of the ion beam and the ratio of the average energy-to-charge of ions in the ion beam at the position where the beam current is measured.

Ion beam 192 can have a relatively low angular convergence with respect to surface 181 of sample 180. For example, in some embodiments, the convergence half angle of ion beam 192 can be 5 mrad or less (e.g., 1 mrad or less, 0.5 mrad or less, 0.1 mrad or less), and/or 0.05 mrad or more. As referred to herein the convergence half angle of an ion beam is determined as follows. A sample that includes a gold island atop a carbon substrate, as described above, is mounted in ion microscope 200 and translated in the z-direction so that the position of the focus of ion beam 192 lies, as nearly as possible, at the highest elevation point along a diameter of the gold island. Ion beam 192 is then translated linearly along the diameter of the gold island and the focused spot size, $s_f$, of the ion beam is measured, as described above. The sample is then translated in the +z direction, away from ion optics 130, by $s_z = 1$ μm, and ion beam 192 is translated linearly along the same diameter of the gold island to measure the defocused spot size, $s_d$, of ion beam 192. The convergence angle η can then be determined trigonometrically from the measurements of the focused and defocused spot sizes, along with the translation distance, as $$\eta = 2\sin^{-1}\left(\frac{s_d - s_f}{2s_z}\right)$$

The convergence half angle of ion micro scope 200 is η/2.

Ion microscope 200 can be highly reliable. As an example, in some embodiments, the He ion source (tip 186, extractor 190 and optionally suppressor 188) is capable of continuously interacting with gas atoms to generate an ion beam for a time period of one week or more (e.g., two weeks or more, one month or more, two months or more) without removing tip 186 from the system. In some embodiments, during the time period that the He ion source is continuously interacting with gas atoms to generate an ion beam, the current of ion beam 192 at surface 181 of sample 180 varies by 10% or less (e.g., 5% or less, 1% or less) per minute.

As another example, in some embodiments, the gas field ion source (tip 186, extractor 190 and optionally suppressor 188) is capable of interacting with gas atoms to generate an ion beam for a time period of one week or more (e.g., two weeks or more, one month or more, two months or more) with a total interruption time of 10 hours or less (e.g., five hours or less, two hours or less, one or less). In such embodiments, the gas field ion source may interact with gas atoms to generate the ion beam continuously for the entire time period (corresponding to a total interruption time of zero hours), but this is not necessary. For example, during the time period, there may be times when the gas field ion microscope is not interacting with gas atoms to generate an ion beam. Such time periods correspond to an interruption time. During the time period, such interruption times may occur one time or more than one time (e.g., two times, three, times, four times, five times, six times, seven times, eight times, nine times, 10 times). The interruptions may be due, for example, to scheduled maintenance, unexpected maintenance, and/or down time between shifts (e.g., overnight down time). During the time period, the total of the interruption times is the total interruption time. As an example, if during the time period there are three interruption times, each of one hour, then the total interruption time is three hours. As another example, if during the time period there is only one interruption time and it is three hours long, then the total interruption time is three hours. As a further example, if during the time period there are two interruption times, with the first interruption time being an hour and the second interruption time being two hours, then the total interruption time is three hours. In some embodiments, for those times during the time period when the gas field ion source is interacting with gas atoms to generate an ion beam, the current of ion beam 192 at surface 181 of sample 180 varies by 10% or less (e.g., 5% or less, 1% or less) per minute.

Ion microscope 200 can have a relatively good resolution. For example, in some embodiments, the resolution of ion microscope 200 can be 10 nm or less (e.g., nine nm or less, eight nm or less, seven nm or less, six nm or less, five nm or less, four nm or less, three nm or less, two nm or less, one nm or less). In certain embodiments, the resolution of ion microscope 200 can be 0.05 nm or more (e.g., 0.1 nm or more, 0.2 nm or more, 0.25 nm or more, 0.5 nm or more, 0.75 nm or more, one nm or more, two nm or more, three nm or more). In some embodiments, the resolution of ion microscope 200 can be from 0.05 nm to 10 nm (e.g., from 0.1 nm to 10 nm, 0.2 nm to 10 nm, 0.25 nm to 3 nm, 0.25 nm to one nm, 0.1 nm to 0.5 nm, 0.1 nm to 0.2 nm). As used herein, the resolution of an ion beam refers to the size of the smallest feature that can be reliably measured from images obtained using the ion microscope. A size of a feature is reliably measured if it can be determined to within an error of 10% or less of the actual size of the feature, and with a standard deviation in the measured size of less than 5% of the actual size of the feature, from ten images of the feature obtained under similar conditions.

Ion microscope 200 can be used to take a good quality image in a relatively short period of time. For example, ion microscope 200 can have a quality factor of 0.25 or more (e.g., 0.5 or more, 0.75 or more, one or more, 1.5 or more, two or more). As referred to herein, the quality factor is determined as follows. A planar sample, one half of which is formed of silicon (Si) and the other half of which is formed of copper (Cu), with a boundary between the materials being a straight line across the sample, is positioned so that the boundary is oriented parallel to the y-axis. The sample is imaged pixel-by-pixel by sub-dividing the surface of the sample into an x-y array of 512 pixels by 512 pixels. The dwell time per pixel is 100 ns during the measurement. The total abundance of secondary electrons from the sample is measured as a function of the position of the ion beam on the surface of the sample. For image pixels that correspond to Si in the sample, an average pixel intensity $G_1$ is determined, along with a standard deviation $SD_1$ from the distribution of Si pixel intensities. For image pixels that correspond to Cu in the sample, an average pixel intensity $G_2$ is determined, along with a standard deviation $SD_2$ from the distribution of Cu pixel intensities. The quality factor is calculated according to the equation $$\frac{G_1 - G_2}{\sqrt{SD_1 \cdot SD_2}}$$

Surface 181 of sample 180 can undergo relatively little damage when exposed to ion beam 192. For example, surface 181 of sample 180 can have a value of 25 nm or less (e.g., 20 nm or less, 15 nm or less, 10 nm or less, five nm or less) according to the damage test. As referred to herein, the damage test is performed as follows. An atomically flat silicon (99.99% purity) sample with a four square μm field of view is imaged for 120 seconds while rastering the ion beam across the surface of the sample pixel-by-pixel using an ion beam current at the sample of 10 pA and a spot size of the ion beam at the sample of 10 nm or less. The four square μm field of view is broken into a 512 pixel by 512 pixel array for rastering purposes. The value of the damage test corresponds to the maximum distance of etching into the imaged portion of the silicon sample resulting from performing the damage test.

Ion microscope 200 can have a relatively large depth of focus. For example, in some embodiments, the depth of focus of ion microscope 200 can be five nm or more (e.g., 10 nm or more, 100 nm or more, one μm or more), and/or 200 μm or less (e.g., 100 μm or less, 10 μm or less). In some embodiments, the depth of focus of ion microscope 200 can be from 200 μm to five nm (e.g., from 500 μm to five nm, from one nm to five nm). As used herein, the depth of focus of an ion beam is measured in the following manner. A sample that includes gold islands formed on a carbon substrate (as discussed previously in connection with measurement of the He ion beam spot size) is inserted into the He ion microscope, and a measurement of the He ion beam spot size is performed as discussed above. The location of the sample along the z-axis is iteratively adjusted so that the position of the sample that yields the smallest He ion beam spot size is determined. This position along the z-axis is denoted $z_f$. The spot size of the He ion beam at $z_f$ is denoted $ss_f$. The sample is then translated in increments along the −z direction relative to $z_f$. Spot size measurements of the He ion beam are performed (at the same location on the sample that was used to determine $z_f$) after successive incremental translations. Translation of the sample is halted when the measured He ion beam spot size is 2 $ss_f$. This position of the sample along the z-axis is denoted $z_u$. Then, the sample is translated in increments along the +z direction relative to $z_u$, and through point $z_f$. Spot size measurements of the He ion beam are performed (at the same location on the sample that was used to determine $z_f$) after successive incremental translations. Translation of the sample is halted when the measured He ion beam spot size is 2 $ss_f$. This position of the sample along the z-axis is denoted $z_1$. The depth of focus of the He ion microscope, $d_f$ is calculated as $d_f = |z_1 - z_u|$.

In some embodiments, a gas field ion microscope (e.g., He ion microscope) as disclosed herein can be used to distinguish elements in a sample having very close atomic numbers (Z values) using, for example, secondary electron yield, scattered ion abundance, and/or angle- and energy-resolved scattered ion detection. For example, in certain embodiments, the gas field ion microscope can be used to distinguish elements having atomic numbers (Z values) that differ only by one.

In certain embodiments, a gas field ion microscope (e.g., He ion microscope) as disclosed herein can be used to distinguish elements in a sample having a very close masses using, for example, secondary electron yield, scattered ion abundance, and/or angle- and energy-resolved scattered ion detection. In certain embodiments, the gas field ion microscope can be used to distinguish elements having masses that differ by one atomic mass unit or less (e.g., 0.9 atomic mass unit or less, 0.8 atomic mass unit or less, 0.7 atomic mass unit or less, 0.6 atomic mass unit or less, 0.5 atomic mass unit or less, 0.4 atomic mass unit or less, 0.3 atomic mass unit or less, 0.2 atomic mass unit or less, 0.1 atomic mass unit or less). In some embodiments, a sample may have domains formed of materials (e.g., alloys) having different average masses. In such embodiments, the gas field ion microscope can, for example, be used to distinguish domains of material having masses that differ only by one atomic mass unit or less (e.g., 0.9 atomic mass unit or less, 0.8 atomic mass unit or less, 0.7 atomic mass unit or less, 0.6 atomic mass unit or less, 0.5 atomic mass unit or less, 0.4 atomic mass unit or less, 0.3 atomic mass unit or less, 0.2 atomic mass unit or less, 0.1 atomic mass unit or less).

H. Optional Features

(i) High Efficiency Gas Use

In some embodiments, a more focused delivery of He gas to tip 206 can increase the efficiency of He gas utilization within microscope system 200. Typically, un-ionized He gas atoms can enter ion optics 130, which can increase the width of the distribution of energies of the ions in ion beam 192. In addition, low energy un-ionized He gas atoms can participate in charge exchange interactions with high energy He ions, which can also increase the width of the energy distribution of ions in ion beam 192.

Figure 21:
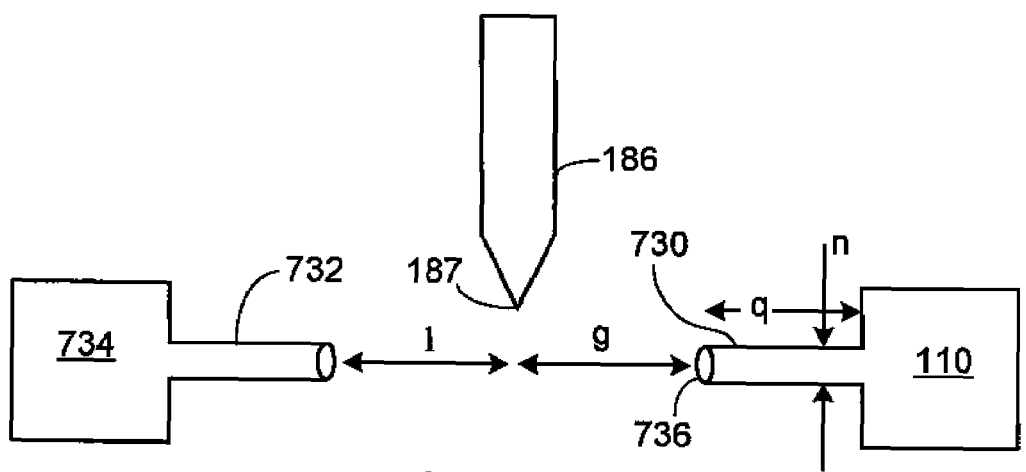
FIG. 21 is a schematic diagram of a portion of a gas field ion microscope including a gas delivery system.

Thus, in some embodiments, a gas delivery system can be designed to provide gas (e.g., He gas) to tip 186 of gas field ion source 120 in a more targeted manner, and to remove unused gas (e.g., un-ionized He gas) from the system in a more efficient manner. For example, FIG. 21 is a schematic diagram of a portion of a gas field ion microscope that includes gas source 110 and a vacuum pump 734. Gas source 110 includes a delivery tube 730 of length q and diameter n terminating in a delivery nozzle 736, and vacuum pump 734 includes an inlet port 732. Nozzle 736 is positioned at a distance g from apex 187 of tip 186, and inlet port 732 is positioned at a distance l from apex 187 of tip 186.

In some embodiments, g can be 10 mm or less (e.g., 9 mm or less, 8 mm or less, 7 mm or less). Typically, g is 3 mm or more (e.g., 4 mm or more, 5 mm or more, 6 mm or more). For example, g can be from 3 mm to 10 mm (e.g., from 4 mm to 9 mm, from 5 mm to 8 mm).

In certain embodiments, l can be 100 mm or less (e.g., 90 mm or less, 80 mm or less, 70 mm or less, 60 mm or less, 50 mm or less). Typically, l is 10 mm or more (e.g., 20 mm or more, 30 mm or more, 40 mm or more). For example, l can be from 10 mm to 100 mm (e.g., from 30 mm to 100 mm, from 40 mm to 80 mm).

In some embodiments, the local pressure of He gas at the position of apex 187 of tip 186 is $10^{-5}$ Torr or more (e.g., $10^{-4}$ Torr or more, $10^{-3}$ Torr or more, $10^{-2}$ Torr or more, $10^{-1}$ Torr or more, 1 Torr or more). At the same time, the overall pressure of He gas in microscope system can be reduced relative to systems that employ background introduction of He gas. For example, the overall He pressure in microscope system 200 can be $10^{-4}$ Torr or less (e.g., $10^{-5}$ Torr or less, $10^{-6}$ Torr or less, $10^{-7}$ Torr or less, $10^{-8}$ Torr or less).

In some embodiments, the distance l and the cross-sectional area of inlet port 732 are selected so that vacuum pump 734 captures unionized He atoms within a particular solid angle region of microscope system 200. For example, for He atoms positioned at apex 187 of tip 186, the solid angle subtended by inlet port 732 is 5° or more (e.g., 10° or more, 15° or more, 20° or more, 30° or more, 40° or more).

In general, the ratio of the length q of delivery tube 730 to the diameter n of tube 730 can be selected to control the distribution of trajectories of He gas atoms delivered to tip 186. For example, in some embodiments, the ratio q/n can be 3 or more (e.g., 4 or more, 5 or more, 6 or more) and/or 10 or less (e.g., 9 or less, 8 or less, 7 or less). In certain embodiments, the ratio q/n can be between 3 and 10 (e.g., between 3 and 9, between 4 and 9, between 4 and 8, between 5 and 8, between 5 and 7).

In some embodiments, the gas delivery system can include more than one delivery tube and nozzle. For example, in certain embodiments, the gas delivery system can include two or more (e.g., three or more, four or more, five or more, six or more) gas delivery tubes. Each of the multiple gas delivery tubes can be positioned to deliver He gas, in a relatively directed fashion, to tip 186. As a result of using multiple gas delivery tubes, the local pressure of He gas at the position of apex 187 of tip 186 can be increased even further. One or more vacuum pumps can be used to remove un-ionized He gas from microscope system 200.

In some embodiments, gas delivery tube 730 can be incorporated into another component of the system. For example, in certain embodiments, gas delivery tube 730 can be formed by one or more passageways (e.g., two or more passageways, four or more passageways, six or more passageways) for gas delivery in extractor 190 and/or suppressor 188. In some embodiments, one or more passageways (e.g., two or more passageways, four or more passageways, six or more passageways) for gas delivery can be provided in posts which support tip 186 (e.g., posts 522*a/b* and 552). As an example, in certain embodiments, extractor 190 can include four passageways for gas delivery to tip 186. The passageways can be equally spaced and arranged radially along a circumference of extractor 190 so that the opening of each passageway directly faces tip 186. The length-to-diameter ratios of each of the passageways can be the same, or different.

A number of advantages can be realized by incorporating gas delivery tubes into other elements of microscope system 200. For example, using a metal tube 730 placed close to tip 186 for gas delivery can perturb electric fields in the vicinity of tip 186. Incorporation of the gas delivery tube into another element of the microscope system can eliminate such perturbations. As another example, the spatial region in the vicinity of tip 186 is typically crowded with electrodes and other devices for operation of microscope system 200. By incorporating gas delivery tube 730 into another element of the system, crowding in the vicinity of tip 186 can be reduced.

In some embodiments, He gas delivered via delivery tube 730 can be pre-cooled so that it is near the operating temperature of tip 186 when it enters microscope system 200. For example, a portion of delivery tube 730 can be placed in contact with a supply reservoir of coolant (e.g., liquid nitrogen) that is used to cool tip 186. As a result of this thermal contact, He gas traveling through tube 730 is cooled to approximately the same temperature as tip 186 before introduction into the chamber where tip 186 is positioned.

(ii) Surface Charge Neutralization

In general, when He ions are incident on a surface of a sample, secondary electrons leave the sample. Many of the secondary electrons leave the sample, resulting in the surface having a net positive charge. Excess positive charges on the surface of the sample can produce a number of undesirable effects. In some embodiments, the material of the sample can be damaged by the positive charges. For example, certain materials are charge sensitive, and can react violently (e.g., explode) in the presence of excess positive (or negative) charge.

In certain embodiments, positive charging of the surface of the sample can limit the ability of detectors to detect secondary electrons that leave the sample due to the interaction of the ion beam with the sample. For example, attractive forces between positive charges at the surface of the sample and the secondary electrons can decelerate the electrons, preventing the electrons from reaching a detector.

In some embodiments, positive charging of the surface of the sample can cause inaccurate ion beam rastering. Deflection and deceleration of the incident ion beam as a result of the electric field created by positive charges at the surface of the sample can reduce the energy of the incident ions, and change their trajectories in difficult-to-predict fashion.

If the net positive charge on the surface of the sample becomes large enough, the surface of the sample can act as an electrostatic mirror for He ions, deflecting He ions away from the surface of the sample before the He ions reach the surface of the sample.

Figure 22:
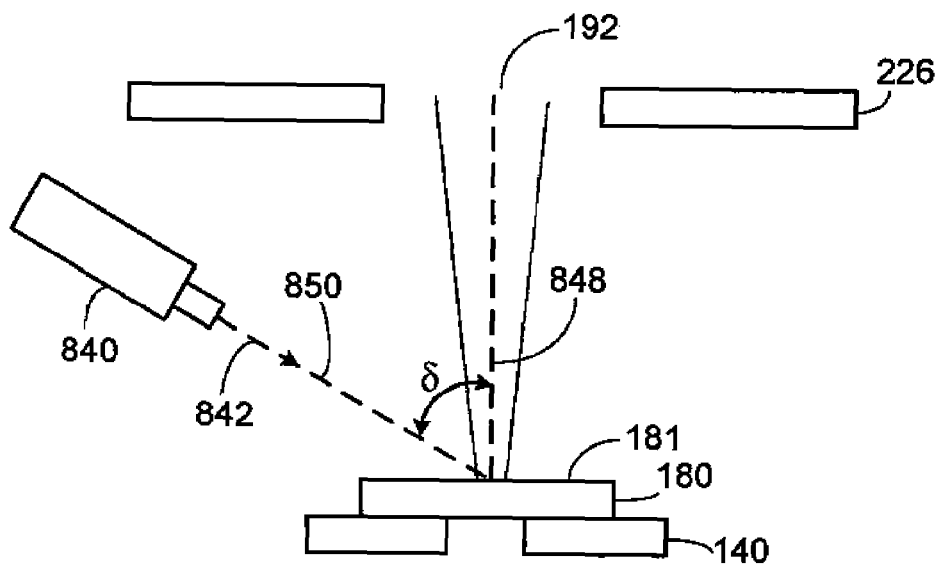
FIG. 22 is a schematic diagram of a portion of a gas field ion microscope including a flood gun.

A flood gun capable of delivering a flux of electrons to the surface of the sample can be used to counteract surface charging effects. FIG. 22 shows a portion of a gas field ion microscope that includes a flood gun 840 configured to deliver an electron beam 842 to surface 181 of sample 180 while He ion beam 192 is incident on surface 181. The electron flux on surface 181 can, in general, be controlled so that surface charging effects are counterbalanced by electron beam 842 to the extent desired.

Figure 23:
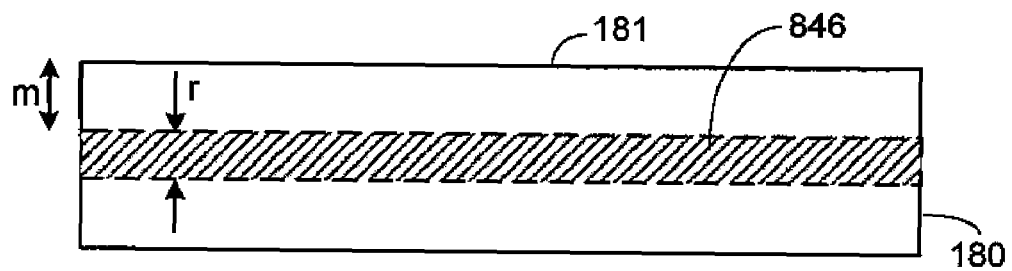
FIG. 23 is a schematic diagram of a sample including a sub-surface charge layer.

While FIG. 22 depicts ion beam 192 and electron beam 842 simultaneously impinging on surface 181 of sample 180, other approaches may be used. For example, prior to exposing surface 181 to He ion beam 192, flood gun 840 can be configured to deliver electron beam 842 to sample 180 to create a charge layer 846 in a sub-surface region of sample 180 (FIG. 23). Layer 846 has an average depth m below surface 181, and layer 846 has a thickness r measured in a direction normal to surface 181. Generally, the depth m and thickness r, as well as the density of electrons in layer 846, can be controlled by the energy of the electrons in electron beam 842, the angle of incidence of the electrons in electron beam 842 with respect to surface 181, and the total dosage of electrons delivered to sample 180.

In some embodiments, when incident on surface 181, the average energy of the electrons in electron beam 842 is adjustable. For example, the average energy of the electrons can be 500 eV or more (e.g., 1 keV or more, 2 keV or more), and/or 20 keV or less (e.g., 15 keV or less, 10 keV or less). For example, when incident on surface 181, the average energy of the electrons in electron beam 842 can be from 500 eV to 20 keV (e.g., from 1 keV to 15 keV, from 2 keV to 10 keV).

The angle of incidence δ of the electrons in electron beam 842 with respect to surface 181 corresponds to the angle between a principal trajectory 850 of electron beam 842 and a normal 848 to surface 181. In general, δ is 0° or more (e.g., 10° or more, 20° or more), and/or 80° or less (e.g., 70° or less, 60° or less). For example, δ can be from 0° to 70° (e.g., from 0° to 10°, from 40° to 60°).

In certain embodiments, the total current of electrons delivered to sample 180 is 10 pA or more (e.g., 100 pA or more, 1 nA or more, 10 nA or more), and/or 100 μA or less (e.g., 10 μA or less, 1 μA or less, 500 nA or less, 100 nA or less). For example, the total current of electrons delivered to sample 180 can be from 10 pA to 1 μA (e.g., from 100 pA to 100 nA, from 1 nA to 10 nA).

In some embodiments, m is 10 nm or more (e.g., 25 nm or more, 50 nm or more, 75 nm or more, 100 nm or more), and/or 500 nm or less (e.g., 400 nm or less, 300 nm or less, 200 nm). For example, m can be from 10 nm to 500 nm (e.g., from 25 nm to 500 nm, from 50 nm to 500 nm, from 75 nm to 400 nm, from 100 nm to 400 nm).

In certain embodiments, multiple flood guns can be used. For example, in some embodiments, different flood guns can be used to expose different portions of surface 181 of sample 180 to electrons. In certain embodiments, each flood gun can be used to expose the same portion of surface 181 to electrons. Optionally, different flood guns can be operated at different times. For example, one or more flood guns can be used to expose surface 181 to electrons before surface 181 is exposed to He ions (e.g., to form a sub-surface charge layer), while one or more different flood guns can be used to expose surface 181 to electrons while surface 181 is also being exposed to He ions. In some embodiments, all the flood guns can be used to expose surface 181 to electrons before surface 181 is exposed to He ions (e.g., to form a sub-surface charge layer), whereas in certain embodiments all the flood guns can be used to expose surface 181 to electrons while surface 181 is also being exposed to He ions. Other combinations may also be used.

Figure 24:
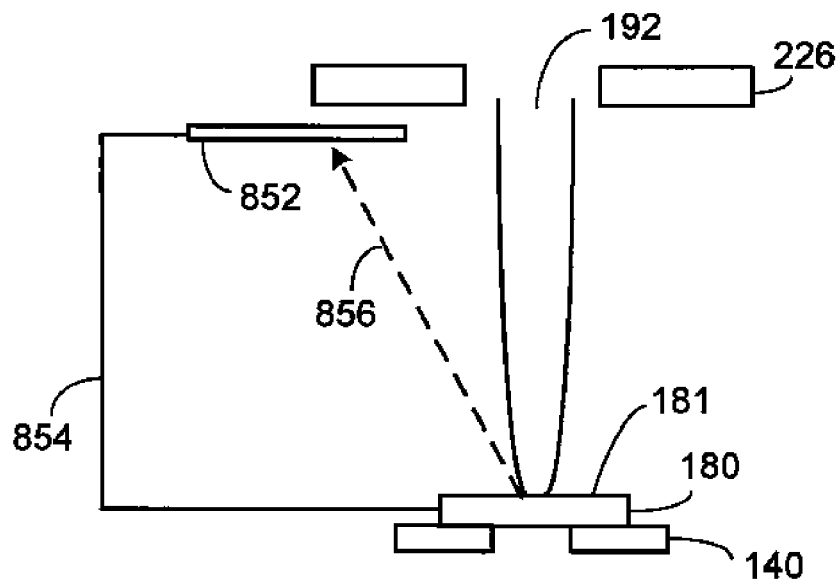
FIG. 24 is a schematic diagram of a collector electrode for reducing surface charge on a sample.

While embodiments have been described in which surface charge neutralization can be achieved using a flood gun, surface charge neutralization can also be achieved using a collector electrode to collect ejected secondary electrons and return them to the surface of the sample to reduce the net positive charge at the surface. Referring to FIG. 24, a collector electrode 852 is connected to sample 180 via conductor 854. When sample 180 is exposed to He ion beam 192, secondary electrons ejected from surface 181 of sample 180 (represented by arrow 856) are incident on collector electrode 852. Electrons 856 are then conveyed, via conductor 854, back to surface 181 to reduce the positive charge at surface 181. Additional collector electrodes 852 can be connected to sample 180 to provide for further surface charge neutralization.

In certain embodiments, combinations of one or more collector electrodes and one or more flood guns can be used. For example, one or more flood guns can be used to expose surface 181 of sample 180 to electrons before surface 181 is exposed to He ions (e.g., to form a sub-surface charge layer), and one or more collector electrodes can be used to neutralize charging at surface 181 while surface 181 is being exposed to He ions. Other combinations are also possible.

Figure 25:
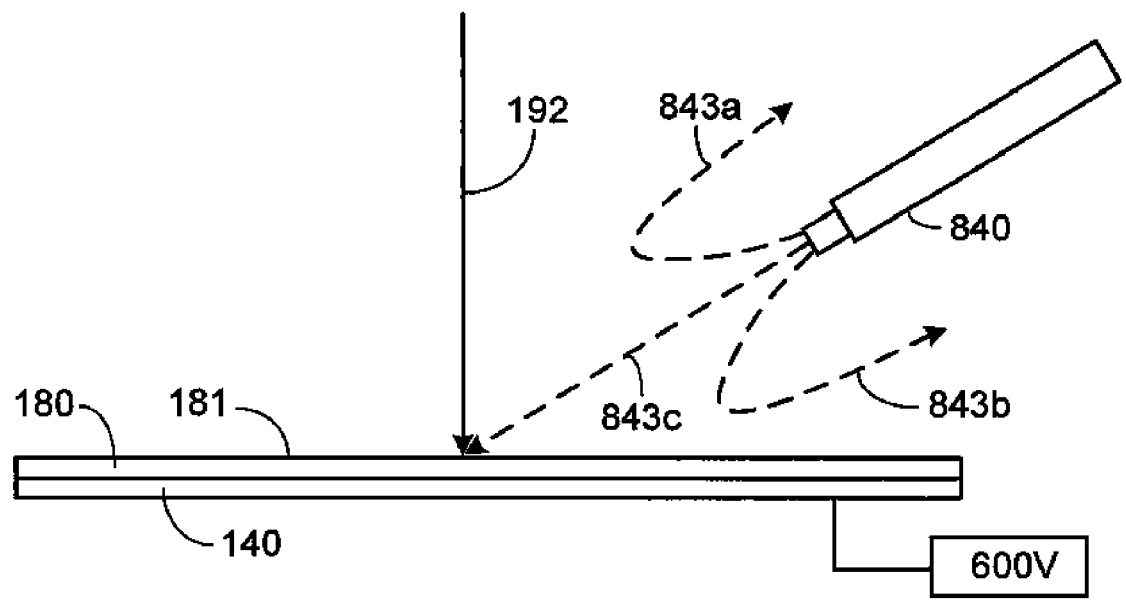
FIG. 25 is a schematic diagram of a flood gun apparatus for reducing surface charge on a sample.

In some embodiments, flood gun 840 can be configured to deliver a very low energy beam of electrons 842 to sample 180. For example, electrons in beam 842 can have an average energy of about 50 eV or less. The low energy electrons have low landing energies, and this limits the amount of negative charge that can accumulate on surface 181. For example, if the average electron energy in electron beam 842 is 50 eV, once sample 180 charges to a potential of −50 V relative to the common ground, electrons from flood gun 840 will no longer land on the surface of the sample. As a result, by adjusting the energy of the low energy electrons from flood gun 840, the maximum accumulated negative charge on surface 181 of sample 180 can be controlled. This method can be used to image non-conducting materials without depositing a layer of conductive material on top of the non-conducting material to prevent charging of the non-conducting material. An example of this method is shown in FIG. 25. Ion beam 192 is incident on surface 181 of sample 180, which is a dielectric material with relatively low electrical conductivity (e.g., sample 180 is not metallic). Sample 180 is supported by sample manipulator 140, which is biased at an electrical potential of −600 V relative to the common external ground of microscope system 200. The electrical potential applied to manipulator 140 creates an electric field at surface 181 of sample 180. Flood gun 840 is configured to deliver an electron beam that includes electrons having an average energy of 500 eV to surface 181 in the vicinity of the impinging ion beam 192. Initially, the electric field at surface 181 due to the bias applied to manipulator 140 causes deflection of the electrons from flood gun 840 along trajectories such as 843a and 843b—the electrons do not land on surface 181. However, as positive charge accumulates on surface 181 due to the incident He ions, sample 180 becomes positively-charged, reducing the electric field strength experienced by electrons from flood gun 840. When the charge on surface 181 of sample 180 accumulates to the point where the effective bias at the surface reaches −500 V relative to the common ground, electrons from flood gun 840 can land on surface 181 and neutralize positive charges thereon, following trajectories such as 843c, for example. As a result, by controlling the bias applied to manipulator 140 and the energy of the electrons delivered by flood gun 840, positive charge accumulation on sample 180 can be controlled. Sample 180, a non-conducting material, can thus be imaged without the accumulation of surface charge, which might otherwise lead to undesirable image contrast due to voltage contrast effects that result from surface charging. Images of non-conducting and semiconducting materials can be obtained without depositing a layer of conductive material on the sample to act as a charge dissipation layer.

In some embodiments, flood gun 840 can be configured to deliver electrons to sample 180 which have a negative landing energy—that is, in the absence of positive charge on the sample surface, electrons that do not land at all on surface 181. When sample 180 acquires surface charge due to incident He ions, electrons from flood gun 840 begin to land on surface 181, neutralizing the positive charge. As a result, surface 181 of sample 180 is maintained in an approximately uncharged state.

In some embodiments, a conversion surface can be used to generate secondary electrons, which can then be used to neutralize positive charges that accumulate at surface 181 of sample 180. For example, a conversion surface formed of a material with a high secondary electron yield (e.g., platinum) can be positioned in proximity to sample 180. High energy He ions and/or neutral atoms, leaving sample 180, can strike the conversion surface, generating secondary electrons. The generated secondary electrons experience attractive forces due to accumulated positive surface charge on sample 180. As a result, the secondary electrons land on the sample surface, neutralizing the positive charges and reducing the electric field due to surface charge. Consequently, secondary electrons are attracted more strongly to surface 181 of sample 180 when there is a greater accumulation of surface positive charge. This provides a self-regulating mechanism for reducing surface charging.

Figure 26:
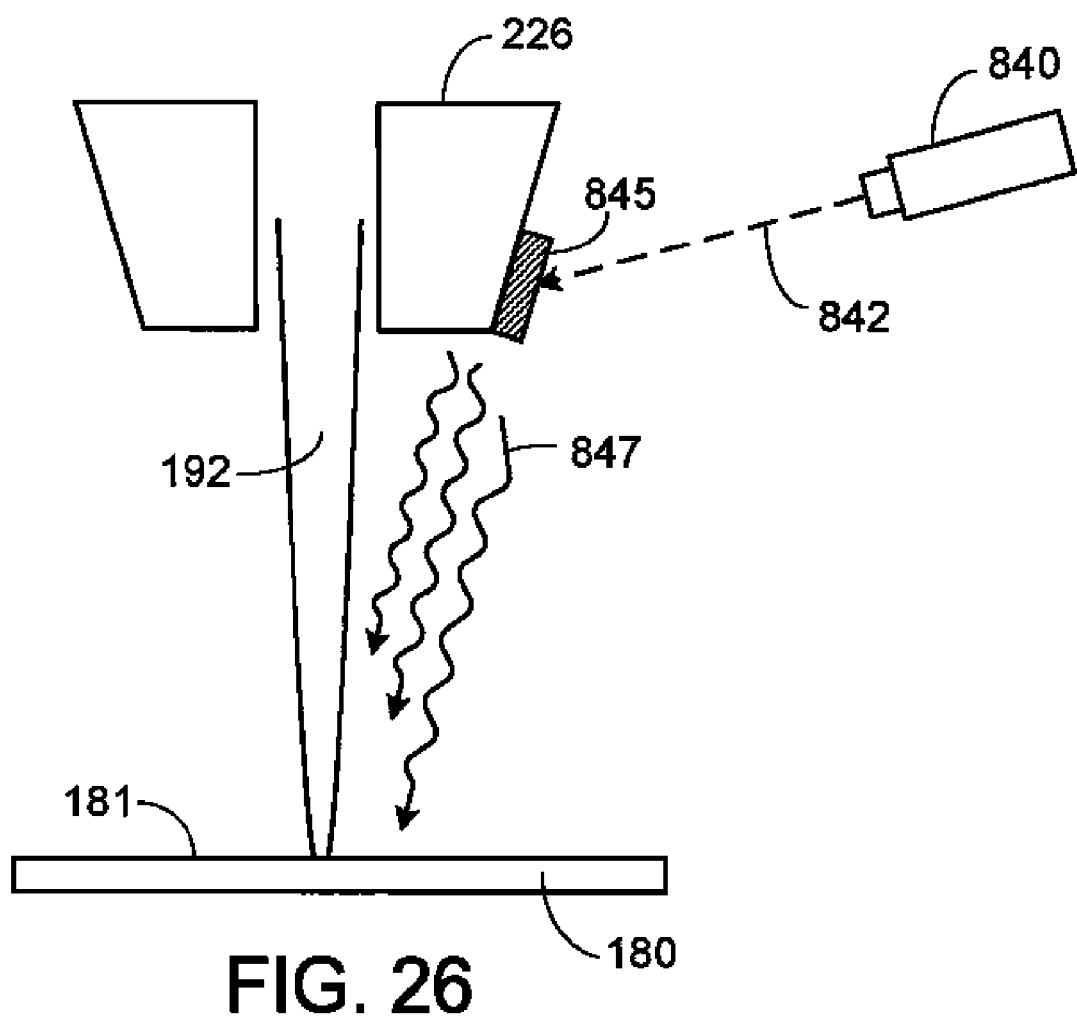
FIG. 26 is a schematic diagram of a flood gun apparatus including a conversion plate for reducing surface charge on a sample.

In some embodiments, a conversion plate can be mounted directly to an element of ion optics 130 to provide secondary electrons for surface charge neutralization of sample 180. For example, in FIG. 26, a conversion plate 845 is attached to a surface of second lens 226. Electrons 842 from flood gun 840 are directed to be incident on the conversion plate, which is formed from a material with a high secondary electron yield. He ion beam 192 is incident on surface 181 of sample 180 and, over time, positive charge accumulates on surface 181 in the region where ion beam 192 is incident. Secondary electrons 847, generated from conversion plate 845, are attracted to surface regions with excess positive charge and land on these regions, neutralizing excess positive charge. Once the excess surface charge is eliminated, further secondary electrons do not land on surface 181. As a result, surface 181 can be maintained in a quasi-neutral state.

In general, flood gun 840 can be configured for either continuous or intermittent operation. In particular, during intermittent operation, flood gun 840 can be turned on and off at a desired rate. For example, in some embodiments, flood gun 840 can be turned on and off to provide charge neutralization of sample 180 at a pixel exposure rate. Ion beam 192 can be rastered across the surface of sample 180 in discrete steps to expose successive portions of the sample surface. After each portion is exposed, flood gun 840 can be used to neutralize surface charge in the exposed region. This corresponds to charge neutralization at a pixel exposure rate. Alternatively, or in addition, flood gun 840 can be used to perform neutralization at a line scan rate (e.g., after an entire line of discrete portions of sample 180 have been exposed to ion beam 192), and/or at a frame rate (e.g., after an entire two-dimensional area of discrete portions of sample 180 have been exposed to ion beam 192).

In some embodiments, flood gun 840 can be used to improve the ease of detection of secondary electrons from sample 180. For example, flood gun 840 can be used to embed a layer of charge (e.g., charge layer 846) within a bulk region of sample 180. The embedded layer of negative charge induces an electric field at surface 181 of sample 180. Secondary electrons that leave sample 180 due to the interaction of sample 180 with the incident ion beam 192 are accelerated away from sample 180 due to the electric field created by charge layer 846, making detection of the secondary electrons by a suitably configured detector relatively easier.

Figure 27A:
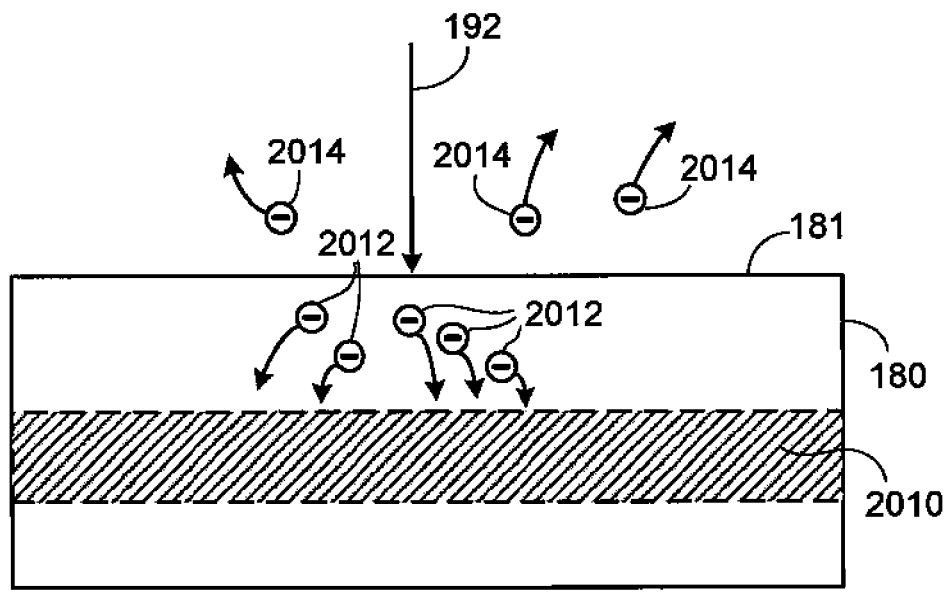
FIG. 27A is a schematic representation of a sample having a positively charged layer disposed therein.
Figure 27B:
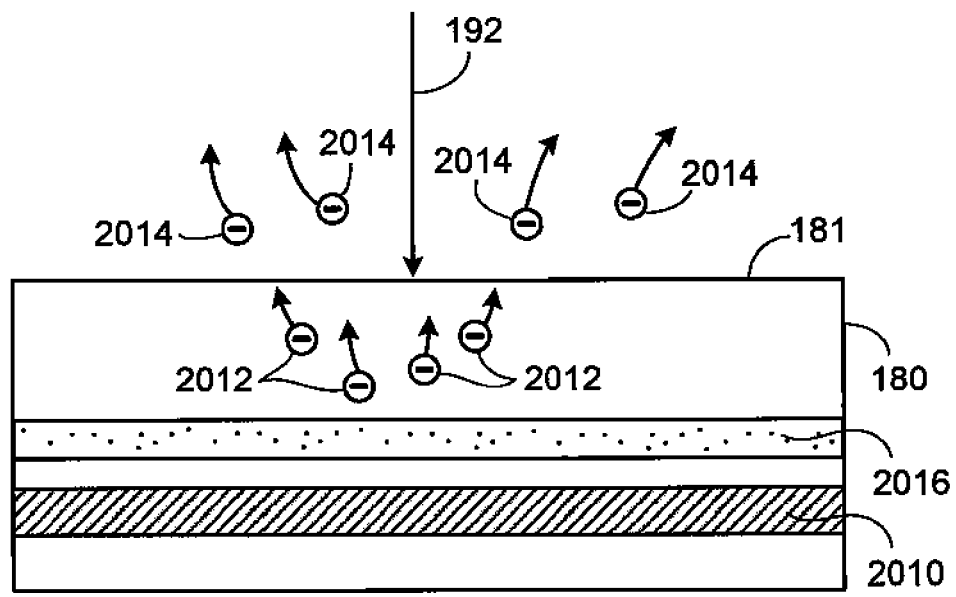
FIG. 27B is a schematic representation of a sample having positively and negatively charged layers disposed therein.

An example of the use of an embedded layer of negative charge is shown schematically in FIGS. 27A and 27B. In FIG. 27A, ion beam 192 is incident on surface 181 of sample 180. A plurality of secondary electrons 2012 are generated within the first few nanometers of sample 180. At first, many of the secondary electrons escape as free electrons 2014, which can be detected by a suitably configured detector. Over time, however, incident He ions implant within sample 180, forming a positively-charged layer 2010 within sample 180. As the net positive charge within layer 2010 increases, secondary electrons 2012 are increasingly attracted toward layer 2010, and fewer and fewer secondary electrons 2012 escape sample 180 as free electrons 2014. As a result, imaging of sample 180 via detection of secondary electrons can become increasingly difficult.

A solution to this problem is shown in FIG. 27B. In the embodiment shown in FIG. 27B, flood gun 840 (not shown) is used to embed a layer of negative charge 2016 (e.g., electrons) within sample 180. The embedded layer of negative charge is similar to layer 846 in FIG. 23. As a result of layer 2016, secondary electrons 2012 generated in sample 180 are accelerated away from sample 180, resulting in an increase in the number of generated secondary electrons 2014 that escape sample 180, and therefore enhancing the detected secondary electron signal front the sample. In effect, layer 2016 acts as an electrostatic mirror for secondary electrons, enhancing their detectability.

In general, flood gun 840 can be used to implant electrons in a sample prior to the analysis of the sample, and/or flood gun 840 can be used to implant electrons in a sample while imaging the sample. In some embodiments, the sample may be exposed to electrons from flood gun 840 at intervals (e.g., regular intervals). This can, for example, assist in maintaining a relatively consistent level of charging. For example, the sample may be exposed to electrons from flood gun 840 at time periods corresponding to a dwell time per pixel (e.g., 100 ns).

(iii) Vibration Decoupling

Figure 28:
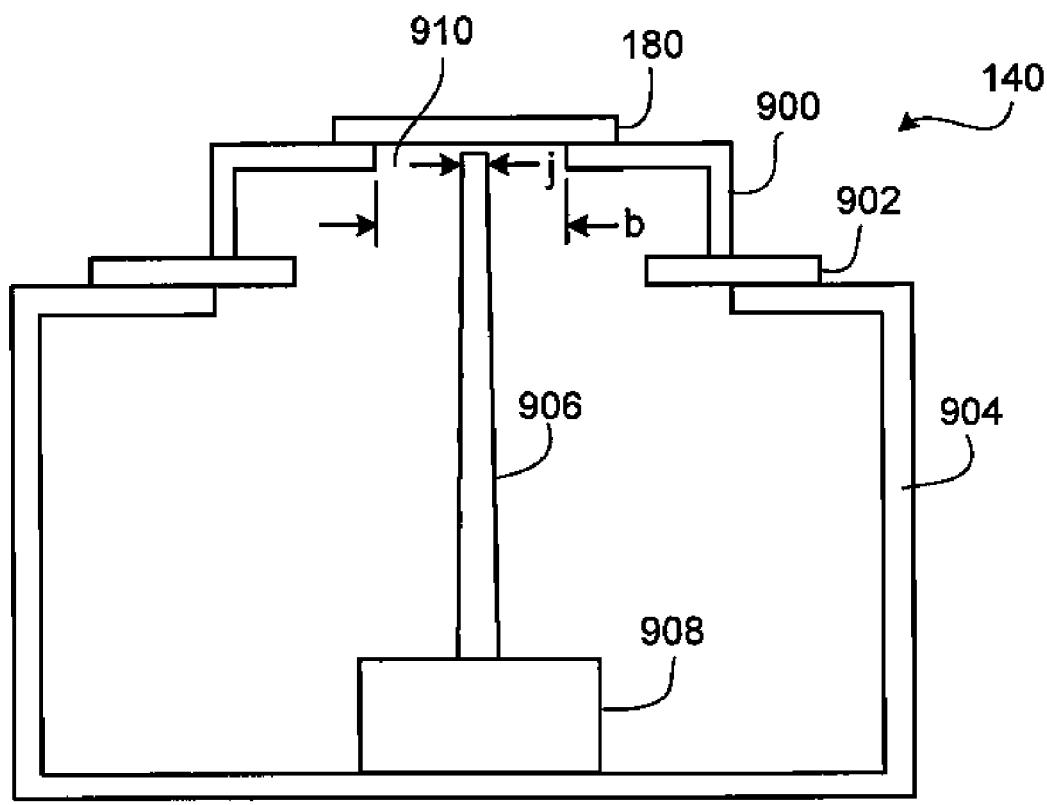
FIG. 28 is a schematic diagram of an embodiment of a vibration-decoupled sample manipulator.

Mechanical vibrations due to vacuum pumps, various moving parts, and background acoustic disturbances can affect certain performance parameters (e.g., imaging resolution, ion beam spot size at sample 180, stability) of a gas field ion microscope system 200. In some embodiments, sample manipulator 140 can be configured to decouple sample 180 from other parts of system 200, thereby reducing the impact of external mechanical disturbances. FIG. 28 shows a vibration-decoupled sample manipulator 140 that includes a guiding needle 906 supported by an actuator 908, with needle 906 and actuator 908 each located within a stage 904. A support disk 902 is positioned atop stage 904, and a friction spider 900, which supports sample 180, is placed atop disk 902.

To move sample 180 in the x-y plane, actuator 908 receives a suitable signal from electronic control system 170 and actuates guiding needle 906. Guiding needle 906 nudges sample 180 and/or spider 900, causing translation in the x-y plane, in response to signals from actuator 908.

A width j of guiding needle 906 at its apex is typically chosen to be slightly smaller than a diameter b of aperture 910 in spider 900. For example, j can be 1 mm, and b can be 1.1 mm. In addition, spider 900 and disk 902 are selected such that the static frictional force between disk 902 and spider 900 is large, but can be overcome by the force applied by actuator 908 to sample 180 through guiding needle 906. Guiding needle 906 is formed of a mechanically compliant material that can deform under an applied stress to reduce transmission of vibrations to sample 180, but is stiff enough to transmit to sample 180 the force applied by actuator 908.

As a result of these system parameters, mechanical vibrations that are coupled into stage 904 can be partially absorbed and dissipated by guiding needle 906 so that there is little or no vibration of spider 900. Additionally, if guiding needle 906 does apply a force to spider 900, guiding needle 906 will preferentially slip against the sides of spider 900, rather than induce vibration of spider 900.

In some embodiments, guiding needle 906 can have a substantially rectangular cross-sectional shape. A rectangular cross-sectional shape may assist in ensuring that rotation of sample 180 and/or of spider 900 does not occur as spider 900 is translated in the x- and/or y-directions by guiding needle 906. If sample manipulator 140 is tilted with respect to axis 132 of ion optics 130 (e.g., so that ion beam 192 is incident upon sample 180 at a non-normal angle), the materials used to form spider 900 and/or disk 902 can be selected so that an even higher static frictional force between these elements is present. Alternatively, or in addition, in certain embodiments, spider 900 and disk 902 can be magnetically coupled to increase the frictional force between these elements. Magnetic field coupling can be carefully implemented to ensure that the magnetic field is localized and does not disturb sample 180 or impinging ion beam 192.

Guiding needle 906 can be completely disengaged from spider 900 when needle 906 is not actuated. For example, after guiding needle 906 has applied a force to spider 900 causing spider 900 and sample 180 to be translated in the x-y plane, a small recoil motion of needle 906 can be induced by electronic control system 170, which introduces a space between guiding needle 906 and spider 900. As a result, guiding needle 906 is completely disengaged from spider 900, and coupling of mechanical vibrations to spider 900 via needle 906 are prevented.

Figure 29:
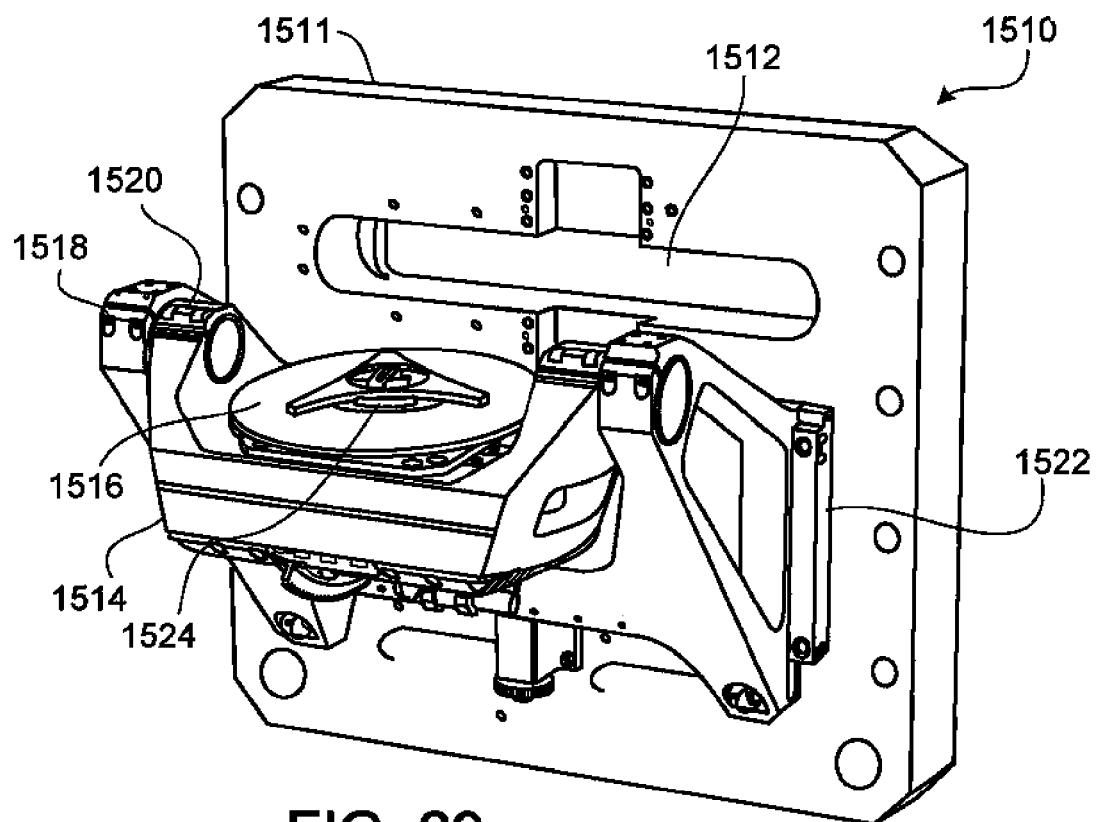
FIG. 29 is a schematic diagram of an embodiment of a vibration-decoupled sample manipulator.

FIG. 29 depicts a sample holder assembly 1510 for a microscope system. Sample holder assembly 1510 reduces the use of bearings and helps reduce low frequency mechanical vibrations in the sample during operation. Assembly 1510 includes a body 1511 having an opening 1512 to insert a sample. Body 1511 is connected to arms 1518 through adjustable connectors 1522. Arms 1518 support a sample stage 1514 using grips 1520. Sample stage 1514 includes a surface disk 1516 having an aperture 1524.

Assembly 1510 may be connected to an ion microscope such that tip 186 is pointed towards aperture 1524 on sample stage 1514. Body 1511 may be formed from suitable rigid materials such as hardened steel, stainless steel, phosphor bronze, and titanium. Body 1511 may be sized and shaped to suit the particular needs of the application. As an example, the size and shape of body 1511 may be chosen for use with the microscope systems disclosed herein. During operation, a sample may be introduced to assembly 1510 through opening 1512.

Sample stage 1514 is supported by arms 1518 connected to body 1511 along adjustable connectors 1522. Adjustable connectors 1522 allow for vertical movement of arms 1518. Arms 1518 and sample stage 1514 can be moved in a vertical direction and locked in a specific position. Connectors 1522 can be pneumatic or vacuum controlled such that arms 1518 and stage 1514 can be tightly locked in a desired vertical position. Connectors 1522 can optionally include other types of connectors.

Sample stage 1514 is connected to arms 1518 using grip 1520. Arm 1518 can have a shaft extending inwards such that grip 1520 of sample stage 1514 can clasp the shaft. Grip 1520 can be pneumatically or vacuum operated such that stage 1514 can be tilted. Grip 1520 can be controlled such that stage 1514 is tilted to a desired position. In some embodiments, after a desired position has been reached, grip 520 can be tightened such that sample stage 1514 is tightly locked in the desired tilted position.

Sample stage 1514 further includes surface disk 1516 having an opening 1524. A sample may be placed on disk 1516 and a sample position control system can be introduced through opening 1524 to move the sample on the plane of disk 1516. In certain embodiments, disk 1516 can be rotated about its center to rotate and move the sample located on the surface of the disk as desired. Disk 1516 may be formed from suitable rigid materials including ceramic, glass and polymers.

Figure 30:
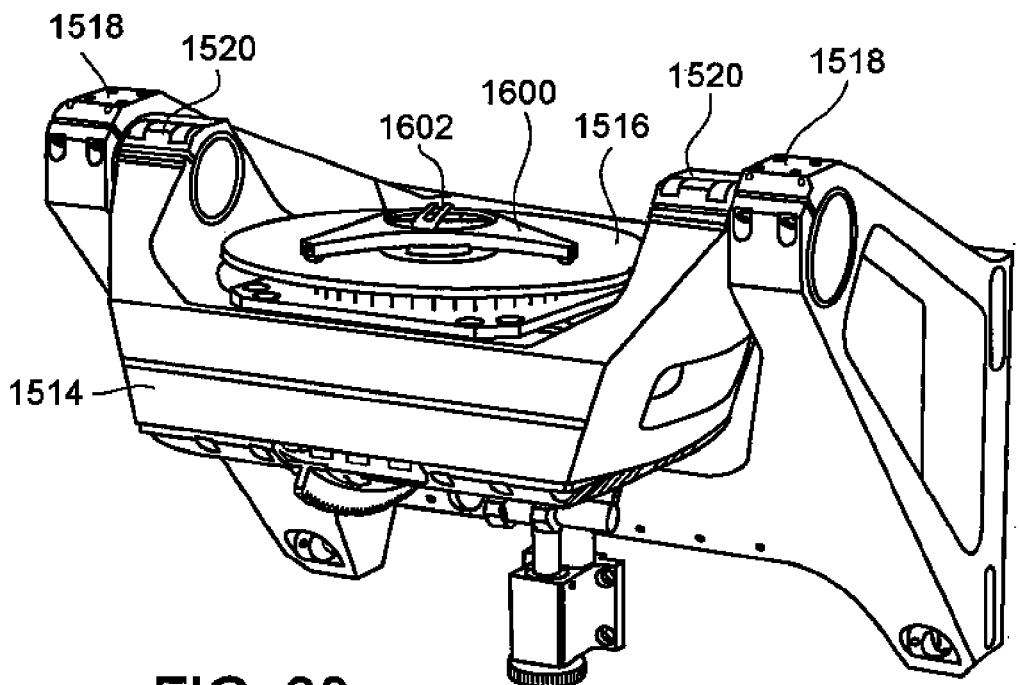
FIG. 30 is a schematic diagram of an embodiment of a vibration-decoupled sample manipulator.

FIG. 30 depicts a sample holder assembly for a microscope system. The sample holder assembly of FIG. 30 is similar to the sample holder assembly of FIG. 29 with a spider 1600 placed on a surface of disk 1516. Spider 1600 can have legs to allow it to be positioned on top of opening 1524. Optionally, spider 1600 can have an opening on a portion of the surface. Spider 1600 can be formed from suitable rigid materials including ceramic, glass and polymers.

During operation of microscope system 200, sample 180 can be moved in the z-direction, tilted, translated in the x-y plane, and rotated. If sample 180 is tilted and the tilt angle (e.g., the angle between ion beam 192 and a normal to the surface of sample 180) is relatively large, the inclined sample may not be in focus over the entire field of view of microscope system 200. As a result, the image of the sample obtained under these conditions may be out of focus and blurred at the areas outside of the center and vertical to the tilt axis.

These can be compensated by changing the focal length of lens 226 as ion beam 192 is scanned over the surface of sample 180. To perform this correction, sample manipulator 140 can transmit tilt angle information for sample 180 to electronic control system 170. Alternatively, tilt angle information can be entered manually by a system operator via a user interface. Electronic control system 170 can determine, based upon the orientation of sample 180, a set of voltage corrections to apply to second lens 226 to dynamically change the focal length of lens 226 as ion beam 192 is scanned over the surface of tilted sample 180.

In addition, the lateral dimensions of the inclined sample are distorted due to the projection of the tilted sample on a plane surface and due to the difference in distance to the ion optics 130. For example, lateral dimensions of inclined sample surfaces may appear shorter that they actually are due to the orientation of sample 180 with respect to ion beam 192. Another example is the keystone distortion of the image. The effect is that a rectangular feature is distorted so that the image of the rectangle appears to be keystone in its shape.

These can be compensated by adjusting the scan amplitude of scanning deflectors 219 and 221 as ion beam 192 is scanned over the surface of sample 180. To perform this correction, the electronic control system 170 can get the information about the tilt angle for sample 180 in the same way as described above. Electronic control system 170 can determine, based upon the tilt of sample 180, adjustments of the scan amplitude to apply to scanning deflectors 219 and 221 to adapt the ion beam deflection as ion beam 192 is scanned over the surface of tilted sample 180 for an undistorted imaging of the surface of tilted sample 180. Alternatively, these two distortion effects can be corrected by digital manipulation of the distorted image.

(iv) Reducing the Presence of Neutral Particles and Doubly-Charged Ions in the Ion Beam As discussed above, neutral particles (e.g., He atoms) can enter ion optics 130 of microscope system 200 as un-ionized neutral atoms from gas field ion source 120. Such neutral particles can negatively impact the performance of the microscope system. Therefore, in some embodiments, it is desirable to reduce the presence of neutral particles in ion beam 192. Doubly-charged He ions (e.g., $He^{2+}$) can also be produced in gas field ion source 120, either via double-ionization of He atoms in the vicinity of tip 186, or by collisions between He ions. The focusing properties of doubly-charged He ions are different from singly-charged ions, and doubly-charged ions present in ion beam 192 can lead to larger spot sizes on sample 180 and other undesirable effects.

One approach to reducing the population of neutral particles in ion beam 192 involves reducing the probability that neutral particles will make their way into the ion beam. Such an approach can involve, for example, using directed gas delivery to tip 186 (see discussion above) to reduce the overall presence of un-ionized He gas atoms in microscope system 200.

Figure 31:
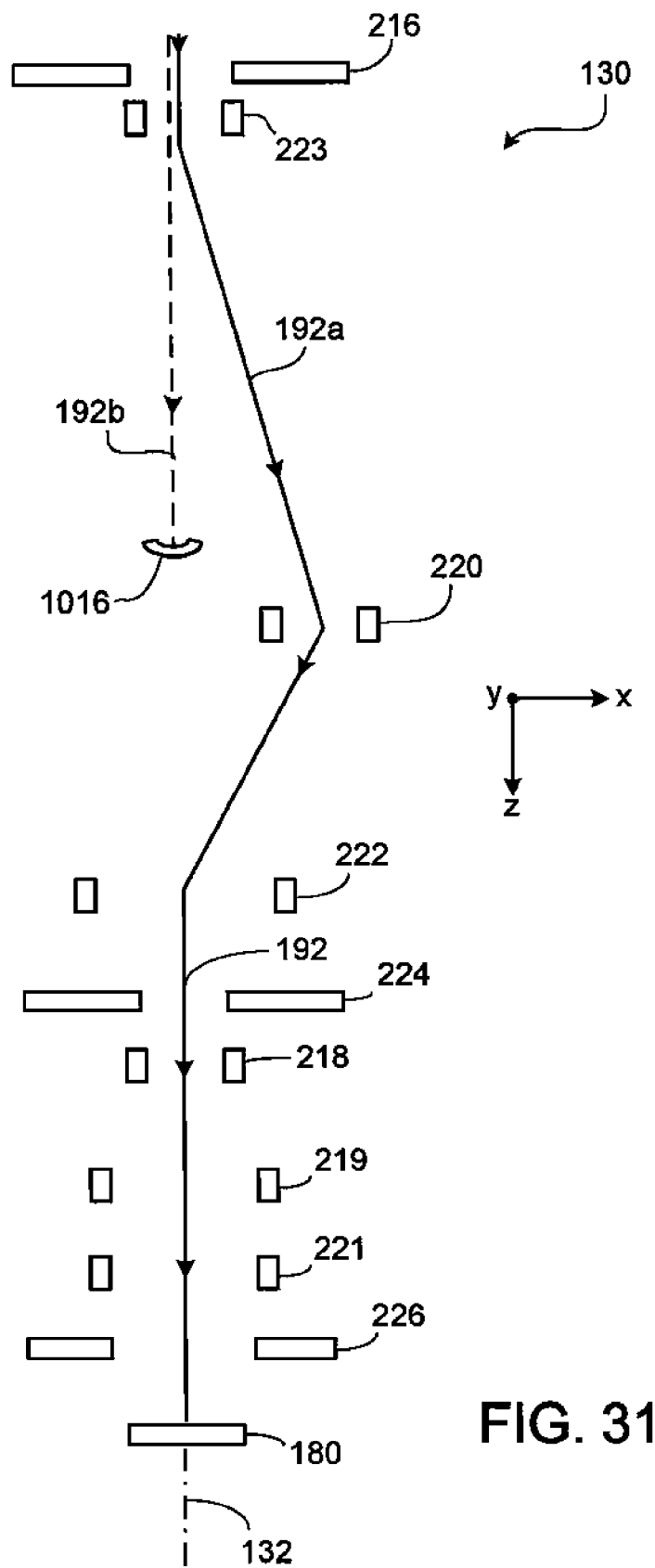
FIG. 31 is a schematic diagram of an electrostatic filtering system for separating ions and neutral atoms in a particle beam.

Another approach to reducing the population of neutral particles in ion beam 192 involves removing neutral particles from the ion beam after the neutral particles are present in ion beam 192. This approach can involve the use of electrostatic lens elements to deflect ions, spatially separating ions and neutrals in ion optics 130. For example, FIG. 31 shows ion optics 130 in which deflector 220 is offset from longitudinal axis 132 of ion optics 130, and in which an additional deflector 223 is disposed. He ion beam 192 includes He ions 192$a$ and He atoms 192$b$. To separate He ions 192$a$ and He atoms 192$b$, the electrical potential applied to deflector 223 is adjusted to cause deflection of He ions 192$a$ in the x-direction. He atoms 192$b$ are unaffected by deflector 223, and are therefore undeflected. He atoms 192$b$ are subsequently intercepted by collector 1016, which prevents He atoms 192$b$ from passing through aperture 224. The electrical potentials applied to deflectors 220 and 222 are also adjusted so that the trajectories of He ions 192$a$ are re-aligned with longitudinal axis 132, and a portion of He ions 192$a$ pass through aperture 224 and are incident on surface 181 of sample 180 as ion beam 192.

Other techniques may also be used to remove neutral particles from an ion beam. Typically, such techniques involve deflecting the ions in the ion beam using electric and/or magnetic field(s), without deflecting the neutral particles. In some embodiments, combinations of electric and magnetic fields can be used to compensate for energy dependent spatial separation of ions resulting from ion deflection in ion optics 130. In addition, various asymmetric ion column geometries (e.g., bent ion columns) can be used to separate He atoms and ions.

Figure 32:
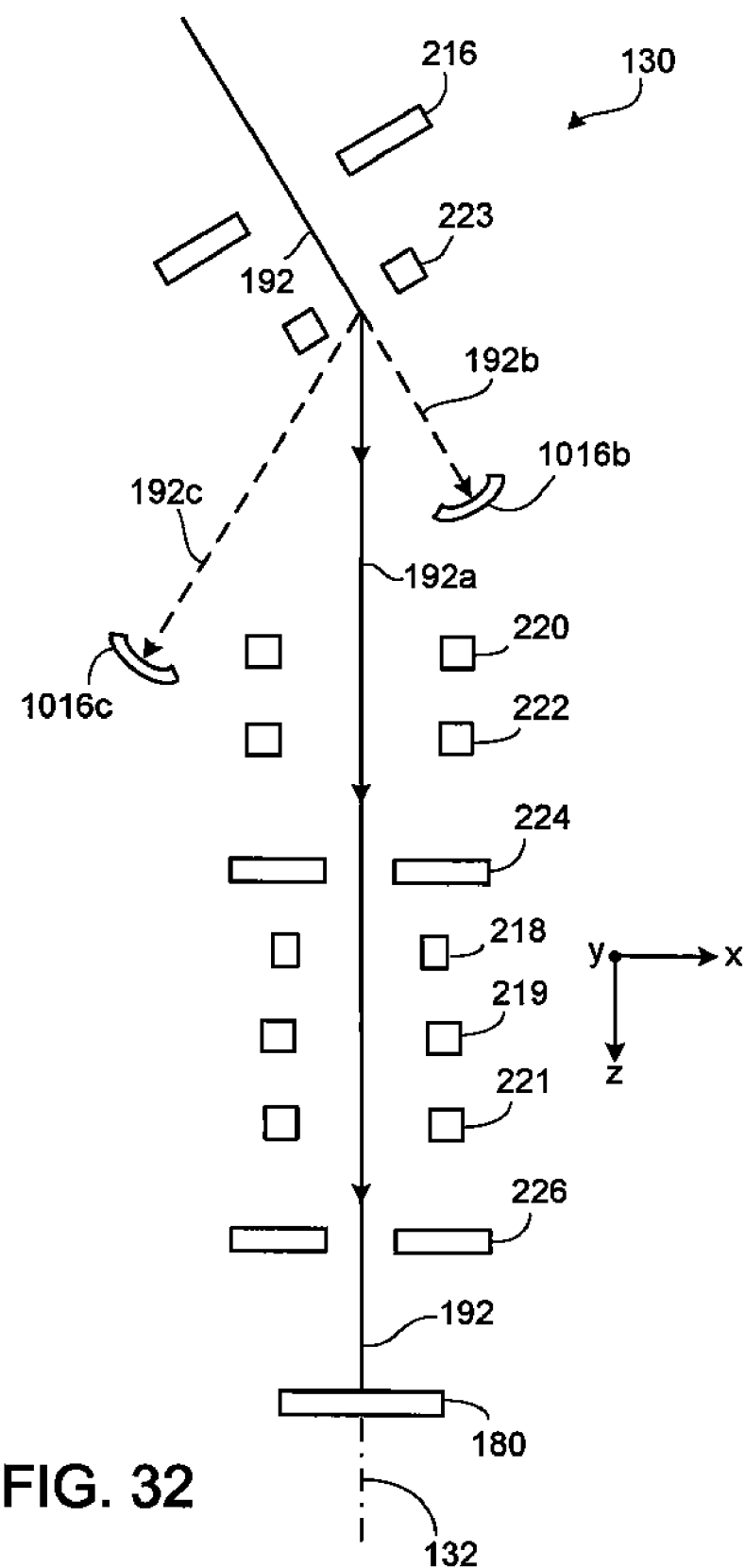
FIG. 32 is a schematic diagram of an electrostatic filtering system for separating neutral atoms, singly-charged ions, and doubly-charged ions in a particle beam.

For example, in FIG. 32, a bent column configuration of ion optics 130 can be used to separate He atoms, singly-charged He ions, and doubly-charged He ions. Ion beam 192 enters ion optics 130 propagating along a direction that is tilted with respect to axis 132 of ion optics 130. Ion beam 192 includes neutral He atoms, $He^+$ ions, and $He^{2+}$ ions. An electrical potential is applied to deflector 223, deflecting $He^+$ ions in ion beam 192 so that after passing through deflector 223, the $He^+$ ions propagate along axis 132 as ion beam 192$a$. However, neutral atoms are undeflected on passing through deflector 223. The neutral atoms are therefore spatially separated from $He^+$ ions, providing a neutral atom beam 192$b$ which is intercepted by collector 1016$b$. $He^{2+}$ ions are deflected to an even greater extent than $He^+$ ions, spatially separating singly- and doubly-charged ions, and providing an ion beam 192$c$ of $He^{2+}$ ions. The $He^{2+}$ ion beam 192$c$ is intercepted by collector 1016$c$. As a result, ion beam 192$a$ which emerges from ion optics 130 includes substantially only $He^{2+}$ ions.

Figure 33:
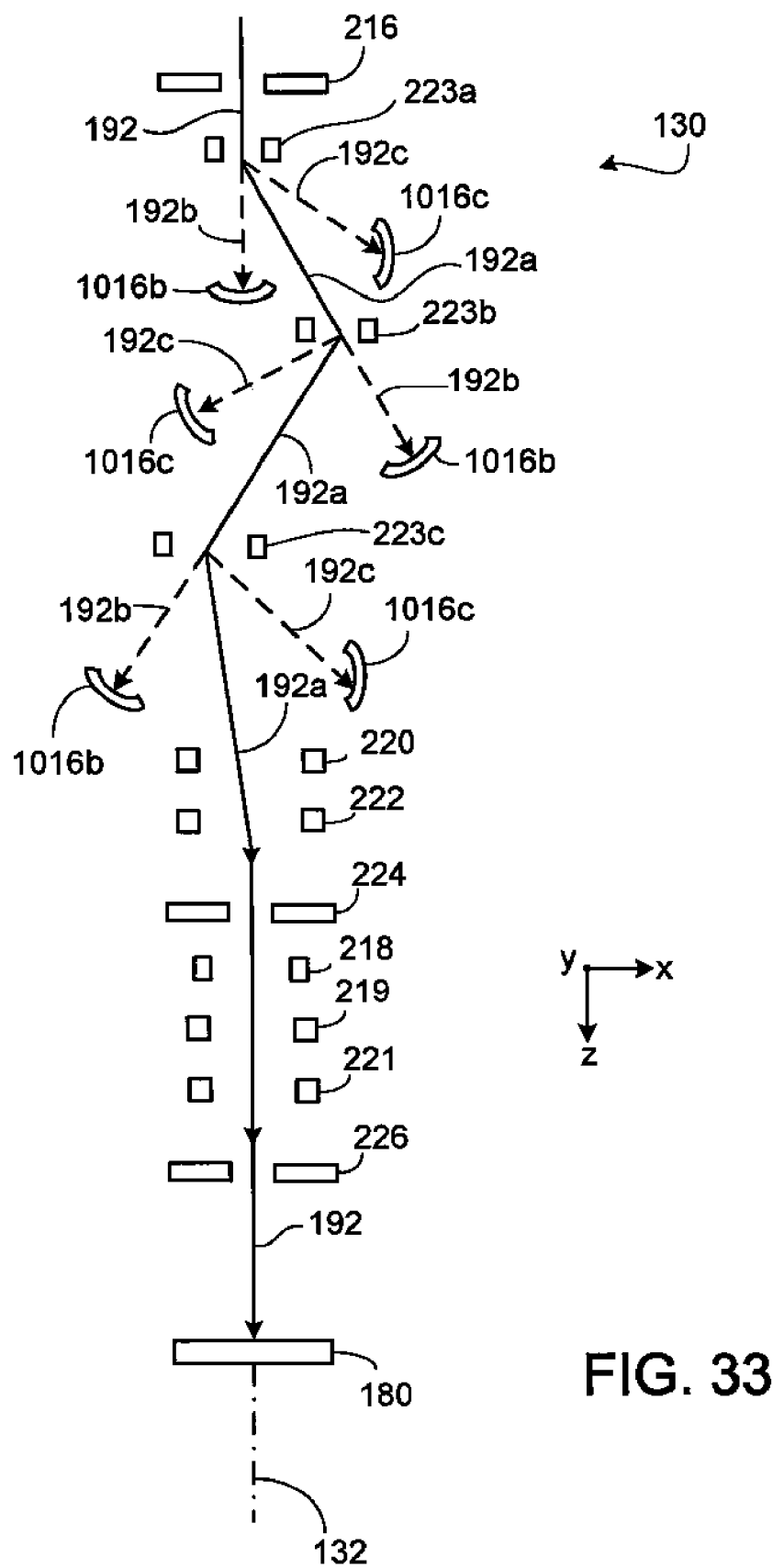
FIG. 33 is a schematic diagram of a filtering system that includes a dispersionless sequence of electric and magnetic fields for separating neutral atoms, singly-charged ions, and doubly-charged ions in a particle beam.

FIG. 33 shows another embodiment of an ion optical system for separating He atoms, $He^+$ ions, and $He^{2+}$ ions. The ion optical system shown in FIG. 33 includes a dispersionless sequence of electric and magnetic fields which are used to isolate He atoms, $He^+$ ions, and $He^{2+}$ ions from one another, and which do not contribute prism-like effects to the particle beams. The ion optical system includes a series of three deflectors 223$a$, 223$b$, and 223$c$, which are configured to deflect and direct $He^+$ ions through ion optics 130 so that ion beam 192$a$, which includes substantially only $He^+$ ions, emerges from ion optics 130. Neutral atom beams 192$b$ are undeflected and are intercepted at positions following each deflector by collectors 1016$b$. Doubly-charged He ions are deflected even further than $He^+$ ions, and multiple $He^{2+}$ beams 192$c$ are intercepted by collectors 1016$c$. As a result, He atoms, $He^+$ ions, and $He^{2+}$ ions are spatially separated from one another, and the $He^+$ ions are directed toward sample 180 as ion beam 192, while the undesired beam constituents are blocked in ion optics 130.

In some embodiments, the use of magnetic fields can lead to spatial separation of the trajectories of ions in ion beam 192 which have the same charge, but which correspond to different isotopes of the gas introduced by gas source 110. For certain gases such as He, which have a dominant naturally occurring isotope (e.g., greater than 90% relative abundance), separation effects due to magnetic fields are typically small. However, for other gases which have two or more naturally occurring isotopes and which lack a dominant isotope, such effects can be greater. As a result, in certain embodiments, an isotope separator (e.g., a block used to prevent undesired isotopes from traversing the length of ion optics 130) can be used. In some embodiments, a collector 1016 that is used to block neutral atoms or doubly-charged ions can also be used to block unwanted isotopes in ion beam 192.

Types of Particles

The interaction of the ion beam with the sample can cause different types of particles to leave the surface through various interactions as described below. Such particles include secondary electrons, Auger electrons, scattered ions, primary neutral particles, X-ray photons, IR photons, visible photons, UV photons, secondary ions and secondary neutral particles. One or more types of particles can be detected and analyzed to determine one or more different types of information about the sample. Such types of information about the sample include topographical information about the surface of the sample, material constituent information about the surface of the sample, material constituent information about a sub-surface region of the sample, crystalline information about the sample, voltage contrast information about the surface of the sample, voltage contrast information about a sub-surface region of the sample, magnetic information about the sample, and optical information about the sample. As used herein, the term surface of a sample refers to the volume up to a depth of five nm or less.

A. Secondary Electrons

A secondary electron, as referred to herein, is an electron that is emitted from a sample species and that has an energy of less that 50 eV. In general, secondary electrons are emitted from the sample surface at a range of angles and energies. However, the information of most interest is usually the total abundance of secondary electrons (as opposed to energy-resolved secondary electron information, or angle-resolved secondary electron information) because, as explained below, the total abundance of the secondary electrons is what can provide information regarding the sample surface.

Secondary electrons can be detected using one or more appropriate detectors capable of detecting electrons (see discussion above regarding types of detectors). If multiple detectors are used, the detectors may all be the same type of detector, or different types of detectors may be used, and may generally be configured as desired. The detectors can be configured to detect secondary electrons leaving surface 181 of sample 180 (the surface on which the ion beam impinges), surface 183 of sample 180 (the surface on the opposite side from where the ion beam impinges) or both (see discussion above regarding configurations of detectors).

Detected secondary electron signals can be used to form an image of a sample. Generally, the ion beam is raster-scanned over a field of view of the surface of the sample, and the secondary electron signal at each raster step (which corresponds to an individual pixel in an image) is measured by one or more detectors. Usually, each detector remains in fixed position relative to the sample as the ion beam is raster-scanned over the field of view of the surface of the sample. In certain embodiments, however, one or more detectors can be moved relative to the sample. For example, if a single detector is being used, moving the detector relative to the sample can yield angle-dependent information about the sample.

In certain embodiments, detecting the total abundance of secondary electrons can provide information regarding the topography of a sample. The secondary electron total abundance at a given location on a surface generally depends upon the slope of the surface relative to the ion beam at that point. In general, the secondary electron total abundance is higher where the slope of the surface relative to the ion beam is higher (i.e., where the angle of incidence of the ion beam as measured from the surface normal is larger). Thus, the change in the total abundance of secondary electrons as a function of the location of the ion beam on the surface of the sample, can be correlated to a change in the slope of the surface, providing information regarding the topography of the surface of the sample.

In some embodiments, detecting the total abundance of secondary electrons can yield material constituent information (e.g., elemental information, chemical environment information) about a sample. In such embodiments, the information is predominantly related to the surface of the sample. In general, each element or material in a given chemical environment will have a particular inherent secondary electron yield. As a result, the secondary electron total abundance at a given location on a surface generally depends on the material present at that location. Therefore, the change in the total abundance of secondary electrons as a function of the location of the ion beam on the surface of the sample, can be correlated to a change in the element(s) and/or material(s) present at the surface of the sample, providing material constituent information about the surface of the sample. In certain embodiments, specific materials in a sample can be identified based on quantitative measurements of secondary electron yields from the sample. For example, materials such as Al, Si, Ti, Fe, Ni, Pt, and Au have known secondary electron yields when exposed to a He ion beam under controlled conditions. An ion microscope (e.g., a gas field ion microscope) can be calibrated based on known secondary electron yields for various materials to identify the presence and relative abundance of a variety of different materials in a sample under study. For example, secondary electron yields for various materials are shown in Table I. The yields were measured at normal incidence of the He ion beam, and at an average ion energy of 21 keV. At non-normal angles of incidence, for example, the yields shown in Table I are typically scaled by a multiplicative factor that corresponds to the secant of the angle of incidence of the ion beam on the surface of the sample. Other experimental conditions are described in the corresponding Example noted below.

TABLE I

| Material | Z | M (amu) | Yield of secondary electrons |
|---|---|---|---|
| Aluminum | 13 | 27.0 | 4.31 |
| Silicon | 14 | 28.1 | 2.38 |
| Titanium | 22 | 47.9 | 3.65 |
| Iron | 26 | 55.8 | 3.55 |
| Nickel | 28 | 58.7 | 4.14 |
| Copper | 29 | 63.4 | 3.23 |
| Indium | 49 | 114.8 | 4.69 |
| Tungsten | 74 | 183.8 | 2.69 |
| Rhenium | 75 | 186.2 | 2.61 |
| Platinum | 78 | 195.1 | 7.85 |
| Gold | 79 | 197.0 | 4.17 |
| Lead | 82 | 207.2 | 4.57 |

In certain embodiments, detecting the total abundance of secondary electrons can yield voltage contrast information, which in turn, can provide information regarding the electrical conductivity properties and/or the electrical potential of an element and/or a material at the surface of a sample. The secondary electron total abundance at a given location on the surface of a sample usually depends on the electrical properties of the material present at the surface of the sample. In general, less electrically conducting materials will tend to become positively charged over time while being exposed to an ion beam over time, whereas more electrically conducting materials will have less of a tendency to become positively charged over time while being exposed to an ion beam. Hence, for example, the secondary electron total abundance at a given location of the surface of a sample will tend to decrease over time for a material that is less electrically conducting (due to more surface charging resulting in fewer secondary electrons escaping the sample), while the secondary electron total abundance at a given location of the surface of the sample that is more electrically conducting will tend to undergo less reduction in secondary electron total abundance over time (due to less surface charging). As a result, the change in the total abundance of secondary electrons as a function of the ion beam location at the sample surface can be correlated to the electrical conductivity of the material at that location, providing voltage contrast information about the surface of the sample.

Sub-surface voltage contrast effects can be provided by He ions which become embedded within sub-surface regions of the sample. As described in connection with FIGS. 27A and 27B, sub-surface He ions can prevent secondary electrons generated in the sample from escaping the sample surface. Thus, contrast in secondary electron images of the sample can be due to sub-surface charging of the sample by incident He ions.

The information provided by these techniques can be used for ion beam testing of semiconductor articles. For example, voltage contrast measurements can be used to determine whether portions of electrical devices and/or circuits are at different potentials when exposed to the ion beam due to the presence or absence of electrical connections between the portions, and therefore whether the devices and/or circuits are operating correctly or not.

In some embodiments, detecting the total abundance of secondary electrons can provide crystalline information about a sample. The total abundance of secondary electrons can vary depending on whether the ion beam is aligned with the crystal structure of the sample (e.g., aligned parallel to one of the unit vectors describing the crystal lattice) or not. If the ion beam is aligned with the crystal structure of the sample, the probability that ions in the ion beam can generally penetrate into a given distance into the sample without undergoing a collision with a sample atom (commonly referred to as channeling) is relatively high, resulting in a lower total abundance of secondary electrons. If, on the other hand, the ion beam is not aligned with the crystal structure, then the ions in the ion beam will have a lower probability of penetrating into the sample the given distance without undergoing a collision with a sample atom, resulting in a higher total abundance of secondary electrons. Therefore, the change in the total abundance of secondary electrons as a function of the ion beam location at the sample surface can be correlated to the crystalline information of the material at that location. For example, there may be regions of the sample surface where the secondary electron total abundance is substantially the same. Such regions can, for example, have the same crystal orientation, and the size of the regions can provide grain size and/or crystal size information (e.g., in a polycrystalline sample that includes multiple, oriented crystal domains), and/or can provide information regarding strained regions of sample (whether amorphous or crystalline) because the magnitude of the secondary electron total abundance for a material of a given chemical composition (e.g., elemental composition, material composition) can depend on the strain of the material.

In certain embodiments, detecting the total abundance of secondary electrons can provide magnetic information about a sample. The total abundance of secondary electrons can depend on the magnitude of a magnetic field adjacent the sample surface. In some embodiments, for example, the magnetic field adjacent to the sample surface varies due to magnetic domains within the sample that produce local magnetic fields at the sample surface. In certain embodiments, a static magnetic field is applied by an external magnetic field source, and magnetic domains within the sample produce local magnetic fields at the surface of the sample that introduce variations in the applied external magnetic field. In either case, variations in the local magnetic field at the surface of the sample can, for example, change the trajectories of secondary electrons ejected from the sample. The change in secondary electron trajectories can correspond to an increase in the total abundance of secondary electrons when the trajectories of the secondary electrons are changed so that more secondary electrons are directed toward the detector(s), or the change in secondary electron trajectories can correspond to a decrease in the total abundance of secondary electrons when the trajectories of the secondary electrons are changed so that more secondary electrons are directed away from the detector(s).

For some samples, the contrast that appears in a secondary electron image of the sample may be due to two or more of the mechanisms discussed above. In other words, secondary electron images of certain samples can include contrast that is due in part to topographic variations in the sample surface, material constituent variations in the sample surface, voltage contrast variations in the sample surface, crystalline variations in the sample surface, and/or magnetic variations in the sample surface. Accordingly, it can be advantageous to combine information gained from measuring the secondary electron total abundance with information gained from measuring other types of particles to qualitatively and/or quantitatively isolate contributions from one or more of these mechanisms. This possibility is discussed in more detail below.

Secondary electron imaging techniques can be applied to a variety of different classes of samples. An example of such a class of materials is semiconductor articles, such as patterned wafers, which can include, for example, multiple electrical conductors surrounded by a matrix of insulating material. Secondary electron imaging techniques can be used to identify defects in the device, such as incomplete electrical connections between conductors, and/or electrical shorts between circuit elements. More generally, secondary electron imaging techniques can be used for a wide range of ion beam testing applications of semiconductor articles. Optionally, this approach can similarly be used for purposes of mask repair.

Another example of a sample class for which secondary electron imaging techniques can be used is metals and alloys. For example, images of samples that contain mixed materials such as alloys can be used to determine the surface distribution of each of the materials in the sample. Yet another example of a sample class where secondary electron imaging techniques can be used is read/write structures for data storage. Additional examples of classes of materials for which secondary electron imaging techniques can be used are biological materials and pharmaceutical materials.

Imaging samples using secondary electrons generated by exposure to a He ion beam can provide a number of advantages relative to secondary electron imaging via other techniques, such as SEM. For example, the spot size of the He ion beam on the sample can be smaller than the spot size of an electron beam from a SEM. As a result of the smaller spot size, the region of the sample that is exposed to the He ion beam is more carefully controlled than the exposed region in a SEM.

Further, in general, because He ions are heavier than electrons, scattering events do not disperse He ions as readily within the sample as electrons are dispersed by scattering. As a result, He ions incident on the surface of a sample can interact with the sample in a smaller interaction volume than electrons in a SEM. As a result, secondary electrons detected in a gas field ion microscope (e.g., a He ion microscope) can arise from a smaller region than the region giving rise to secondary electrons in a SEM with a similar spot size. Consequently, the secondary electrons which are generated by the He ion beam can correspond to a more localized interrogation of the surface of the sample (e.g., with less lateral averaging of material properties) than the secondary electrons generated in a SEM.

In addition, the He ion source also provides a greater depth of focus than an electron source. As a result, images of a sample obtained using an ion microscope (e.g., a gas field ion microscope) can show a larger portion of the sample, measured along the direction perpendicular to the sample surface, in focus than comparable images obtained from secondary electrons in a SEM.

He ion beams can also provide a more sensitive contrast mechanism for secondary electron images of a sample due to a larger range of secondary electron yields for different materials available when causing the secondary electrons to leave the sample due to the interaction of the ion beam with the sample, as compared to when causing the secondary electrons to leave the surface due to the interaction of an electron beam with the sample. Typically, for example, secondary electron yields for common materials such as semiconductors and metals vary from 0.5 to 2.5 for an incident electron beam. However, secondary electron yields for the same materials exposed to a He ion beam can vary from 0.5 to 8. Thus, identification of different materials from secondary electron images can be performed more accurately using a gas field ion microscope (e.g., a He ion microscope) than in comparable SEM systems.

B. Auger Electrons

As referred to herein, an Auger electron is an electron generated as follows. An inner shell atomic electron is removed to form a vacancy, followed by filling of the vacancy by a second atomic electron from a higher shell with the release of energy. This energy is released via another electron called an Auger electron. In general, Auger electrons are emitted from the sample surface at a range of angles and energies. However, the information of most interest is usually the energy of the Auger electrons (as opposed to angle-resolved Auger electron information) because, as explained below, the energy of the Auger electrons is what can provide information regarding the sample surface. Auger electrons can be detected using one or more appropriate detectors capable of detecting electrons in an energy-resolved fashion (see discussion above regarding types of detectors). If multiple detectors are used, the detectors may all be the same type of detector, or different types of detectors may be used, and may generally be configured as desired. The detectors can be configured to detect Auger electrons leaving surface 181 of sample 180 (the surface on which the ion beam impinges), surface 183 of sample 180 (the surface on the opposite side from where the ion beam impinges) or both (see discussion above regarding configurations of detectors). To enhance the signal to noise of the detected Auger electrons, it can be desirable to use a detector that can collect a relatively large solid angle of Auger electrons. Additionally or alternatively, electron collection optics (e.g., an electrostatic lens system) that are adjacent the surface of the sample and that can direct the electrons to the detector can be used (e.g., to increase the effective solid angle of detection for the Auger electrons).

In general, detecting the energy of Auger electrons can yield material constituent information (e.g., elemental information, chemical environment information) about a sample. In such embodiments, the information is predominantly related to the surface of the sample. In general, for each element or material in a given chemical environment, the Auger electrons emitted by the element or material will have a particular energy or band of energies. As a result, the energy of the Auger electrons at a given location on a surface generally depends on the material present at that location. Therefore, the change in the energy of the Auger electrons as a function of the location of the ion beam on the surface of the sample, can be correlated to a change in the element(s) and/or material(s) present at the surface of the sample, providing material constituent information about the surface of the sample.

Auger electron imaging techniques can be applied to a variety of different classes of samples. An example of such a class of materials is semiconductor articles, such as patterned wafers, which can include, for example, multiple electrical conductors surrounded by a matrix of insulating material. Optionally, this approach can similarly be used for purposes of mask repair. Another example of a sample class for which Auger electron imaging techniques can be used is metals and alloys. For example, images of samples that contain mixed materials such as alloys can be used to determine the surface distribution of each of the materials in the sample. Yet another example of a sample class where Auger electron imaging techniques can be used is read/write structures for data storage. Additional examples of classes of materials for which Auger electron imaging techniques can be used are biological materials and pharmaceutical materials.

Imaging samples using Auger electrons that leave the surface due to the interaction of the sample and the He ion beam can provide a number of advantages relative to Auger electron imaging via other techniques, such as SEM. For example, the spot size of the He ion beam on the sample can be smaller than the spot size of an electron beam from a SEM. As a result of the smaller spot size, the region of the sample that is exposed to the He ion beam is more carefully controlled than the exposed region in a SEM.

Further, in general, because He ions are heavier than electrons, scattering events do not disperse He ions as readily within the sample as electrons are dispersed by scattering. As a result, He ions incident on the surface of a sample can interact with the sample in a smaller interaction volume than electrons in a SEM. As a result, Auger electrons detected in a gas field ion microscope (e.g., a He ion microscope) can arise from a smaller region than the region giving rise to Auger electrons in a SEM with a similar spot size. Consequently, the Auger electrons which leave the surface due to the interaction of the sample and the He ion beam can correspond to a more localized interrogation of the surface of the sample (e.g., with less lateral averaging of material properties) than the Auger electrons generated in a SEM.

In addition, the He ion source also provides a greater depth of focus than an electron source. As a result, images of a sample obtained using an ion microscope (e.g., a gas field ion microscope) can show a larger portion of the sample, measured along the direction perpendicular to the sample surface, in focus than comparable images obtained from Auger electrons in a SEM.

Another advantage of using an ion beam, as opposed to an electron beam, for Auger electron detection is that when using an electron beam the Auger electrons are detected on a baseline of backscattered electrons, and, using an ion beam, the backscattered electrons are not present. As a result, it can be possible to obtain a relatively high signal to noise ratio for detected Auger electrons while collecting a relatively small number of Auger electrons, which can reduce the amount of time it takes to obtain a relatively good quality Auger electron spectrum from a sample when using an ion beam.

C. Scattered Ions

As referred to herein, a scattered ion is generated when an ion from the ion beam (e.g., a He ion) interacts with the sample and is scattered from the sample while remaining an ion (e.g., a He ion). Because the probability that a scattered ion can travel from the sub-surface region of a sample to the surface of the sample and then be emitted from the sample is very low, scattered ions generally provide information about the surface of the sample. As explained in more detail below, when detecting scattered ions, the particular arrangement of the detector(s) generally depends on the type of information that is desired to be obtained.

Figure 34A:
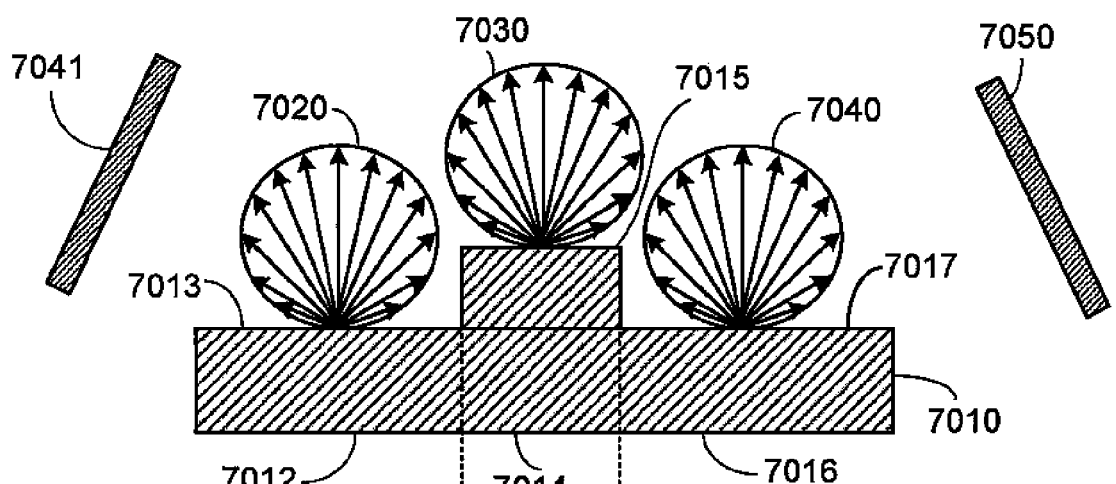
FIG. 34A is a schematic diagram showing an embodiment of helium ion scattering patterns from a surface.
Figure 34B:
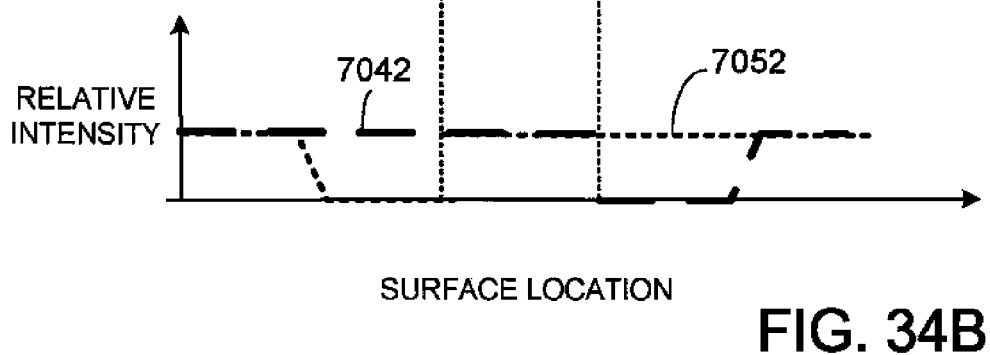
FIG. 34B is a diagram showing plots of the relative abundance of scattered helium ions detected by the detectors in FIG. 34A.

In some embodiments, topographical information about a sample surface can be obtained via detected scattered ions. FIG. 34A generally depicts an embodiment of an approach to detecting scattered ions from different regions of a surface to determine topographical information about the surface of a sample. In particular, FIG. 34A shows a sample 7010 having regions 7012, 7014 and 7016 with surfaces 7013, 7015 and 7017, respectively. Scatter patterns 7020, 7030 and 7040 represent the angular distribution of ions scattered from surfaces 7013, 7015 and 7017, respectively, when the ion beam is perpendicularly incident thereon. As shown in FIG. 34A, each of scatter patterns 7020, 7030 and 7040 is a cosine-type distribution. FIG. 34B depicts the contribution to the relative intensities 7042 and 7052 (dashed line and dotted line, respectively) of scattered ions detected by detectors 7041 and 7050, respectively, arising from topographical effects. Thus, for example, assuming that sample 7010 is formed of the identical material across its entire surface, the relative total abundance profiles from detectors 7041 and 7050 can be used to determine the topography of sample 7010. Alternatively, assuming that the topography of sample 7010 is known, then the contribution to the total abundance of the scattered ions detected that is due to topography alone (relative intensities 7042 and 7052) can be removed from the total abundance of the detected scattered ions to determine the contribution to the total detected scattered ions due to other effects (e.g., changing material across the surface of sample 7010). Although the detectors can be positioned as desired with respect to the surface, in certain embodiments, for a detector system of the type shown in FIG. 34A, topographic information is obtained from He ions that are scattered at large scattering angles. As an example, in some embodiments, topographic information from scattered ions is determined by detecting scattered ions at an angle of 60° or greater (e.g., 65° or greater, 70° or greater, 75° or greater) relative to the direction of the ion beam. While FIG. 34A depicts the use of two detectors, in some embodiments a single detector is used (e.g., detector 7041 or detector 7050). Alternatively, in certain embodiments, more than two (e.g., three, four, five, six, seven, eight) detectors can be used. In general, when multiple detectors are used to detect scattered ions, the detectors are equally spaced from each other with respect to their solid angle relative to the surface of the sample. The use of more than two detectors (e.g., four detectors) that are symmetrically positioned with respect to the surface of the sample can allow for detecting surface features in both orthogonal directions with respect to the nominal plane of the sample surface.

FIGS. 35A-35I generally depict various embodiments of approaches to detecting scattered ions from different regions of a surface to determine topographical information about the surface of a sample. In particular, FIGS. 35A, 35D and 35G shows a sample 8050 having regions 8052, 8054, 8056 and 8058 with surfaces 8053, 8055, 8057, 8059 and 8061, respectively. As shown in FIGS. 35A, 35D and 35G, surfaces 8055 and 8059 are oblique relative to surfaces 8053, 8057 and 8061. Scatter patterns 8070, 8090 and 80110 represent the angular distribution of ions scattered from surfaces 8053, 8057 and 8061, respectively, when the ion beam is perpendicularly incident thereon. As shown in FIGS. 35A, 35D and 35G, each of scatter patterns 8070, 8090 and 80110 is a cosine-type distribution. Scatter patterns 8080 and 80100 represent the angular distribution of ions scattered from surfaces 8055 and 8059 when the ion beam is perpendicular with respect to regions 8054 and 8058. As shown in FIGS. 35A, 35D and 35G, because the ion beam is not perpendicularly incident on surfaces 8055 and 8059, the angular distribution of scatter patterns 8080 and 80100 is not a cosine-type distribution.

FIGS. 35B and 35C depict the total yield of scattered ions and the relative abundance of detected scattered ions when a hemispherical detector (which may be capable of angularly resolving the scattered ions, spectrally-resolving the scattered ions, or both) 80120 is used to detect the scattered ions. As shown in FIG. 35C, there is a shadow effect in the relative abundance of the detected ions when using detector 80120. Thus, for example, assuming that sample 8050 is formed of the identical material across its entire surface, the relative abundance profiles from detector 80120 can be used to determine the topography of sample 8050. Alternatively, assuming that the topography of sample 8050 is known, then the contribution to the total abundance of the scattered ions detected that is due to topography alone (the relative abundance in FIG. 35D) can be removed from the total abundance of the detected scattered ions to determine the contribution to the total detected scattered ions due to other effects (e.g., changing material across the surface of sample 8050).

FIGS. 35E and 35F depict the total yield of scattered ions and the relative abundance of detected scattered ions when a top detector 80130 having a relatively small acceptance angle for scattered ions is used to detect the scattered ions. As shown in FIG. 35F, because the scatter yield into the acceptance angle of detector 80130 is substantially smaller at regions 8054 and 8056 (despite the fact that, as shown in FIG. 35E the total yield of scattered ions is higher at these regions), the relative abundance of scattered ions decreases at regions 8054 and 8056. Thus, for example, assuming that sample 8050 is formed of the identical material across its entire surface, the relative abundance profiles from detector 80130 can be used to determine the topography of sample 8050. Alternatively, assuming that the topography of sample 8050 is known, then the contribution to the total abundance of the scattered ions detected that is due to topography alone (the relative abundance in FIG. 35D) can be removed from the total abundance of the detected scattered ions to determine the contribution to the total detected scattered ions due to other effects (e.g., changing material across the surface of sample 8050).

FIGS. 35H and 35I depict the total yield of scattered ions and the relative abundance of detected scattered ions when a top detector 80140a relatively large acceptance angle for scattered ions is used to detect the scattered ions. As shown in FIG. 35I, by selecting the appropriate acceptance angle of detector 80140, the relative abundance of the detected scattered ions is substantially the same across the sample. Changes in the total abundance of detected scattered ions would be due to effects other than changes in surface topography (e.g., changing material across the surface of sample 8050).

In certain embodiments, the detection of scattered ions can be used to determine material constituent information about the surface of the sample. One such approach involves measuring the total abundance of scattered ions. The total abundance of scattered ions can be detected using a single detector (e.g., a hemispherical detector) configured to detect scattered ions leaving surface 181 of sample 180 (the surface on which the ion beam impinges), or multiple detectors (e.g., located at different solid angles with respect to the surface of the sample) configured to detect scattered ions leaving surface 181 of sample 180 (the surface on which the ion beam impinges the sample surface at a range of angles and energies). In general, the scattering probability of a He ion (and therefore the total abundance of scattered He ions, assuming no effects from other factors, such as topographical changes in the surface sample) is approximately proportional to the square of the atomic number (Z value) of the surface atom from which the He ion scatters. Thus, as an example, when trying to distinguish a copper (atomic number 29) line from silicon (atomic number 14) in a semiconductor article, the total abundance of scattered He ions from a copper atom at a surface of the semiconductor article will be approximately four times the total abundance of scattered ions from a silicon atom at the surface of the semiconductor article. As another example, when trying to distinguish a tungsten (atomic number 74) plug from silicon (atomic number 14) in a semiconductor article, the total abundance of scattered He ions from a tungsten atom at a surface of the semiconductor article will be approximately 25 times the total abundance of scattered ions from a silicon atom at the surface of the semiconductor article. As a further example, when trying to distinguish gold (atomic number 79) region from silicon (atomic number 14) in a semiconductor article, the total abundance of scattered He ions from a gold atom at a surface of the semiconductor article will be approximately 25 times the total abundance of scattered ions from a silicon atom at the surface of the semiconductor article. As an additional example, when trying to distinguish indium (atomic number 49) from silicon (atomic number 14) in a semiconductor article, the total abundance of scattered He ions from a indium atom at a surface of the semiconductor article will be approximately 10 times the total abundance of scattered ions from a silicon atom at the surface of the semiconductor article.

Figure 36:
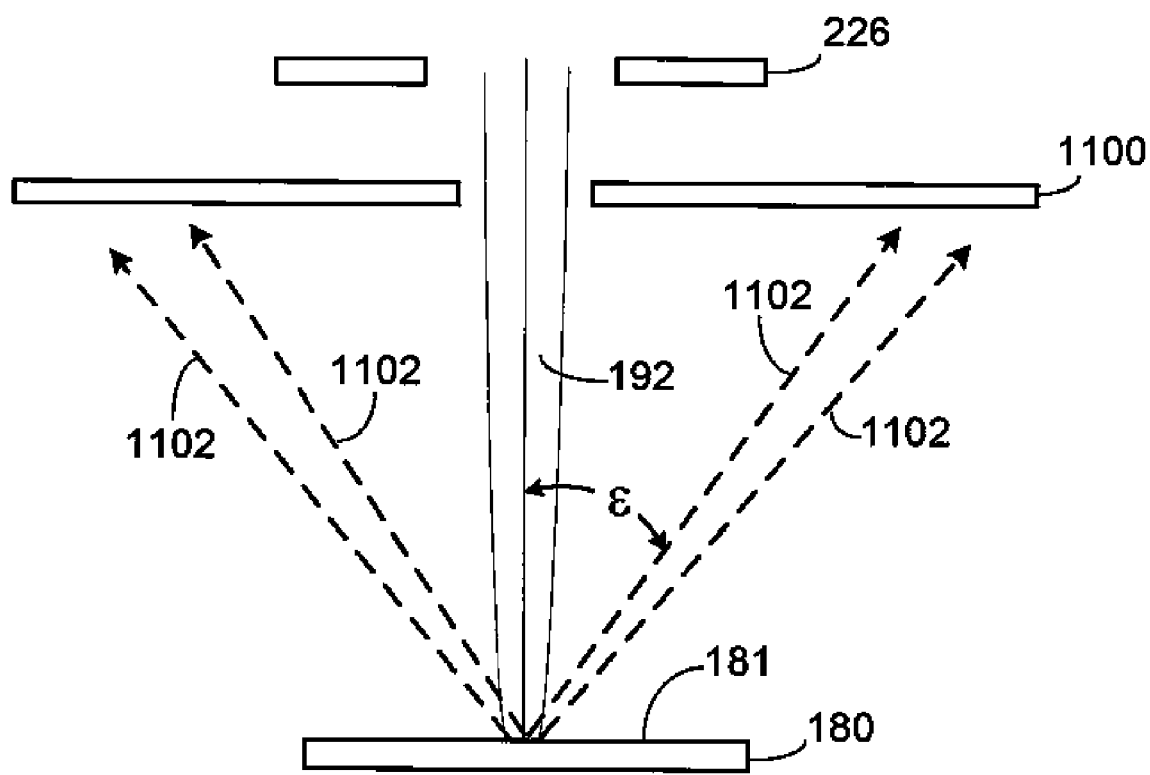
FIG. 36 is a schematic diagram showing a portion of a gas field ion microscope including an arrangement of detectors for measuring scattered ions from a sample.
Figure 37:
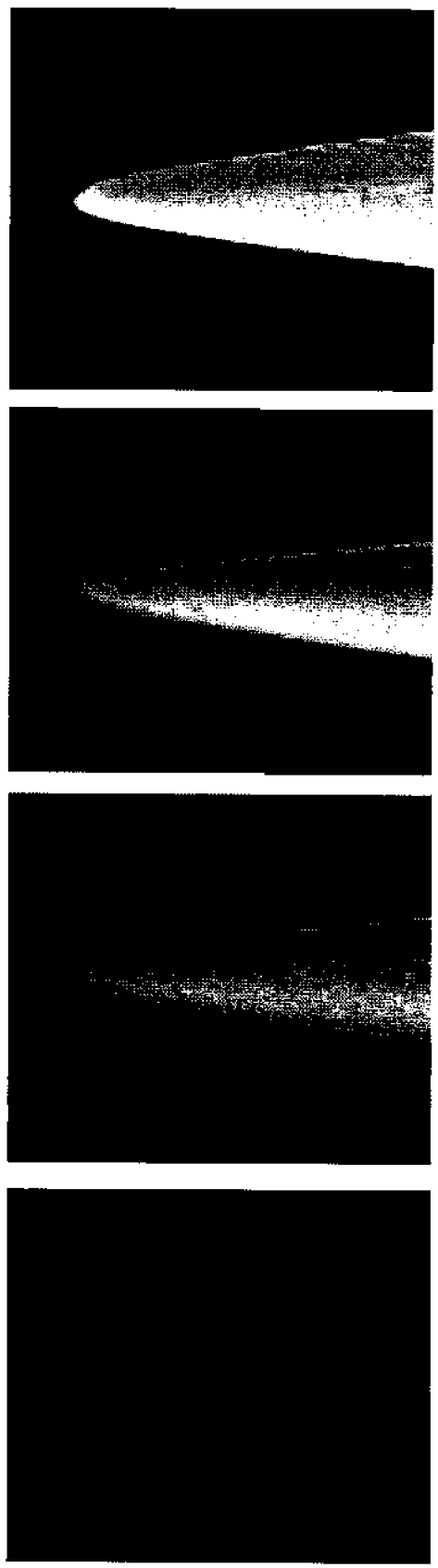
FIGS. 37A-37D are scanning electron microscope images an electrically conductive tip.

Another approach to determining material constituent information about the surface of a sample by detecting scattered He ions (which may be used in combination with or instead of total abundance detection) involves measuring the scattered He ions in an energy-resolved and angle-resolved fashion. For example, as shown in FIG. 36, second lens 226 focuses He ion beam 192 onto surface 181 of sample 180. He ions 1102 scatter from surface 181 and are detected by detector 1100. Detector 1100 is designed so that the angle and energy of each detected scattered He ion is known for each angle $\epsilon$ within the acceptance angle of detector 1100. By measuring the energy and scattering angle of the scattered He ion, the mass of the atom at the surface that scatters the scattered He ion can be calculated based on the following relationship:

$$\frac{E_s}{E_i} = 1 - \frac{2M_{He}M_a}{(M_{He}+M_a)^2}(1-\cos\theta_s)$$

where $E_s$ is the energy of the scattered He ion, $E_i$ is the incident energy of the He ion, $M_{He}$ is the mass of the He ion, $\theta_s$ is the scattering angle, and $M_a$ is the mass of the atom that scatters the He ion.

Detector 1100 can, for example, be an energy-resolving phosphor-based detector, an energy-resolving scintillator-based detector, a solid state detector, an energy-resolving electrostatic prism-based detector, an electrostatic prism, an energy-resolving ET detector, or an energy-resolving microchannel. In general, it is desirable for detector 1100 to have a substantial acceptable angle. In some embodiments, detector 1100 is stationary (e.g., an annular detector). In certain embodiments, detector 1100 can sweep through a range of solid angles. Although a system for detecting energy-resolved and angle-resolved scattered He ions that includes a single detector has been described, such a system can contain multiple (e.g., two, three, four, five, six, seven, eight) detectors. Often, the use of multiple detectors is desirable because it can allow for a larger acceptance angle of detected scattered He ions.

In some embodiments, detecting the total abundance of scattered He ions can provide crystalline information about a sample. The total abundance of scattered He ions can vary depending on whether the ion beam is aligned with the crystal structure of the sample or not. If the ion beam is aligned with the crystal structure of the sample, the probability that ions in the ion beam can generally penetrate into a given distance into the sample without undergoing a collision with a sample atom (commonly referred to as channeling) is relatively high, resulting in a lower total abundance of scattered He ions. If, on the other hand, the ion beam is not aligned with the crystal structure, then the ions in the ion beam will have a lower probability of penetrating into the sample the given distance without undergoing a collision with a sample atom, resulting in a higher total abundance of scattered He ions. Therefore, the change in the total abundance of scattered He ions as a function of the ion beam location at the sample surface can be correlated to the crystalline information of the material at that location. For example, there may be regions of the sample surface where the scattered He ions' total abundance is substantially the same. Such regions can, for example, have the same crystal orientation, and the size of the regions can provide grain size and/or crystal size information (e.g., in a polycrystalline sample that includes multiple, oriented crystal domains), and/or can provide information regarding strained regions of sample (whether amorphous or crystalline) because the magnitude of the scattered He ions' total abundance for a material of a given chemical composition (e.g., elemental composition, material composition) can depend on the strain of the material.

Alternatively or additionally, crystalline information about the surface of a sample can be obtained by exposing a region of the surface to an ion beam (without rastering the ion beam) and then measuring a pattern of the scattered He ions (e.g., similar to a Kikuchi pattern obtained due to backscattered electrons from a sample surface exposed to an electron beam). The pattern of the scattered He ions can be analyzed to determine, for example, the orientation, lattice spacing, and/or crystal type (e.g., body centered cubic, face centered cubic) of the material at the location of the sample surface that is exposed to the ion beam.

Scattered ion imaging techniques can be applied to a variety of different classes of samples. An example of such a class of materials is semiconductor articles, such as patterned wafers, which can include, for example, multiple electrical conductors surrounded by a matrix of insulating material. Scattered ion imaging techniques can be used to identify defects in the device, such as incomplete electrical connections between conductors, and/or electrical shorts between circuit elements. Optionally, this approach can similarly be used for purposes of mask repair. Another example of a sample class for which scattered ion imaging techniques can be used is metals and alloys. For example, images of samples that contain mixed materials such as alloys can be used to determine the surface distribution of each of the materials in the sample. Yet another example of a sample class where scattered ion imaging techniques can be used is read/write structures for data storage. Additional examples of classes of materials for which scattered ion imaging techniques can be used are biological materials and pharmaceutical materials.

In general, scattered ions are not formed when a sample surface is exposed to an electron beam of the type used in conventional SEMs, and thus none of the crystalline information or material constituent information obtainable via detected scattered He ions is available with such SEMs. This is a significant advantage of a gas field ion microscope (e.g., a He ion microscope) as described herein relative to a conventional SEM.

Measurement of scattered He ions using a gas field ion microscope (e.g., a He ion microscope) as described herein can offer a number of advantages relative to conventional Rutherford backscattering measurement devices. The spot size to which the incident He ions can be focused at the surface of the sample can be significantly smaller than the spot size of conventional Rutherford backscattering measurement devices (typical spot sizes of 100 μm to 1 mm or more), allowing for the material constituent information about the sample surface to be more precisely localized than achieved with conventional Rutherford backscattering measurement devices. Further, a gas field ion microscope (e.g., a He ion microscope) as described herein allows for pixel-by-pixel rastering across the sample surface, whereas Rutherford backscattering measurement devices do not have this capability. This can reduce the cost and/or complexity associated with material constituent information about the sample surface at various locations of the surface.

D. Primary Neutral Particles

As referred to herein, a primary neutral particle is a neutral particle generated when the ion beam interacts with the sample and an ion (e.g., a He ion) from the ion beam leaves the sample as an un-charged neutral particle (e.g., an un-charged He atom). In contrast to scattered He ions, primary He atoms are a relatively sensitive probe of the sub-surface region of a sample. As used herein, the sub-surface region is the region of a sample that is more than five nm beneath the sample surface (e.g., 10 nm or more beneath the sample surface, 25 nm or more beneath the sample surface, 50 nm or more beneath the sample surface), and 1000 nm or less beneath the sample surface (e.g., 500 nm or less beneath the sample surface, 250 nm or less beneath the sample surface, 100 nm or less beneath the sample surface). In general, the probe depth of the ion beam increases as the energy of the ions increase. Thus, to determine deeper sub-surface information about a sample, a higher energy ion beam can be used. A depth profile of material constituent information can be obtained by taking multiple He atom images of a sample at varying ion beam energies (probe depths). In some embodiments, tomographic reconstruction algorithms and/or techniques can be applied to the depth dependent information to perform tomographic reconstruction of the structure of the sample.

In general, material constituent information based on the detection of primary He atoms can be determined using total abundance detection, energy-resolved/angle-resolved detection, or both, using detector arrangements as described above with respect to the corresponding techniques for scattered He ions and also using the same mathematical relationships as described above for scattered He ions. Typically, however, the detector(s) used for primary He atoms is capable of detecting a neutral species. Examples of such detectors include microchannel plates, channeltrons and scintillator/PMT detectors.

Primary neutral particle (e.g., He atom) techniques can be applied to a variety of different classes of samples. An example of such a class of materials is semiconductor articles, such as patterned wafers, which can include, for example, multiple electrical conductors surrounded by a matrix of insulating material. Primary neutral particle techniques can be used to identify defects in the device, such as incomplete electrical connections between conductors, and/or electrical shorts between circuit elements. Optionally, this approach can similarly be used for purposes of mask repair. Another example of a sample class for which primary neutral particle imaging techniques can be used is metals and alloys. For example, images of samples that contain mixed materials such as alloys can be used to determine the surface distribution of each of the materials in the sample. Yet another example of a sample class where primary neutral particle imaging techniques can be used is read/write structures for data storage. Additional examples of classes of materials for which primary neutral particle imaging techniques can be used are biological materials and pharmaceutical materials.

Primary neutral particles are generally not generated when a sample surface is exposed to an electron beam of the type used in conventional SEMs, and thus none of the crystalline information or material constituent information obtainable via detected scattered He ions is available with such SEMs. This is a significant advantage of a gas field ion microscope (e.g., a He ion microscope) as described herein relative to a conventional SEM.

E. Photons

Typical photons of interest include X-ray photons, UV photons, visible photons and IR photons. As referred to herein, an IR photon is a photon having a wavelength of more than 700 nm to 100,000 nm (e.g., from $1.2 \times 10^{-5}$ keV to $1.7 \times 10^{-3}$ keV), a visible photon is a photon having a wavelength of from more than 400 nm to 700 nm (e.g., from $1.8 \times 10^{-3}$ keV to $3 \times 10^{-3}$ keV), a UV photon is a photon having a wavelength of more than 10 nm to 400 nm (e.g., from $3.1 \times 10^{-3}$ keV to 125 eV) and an X-ray photon is a photon having a wavelength of from 0.01 nm to 10 nm (e.g., from 125 eV to 125 keV). In general, such photons are emitted from the sample surface at a range of angles and energies/wavelengths. However, the information of most interest is usually the wavelength and/or energy of the photons (as opposed to angle-resolved photon information) because, as explained below, the wavelength and/or energy of the photons is what can provide information regarding the sample surface. The photons can be detected using one or more appropriate detectors capable of detecting photons in a wavelength-resolved or energy-resolved fashion (see discussion above regarding types of detectors). If multiple detectors are used, the detectors may all be the same type of detector, or different types of detectors may be used, and may generally be configured as desired. The detectors can be configured to detect photons leaving surface 181 of sample 180 (the surface on which the ion beam impinges), surface 183 of sample 180 (the surface on the opposite side from where the ion beam impinges) or both (see discussion above regarding configurations of detectors). To enhance the signal to noise of the detected photons, it can be desirable to use a detector that can collect a relatively large solid angle of photons. Additionally or alternatively, the system can include one or more optical elements (e.g., one or more lenses, one or more mirrors) that are adjacent the surface of the sample and that can direct the photons to the detector can be used (e.g., to increase the effective solid angle of detection of the detected photons).

In general, detecting the energy and/or wavelength of the photons can yield material constituent information (e.g., elemental information, chemical environment information) about a sample. In such embodiments, the information is predominantly related to the surface of the sample. In general, for each element or material in a given chemical environment, the photons emitted by the element or material will have a particular energy/band of energies and wavelength/band of wavelengths. As a result, the energy and wavelength of the photons emitted from a given location on a surface generally depends on the material present at that location. Therefore, the change in the energy or wavelength of the photons as a function of the location of the ion beam on the surface of the sample, can be correlated to a change in the element(s) and/or material(s) present at the surface of the sample, providing material constituent information about the surface of the sample.

Alternatively or additionally, material constituent information about the sample can be obtained detecting photons by determining the de-excitation time of the sample material. This can be achieved, for example, by pulsing the ion beam to expose the sample to the ion beam for a brief period, followed by measuring the amount of time it takes to detect the photons, which relates to the de-excitation time of the sample material that emits the photons. In general, each element or material in a given chemical environment will have a particular de-excitation time period.

Crystalline information about a sample can be obtained using photon detection in combination with a polarizer because the polarization of the photons can depend upon the crystal orientation of the material in the sample. Thus, via the use of a polarizer, the polarization of the photons emitted by a sample can be determined, providing information relating to the crystal orientation of the sample.

In general, the information contained in the detected photons will predominantly be information about the surface of the sample. However, because photons can escape from a sub-surface region of a sample, detected photons can contain information relating to the sub-surface region of the sample. Thus, detected photons can be used to determine optical properties of the sample. For example, the transparency of the sample to the photons can be investigated by manipulating the energy of the ions in the ion beam, and therefore their probe depth, and determining the corresponding impact on the intensity of the detected photons. The detected photon intensity as a function of ion energy (probe depth) can yield information regarding the transparency of the sample to the photons.

Photon imaging techniques can be applied to a variety of different classes of samples. An example of such a class of materials is semiconductor articles, such as patterned wafers, which can include, for example, multiple electrical conductors surrounded by a matrix of insulating material. Photon imaging techniques can be used to identify defects in the device, such as incomplete electrical connections between conductors, and/or electrical shorts between circuit elements. Optionally, this approach can similarly be used for purposes of mask repair. Another example of a sample class for which photon imaging techniques can be used is metals and alloys. For example, images of samples that contain mixed materials such as alloys can be used to determine the surface distribution of each of the materials in the sample. Yet another example of a sample class where photon imaging techniques can be used is read/write structures for data storage. Additional examples of classes of materials for which photon imaging techniques can be used are biological materials and pharmaceutical materials.

Imaging samples using photons generated by exposure to a He ion beam can provide a number of advantages relative to photon imaging via other techniques, such as SEM. For example, the spot size of the He ion beam on the sample can be smaller than the spot size of an electron beam from a SEM. As a result of the smaller spot size, the region of the sample that is exposed to the He ion beam is more carefully controlled than the exposed region in a SEM.

Further, in general, because He ions are heavier than electrons, scattering events do not disperse He ions as readily within the sample as electrons are dispersed by scattering. As a result, He ions incident on the surface of a sample can interact with the sample in a smaller interaction volume than electrons in a SEM. As a result, photons detected in a gas field ion microscope (e.g., a He ion microscope) can arise from a smaller region than the region giving rise to photons in a SEM with a similar spot size. Consequently, the photons which are generated by the interaction of the sample and the He ion beam can correspond to a more localized interrogation of the surface of the sample (e.g., with less lateral averaging of material properties) than the photons generated in a SEM.

In addition, the He ion source also provides a greater depth of focus than an electron source. As a result, images of a sample obtained using an ion microscope (e.g., a gas field ion microscope) can show a larger portion of the sample, measured along the direction perpendicular to the sample surface, in focus than comparable images obtained from photons in a SEM.

F. Secondary Ions

As referred to herein, a secondary ion is an ion formed when the ion beam interacts with the sample to remove a mono-atomic or poly-atomic species from the sample in a charged state. Interactions between the incident ion beam and the sample can produce secondary ions. Typically, this method is more effective when using a noble gas ion of mass greater than He (Ar ions, Ne ions, Kr ions, Xe ions).

Detection of secondary ions from the sample can provide material constituent information about the sample via calculation of the masses of detected particles. In general, this information will correspond to material at the surface of the sample. In some embodiments, the mass(es) of the secondary ions is(are) determined using a combination of time-of-flight and a mass-resolved detector, such as a quadrupole mass spectrometer. Such secondary ion detection can be performed as follows. The ion beam is operated in pulsed mode by changing the electrical potentials applied to ion optical elements in the ion optics. Pulses of incident ions are incident on a surface of the sample. A clock signal, which determines the rate at which the ion optical element potentials are switched to turn the ion beam on and off, is also used as a reference time signal for the detector (see discussion above regarding detectors). In this manner, the time of flight of secondary ions from the sample to the detector can be accurately determined.

Based upon a detected secondary ions' time of flight, its distance traveled (e.g., the distance between the detector and the sample), and its energy, the mass of the particle can be calculated, and the type of chemical species (e.g., atom) can be identified. This information is used to determine material constituent information for the sample.

Secondary ion imaging techniques can be applied to a variety of different classes of samples. An example of such a class of materials is semiconductor articles, such as patterned wafers, which can include, for example, multiple electrical conductors surrounded by a matrix of insulating material. Secondary ion imaging techniques can be used to identify defects in the device, such as incomplete electrical connections between conductors, and/or electrical shorts between circuit elements. Optionally, this approach can similarly be used for purposes of mask repair. Another example of a sample class for which secondary ion imaging techniques can be used is metals and alloys. For example, images of samples that contain mixed materials such as alloys can be used to determine the surface distribution of each of the materials in the sample. Yet another example of a sample class where secondary ion imaging techniques can be used is read/write structures for data storage. Additional examples of classes of materials for which secondary ion imaging techniques can be used are biological materials and pharmaceutical materials.

Secondary ions are generally not generated when a sample surface is exposed to an electron beam of the type used in conventional SEMs, and thus none of the material constituent information obtainable via detected secondary ions is available with such SEMs. This is a significant advantage of a gas field ion microscope (e.g., a He ion microscope) as described herein relative to a conventional SEM.

G. Secondary Neutral Particles

A secondary neutral particle is a neutral particle generated when the ion beam interacts with the sample to remove a mono-atomic or poly-atomic species from the sample in an un-charged state. Interactions between the incident ion beam and the sample can produce secondary neutral particles. Typically, this method is more effective when using a noble gas ion of mass greater than He (Ar ions, Ne ions, Kr ions, Xe ions). In general, to access the information available from secondary neutral particles, the particles are ionized (e.g., via laser induced ionization, electron induced ionization) prior to detection.

Detection of secondary neutral particles (post-ionization) from the sample can provide material constituent information about the sample via calculation of the masses of detected particles. In general, this information will correspond to material at the surface of the sample. In some embodiments, the mass(es) of the secondary neutral particles (post-ionization) is(are) determined using a combination of time-of-flight and a mass-resolved detector, such as a quadrupole mass spectrometer. Such secondary neutral particle (post-ionization) detection can be performed as follows. The ion beam is operated in pulsed mode by changing the electrical potentials applied to ion optical elements in the ion optics. Pulses of incident ions are incident on a surface of the sample. A clock signal which determines the rate at which the ionization device (e.g., laser, electron beam) and/or ion optical element potentials are switched is also used as a reference time signal for the detector (see discussion above regarding detectors). In this manner, the time of flight of secondary neutral particles (post ionization) from the sample to the detector can be accurately determined.

Based upon a detected secondary ions' time of flight, its distance traveled (e.g., the distance between the detector and the sample), and its energy, the mass of the particle can be calculated, and the type chemical species (e.g., atom) can be identified. This information is used to determine material constituent information for the sample.

Secondary neutral particle imaging techniques can be applied to a variety of different classes of samples. An example of such a class of materials is semiconductor articles, such as patterned wafers, which can include, for example, multiple electrical conductors surrounded by a matrix of insulating material. Secondary neutral particle imaging techniques can be used to identify defects in the device, such as incomplete electrical connections between conductors, and/or electrical shorts between circuit elements. Optionally, this approach can similarly be used for purposes of mask repair. Another example of a sample class for which secondary neutral particle imaging techniques can be used is metals and alloys. For example, images of samples that contain mixed materials such as alloys can be used to determine the surface distribution of each of the materials in the sample. Yet another example of a sample class where secondary neutral particle imaging techniques can be used is read/write structures for data storage. Additional examples of classes of materials for which secondary neutral particle imaging techniques can be used are biological materials and pharmaceutical materials.

Secondary neutral particle are generally not generated when a sample surface is exposed to an electron beam of the type used in conventional SEMs, and thus none of the material constituent information obtainable via detected secondary neutral particle is available with such SEMs. This is a significant advantage of a gas field ion microscope (e.g., a He ion microscope) as described herein relative to a conventional SEM.

Exemplary Applications

A. Semiconductor Fabrication
   (i) General

Semiconductor fabrication typically involves the preparation of an article that includes multiple layers of materials sequentially deposited and processed to form an integrated electronic circuit, an integrated circuit element, and/or a different microelectronic device. Such articles typically contain various features (e.g., circuit lines formed of electrically conductive material, wells filled with electrically non-conductive material, regions formed of electrically semiconductive material) that are precisely positioned with respect to each other (e.g., generally on the scale of within a few nanometers). The location, size (length, width, depth), composition (chemical composition) and related properties (conductivity, crystalline orientation, magnetic properties) of a given feature can have an important impact on the performance of the article. For example, in certain instances, if one or more of these parameters is outside an appropriate range, the article may be rejected because it cannot function as desired. As a result, it is generally desirable to have very good control over each step during semiconductor fabrication, and it would be advantageous to have a tool that could monitor the fabrication of a semiconductor article at various steps in the fabrication process to investigate the location, size, composition and related properties of one or more features at various stages of the semiconductor fabrication process. As used herein, the term semiconductor article refers to an integrated electronic circuit, an integrated circuit element, a microelectronic device or an article formed during the process of fabricating an integrated electronic circuit, an integrated circuit element, a microelectronic device. In some embodiments, a semiconductor article can be a portion of a flat panel display or a photovoltaic cell.

Regions of a semiconductor article can be formed of different types of material (electrically conductive, electrically non-conductive, electrically semiconductive). Exemplary electrically conductive materials include metals, such as aluminum, chromium, nickel, tantalum, titanium, tungsten, and alloys including one or more of these metals (e.g., aluminum-copper alloys). Exemplary electrically non-conductive materials include borides, carbides, nitrides, oxides, phosphides, silicides, and sulfides of one or more of the metals (e.g., nickel silicides, tantalum borides, tantalum germaniums, tantalum nitrides, tantalum silicides, tantalum silicon nitrides, and titanium nitrides). Exemplary electrically semiconductive materials include silicon, germanium and gallium arsenide. Optionally, a electrically semiconductive material can be doped (p-doped, n-doped) to enhance the electrical conductivity of the material.

As noted above, in general, fabrication of a semiconductor article involves sequentially depositing and processing multiple layers of material. Typical steps in the deposition/processing of a given layer of material include imaging the article (e.g., to determine where a desired feature to be formed should be located), depositing an appropriate material (e.g., an electrically conductive material, an electrically semiconductive material, an electrically non-conductive material) and etching to remove unwanted material from certain locations in the article. Often, a photoresist, such as a polymer photoresist, is deposited/exposed to appropriate radiation/selectively etched to assist in controlling the location and size of a given feature. Typically, the photoresist is removed in one or more subsequent process steps, and, in general, the final semiconductor article desirably does not contain an appreciable amount of photoresist.

The gas field ion microscope (e.g., He ion microscope) described herein can be used to investigate a semiconductor article at various steps (e.g., each step) in the fabrication process. In particular, by detecting and analyzing one type of particle or multiple different types of particles (see discussion above), the gas field ion microscope (e.g., He ion microscope) can be used to determine topographical-information about the surface of the semiconductor article, material constituent information of the surface of the semiconductor article, material constituent information about the sub-surface region of the semiconductor article, crystalline information about the semiconductor article, voltage contrast information about the surface of the semiconductor article, voltage contrast information about a sub-surface region of the sample, magnetic information about the semiconductor article, and/or optical information about the semiconductor article.

Using an ion microscope or ion beam as described herein can provide a variety of different advantages, which, in general, can reduce the time, cost and/or complexity associated with semiconductor article fabrication. Exemplary advantages associated with using the ion microscope or ion beam described herein include relatively high resolution, relatively small spot size, relatively little undesirable sample damage, relatively little undesirable material deposition and/or implantation, relatively high quality imaging in a relatively short time period, relatively high throughput.

Certain examples of process steps in semiconductor fabrication are discussed below.

(ii) Maskless Lithography

Semiconductor articles are typically prepared using a lithography process that involves putting a layer of photoresist (e.g., polymer photoresist, such as poly(methyl methacrylate) (PMMA) or epoxy-based photoresists, allyl diglycol carbonate, or photosensitive glasses) on a surface, patterning the material so that certain regions of the photoresist are resistant to an etchant (and some regions are not resistant to an etchant), etching the non-etch resist regions of the material, depositing appropriate materials (e.g., one or more electrically conductive materials, one or more non-electrically conductive materials, one or more semiconductive materials), and optionally removing undesired regions of material. Typically, the patterning step involves exposing the photoresist to a radiation pattern of an appropriate wavelength so that some regions of the photoresist are etch resistant and other regions of the photoresist are not etch resistant. The radiation pattern can be formed on the photoresist by forming an image of a mask onto the photoresist or covering certain regions of the photoresist with a mask, and exposing the uncovered regions of the photoresist through the mask.

However, rather than using a mask to cover regions of photoresist prior to exposure to radiation, an ion beam generated by the interaction of gas atoms with the gas field ion source (e.g., He ion source) described herein can be used to irradiate to pattern the photoresist to create desired etch-resistant regions and non-etch resistant regions. This can be achieved, for example, by rastering the ion beam across the photoresist so that desired regions of material are exposed to the ions (e.g., by turning the ion beam on at regions where exposure of the photoresist to radiation is desired and by turning the ion beam off at regions where exposure of the photoresist to radiation is not desired). As a result, a semiconductor article can be fabricated in a maskless process.

Using the ion beam generated via the interaction of gas atoms with the gas field ion source (e.g., He ion source) disclosed herein can offer one or more of the following advantages. As noted, the process can be performed without the use of mask, which can decrease the time, cost and/or complexity associated with fabrication of semiconductor articles. The relatively large depth of focus of the ion beam can allow for patterning relatively thick photoresist materials (e.g., 2 µm or more thick, 5 µm or more thick, 10 µm or more thick, and or 20 µm or less thick). The relatively deep penetration depth of ions that can be achieved with the ion beam can further assist in processing relatively thick photoresist materials, as well as assisting in good quality processing of more standard thickness photoresist materials. In addition, the ion beam has higher resolution relative to what is generally achieved with an electron beam, allowing for the fabrication of smaller sized features with higher precision. Further, ion beam patterning of photoresist can be faster than electron beam patterning of photoresist.

(iii) Combination of Ion Microscope and Focused Ion Beam

A focused ion beam (FIB) is commonly used during the fabrication of a semiconductor article to obtain a sample for inspection. Gallium (Ga) ions are commonly used in the FIB. A FIB can be used for a variety of reasons, such as cross-sectional imaging through a semiconductor article, circuit editing, failure analysis of a semiconductor articles, preparation of a semiconductor article specimen for transmission electron microscopy (TEM) and mask repair. Optionally, a FIB can be used to deposit one or more materials on a sample (e.g., as an ion source in a chemical vapor deposition process). Typically, the FIB is used to remove material from a semiconductor article via sputtering. For example, in some embodiments, the FIB is used to slice through a semiconductor article to expose a cross-section of the article for subsequent imaging using the ion microscope. In certain embodiments, the FIB is used to sputter away material from an article to form a trench or via in the article. This technique can be used, for example, to expose portions of the article that are underneath the article's surface. The ion microscope can then be used to deposit new material, or etch away existing material exposed by the FIB, using gas assisted chemical techniques. In some embodiments, a FIB can also be used as a selective sputtering tool to remove portions of a semiconductor article, such as portions of conductive material on the article. In certain embodiments a FIB is used to cut out a portion of a sample so that the portion can be subsequently analyzed (e.g., using TEM).

It is generally desirable to precisely locate the FIB on the sample. A gas field ion microscope (e.g., a He ion microscope) as described herein can be used for this purpose. For example, a cross-beam tool with both a FIB instrument and a gas field ion microscope can be used so that the location of the FIB can be determined using the gas field ion microscope without moving the sample. With such a tool, the gas field ion source can be used to image the sample and provide information that can be used to precisely position the FIB as desired. Such an arrangement can offer numerous advantages relative to using a SEM to determine location of the FIB. As an example, use of a SEM can result in a magnetic field adjacent the sample surface, which can result in isotope separation of the Ga ions, resulting more than one location of the FIB at the sample. In many instances, this problem results in the FIB and SEM being used in series rather than simultaneously. In contrast, however, a gas field ion microscope can be operated in the absence of such a magnetic field, thereby eliminating complications associated with Ga ion isotope separation, while also allowing the FIB and gas field ion microscope to be used simultaneously. This can be desirable, for example, when preparing a sample for subsequent inspection (e.g., for TEM inspection) where it may be desirable for the thickness of the sample to satisfy relatively strict tolerances. An additional advantage for using a gas field ion microscope (e.g., a He ion microscope) is that it has a longer working distance than typically used with a SEM, while still maintaining very good resolution because the ion beam has a smaller virtual source than the electron beam. This can relieve certain spacing constraints that may exist for a tool that combines a FIB instrument and a SEM. A further advantage of a gas field ion microscope as described herein is that it can be used to obtain sub-surface information about a sample, which can enhance the ability to precisely locate the FIB, whereas a SEM generally cannot provide such sub-surface information.

(iv) Gas Assisted Chemistry

Gas assisted chemistry is commonly used during semiconductor fabrication to add material to and/or remove material from a given layer. For example, gas assisted chemistry can be used for semiconductor circuit editing—to repair damaged or incorrectly fabricated circuits formed in semiconductor articles. Gas assisted chemistry can also be used in photolithographic mask repair, where material can be added to or removed from masks to repair defects which result from use or incorrect fabrication.

The process generally involves interacting electrons with an activating gas to form a reactive gas that can then participate in chemistry at the surface of a semiconductor article to add material to the surface, remove material from the surface, or both. Typically, the electrons are generated as secondary electrons resulting from the interaction of a Ga ion beam with the sample and/or the electrons are generated as secondary electrons resulting from the interaction of an electron beam (e.g., produced by a SEM) with the sample. Optionally, an appropriate pumping system can be used to remove undesirable volatile products of the surface chemistry.

Examples of activating gases that can be used to remove material from the surface include $Cl_2$, $O_2$, $I_2$, $XeF_2$, $F_2$, $CF_4$ and $H_2O$. As an example, in some embodiments, a surface region formed of chrome, chrome oxide, chrome nitride and/or chrome oxynitride can be at least partially removed by interacting electrons with $Cl_2$ and/or $O_2$, and allowing the resulting chemical species to etch the surface region. As another example, in certain embodiments, a surface region formed of a tantalum nitride can be at least partially removed by interacting electrons with $XeF_2$, $F_2$ and/or $CF_4$, and allowing the resulting chemical species to etch the surface region. As a further example, in certain embodiments, a surface region formed of a carbon-containing material can be at least partially removed by interacting electrons with $H_2O$ and/or $O_2$, and allowing the resulting chemical species to etch the surface region.

An example of an activating gas that can be used to deposit a material on the surface is $WF_6$ (to deposit W, such as a W plug).

An ion beam generated by the interaction of gas atoms with the gas field ion source (e.g., the He ion source) described herein can be used to perform gas assisted chemistry. In such a process, for example, the secondary electrons that leave the sample due to the interaction of the ion beam with the sample can be the electrons used to assist in the chemistry. Using such an ion beam can offer several advantages relative to using a Ga ion beam. As an example, undesirable ion implantation can be reduced (e.g., eliminated) using a He ion beam, whereas undesirable implantation of Ga is a common problem when a Ga ion beam is used. As another example, a gas field ion beam (e.g., a He ion beam) can provide improved resolution relative to a Ga ion beam and/or an incident electron beam (e.g., an incident electron beam produced by a SEM), which can allow for the more precise and/or controllable use of the chemistry. This can, for example, reduce (e.g., eliminate) the undesirable interaction of ions with certain portions of a sample (e.g., such as can occur with a Ga ion beam where the beam profile has tails that extend to undesirable regions of the sample where Ga implantation can create problems with the performance of the semiconductor article).

(v) Sputtering

In the process of fabricating semiconductor articles, it can be desirable during certain steps to remove materials. An ion beam can be used for this purpose where the ion beam sputters material from the sample. In particular, an ion beam generated via the interaction of gas atoms with a gas field ion source as described herein can be used for sputtering a sample. Although He gas ions may be used, it is typically preferable to use heavier ions (e.g., Ne gas ions, Ar gas ions, Kr gas ions, Xe gas ions) to remove material. During the removal of material, the ion beam is focused on the region of the sample where the material to be removed is located.

An advantage to using an ion beam to remove material is that the material can be removed in a relatively controlled and/or precise manner. An additional advantage is that sputtering can be achieved without undesirable implantation of ions (e.g., such as often results when using Ga ion sputtering, where Ga implantation is a common undesired side effect of sputtering).

(vi) Detection of Voids

During the fabrication of a semiconductor article, voids in certain features or layers may be inadvertently formed. In some embodiments, the voids can undesirably impact the properties (e.g., electrical, mechanical) of the feature and/or the overall device. In certain embodiments, subsequent processing steps may open the void, and the void may, for example, fill with liquid and/or gaseous components. This can cause corrosion of the underlying structures, particle defects and/or residue defects on the surrounding wafer surface.

As an example, during W plug deposition from $WF_6$, a $TiN_x$ protective layer is commonly used to protect an adjacent dielectric material (e.g., boron and phosphor doped silicon glass) from corrosion (e.g., from HF that is liberated during W formation). Discontinuities in the $TiN_x$ layer can result in significant void formation. As another example, material (e.g., dielectric material) deposition in trenches (e.g., relatively high aspect ratio trenches) can result in the formation of a bottleneck with subsequent void formation. As an additional example, void formation can occur during dielectric filling of shallow trench isolation structures. As a further example, voids can be formed during the formation of electrically conductive lines of material (e.g., copper lines), which can result in undesirable reduction in electrical conductance. In some cases, such voids can result in a lack of electrical conductance where electrical conductance is desired.

A gas field ion microscope (e.g., a He ion microscope) as described herein can be used to investigate void formation by taking advantage of its ability to provide sub-surface information about a sample, such as a semiconductor article. This property can be used during the semiconductor article fabrication process to determine the existence and/or location of voids.

This is a distinct advantage over using an electron beam because an electron beam generally does not provide this kind of sub-surface information for a sample.

(vii) Overlay Shift Registration

Overlay shift registration generally refers to the alignment of a feature of a given layer of a semiconductor article with a feature in a different layer of the semiconductor article. As noted above, the formation of a semiconductor article generally involves the proper formation of many layers. Typically, a semiconductor article contains well over 20 layers. Often, each layer can contain multiple different features, each of which is desirably located with high precision so that the semiconductor article can function properly. As an example, a semiconductor article can contain lateral features, such as electrically conductive wires, which are in different layers and connected to each other by a via. In general, it is desirable to have features within the semiconductor article aligned with each other to within 100 nm (e.g., 75 nm, 50 nm, 25 nm, 15 nm, 10 nm, nine nm, eight nm, seven nm, six nm, five nm, four nm, three nm, two nm, 1 nm). Misalignment of a single one of these many features can render the entire semiconductor article useless.

Overlay shift registration is commonly performed using optical techniques using test structures, which are μm-sized structures (significantly larger than microelectronic circuit feature sizes). As such, optical test structures typically cannot be placed intra-dye on a wafer due to the amount of wafer space they occupy. The test structures can be placed, for example, nearer to the edges of wafer, but they still occupy valuable space on the wafer surface. Optical test structures are also expensive, because they are manufactured only for alignment purposes. Finally, the use of optical test structures for alignment has limitations regarding the precision with which the alignment of features in different layers can be determined.

The ability of a gas field ion microscope (e.g., a He ion microscope) as described herein to provide a variety of types of information (e.g., topographical information, material constituent information about the surface, material constituent information about a sub-surface region, crystalline information, voltage contrast information about the surface, voltage contrast information about a sub-surface region, magnetic information, and optical information) about the sample with relatively high precision allows for the microscope to be advantageously used during the fabrication of a semiconductor article to assist in assuring that the features in the device are positioned and dimensioned properly and with high precision within the device. In particular, the He ion microscope can permit alignment of circuit features in multiple layers at higher resolution than can typically be achieved using optical test structures. Further, overlay shift registration can be performed without using purpose-fabricated test structures (e.g., optical test structures) because, for example, the gas field ion microscope (e.g., He ion microscope) described herein can image sub-surface features of samples, such as semiconductor articles. Accordingly, the wasted space on a wafer taken up by purpose-fabricated test structures (e.g., optical test structures) can be avoided, as well as the associated cost and/or complexity associated with including such test structures.

(vii) Critical Dimension Metrology

Critical dimension metrology refers to the measurement of the linear dimensions of features in a semiconductor article that can have a critical impact on the performance of the device. Examples of such features can include lines (e.g., lines of electrically conductive material, lines of electrically semiconductive conductive material, lines of electrically non-conductive material). A semiconductor article can contain one or more features having a size dimension of 20 nm or less (e.g., 10 nm or less, five nm or less, four nm or less, three nm or less, two nm or less, one nm or less). In some embodiments, the size of the feature is measured multiple times to provide statistical information regarding the size of the feature. Critical dimension measurements frequently involve, e.g., the determination of the length of a patterned feature on a wafer, for example. Wafers (containing multiple dies, with each die forming a semiconductor article) may be selected at random from a fabrication line for inspection, or all wafers on the line can be inspected. An imaging instrument can be used to measure selected critical dimensions at a relatively high throughput rate. If the measured critical dimension does not fall within acceptable limits, the wafer may be discarded. If multiple samples originating from a particular fabrication machine have critical dimensions outside acceptable limits, the machine may be taken out of service, or its operating parameters changed.

The He ion microscope systems disclosed herein can be used for critical dimension measurement. In particular, the He ion beam can be raster-scanned over a region of a wafer, and the resulting image(s) of the wafer can be used to determine the critical dimension(s). With regard to critical dimension measurement, He ion microscope systems can provide a number of advantages relative to SEMs and other inspection systems. He ion microscope images generally exhibit less edge blooming (generally, excessive signal, approaching the point of saturation of the detector, due to enhanced yield at topographic features with slopes nearly parallel to the beam) than comparable SEM images. The reduced edge blooming is a result of the smaller interaction volume between He ions and the surface of the sample, relative to the interaction volume of electrons with the surface.

In addition, the incident He ions can be focused to a smaller spot size than a comparable incident electron beam. The smaller beam spot size, in combination with the smaller interaction volume, results in images of the sample having resolution that is superior to images produced with SEMs, and more accurate determination of critical dimensions of samples.

The depth of focus of a He ion beam is relatively large compared to a SEM. As a result, the resolution of sample features at varying depths is more consistent when using an ion beam, as compared to an electron beam. Therefore, using an ion beam can provide information at various sample depths with better and more consistent lateral resolution than can be provided using an electron beam. As an example, better critical dimension profiles can be achieved using an ion beam than can be achieved with an electron beam.

Further, in embodiments in which information is obtained based at least in part on secondary electrons, the relatively high yield of secondary electrons provided by an ion beam, as compared to an electron beam, can result in a relatively high signal to noise ratio for a given current. This can, in turn, allow for sufficient information about the sample to be obtained in a relatively short period of time, increasing throughput for a given current.

Imaging of the samples for determination of critical dimensions can be performed using scattered He ions. This provides the added advantage of material information in addition to high resolution distance determination.

During use of the ion microscope systems for critical dimension measurements, a flood gun can be used to prevent excessive charging of the sample surface (see discussion above). Alternatively or additionally, very low He ion beam currents (e.g., 100 fA or less) can be used. In addition to reducing surface charge and maintaining image fidelity, the use of low ion currents reduces ion beam-induced damage to certain resist materials.

In some embodiments, wafer samples selected for critical dimension measurement may first need to be sectioned (e.g., to measure a cross-sectional dimension of the sample). For this purpose, heavier gases such as Ne and Ar can be used in the ion microscope to form an ion beam which can be used to slice through the sample. Alternatively, a Ga-based FIB can be used to section the sample. Then, the microscope system can be purged of these gases and He can be introduced, so that critical dimension measurements are made with a He ion beam, avoiding sample damage during metrology.

(viii) Line Edge Roughness and Line Width Roughness

Line edge roughness generally refers to the roughness of the edge of a line of material in a semiconductor article, and line width roughness generally refers to the roughness of the width of a line of material in a semiconductor article. It can be desirable to understand these values to determine whether actual or potential problems exist in a given semiconductor article. For example, if adjacent lines formed of electrically conductive material have edges that bulge outward toward each other, the lines may contact each other resulting in a short. It can be desirable to understand the dimensions of line edge roughness and/or line width roughness to within five nm or less (e.g., four nm or less, three nm or less, two nm or less, one nm or less, 0.9 nm or less, 0.8 nm or less, 0.7 nm or less, 0.6 nm or less, 0.5 nm or less). In some embodiments, the line edge roughness and/or line edge width is measured multiple times to provide statistical information regarding the size of the feature. In addition, fabrication tolerances for parameters such as line edge roughness can be very high. For example, line edge roughness of semiconductor article features may have to be controlled within 5 nm or less (e.g., within 4 nm or less, within 3 nm or less, within two nm or less, within one nm or less, within 0.5 nm or less, within 0.1 nm or less, within 0.05 nm or less, within 0.01 nm or less).

When determining line edge roughness and line width roughness, wafers may be selected at random from a fabrication line for inspection, or all wafers on the line can be inspected. An imaging instrument can be used to measure line edge roughness and line width roughness at a relatively high throughput rate. If the measured line edge roughness and line width roughness does not fall within acceptable limits, the wafer may be discarded. If multiple samples originating from a particular fabrication machine have line edge roughness and line width roughness outside acceptable limits, the machine may be taken out of service, or its operating parameters may be changed.

The gas field ion microscope (e.g., He ion microscope) disclosed herein can be used for metrology of line edge roughness and line width roughness. In particular, the He ion beam can be raster-scanned along the length of a feature, and the resulting information can be used to determine the line edge roughness and line width roughness with relatively high precision.

With regard to line edge roughness and line width roughness measurement, He ion microscope systems can provide a number of advantages relative to SEMs and other inspection systems. He ion microscope images generally exhibit less edge blooming (generally, excessive signal, approaching the point of saturation of the detector, due to enhanced yield at topographic features with slopes nearly parallel to the beam) than comparable SEM images. The reduced edge blooming is a result of the smaller interaction volume between He ions and the surface of the sample, relative to the interaction volume of electrons with the surface.

In addition, the incident He ions can be focused to a smaller spot size than a comparable incident electron beam. The smaller beam spot size, in combination with the smaller interaction volume, results in images of the sample having resolution that is superior to images produced with SEMs, and more accurate determination of line edge roughnesses and line width roughnesses of samples.

The depth of focus of a He ion beam is relatively large compared to a SEM. As a result, the resolution of sample features at varying depths is more consistent when using an ion beam, as compared to an electron beam. Therefore, using an ion beam can provide information at various sample depths with better and more consistent lateral resolution than can be provided using an electron beam. As an example, better line width profiles than can be achieved using an ion beam than can be achieved with an electron beam.

Further, in embodiments in which information is obtained based at least in part on secondary electrons, the relatively high yield of secondary electrons provided by an ion beam, as compared to an electron beam, can result in a relatively high signal to noise ratio for a given current. This can, in turn, allow for sufficient information about the sample to be obtained in a relatively short period of time, increasing throughput for a given current.

Imaging of the samples for determination of critical dimensions can be performed using scattered He ions. This provides the added advantage of material information in addition to high resolution distance determination.

During use of the ion microscope systems for line edge roughness and line width roughness measurements, a flood gun can be used to prevent excessive charging of the sample surface (see discussion above). Alternatively or additionally, very low He ion beam currents (e.g., 100 fA or less) can be used. In addition to reducing surface charge and maintaining image fidelity, the use of low ion currents reduces ion beam-induced damage to certain resist materials.

In some embodiments, wafer samples selected for line edge roughness and line width roughness measurement may first need to be sectioned (e.g., to measure a cross-sectional dimension of the sample). For this purpose, heavier gases such as Ne and Ar can interact with a gas field ion source to generate an ion beam which can be used to slice through the sample. Then, the microscope system can be purged of these gases and He can be introduced, so that critical dimension measurements are made with a He ion beam, avoiding sample damage during metrology.

(ix) Circuit Editing

As discussed previously, the process of forming a semiconductor article typically involves stacking many different layers of material in a desired fashion, and performing appropriate processes on each layer. Generally, this involves depositing on and/or removing material from a given layer. The final semiconductor article includes many different features in different layers (e.g., to form a desired circuit). In general, it is desirable for the features to be properly aligned for the final device to function as desired. Alignment marks are commonly used in semiconductor articles to assist in properly aligning features in a given layer with features in a different layer. However, using alignment marks can add extra steps to the overall fabrication process, and/or can introduce other complexities or expenses to the fabrication process. Further, the mere presence of the alignment marks means that there are areas and/or volumes of the semiconductor article that are not available for use (e.g., for the fabrication of active components).

As noted above, an ion beam can be used to investigate the sub-surface region of a material. This property can be used to determine the location of certain features in a layer beneath a surface layer, allowing features in different layers of the semiconductor article to be aligned as desired without the use alignment marks.

The gas field ion microscope (e.g., the He ion microscope) described herein can be used to remove and/or deposit material (e.g., from an electrical circuit) using, for example, the gas assisted chemistry and/or sputtering techniques noted above. An advantage of using an ion microscope to perform these processes is that the ion beam can also be used to assess the resulting product to determine, for example, whether the desired material was properly deposited or removed. This can reduce the cost and/or complexity associated with device fabrication, and/or increase the throughput of device fabrication. Removal and/or addition of material capabilities can be combined to perform sub-surface circuit repair. To repair a sub-surface defect, material from the device is first removed down to a depth that exposes the defect. The defect is then repaired by either adding or removing material from the device. Finally, the overlying layers of the device are repaired, layer-by-layer, by adding appropriate thicknesses of new material.

The gas field ion microscope (e.g., the He ion microscope) described herein can provide particular advantages for circuit editing applications including small spot sizes and low ion currents for controlled and highly accurate editing of fabricated devices.

(x) Mask Repair

Semiconductor articles are typically prepared using a lithography process that involves putting a layer of photoresist (e.g., polymer photoresist, such as poly(methyl methacrylate) (PMMA) or epoxy-based photoresists, allyl diglycol carbonate, or photosensitive glasses) on a surface, patterning the material so that certain regions of the photoresist are resistant to an etchant (and some regions are not resistant to an etchant), etching the non-etch resist regions of the material, depositing appropriate materials (e.g., one or more electrically conductive materials, one or more non-electrically conductive materials, one or more semiconductive materials), and optionally removing undesired regions of material. Typically, the patterning step involves exposing the photoresist to a radiation pattern of an appropriate wavelength so that some regions of the photoresist are etch resistant and other regions of the photoresist are not etch resistant. The radiation pattern can be formed on the photoresist by forming an image of a mask onto the photoresist or covering certain regions of the photoresist with a mask, and exposing the uncovered regions of the photoresist through the mask.

Photolithographic masks used to fabricated integrated circuits and other microelectronic devices in the semiconductor industry can be fragile and/or expensive. In addition, mask fabrication processes can be time-consuming and/or delicate. In some circumstances, despite the care which is typically used during the manufacturing of such masks, fabrication errors produce mask defects. In other circumstances, mask defects can arise from handling and general use. If circuits or other devices were produced using the defective masks, the circuits or devices may not operate correctly. Given the time and expense required to fabricate a new mask, it may be more cost-effective to edit a defective mask than to fabricate an entirely new mask.

Mask defects generally include an excess of mask material in a region of the mask where there should be no material, and/or an absence of mask material where material should be present. In either situation, the gas field ion microscope (e.g., the He ion microscope) described herein may be used to inspect and/or repair a mask.

In some embodiments, the gas field ion microscope (e.g., He ion microscope) disclosed herein can be used to inspect the mask to determine whether a defect and present, and, if a defect is present, where the defect is. Many of the various advantageous featured provided by the gas field ion microscope (e.g., He ion microscope) disclosed herein are desirably used to image the mask.

In certain embodiments, in addition to imaging the mask during mask repair, the gas field ion microscope (e.g., He ion microscope) can be used during the repair process. As an example, the gas field ion microscope can be used to position the mask relative to a FIB so that the FIB can be used to add and/or remove material from the mask using gas surface chemistry process and/or etching processes, such as described above. As another example, the gas field ion microscope, in addition to initially imaging the mask to determine the existence and/or location of a defect, can be used to add and/or remove material from the mask using gas surface chemistry process and/or etching processes, such as described above. Optionally, the gas field ion microscope can be used to conduct certain repair steps (add material, remove material) while another instrument (e.g., a FIB) is used to conduct other repair steps (add material, remove material).

(xi) Defect Inspection

In general, during the process of fabricating a semiconductor article, the article is inspected for potential defects. Typically, the inspection is performed using an in-line tool which is always running and being fed wafers and that is fully automatic. The tool is often used to examine a small area of wafer whether there are regions where a defect will occur. This inspection is performed prior to defect review (see discussion below). The goal of defect inspection typically is to determine whether a defect may exist, as opposed to determining the exact nature of a given defect. During defect inspection, a region of a wafer is analyzed to see whether certain anomalous properties (e.g., voltage contrast properties, topographical properties, material properties) are exhibited by the sample, relative to other regions of the same wafer and/or to regions of other wafers. Typically, for a potential defect, the coordinates (e.g., X,Y coordinates) on the wafer are noted, and the location of the wafer is more carefully inspected during defect review.

A gas field ion microscope (e.g., a He ion beam) as described herein can be used to gather information about a sample during defect inspection. Such a microscope can be used for relatively high throughput and high quality defect inspection. The different contrast mechanisms provided by the gas field ion microscope (e.g., He ion microscope) can permit visualization of different types of defects and at higher resolution than can generally be observed using optical imaging techniques.

(xii) Defect Review

In general, if a sample is noted as having a potential defect during defect inspection, that sample is then submitted to defect review where the particular region(s) of the sample having the potential defect is(are) investigated to determine the nature of the defect. Based on this information, modifications to the process may be implemented to reduce the risk of defects in final product. Typically, defect inspection is conducted at slower speed and higher magnification than defect review, and may be automated or conducted manually to obtain specific information regarding one or more defects. The information is used to attempt to understand why anomalous results were obtained during defect review, and the nature and cause of the defects that gave rise to the anomalous results.

The gas field ion microscope (e.g., He ion microscope) described herein can be used to investigate a semiconductor article at various steps (e.g., each step) in the fabrication process. In particular, by detecting and analyzing one type of particle or multiple different types of particles (see discussion above), the gas field ion microscope (e.g., He ion microscope) can be used to determine topographical information about the surface of the semiconductor article, material constituent information of the surface of the semiconductor article, material constituent information about the sub-surface region of the semiconductor article, crystalline information about the semiconductor article, voltage contrast information about the surface of the semiconductor article, voltage contrast information about a sub-surface region of the semiconductor article, magnetic information about the semiconductor article, and/or optical information about the semiconductor article. The different contrast mechanisms provided by the He ion microscope can permit visualization of defects that would otherwise not appear using SEM-based techniques.

Using an ion microscope or ion beam as described herein can provide a variety of different advantages, which, in general, can reduce the time, cost and/or complexity associated with semiconductor article fabrication. Exemplary advantages associated with using the ion microscope or ion beam described herein include relatively high resolution, relatively small spot size, relatively little undesirable sample damage, relatively little undesirable material deposition and/or implantation, relatively high quality imaging in a relatively short time period, relatively high throughput.

(xiii) Circuit Testing

During the fabrication of a semiconductor article, the electrical conductivity and functionality of one or more features of the article may be tested. This process generally involves exposing the feature(s) to charged particles and then monitoring the rate at which the charge is accumulated. An open circuit will charge at a different rate relative to a closed circuit, allowing an open circuit to be identified and considered for more detailed inspection. A gas field ion microscope (e.g., a He ion microscope) as described herein may be used to apply the charge to the feature using the ion beam, and/or may be used to monitor whether the charge has leaked away (e.g., by monitoring the voltage contrast characteristics). Optionally, a flood gun can be used to apply the charge (see discussion above), and the gas field ion microscope can be used to monitor whether the charge has leaked away (e.g., by monitoring the voltage contrast characteristics).

B. Metal and Alloy Corrosion

He ion microscopes can be used to identify and examine metal corrosion in various devices and material. For example, metal fixtures and devices used in nuclear power plants, military applications, and biomedical applications can undergo corrosion due to the harsh environments in which they are deployed. He ion microscopes can be used to construct images of these and other devices based on the relative abundance of hydrogen (H) in the devices, which serves as reliable indicator of corrosion.

Typically, to construct images based on scattered H ions or atoms, a detector for these ions or atoms is positioned on the back side of a sample, opposite to an incident He ion beam. Exposing the sample to He ions generates scattered H atoms and ions from within the sample, and these scattered H atoms and ions can be detected and used to construct images of the sample. The H abundance images can then be used to assess the extent of corrosion within the sample. The small spot size and interaction volume of the He ion beam can result in high resolution H images of the sample to be obtained without damaging the sample.

C. Read/Write Structures for Data Storage

Read/write heads used in magnetic storage devices such as hard disks are fabricated to extremely high tolerances and must be inspected for manufacturing defects prior to installation. These devices frequently have very high aspect ratios; the short sides of such devices can be as small as 1 nm. He ion microscopes provide numerous advantages when used to image these devices during inspection. Among these are small spot sizes and interaction volumes, which can result in high resolution imaging of these tiny devices, a large depth of focus, which can allow in-focus imaging of the entire high-aspect-ratio device along its long dimension, and material information provided by measurement of scattered He ions and/or neutral atoms, which is used to verify that tiny circuit elements are properly connected.

D. Biotechnology

It is often desirable to determine elemental and/or chemical compositional information about a biological sample using a non-destructive technique. Examples of biological samples include tissue, nucleic acids, proteins, carbohydrates, lipids and cell membranes.

A gas field ion microscope (e.g., a He ion microscope) as described herein can be used to determine, for example, topographical information about a biological sample, material constituent information of a surface of a biological sample, material constituent information about the sub-surface region of a biological sample and/or crystalline information about a biological sample. For example, the gas field ion microscope can be used to image immuno-labeled cells and internal cell structures. The microscope can be used in this manner while providing certain advantages disclosed herein.

E. Pharmaceutical

Often, a therapeutic agent (e.g., small molecule drug) will form as a crystal (e.g., as it comes out of solution). It can be desirable to determine the crystalline structure of the crystallized small molecule because this can, for example, provide information regarding the degree of hydration of the small molecule, which, in turn, can provide information regarding the bioavailability of the small molecule. In certain instances, the crystalline information may turn out to demonstrate that the small molecule is actually in an amorphous (as opposed to crystalline) form, which can also impact the bioavailability of the small molecule.

Additionally or alternatively, it is often desirable to determine elemental and/or chemical compositional information about a biological sample using a non-destructive technique.

A gas field ion microscope (e.g., a He ion microscope) as described herein can be used to determine, for example, topographical information about a biological sample, material constituent information of a surface of a biological sample, material constituent information about the sub-surface region of a biological sample and/or crystalline information about a biological sample. The microscope can be used in this manner while providing certain advantages disclosed herein.

Computer Hardware and Software

In general, any of the analysis methods described above can be implemented in computer hardware or software, or a combination of both. The methods can be implemented in computer programs using standard programming techniques following the methods and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis methods can also be implemented as a computer-readable storage medium, configured with a computer program, where the storage medium so configured causes a computer to operate in a specific and predefined manner to perform the functions described herein.

Other Embodiments

While certain embodiments have been described, other embodiments are possible.

As an example, a SEM can be used in one or more of the preceding embodiments in combination with a gas field ion microscope. For example, a SEM can be used to produce secondary electrons, Auger electrons, X-ray photons, IR photons, visible photons and/or UV photons. Optionally, a SEM can be used to promote gas assisted chemistry. The gas field ion microscope can be configured in any of the operating modes disclosed herein, so that the SEM and the gas field ion microscope perform complementary functions.

As another example, while a W(111) tip has been disclosed, different crystallographic orientations of W can also be used in a tip. For example, a W(112), W(110) or W(100) tip may be used.

As a further example, in some embodiments, the ion microscope (e.g., gas field ion microscope) can include appropriate componentry to allow the microscope to be used in-line for the analysis of samples, such as samples relevant to the semiconductor industry (e.g., wafer samples). In certain embodiments, for example, the ion microscope may be automated with a high-speed loadlock for standard sized semiconductor wafers. In some embodiments, the system may include a wafer stage capable of putting a portion of a sample wafer under the ion microscope at high speed. The ion microscope may also include a scan system capable of high-speed rastering of metrology patterns. Optionally, the ion microscope may also include a charge neutralization scheme to reduce sample charging. The ion microscope may also include a wafer height control module for adjusting working distances. In certain embodiments, the system may be configured so that individual dies (e.g., having lengths on the order of 50 mm) can be imaged.

EXAMPLES

The following examples are illustrative and not intended as limiting.

1

A 25 mm length of emitter wire formed of single crystal W(111) (diameter 250 μm) was obtained from FEI Company (Hillsboro, Oreg.). The emitter wire was trimmed to a 3 mm length and set aside. A V-shaped heater wire was prepared as follows. A 13 mm length of polycrystalline tungsten wire (diameter 180 μm) was obtained from Goodfellow (Devon, Pa.) and cleaned by sonication for 15 minutes in distilled water to remove the carbon residue and other impurities. The wire was bent at its midpoint to form an angle of 115 degrees. The region near the apex of the "V" was electrochemically etched to prepare it for welding in a 1N aqueous solution of sodium hydroxide (NaOH) with an applied AC potential of 1 V and frequency 60 Hz for a duration of approximately 15 seconds. The heater wire was then removed from the etching solution, rinsed with distilled water, and dried.

The V-shaped heater wire was mounted in a fixture to ensure that the ends of the wire remained coplanar. The emitter wire was spot welded to the V-shaped apex of the heater wire. Then, the two ends of the heater wire were spot welded to two posts of a support base of the type shown in FIGS. 11A and 11B. The support base was obtained from AEI Corporation (Irvine, Calif.). The resulting assembly was then cleaned ultrasonically in distilled water and dried.

Following mounting of the emitter wire on the support base and cleaning of the support base, the end of the emitter wire was etched by an electrochemical process as follows. First, a resist material (e.g., nail polish obtained from Revlon Corporation, New York, N.Y.) was applied to a 0.5 mm length of the emitter wire, starting from the free end of the wire. A drop of resist was placed on the surface of a clean glass microscope slide, and the wire was dipped ten times into the resist solution, allowing the resist to dry slightly between each dipping. Care was taken to assure that the upper boundary of the resist was in the shape of a circle, and that the plane of the circle was maintained perpendicular to the axis of the wire. Following the last dip of the end of the emitter wire into the resist material, the wire was allowed to dry for 1 hour in air.

The support base with the resist-coated emitter wire attached was then attached to an etching fixture that included: (a) a translation apparatus for vertically translating the support base; (b) a dish; and (c) a counter electrode, formed of stainless steel to minimize undesired chemical reactions, that extended into the dish. The dish was filled with an etching solution to a level such that the solution was in contact with the counter electrode. Approximately 150 mL of solution was present in the etching fixture dish. The orientation of the support base was adjusted to ensure that the longitudinal axis of the emitter wire was approximately parallel to the vertical direction (e.g., the direction along which the translation apparatus provided for translation of the support base). Then, the support base was lowered toward the dish using the translation apparatus until the exposed emitter wire just contacted the etching solution. A high magnification camera mounted to the etching fixture allowed the resist layer and etching solution surface to be seen easily, and permitted accurate positioning of the emitter wire with respect to the solution surface.

Then, the wire was lowered an additional 0.2 mm into the etching solution. In this position, the resist coated portion of the emitter wire was fully immersed in etching solution.

The etching solution consisted of 150 mL of 2.5 M aqueous NaOH. To facilitate wetting, 1 drop of surfactant (PhotoFlo 200, obtained from Eastman Kodak, Rochester, N.Y.) was added to the etching solution. Gentle stirring of the etching solution using a magnetic stirrer was also employed during the etching process.

An external power supply was connected to the support base posts and the counter electrode. The voltage maximum amplitude, pulse duration, and waveform shape of the external power supply could be controlled to provide particular etching conditions in the etching fixture.

A sequence of AC pulses at a frequency of 60 Hz was applied to the emitter wire to facilitate the electrochemical etching process. First, one hundred pulses of duration 580 ms and amplitude 10 V were applied over a total time window of 5 minutes. The effect of the applied pulses was to increase the rate of the etching process. Portions of the emitter wire which were immersed in solution but not covered by resist material began to etch away. Because the emitter wire was positioned so that only a small uncoated region of the wire above the edge of the photoresist material was immersed in solution, localized etching of the emitter wire in this region was observed. As the electrochemical reaction proceeded, the diameter of the wire in this region began to get narrower due to the etching process.

Next, the pulse duration of the external power supply was adjusted to 325 ms, and sixty pulses of this duration were applied to the emitter wire over a total time window of 5 minutes. These pulses further promoted the electrochemical etching process, resulting in an etched region of the emitter wire with a very small diameter.

Finally, the pulse duration of the external power supply was adjusted to 35 ms, and individual pulses were applied to the emitter wire until etching was complete and the resist-coated portion of the emitter wire dropped off into the etching solution. The support base was then removed from the etching fixture, rinsed with distilled water, and dried under a flow of nitrogen.

The emitter wire—still attached to the support base—was then examined using a SEM to verify that the etched tip had suitable geometrical features. An AMRAY Model 1860 SEM operating at 5 keV and with a probe size of 3 nm was used to image the emitter wire tip. The support base was installed in a sample region of the SEM, on a sample manipulator equipped with a tilt and rotate manual stage. Images of the source were acquired from several different observation perspectives and magnifications to verify that the tip was approximately correctly shaped.

The SEM images were then used to characterize the average full cone angle, the average tip radius, and average cone direction, as discussed previously of the apex of the tip of the wire. The images used for these measurements were taken at a magnification of 65,000×, and along a viewing axis oriented at right angles to the axis of the emitter wire. The emitter wire tilt was adjusted using the SEM sample manipulator to ensure that the emitter wire was oriented orthogonally with respect to the viewing axis. To make average measurements of the tip's cone angle, cone direction, and radius, the SEM sample manipulator was used to rotate the tip by 45° (about the axis of the emitter wire) between successive images. This yielded a set of eight images of the tip—each from a different perspective—which were then used to determine the cone angle, radius of curvature, and cone direction of the tip.

Figure 38:
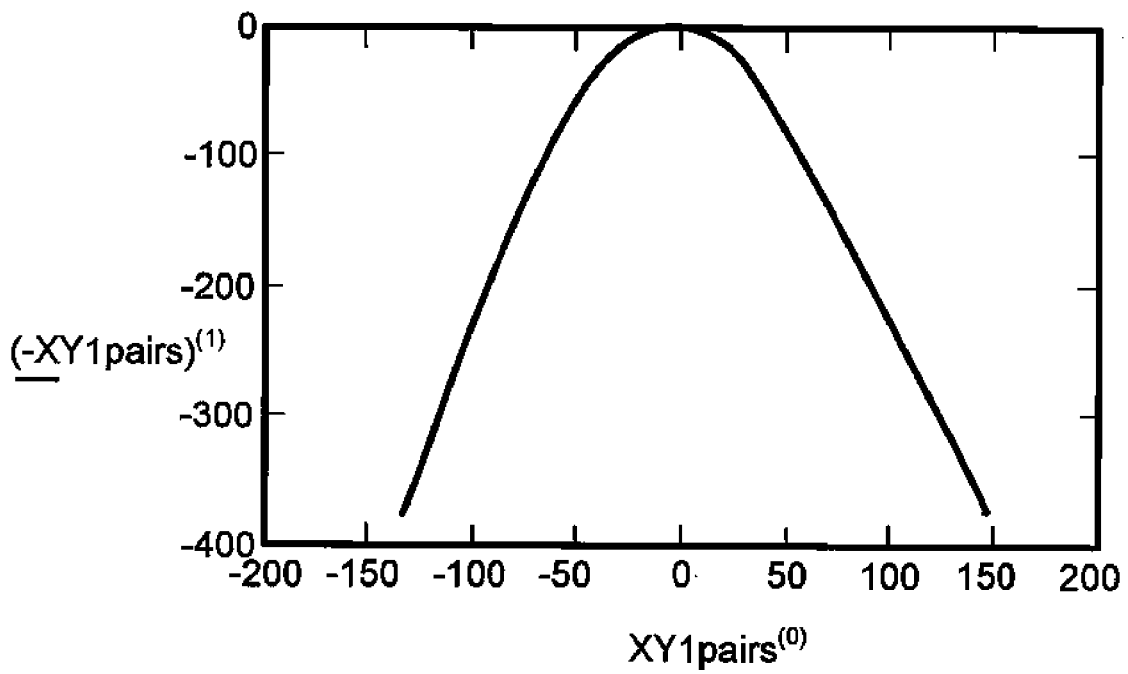
FIG. 38 is a digitized representation of the surface of an electrically conductive tip.

Four of the eight perspective images are shown in FIGS. 37A-37D. Each of the SEM images was digitized into bitmap format and then analyzed using custom algorithms developed using the MathCAD software package (PTC Inc., Needham, Mass.). First, each of the images was smoothed by applying a Gaussian convolution algorithm to reduce image noise, particularly noise due to vibrations of the SEM that occurred during imaging. A filtering step based upon a threshold intensity value was then applied to each of the images to emphasize the boundary between the tungsten tip and the black background. The tip boundary in each image was then determined as the set of nonzero-intensity (X,Y) points that formed a demarcation between image pixels corresponding to the tip and image pixels corresponding to the black (e.g., zero-intensity) background. One such set of (X,Y) points for one of the views of the tip is shown in FIG. 38. Similar sets of boundary points were determined for each of the eight perspective views of the tip.

Prior to calculating the slope of a given boundary curve, a smoothing algorithm was applied to the curve to ensure that the local slope of the curve was relatively insensitive to noise and other small signal variations. The smoothing algorithm consisted of fitting the raw (X,Y) data points to a fourth-order polynomial, which has been found to describe the shape of the tip well. The effect of the smoothing algorithm was to ensure that, on either side of the apex position, the first derivative of this curve is not excessively influenced by small variations in the shape.

Figure 39:
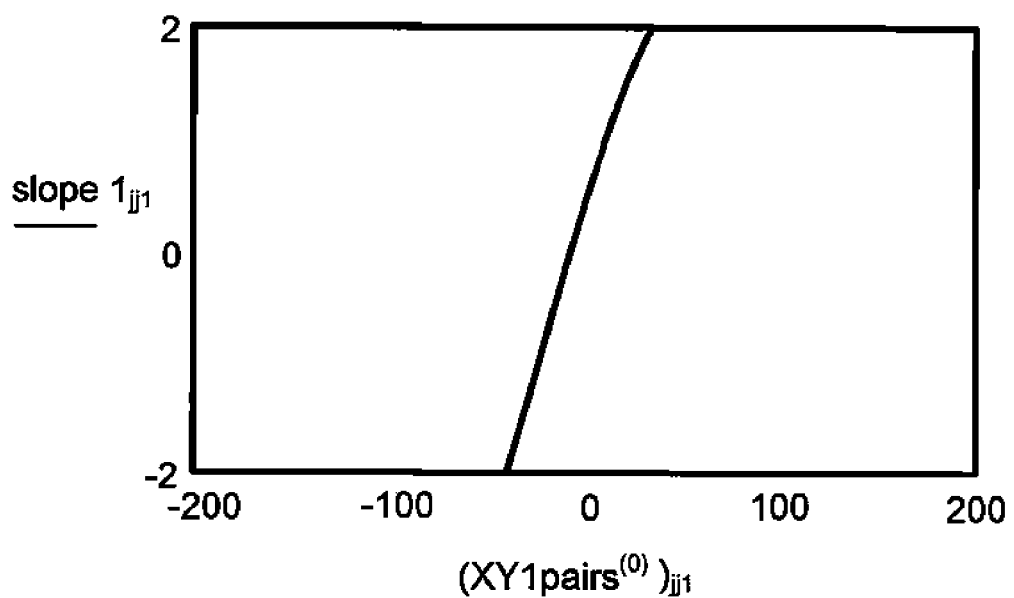
FIG. 39 is a plot of the slope of the slope of the surface shown in FIG. 38.

Following the smoothing step, the slope dY/dX was calculated at each X point along the boundary curves for each view using a finite difference algorithm. FIG. 39 shows a graph of the calculated slope at points along the boundary curve as a function of X for the boundary curve shown in FIG. 38.

For a particular view of the tip, the position on the boundary curve corresponding to that view where the slope acquired a zero value was identified as the tip apex and given the label $X_{apex}$. The position on the boundary curve corresponding to the (X,Y) point, closest to the tip apex, where the slope of the boundary curve acquired a value of 1 was given the label $X_{+1}$. The position on the boundary curve corresponding to the (X,Y) point, closest to the tip apex, where the slope of the boundary curve acquired a value of −1 was given the label $X_{-1}$.

These measured points were then used to determine geometrical parameters of the tip. The left radius of the tip in a particular view was calculated as the absolute value of the difference between $X_{+1}$ and $X_{apex}$, multiplied by 1.414. The right radius of the tip in a particular view was calculated as the absolute value of the difference between $X_{-1}$ and $X_{apex}$, multiplied by 1.414. Then, based on the left and right radius values, the radius of curvature of the tip in a particular view was calculated as the average of the left radius and the right radius values.

The calculations of the right radius, left radius, and tip radius of curvature were repeated for each of the eight perspective views of the tip. The average tip radius was then calculated as the average of the tip radius of curvature measurements in all of the views of the tip. For the tip shown in FIGS. 37A-37D, the average tip radius was determined to be 62 nm.

The standard deviation of all of the tip left and right radii was also calculated, and expressed as a percentage of the average tip radius. For the tip shown in FIGS. 37A-37D, the eccentricity was determined to be 11.9%.

The cone angle of the tip in each of the eight perspective views was also determined. In the boundary curve corresponding to each view, left and right tangent points on the boundary curve were located on the left and right sides of the tip apex, respectively, at positions 1 μm from the tip apex, measured along the Y direction, as discussed previously. The left cone angle of the tip in a particular view was then determined as the angle between a tangent to the boundary curve at the left tangent point and a line parallel to the Y axis and extending through the left tangent point. The right cone angle of the tip in a particular view was determined as the angle between a tangent to the boundary curve at the right tangent point and a line parallel to the Y axis and extending through the right tangent point. Finally, the full cone angle was determined as the sum of the magnitudes of the left and right cone angles.

The average full cone angle of the tip was then determined by calculating the average of the eight measurements of the full cone angle of the tip from the eight perspective views of the tip. For the tip shown in FIGS. 37A-37D, for example, the average full cone angle was determined to be 34.5°.

For a particular view of the tip, the cone direction was calculated as the half of the absolute value of the difference between the magnitudes of the left and right cone angles. Repeating this determination for each of the eight views of the tip yielded eight measurements of the cone direction of the tip. The average cone direction of the tip was then calculated as the average of these eight measurements of the cone direction. For the tip shown in FIGS. 37A-37B, the average cone direction was determined to be 2.1°.

A set of criteria based on the measurements of average tip radius, radius eccentricity, average cone angle, and average cone direction were used to determine whether a given tip would be accepted for use in the He ion microscope. In general, these criteria were as follows. The tip was accepted for use if the measured average cone angle was between 15° and 45°, the average tip radius was between 35 nm and 110 nm, the standard deviation of the tip radius of curvature measurements was less than 30%, and the average cone direction was less than 7°. Ultimately, the tip shown in FIGS. 37A-37D satisfied each of these criteria, and so this tip was accepted for use in the He ion microscope.

After verification of the tip geometrical properties, the tip was inspected in a custom-built FIM. The FIM included a mounting area for the support assembly supporting the tip, a high voltage power supply for biasing the tip, an extractor adjacent to the tip, and a detector for recording ion emission patterns from the tip.

The extractor was spaced from the tip by a distance of 5 mm and had an opening of 10 mm. The extractor was grounded to an external ground. The detector, a combination microchannel plate (MCP) and image intensifier (obtained from Burle Electro-Optics Inc., Sturbridge, Mass.) was positioned at a distance of 75 mm from the extractor.

The support assembly including the tip was installed in the FIM and the FIM chamber was evacuated to a background pressure of $1 \times 10^{-8}$ Torr. The tip was cooled to 77 K using liquid nitrogen as a coolant. After temperature equilibration, the source was heated to 900 K for 5 minutes to desorb condensates or other impurities that had formed on the tip during processing. Heating of the tip was accomplished by applying an electrical current to the heater wire to which the tip was welded. The current was applied using a power supply with constant power capabilities (Bertan Model IB-30A, available from Spellman High Voltage Inc., Hauppauge, N.Y.). Temperature measurements were made using an optical pyrometer (obtained from Pyro Corporation, Windsor, N.J.).

Subsequently, the tip was then allowed to cool again to 77 K, and the FIM extractor was grounded and the tip was biased to +5 kV relative to the extractor. High purity He gas (99.9999% pure) was introduced into the FIM chamber at a pressure of $1 \times 10^{-5}$ Torr. The tip bias was progressively increased to +29 kV in increments until a He ion image corresponding to He ions leaving the tip was observed on the detector. The FIM emission pattern corresponded to about 300 atoms on the surface of the tip. Based on the FIM pattern, the single crystal composition and W(111) orientation of the tip were verified.

Next, the tip was sharpened to obtain a terminal atomic trimer at the tip apex. Helium gas was pumped out of the FIM chamber until the background pressure in the chamber was less than $1.2 \times 10^{-8}$ Torr. The tip was then heated, via application of current to the heater wires as described above, to a temperature of 1500 K for 2 minutes. Oxygen gas was introduced into the FIM chamber in the vicinity of the tip at a pressure of $1 \times 10^{-5}$ Torr. After 2 minutes, the tip temperature was reduced to 1100 K. After 2 minutes at 1100 K, the oxygen supply was shut off and the tip was allowed to cool to approximately 77 K. During cooling, and about 15 minutes after the oxygen supply was shut off, the residual oxygen gas was pumped out of the FIM chamber until the background pressure in the chamber was less than $1.2 \times 10^{-8}$ Torr.

Once cooled to liquid nitrogen temperature, the extractor was biased as above, and the tip was again biased at +5 kV relative to the extractor. He gas at a pressure of $1 \times 10^{-5}$ Torr was introduced into the FIM chamber, and the FIM was once again operated as described above to acquire He emission images of the tip. The tip voltage was progressively increased until a FIM image of the tip was captured by the detector at a bias potential of about +18 kV on the tip.

The observed FIM pattern included adatoms—extra atoms in addition to the desired three atom trimer structure at the tip apex. The adatoms were slowly removed by field evaporation at the tip bias potential of +18 kV. During field evaporation, images of the tip were captured periodically and monitored to determine when to halt the field evaporation process. The adatoms were removed one by one until a clear FIM image of an atomic trimer at the tip apex was observed. In addition to the atomic trimer, the ridges of a 3 sided pyramid were also clearly observed.

The atomic trimer was slowly removed by further field evaporation of the tip. By increasing the tip bias slowly beyond +18 kV, the trimer atoms were removed one by one, resulting in rounded tip that was observed in FIM images recorded by the detector.

Figure 40:
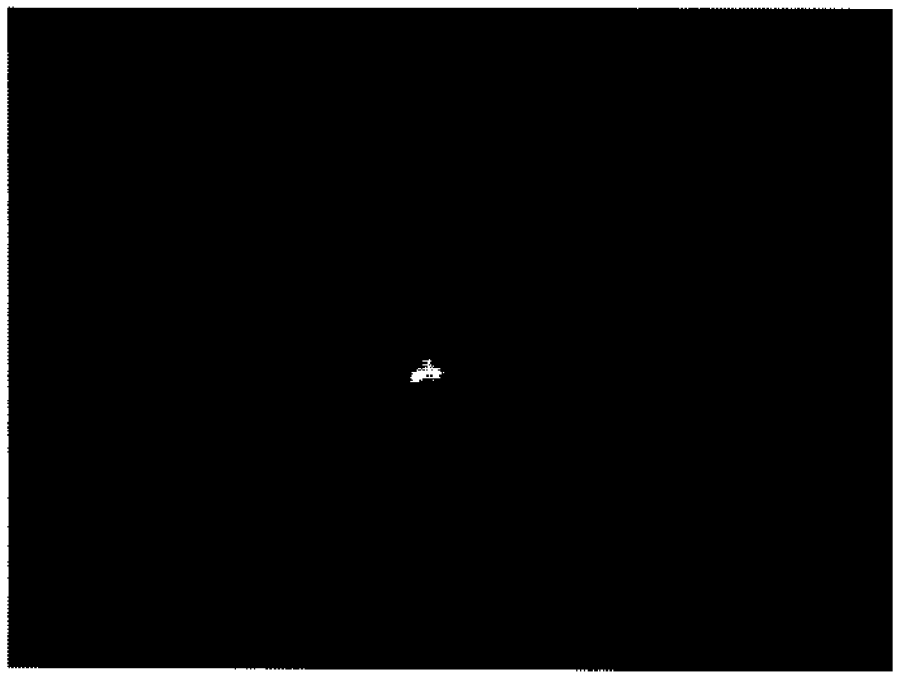
FIG. 40 is a field ion microscope image of an electrically conductive tip having a trimer as the terminal shelf at its apex.

The tip bias potential was further increased up to +28 kV. Field evaporation of the tip atoms continued during this process. At a bias potential of +28 kV, another atomic trimer was obtained at the apex of the tip. A FIM image of the second trimer is shown in FIG. 40. After the second trimer was obtained, the tip bias potential was reduced to attain the highest angular intensity in the FIM emission pattern. This occurred at a tip bias of +23 kV. The highest angular intensity was determined by adjusting the tip bias to obtain the largest observed brightness of a selected atom in the FIM emission pattern. The bias at which the highest angular emission intensity occurred was verified by measuring the He ion current from the trimer as the potential bias of the tip was adjusted. The He ion current was measured using a Faraday cup positioned in the path of the He ion beam.

The tip was then blunted to a nearly spherical end-shape by slowly increasing the bias potential of the tip above +28 kV and field evaporating atoms from the tip apex. Field evaporation was continued until another atomic trimer was obtained at the surface of the tip at a bias potential of +34 kV. To verify the repeatability of the tip re-building procedure, the sharpening process was repeated twice more to obtain new atomic trimers at the tip apex. After two successive trimer re-builds, the Helium gas supply was shut off, the applied tip bias was removed, the tip was allowed to warm to room temperature, and the FIM chamber pressure was slowly equalized to atmospheric pressure. The tip, still mounted in the support assembly, was stored on a shelf for a period of 2 weeks until it was used in a helium ion microscope.

The support assembly including the tip was installed in a helium ion microscope system similar to the system shown in FIGS. 1 and 5. The elements of the system were configured as follows. The extractor was positioned 1 mm from the tip, and had an opening of diameter 3 mm. The first lens of the ion optics was positioned at a distance 30 mm from the extractor. After passing through the first lens, ions passed through the alignment deflectors, which were configured as quadrupole electrodes. An aperture with an opening of diameter of 20 μm was positioned further along the path of the ions to selectively block a portion of the ion beam. A cross-over point of the ion trajectories was positioned at a distance of 50 mm in front of the aperture. The astigmatism corrector, configured as an octupole electrode, was positioned after the aperture to adjust astigmatism of the ion beam. Scanning deflectors, configured as octupole electrodes, were positioned after the astigmatism corrector to permit rastering of the ion beam across the surface of a sample. The second lens was positioned at a distance 150 mm from the aperture, and was used to focus the ion beam onto the surface of a sample. The second lens was shaped as a truncated right-angled cone, with a full cone angle of 90°.

Initially, the ion microscope system was evacuated so that the base pressure in the tip area was about $2\times10^{-9}$ Torr. The tip was cooled to about 80 K using liquid nitrogen. The extractor was grounded, and a bias of +5 kV, relative to the extractor, was then applied to the tip.

The tip was heated by applying electrical power of 8 W to the heater wire, until it was visibly glowing (corresponding to a tip temperature of about 1100 K). Photons emitted from the glowing tip were observed from a side port of the ion optics, using a mirror tilted at 45° with respect to a plane perpendicular to the longitudinal axis of the ion optics. The mirror was introduced for this purpose into the ion optics, in a position just below the alignment deflectors, via a side port in the ion column. The tip was tilted and shifted iteratively until the glowing tip was aimed roughly along the longitudinal axis of the ion optics. Proper alignment of the tip with the longitudinal axis was achieved when the glowing tip appeared as a circular point source. The tip was misaligned if it appeared to be rod-shaped.

The tip was allowed to cool while maintaining the tip at a potential bias of +5 kV relative to the extractor. Once the tip had cooled to liquid nitrogen temperature, He gas was introduced into the tip region at a pressure of $1\times10^{-5}$ Torr. The ion microscope system was run in SFIM mode, as described above, to generate an image showing the He ion emission pattern of the tip. The image indicated the shape of the tip to atomic precision. The alignment electrodes were used to raster the ion beam generated from the tip over the surface of the aperture. Sawtooth voltage functions were applied to each of the alignment deflectors to achieve rastering at a frame rate of 10 Hz, with a maximum voltage of the sawtooth functions of 150 V relative to the common external ground of the microscope system. The raster pattern scanned 256 points in each of two orthogonal directions transverse to the axis of the ion optics. The astigmatism corrector and the scanning deflectors were not used in this imaging mode.

To detect the ions that passed through the aperture, a sample of copper was placed under the second lens, and a MCP detector was positively biased (+300 V relative to the common external ground) to measure secondary electrons that left the copper sample due to the interaction between the sample and the He ions incident on the sample. The detector was positioned at a distance of 10 mm from the sample and oriented parallel to the plane of the sample.

Figure 41:
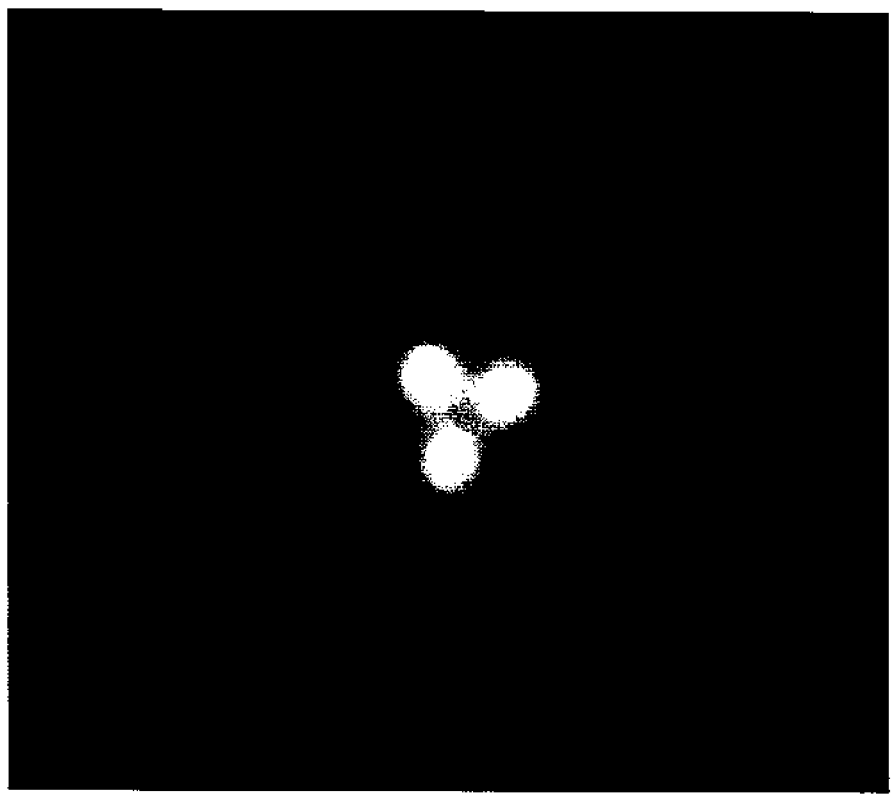
FIG. 41 is a scanning field ion microscope image of an electrically conductive tip having a trimer as the terminal shelf at its apex.

The acquisition system sampled the detector signal at each raster point and generated a SFIM image of the tip, which was displayed on a monitor. To facilitate imaging, the potential of the first lens in the ion column was set to be 77% of the tip bias. Then, as the tip bias was increased, the SFIM image was maintained with roughly constant magnification and intensity. While observing the SFIM image, the tip bias was slowly increased to eliminate undesired adatoms and to produce a tip with an atomic trimer at its apex. This trimer was removed by further increasing the tip bias potential to cause field evaporation of the tip atoms. Field evaporation continued until a new atomic trimer was formed on the apex of the tip at an applied tip potential of +23 kV. The resulting SFIM image of this tip is shown in FIG. 41.

With the alignment deflectors, astigmatism corrector, scanning deflectors, and second lens off (e.g., at zero potential relative to the common external ground of the microscope system), one atom of the trimer was selected and the tip was tilted and translated while the strength of the first lens was modulated by 100 V. The microscope system was operated in FIM mode and the detector collected FIM emission images of the tip. The tip was tilted and translated iteratively until the position of the center of the tip on the FIM images was unchanged from one image to another when the strength of the first lens was modulated.

Next, the aperture was put in place and the potentials applied to the alignment deflectors were adjusted to control the position of the ion beam at the aperture. The portion of the ion beam transmitted through the aperture was imaged by the detector, and the detector images were used to iteratively adjust the alignment deflectors.

The scanning deflectors were used to raster the ion beam transmitted through the aperture over the surface of the sample. A recognizable, high contrast feature (a copper grid) on the surface of the sample (part number 02299C-AB, obtained from Structure Probe International, West Chester, Pa.) was placed in the path of the ion beam under the second lens, and secondary electron images of the feature were measured by the detector using the configuration discussed above.

The strength of the second lens was adjusted to roughly focus the ion beam on the sample surface; the potential bias applied to the second lens was about 15 kV, relative to the common external ground. The quality of the focus was assessed visually from the images of the sample recorded by the detector. The alignment of the ion beam with respect to the axis of the second lens was evaluated by slowly modulating the strength of the second lens—at a frequency of 1 Hz and an modulation amplitude of about 0.1% of the operating voltage of the second lens—and observing the displacement of the feature. The beam alignment in the final lens was optimized by adjusting the voltages of the alignment deflectors. The alignment was optimized when the position of the center of the image measured by the detector did not change significantly during modulation of the strength of the second lens.

Then, the sample was imaged at a higher magnification by adjusting the strength of the second lens, so that the field of view on the sample was about 2 μm square. The asymmetry of the focus was minimized by adjusting the astigmatism corrector controls. These controls were adjusted while observing the image and specifically the sharpness of edges in all directions. The astigmatism correction was complete when the sharpness of the focused image was the same in all directions. Typically, no more than 30 volts were applied to the astigmatism corrector to achieve this condition. At this point, the helium ion microscope was fully operational.

Figure 42:
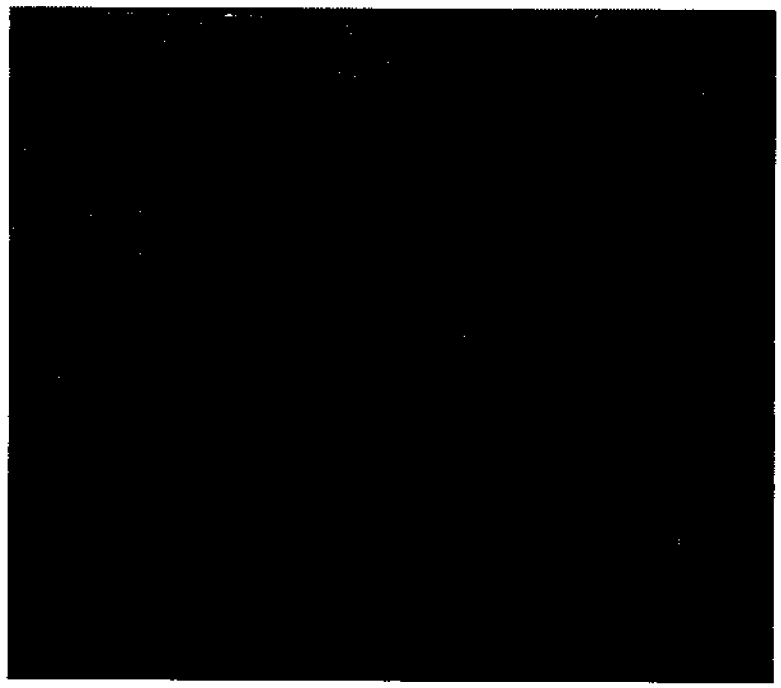
FIG. 42 is an image of a sample taken with a helium ion microscope configured to detect secondary electrons.
Figure 43:
FIG. 43 is an image of a sample taken with a helium ion microscope configured to detect secondary electrons.

The operational microscope was used to image a variety of samples. Sample images recorded by measuring secondary electrons are shown in FIGS. 42 and 43.

The imaging conditions included a wide range of beam currents (100 pA to 1 fA). The beam current was controlled by several methods. First, different apertures with different diameter holes were put into position using a motorized aperture mechanism. The aperture mechanism included apertures whose diameters ranged from 5 μm to 100 μm. Second, the first lens focus strength was adjusted to move the beam crossover closer to the aperture plane in the ion optics so that a larger ion current reached the sample. Conversely, the first lens focus strength was adjusted to move the beam further from the aperture plane so that less ion current passed through the aperture. Third, the helium gas pressure in the tip region was increased or decreased to increase or decrease the ion beam current, respectively.

The beam energy was typically selected for best angular intensity; the beam energy was typically in a range from 17 keV to 30 keV. The beam energy changed over time in response to the changing shape of the tip.

The type of detector used, and the detector's settings, were selected according to the type of sample that was examined with the ion microscope. To measure secondary electron images of a sample, an ET detector was used with a metal grid biased at about +300 V relative to the common external ground. A scintillator internal to the ET detector was biased at +10 kV relative to the external ground, and the gain of the internal PMT adjusted to produce the largest possible signal without saturation.

A MCP detector (obtained from Burle Electro-Optics, Sturbridge, Mass.) was also used to detect secondary electrons and/or scattered He from samples. The MCP grid, front face, and back face could each be biased relative to the external ground. The gain of the detector was attained by biasing the back face of the MCP positive with respect to the front end. Typical gain voltages were 1.5 kV. A collector plate adjacent to the back face was biased at +50 V with respect to the back face. From the collector plate, the detection signal was in the form of a small varying current which was superimposed on the large positive voltage. For collection of secondary electrons, the front face and grid of the MCP were biased to +300 V. For collection of scattered He, the front face and grid were biased to −300 V.

The raster speed was adjusted as necessary for best imaging conditions for each sample. The dwell time per pixel ranged from 100 ns to 500 µs. For shorter dwell times, the noise was reduced by averaging multiple scans. This was done for successive line scans, and for successive frame scans.

The image shown in FIG. 42 is an image of a plurality of carbon nanotubes on a silicon substrate. The image was acquired by detecting secondary electrons from the surfaces of the nanotubes. An ET detector was positioned at a distance of 8 mm from the sample and 15 mm off-axis from the ion beam, and oriented at an angle of 20° with respect to the plane of the sample. The He ion beam current was 0.5 pA and the average ion energy was 21 keV. The ion beam was raster-scanned with a dwell time of 200 µs per pixel, and the total image acquisition time was 200 s. The field of view of the image was 4 µm.

The image shown in FIG. 43 is an image of an aluminum post on a silicon substrate. The image was acquired by detecting secondary electrons from the surfaces of the nanotubes. A MCP detector of type described above, with the grid and front face biased at +300 V relative to the external ground, was positioned at a distance of 10 mm from the sample and oriented parallel to the plane of the sample. The He ion beam current was 0.5 pA and the average ion energy was 24 keV. The ion beam was raster-scanned with a dwell time of 200 µs per pixel. The field of view at the surface of the sample was 1 µm, obtained by applying a maximum voltage of 1 V to the scanning deflectors.

Figure 44:
FIG. 44 is a scanning field ion microscope image of an electrically conductive tip.
Figure 45:
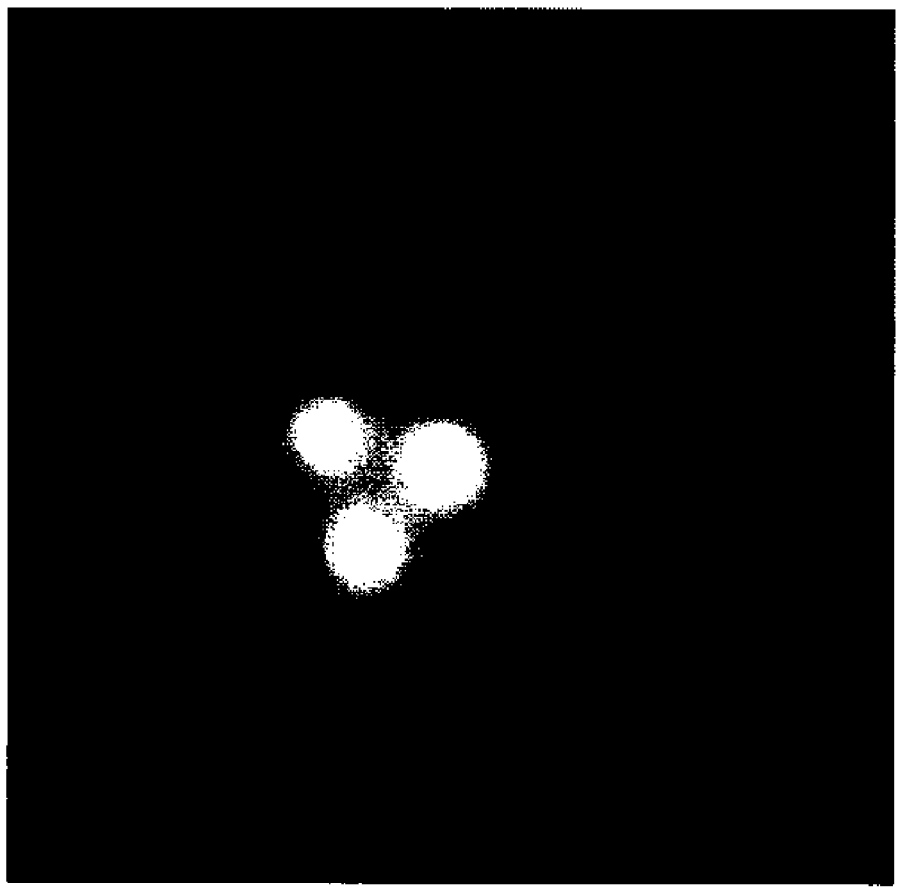
FIG. 45 is a field ion microscope image of an electrically conductive tip having a trimer as the terminal shelf at its apex.

Operation with this tip in the helium ion microscope continued for a period of weeks without any need to vent the system to service the ion source. As trimer atoms were removed, either intentionally or through normal usage, the end form of the tip became more spherical, as indicated in the SFIM image shown in FIG. 44. In-situ pyramid re-building (sharpening) was performed as needed by using the same heat and oxygen build recipe as was performed originally in the FIM to sharpen the tip. In general, each rebuilding process consumed less than 5 minutes of time, and the system was otherwise usable during this period of weeks. Overall, the tip was rebuilt more than eight times. An image of a rebuilt atomic trimer at the apex of the tip is shown in FIG. 45.

2

Figure 46:
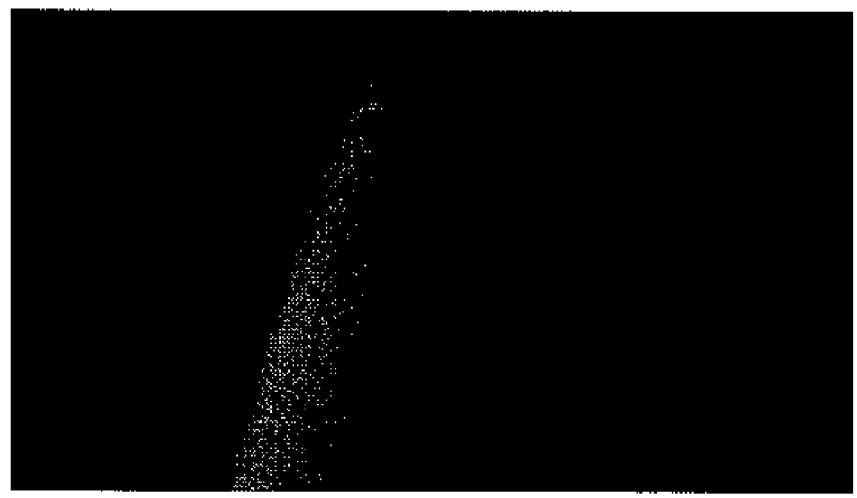
FIG. 46 is a scanning electron microscope image of an electrically conductive tip.

A W(111) tip was mounted in a support assembly and electrochemically etched following the procedure described in Example 1. A SEM image of the tip is shown in FIG. 46. Geometrical characterization of the tip was performed according to the procedure in Example 1. For this tip, the average tip radius was determined to be 70 nm. The tip was accepted for use based on the criteria in Example 1.

Figure 47:
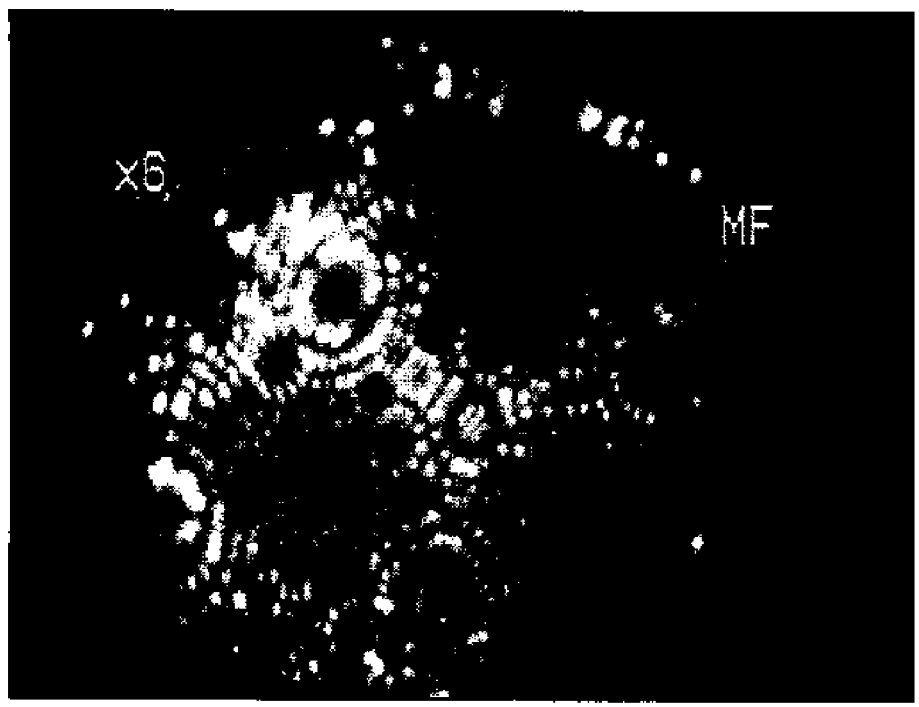
FIG. 47 is a field ion microscope image of an electrically conductive tip.

After verifying that the tip's geometrical properties were within acceptable limits, the source assembly including the etched tip was installed into the FIM described in Example 1. The configuration of the FIM was the same as the configuration discussed in Example 1, except where noted below. The potential bias on the tip, relative to the extractor, was slowly increased up to a potential of +21.8 kV. Field evaporation of tip atoms occurred as the potential was increased. After reaching +21.8 kV, the tip potential was reduced to +19.67 kV. The FIM image of the tip shown in FIG. 47 was acquired with the tip maintained at this potential. Using this image, the single crystal structure and correct orientation of the tip were verified.

Next, the tip was sharpened to produce an atomic trimer at the apex. Helium was pumped out of the FIM chamber, and the tip was heated by applying a constant current of 4.3 A to the tip for 20 seconds. A tilted mirror, installed in the FIM column and angled to re-direct light propagating along the column axis to a side port of the column, was used to observed the tip. No glow (e.g., photons emitted from the tip) was visible to the eye, so the tip was allowed to cool for 5 minutes. Then the tip was heated by applying a constant current of 4.4 A to the tip for 20 seconds. No glow was visible to the eye, so the tip was allowed to cool for 5 minutes. Then the tip was heated by applying a constant current of 4.5 A to the tip for 20 seconds. No glow was visible to the eye, so the tip was allowed to cool for 5 minutes. Then the tip was heated by applying a constant current of 4.6 A to the tip for 20 seconds. At this temperature, a glow was clearly visible from the tip. Thus, the current necessary to induce tip glow was established to be 4.6 A. The source was then allowed to cool for 5 minutes.

Next, a negative bias was applied to the tip while monitoring electron emission current from the tip. The bias was made increasingly negative until an electron emission current of 50 pA from the tip was observed. The tip bias at this current was −1.98 kV. With this bias still applied to the tip, the heating current of 4.6 A was applied to the tip. Tip glow was again observed after about 20 seconds. Heating of the tip extended another 10 seconds after tip glow was observed. The bias potential and heating current applied to the tip were then removed from the tip, and the tip was allowed to cool to liquid nitrogen temperature.

Figure 48:
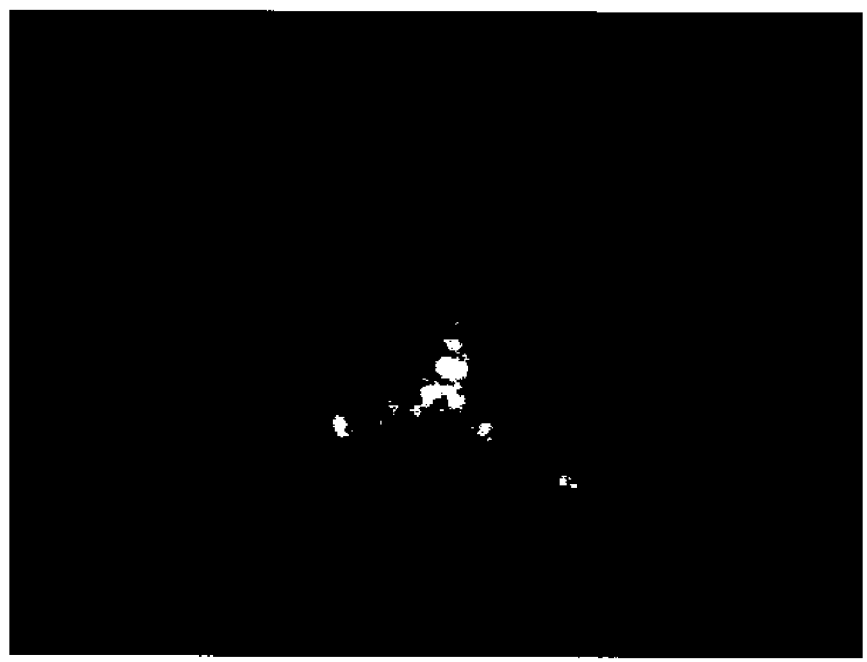
FIG. 48 is a field ion microscope image of an electrically conductive tip.

Once the tip had cooled, a positive bias of +5 kV relative to the extractor was applied to the tip. He gas was admitted to the FIM chamber in the vicinity of the tip, at a pressure of $1 \times 10^{-5}$ Torr. FIM images of the tip apex were acquired as described in Example 1. The FIM image was seen more clearly as the bias was increased. The image in FIG. 48 was observed at a tip bias of +13.92 kV. The image shows ridges of a pyramid and a bright central apex corresponding to an atomic trimer.

Figure 49:
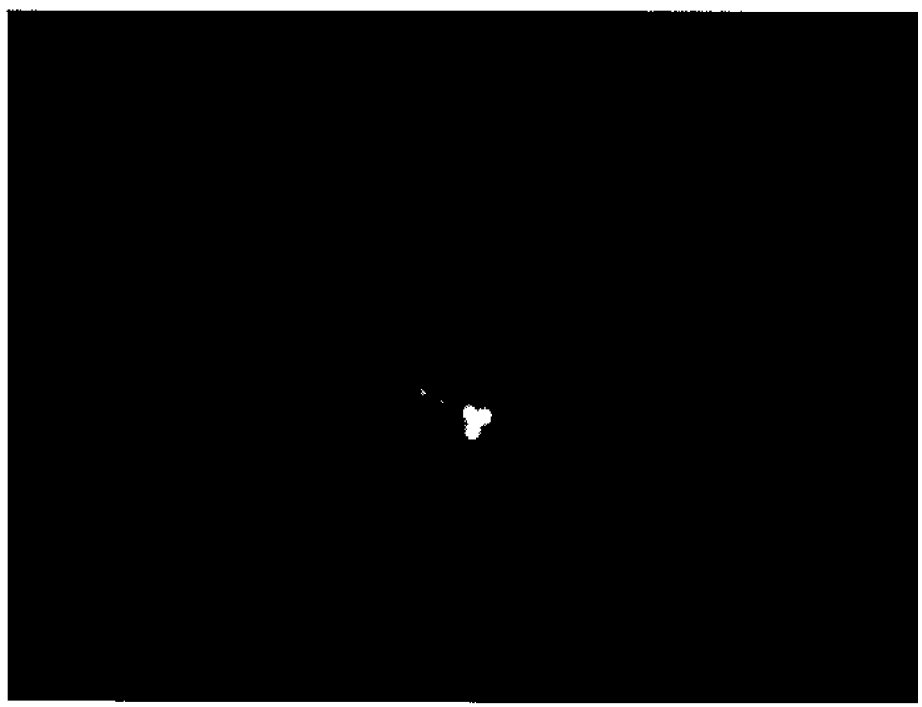
FIG. 49 is a field ion microscope image of an electrically conductive tip.

Some of the emitting atoms on the tip were loosely bound adatoms and were removed with increased field strength via field evaporation of tip atoms. The tip bias was further increased, and first and second trimers were removed by field evaporation to +21.6 kV. After reaching this potential, the tip bias was reduced to +18.86 kV and the FIM image of the tip in FIG. 49 was recorded.

Figure 50:
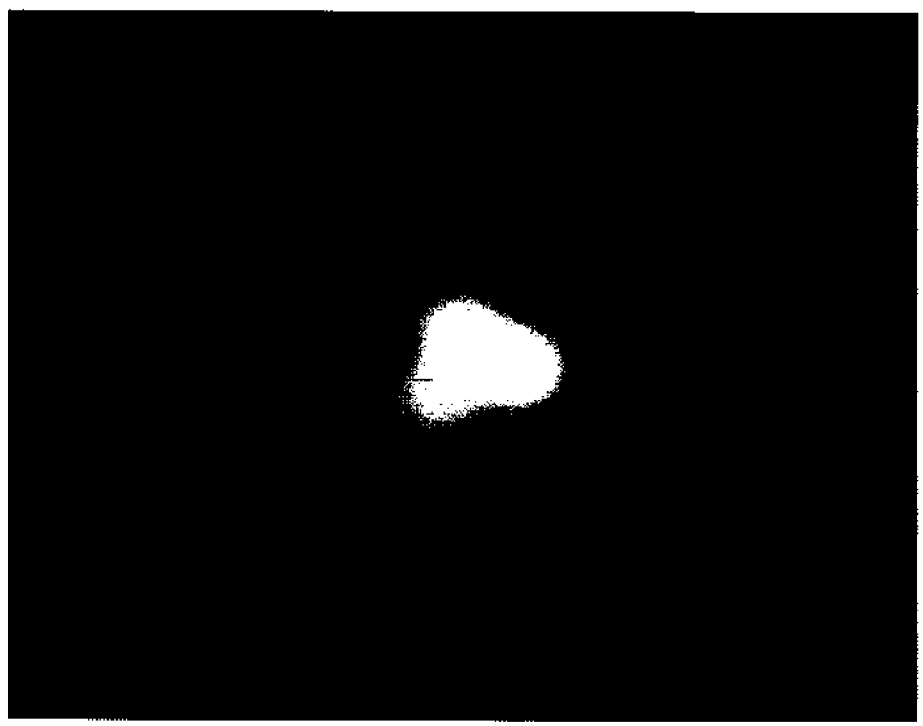
FIG. 50 is a scanning field ion microscope image of an electrically conductive tip having a trimer as the terminal shelf at its apex.

Based on the criteria identified in Example 1, the tip was identified as viable and removed from the FIM. About one month later, the tip was mounted into a helium ion microscope configured as described in Example 1. The trimer was re-built and evaporated multiple times in a process as described in Example 1, except that no oxygen gas was used. Instead, the trimer rebuild process relied upon applying a specific negative potential bias to the tip (to produce an electron emission current of 50 pA), while simultaneously heating the tip with a 4.6 A current applied to the heater wire, resulting in visible glow of the heater wire for 20 seconds. The tip remained in the helium ion microscope and provided over four weeks of usage without the need to vent the system to service the tip. During this period, the tip was rebuilt multiple times using the procedure involving a negative applied potential bias and heating, as discussed above. A SFIM image of a re-built trimer of the tip is shown in FIG. 50.

Figure 51:
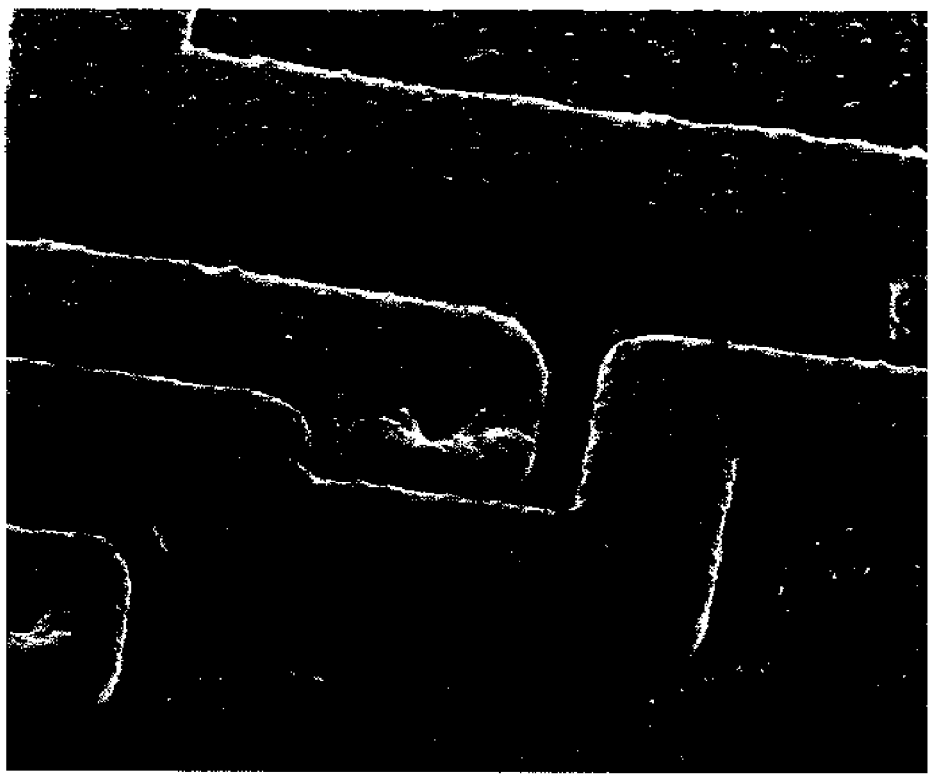
FIG. 51 is an image of a sample taken with a helium ion microscope configured to detect secondary electrons.

An image of a semiconductor sample recorded using a He ion microscope with this tip is shown in FIG. 51. The sample was included lines of aluminum metal deposited on the surface of a silicon oxide substrate. An unknown coating was deposited atop each of these materials.

Scan voltages of maximum amplitude 1 V were introduced on the scanning deflectors to produce a 10 μm field of view on the sample. The potentials of the first and second lenses, the alignment deflectors, and the astigmatism corrector were adjusted to control the portion of the He ion beam that passed through the aperture, and to control the quality of the beam focus at the sample position, as described in Example 1. The sample was tilted and rotated during imaging to reveal the three dimensional nature and the details of the sidewalls.

The image shown in FIG. 51 was recorded by measuring secondary electrons from the surface of the sample. A MCP detector was positioned at a distance of 10 mm from the sample, and oriented parallel to the surface of the sample. The MCP grid and front surface were biased at +300 V, relative to the common external ground. The He ion beam current was 4 pA and the average ion energy was 21.5 keV. The total image acquisition time was 30 s.

Figure 52:
FIG. 52 is an image of a sample taken with a helium ion microscope configured to detect secondary electrons.

An image of another semiconductor sample taken using this tip is shown in FIG. 52. The sample was a multilayer semiconductor device with surface features formed of a metal. The image was recorded by measuring secondary electrons that left the sample of the sample due to the interaction of the sample with the incident He ions. Maximum scan voltages of 150 volts were applied to the scanning deflectors to produce a 1.35 mm field of view at the sample surface.

The sample was observed from a top down perspective, which shows many features on the surface of the sample. To record the image, a MCP detector with grid and front surface biased at +300 V relative to the common external ground was positioned at a distance 10 mm from the sample, and oriented parallel to the surface of the sample. The He ion beam current was 15 pA and the average ion energy was 21.5 keV. The ion beam was raster-scanned with a dwell time of 10 μs per pixel.

3

The tip in this example was prepared and aligned in the helium ion microscope using a procedure as described in Example 2. Geometrical characterization of the tip was performed according to the procedure in Example 1. The tip was accepted for use based on the criteria in Example 1.

By direct or extrapolated measurement, it was possible to acquire images of a sample at a known beam current and for a known acquisition time. The beam current was carefully monitored using a Faraday cup in conjunction with a picoammeter (Model 487, Keithley Instruments, Cleveland, Ohio). The He pressure in the tip region was also carefully monitored using a Baynard Alpert-type ionization gauge (available from Varian Vacuum Inc, Lexington, Mass.). In a regime in which the He ion current was too low to be accurately measured (e.g., less than about 0.5 pA), the ion current was determined by extrapolation based on the measured He gas pressure. Typically, the He gas pressure and He ion current are linearly proportional to one another, and the linear relationship is consistent from one tip to another.

Figure 66:
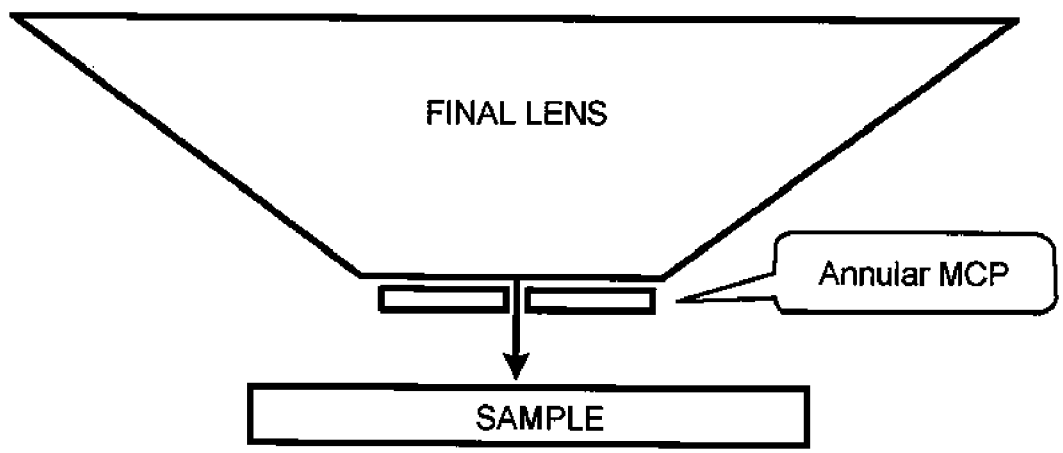
FIG. 66 is an embodiment of a detector configuration configured to detect secondary electrons.

The sample was a gold grid sample with topographic features (part number 02899G-AB, obtained from Structure Probe International, West Chester, Pa.). The sample was imaged by measuring secondary electron emission from the sample surface in response to incident He ions. To record images, a 40 mm diameter annual, chevron-type MCP detector (obtained from Burle Electro-Optics, Sturbridge, Mass.) was positioned at a distance 10 mm from the sample, and oriented parallel to the surface of the sample. The detector consumed a solid angle of about 1.8 steradians and was symmetric with respect to the ion beam. The detector was mounted directly to the bottom of the second lens, as shown in FIG. 66. The front surface of the MCP was biased positively (+300 V) with respect to the common external ground, and there was also a positively biased (with respect to the common external ground) internal metal grid (+300 V).

Figure 53:
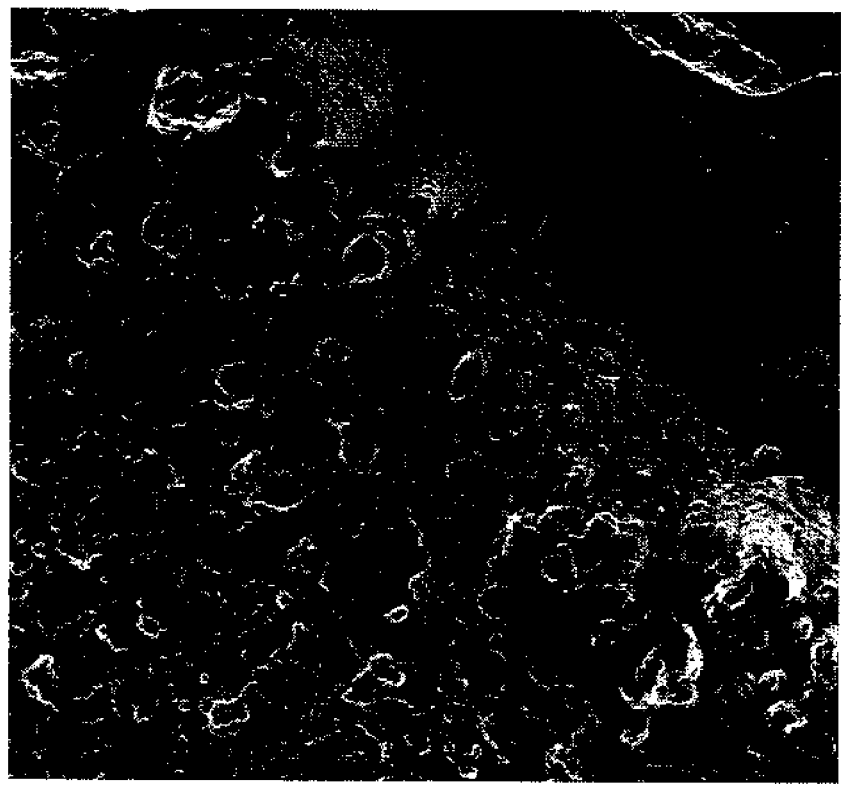
FIG. 53 is an image of a sample taken with a helium ion microscope configured to detect secondary electrons.
Figure 54:
FIG. 54 is an image of a sample taken with a helium ion microscope configured to detect secondary electrons.
Figure 55:
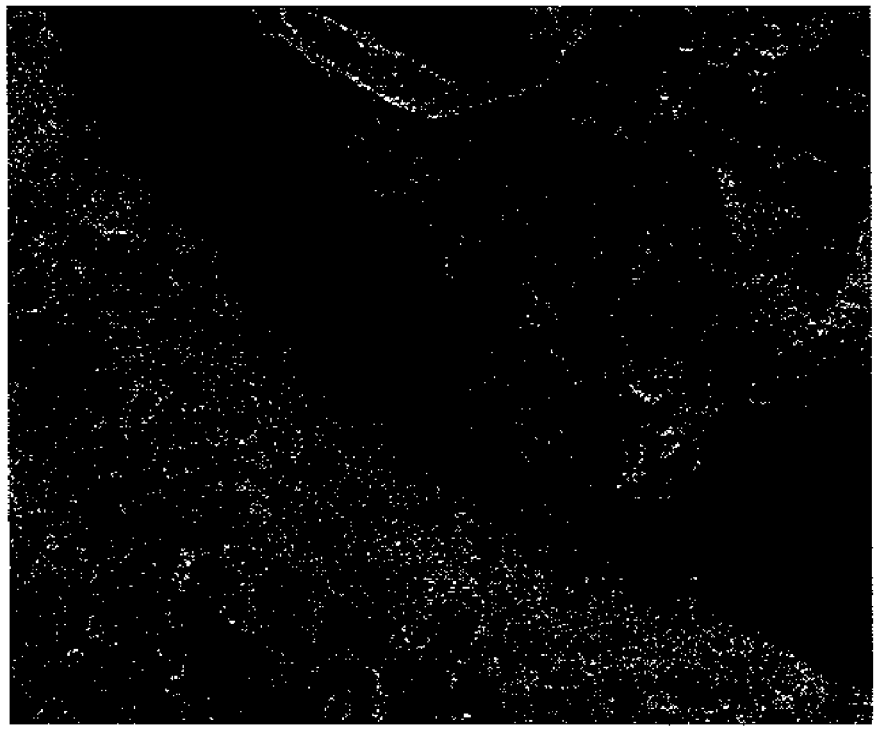
FIG. 55 is an image of a sample taken with a helium ion microscope configured to detect secondary electrons.

The average ion energy was 20 keV. Images of the sample were measured with beam currents of 1 pA, 0.1 pA and 0.01 pA, respectively, and are shown in FIGS. 53, 54, and 55, respectively. The total image acquisition times were 33 seconds, 33 seconds, and 67 seconds, respectively.

For the first two images (FIGS. 53 and 54), the image size was 1024×1024 pixels. For the third image (FIG. 55), the image size was 512×512 pixels. In each image, maximum scan voltages of about 2 V were applied to the scanning deflectors to produce a 20 μm field of view at the sample surface.

To confirm that scattered helium ions and/or neutral atoms did not contribute significantly to these recorded images, the grid and MCP bias potentials were changed to −50 V, whereupon no signal was observed. The noise content of these images was recognized as being lower than the noise content that would be attained with SEM images of the sample for the same current, the same number of pixels, and the same total acquisition time.

4

Figure 56:
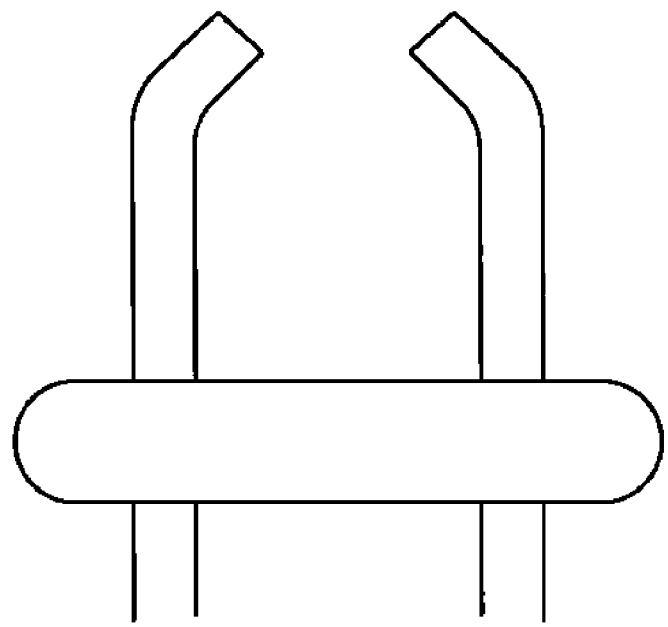
FIG. 56 is a schematic representation of a support for a tip.

A tip was mounted in a support assembly and fabricated using methods as described in Example 1, except that in the support assembly, the two posts attached to the source base were pre-bent towards each other, as shown in FIG. 56. The bend permitted the heater wire to span a significantly shorter length. The heater wire was as described in Example 1, a polycrystalline tungsten wire with a diameter of 180 μm. With the bent posts, a heater wire length of 5 mm was used. The advantage of a shorter heater wire length that the stiffness of a length of wire increases as the length of the wire decreases. The emitter wire was affixed in the usual way as described in Example 1.

The increased stiffness of the shorter heater wire was observed by applying the same force to a two different tips, one mounted in a support assembly of the type described in Example 1, and the other mounted in the support assembly shown in FIG. 56. The deflections of the two tips in response to the applied force were compared. In comparison to the Example 1-type support base, the bent post support assembly was deflected by an amount that was a factor of 6 smaller. Consequently the natural vibration frequency of the bent post-type support assembly (approximately 4 kHz) was about 2.5 times higher than the natural frequency of the support assembly of Example 1. With a higher frequency, the support base and the tip moved in unison (e.g., with negligible phase shift) when excited at vibrational frequencies substantially below the natural vibration frequency. When implemented in a He ion microscope, the relatively low vibration of the tip in the bent post source assembly reduced the likelihood that ion microscope images would have appreciable image artifacts, such as beam landing errors, due to tip vibrations.

5

A tip was prepared according to the procedure described in Example 1, except that a different heater wire was used. The heater wire used in this example had a diameter that was larger than the diameter of the heater wire in Example 1 by about 25%. The thicker heater wire was less compliant with respect to vibrational motion, because, in general, the stiffness of a wire increases with increasing diameter. In addition, the thicker heater wire was formed from a tungsten-rhenium alloy (74% Tungsten, 26% Rhenium). The alloy wire had a significantly higher electrical resistivity than the tungsten heater wire of Example 1; the overall heater wire resistance was measured to be approximately 0.5 ohms. Suitable tungsten-rhenium alloy wires were obtained from Omega Engineering (Stamford, Conn.).

The thicker heater wire increased the natural frequency of the support assembly, including the tip, from about 1.5 kHz (Example 1) to about 2.2 kHz (this example). When implemented in the He ion microscope, the relatively low vibration of the tip in the source assembly with this heater wire assembly reduced the likelihood that ion microscope images would have appreciable image artifacts, such as beam landing errors, due to tip vibrations.

6

Figure 57:
FIG. 57 is a schematic representation of a support for a tip.

A tip was formed by a process as described in Example 1, except that the heater wire was replaced by blocks of pyrolytic carbon (obtained from MINTEQ International Pyrogenics Group, Easton, Pa.). The posts of the source assembly were bent towards one another and were machined to have parallel flat surfaces. To mount the emitter wire, the posts were pried apart and two blocks of pyrolytic carbon were inserted between the posts. The emitter wire was placed between the carbon blocks and then the posts were released. The compressive force applied to the carbon blocks by the posts held the blocks and the emitter wire in place on the support assembly, preventing relative motion of the emitter wire with respect to the support base. A portion of the support assembly, including the bent posts, the two carbon blocks, and the emitter wire, is shown in FIG. 57.

The size of the pyrolytic carbon blocks was chosen so that the carbon blocks and the emitter wire were in compression. Without the carbon blocks in place, the space between the bent posts was 1.5 mm. The carbon blocks each had a length 700 μm along a direction between the two bent posts. The emitter wire had a diameter of 250 μm.

The pyrolytic carbon blocks were oriented with respect to the bent posts for maximum electrical resistance and minimum thermal conductivity (e.g., with carbon planes in the pyrolytic carbon blocks oriented approximately perpendicular to a line joining the posts). The electrical resistance of the support assembly was measured to be 4.94 ohms at 1500 K, which is larger than the resistance of the support assembly of Example 1 (0.56 ohms). The power required to heat the tip to 1500 K was 6.4 W (compared to about 11 W required to heat the tip in Example 1 to 1500 K). The tip was held relatively rigid with respect to the source base, due to the absence of a heater wire. The natural vibration frequency of the support assembly was greater than 3 kHz.

When implemented in the helium ion microscope, the relatively low vibration of the tip in this source assembly—held in position by compressive force applied to pyrolytic carbon blocks on either side of the tip—reduced the likelihood that ion microscope images would have appreciable image artifacts, such as beam landing errors, due to tip vibrations.

7

A tip was prepared following a procedure as described in Example 1, and characterization of geometrical tip properties was performed in as described in Example 1. The tip was accepted for use based on the criteria in Example 1.

The tip was sharpened in the FIM using the procedure described in Example 1. The tip was then installed and configured in the He ion microscope. The microscope system was configured as described in Example 1, with changes to the configuration noted below.

The microscope system was configured to measure secondary electrons that left the sample due to the interaction of the sample with the incident He ions. A MCP detector (similarly configured to the detector described in Example 3) was used to record sample images.

The sample was steel, and was spherical in shape and of uniform composition. The He ion beam current was 1.0 pA and the average ion energy was 20 keV. The ion beam was raster-scanned with a dwell time of 10 μs per pixel. The maximum potentials applied to the scanning deflectors (about 100 V) yielded a field of view at the surface of the sample of about 1 mm.

Figure 58:
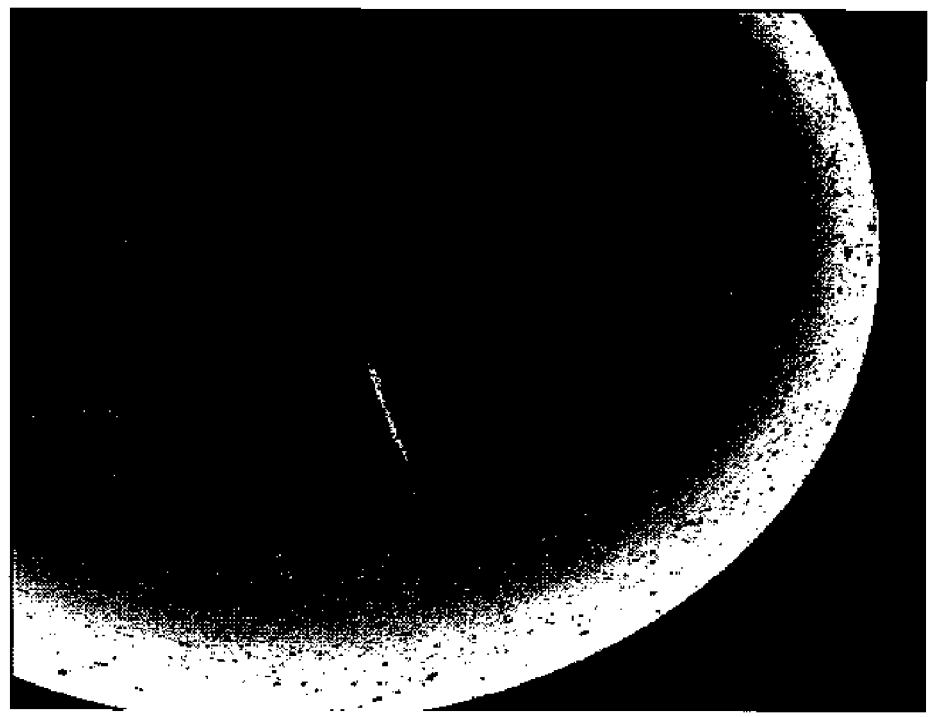
FIG. 58 is an image of a sample taken with a helium ion microscope configured to detect secondary electrons.

An image of the sample is shown in FIG. 58. The image reflects a measurement of the total secondary electron yield for the sample. The image reveals enhanced secondary electron yield at the right-hand edge. The enhanced yield resulted from the increased path length of the ion beam near the surface of the sample, where secondary electrons can escape. The secondary electron yield was found to increase approximately in proportion to $\sec(\alpha)$, where $\alpha$ represents the angle between the incident He ion beam and a normal to the surface of the sample.

Figure 59A:
FIG. 59A is an image of a sample taken with a helium ion microscope configured to detect secondary electrons.
Figure 59B:
FIG. 59B is an image of a sample taken with a scanning electron microscope.

Images of a second sample are shown in FIGS. 59A and 59B. The imaging conditions for the sample shown in FIG. 59A were as discussed above in connection with the first sample in this example.

At energies of 20 keV, the He ion beam penetrated deeply into the sample (about 100 nm) before diverging significantly.

As a result, the edges of sample images showed a relatively narrower bright edge effect (e.g., reduced edge blooming). For example, the image in FIG. 59A was recorded from the He ion microscope, while the image in FIG. 59B was recorded using a standard SEM. In both images, the signal arises from a measurement of secondary electrons only. In the SEM image shown in FIG. 59B, the SEM was operated under imaging conditions which were 2 keV electron beam energy and 30 pA beam current.

The bright edges were observed to be appreciably narrower in the He ion microscope images, which is believed to be a consequence of the smaller interaction volume of He ions at the surface of the sample in comparison to incident electrons. The He ion beam remains relatively collimated as it passes into the sample. In contrast, the SEM's electron beam yields an interaction volume which is considerably wider immediately adjacent to the surface of the sample. As a result, secondary electrons generated by the incident electron beam arise from a surface region that extends several nanometers from the nominal electron beam position on the surface. Consequently, the SEM's bright edge effect was substantially wider, as can be seen by visually comparing the images in FIGS. 59A and 59B.

Figure 67A:
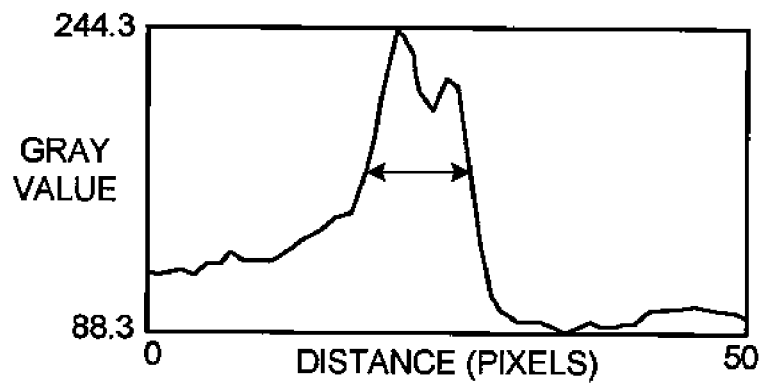
FIG. 67A is a graph of secondary electron intensity at varying sample locations based on the image in FIG. 59A.
Figure 67B:
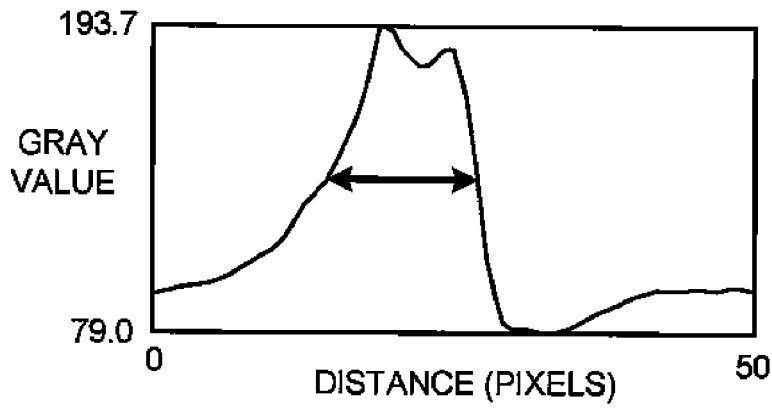
FIG. 67B is a graph of secondary electron intensity at varying sample locations based on the image in FIG. 59B.

To numerically compare the bright edge effect in these two images, a line scan was performed across a common edge feature in each of the images. The results are shown in FIGS. 67A and 67B, which correspond to FIGS. 59A and 59B, respectively. The line scan area was 1 pixel wide by 50 pixels long. The intensity peak in the line scan—which corresponds to the edge feature—has a full width at half-maximum (FWHM) that is 40% wider in the SEM image than in the corresponding He ion microscope image. As noted above, the reduced edge width observed in the He ion microscope image is a result of the smaller interaction volume of He ions at the surface of the sample, relative to electrons.

8

A tip was prepared following a procedure as described in Example 1, and characterization of geometrical tip properties was performed as described in Example 1. The tip was accepted for use based on the criteria in Example 1.

The tip was sharpened in the FIM using the procedure described in Example 1. The tip was then installed and configured in the He ion microscope. The microscope system was configured as described in Example 1, with changes to the configuration noted below.

The microscope system was configured to measure secondary electrons that left the sample due to the interaction of the sample with the incident He ions. A MCP detector (as described in Example 3) was used to record sample images.

A variety of samples were measured to quantitatively determine the secondary electron yield for a number of materials. Each sample consisted of a flat piece of the material to be tested. Positioned above the sample, at a distance of 2 mm was a metal screen with a low fill-factor (e.g., mostly open space). A pico-ammeter (Keithley Instrument Corporation, Cleveland, Ohio) was used measured the sample current in conjunction with a Faraday cup, which was integrated into each sample by machining a groove into the surface of each sample.

Each experiment began with a measurement of the He ion current by positioning the He ion beam such that it was incident on the Faraday cup in each sample. Next, the He ion beam was rastered over the sample while a variable bias, relative to the common external ground, was applied to the screen, and the secondary electron current from the sample was measured.

Figure 60:
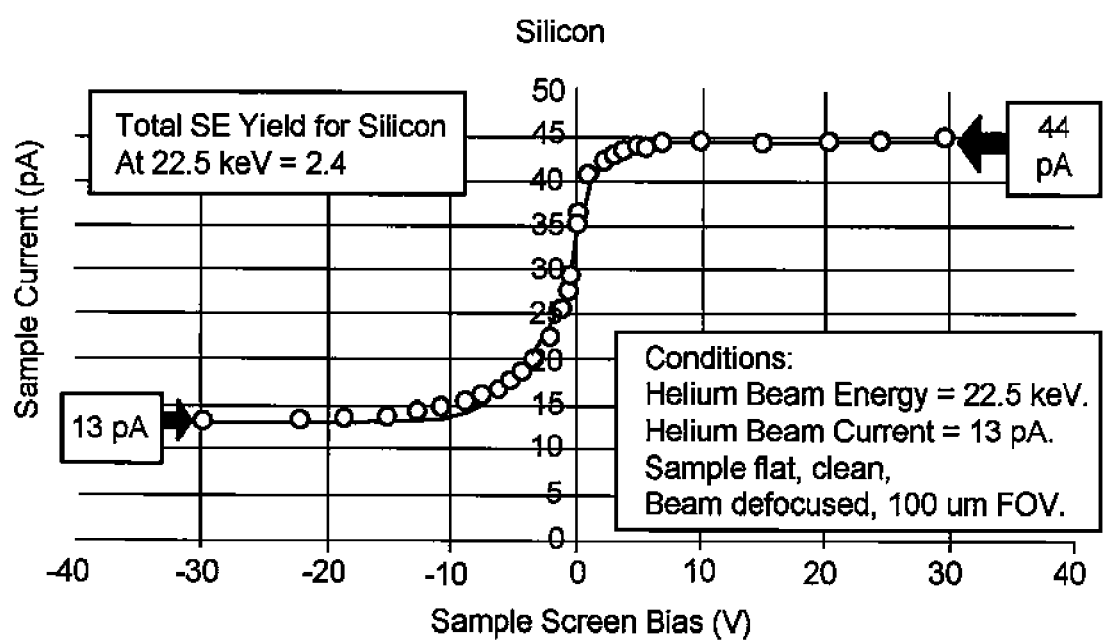
FIG. 60 is a graph of secondary electron current from a sample.

The He ion beam was intentionally defocused (to a spot size of 100 nm) to minimize any contamination or charging artifacts. The screen bias potential was adjusted in increments from −30 V to +30 V, and the secondary electron current was measured for each bias potential. Each measurement was conducted with a He ion beam energy of 22.5 keV and a beam current of 13 pA. The graph in FIG. 60 shows the results for a silicon sample.

On the left of the graph, where the screen was biased negatively, all of the secondary electrons that left the sample due to the interaction of the sample with the incident He ions were returned to the silicon sample. The He ion beam current and the secondary electron current were approximately equal, so that negligible amounts of free secondary ions and scattered helium ions were produced. On the right of the graph, where the screen was biased positively, all of the secondary electrons that left the sample due to the interaction of the sample with the incident He ions were accelerated away from the sample. The measured sample current was the sum of the He ion current and the secondary electron current. Based on these measurements, the secondary electron yield for a 22.5 keV helium beam incident (at a normal incidence) on a flat silicon sample is approximately (44−13)/13=2.4.

A similar measurement procedure was followed for a variety of materials under similar measurement conditions. The results are summarized in the table below.

| Material | Secondary Electron Yield |
| --- | --- |
| Aluminum | 4.31 |
| Silicon | 2.38 |
| Titanium | 3.65 |
| Iron | 3.55 |
| Nickel | 4.14 |
| Copper | 3.23 |
| Indium | 4.69 |
| Tungsten | 2.69 |
| Rhenium | 2.61 |
| Platinum | 7.85 |
| Gold | 4.17 |
| Lead | 4.57 |

Figure 61A:
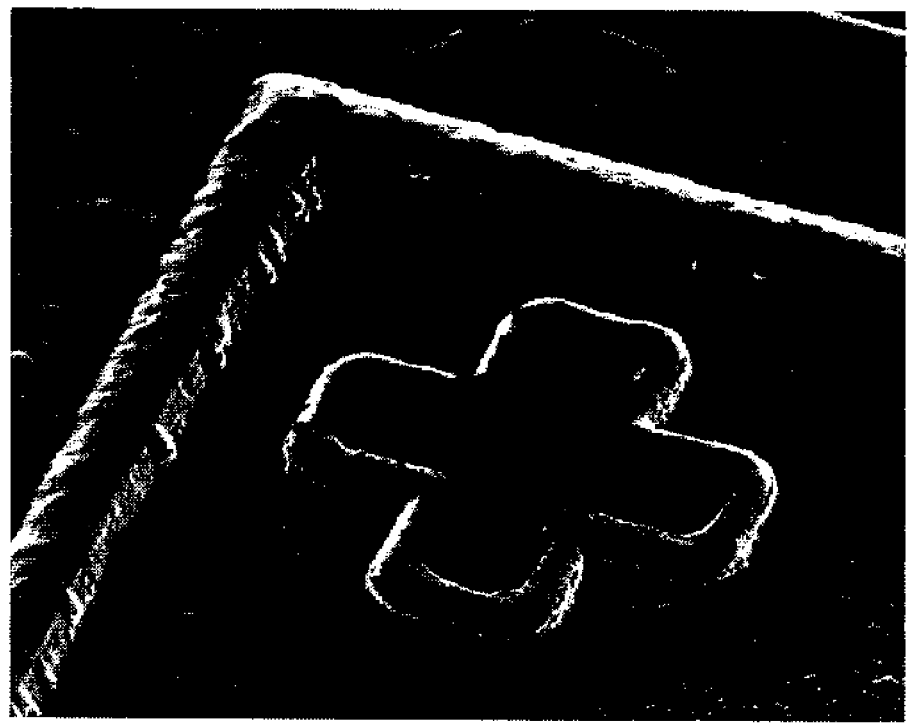
FIG. 61A is an image of a sample taken with a helium ion microscope configured to detect secondary electrons.

These relatively large secondary electron yields, and the wide range of values for different materials, account for the general observation that He ion microscope images based on detection of secondary electrons provide a good way to distinguish different materials. As an example, FIG. 61A is a secondary electron image of an alignment cross on the surface of a substrate, recorded using the helium ion microscope. Scan voltages of maximum amplitude of about 1.5 V were introduced on the scanning deflectors to produce a 15 μm field of view on the sample. A MCP detector was positioned at a distance of 10 mm from the sample, and oriented parallel to the surface of the sample. The grid and front face of the MCP were biased at +300 V, relative to the common external ground. The He ion beam current was 5 pA and the average ion energy was 27 keV. The ion beam was raster-scanned with a dwell time of 150 μs per pixel.

Figure 61B:
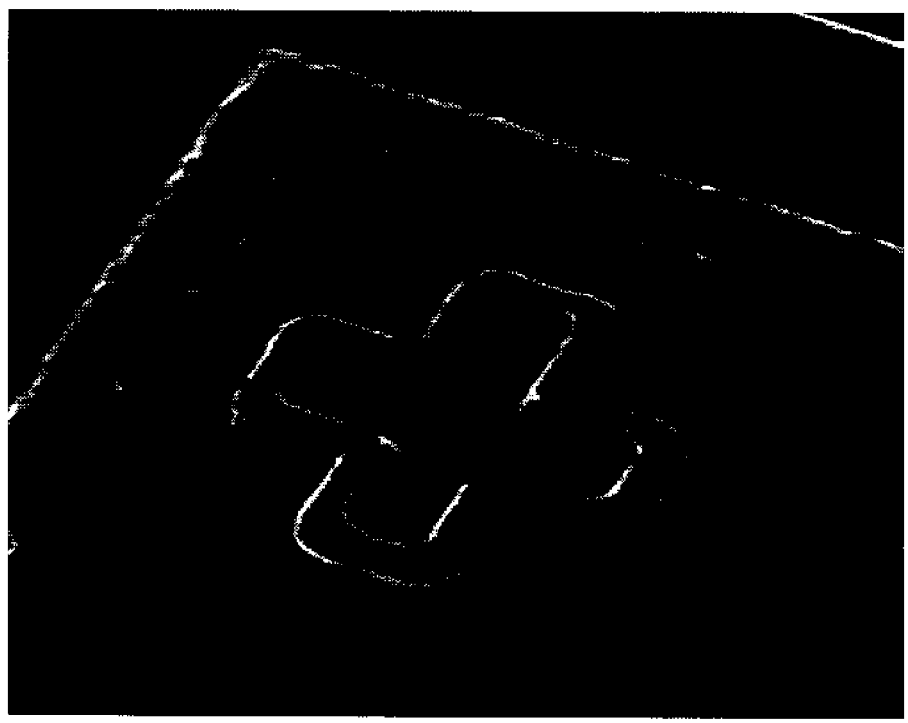
FIG. 61B is an image of a sample taken with a scanning electron microscope.

FIG. 61B is a SEM secondary electron image taken of the same feature. The SEM was operated under experimentally determined optimum imaging conditions, which were 2 keV electron beam energy and 30 pA beam current. Other beam currents, scan speeds, and beam energies were tried, but none of them offered a better contrast.

The He ion microscope image shows greater contrast between the different materials that form the alignment cross because of the larger differences in secondary electron yield for an incident He ion beam, relative to an incident electron beam. The two materials in the alignment cross can readily be distinguished visually in the image of FIG. 61A. However, as observed qualitatively in FIG. 61B, the two materials have similar secondary electron yields for the incident electron beam of the SEM.

9

A tip was prepared following a procedure as described in Example 1, and characterization of geometrical tip properties was performed as described in Example 1. The tip was accepted for use based on the criteria in Example 1.

The tip was sharpened in the FIM using the procedure described in Example 1. The tip was then installed and configured in the He ion microscope. The microscope system was configured as described in Example 1, with changes to the configuration noted below.

The microscope system was configured to measure secondary electrons that left the sample due to the interaction of the sample with the incident He ions. A MCP detector (as described in Example 3) was used to record sample images. The front end of the MCP was biased to +100 V, relative to the common external ground, as was the grid in front of it. In this configuration, the MCP was capable of collecting nearly all of the secondary electrons that left the sample due to the interaction of the sample with the incident He ions, except for secondary electrons which were produced in a region of the sample which was biased positively. These electrons returned back to the sample due to the positive voltage bias instead of being fully liberated from the sample and detected by the MCP.

Regions of the sample were positively biased due both to arriving positive charges from the incident He ion beam, and to departing negative charges (secondary electrons). The magnitude of the induced voltage bias on the sample for a given He ion beam current was dependent upon the electrical capacitance and/or resistance of the exposed region of the sample, relative to the surrounding portions of the sample. These differences lead to different secondary electron collection for different regions of the sample, according to capacitive and/or resistive properties of the sample. The differences in detected secondary collection produces contrast in images of the sample recorded using the He ion microscope. In this manner, electrical properties of the sample were determined based on secondary electron images.

Figure 62:
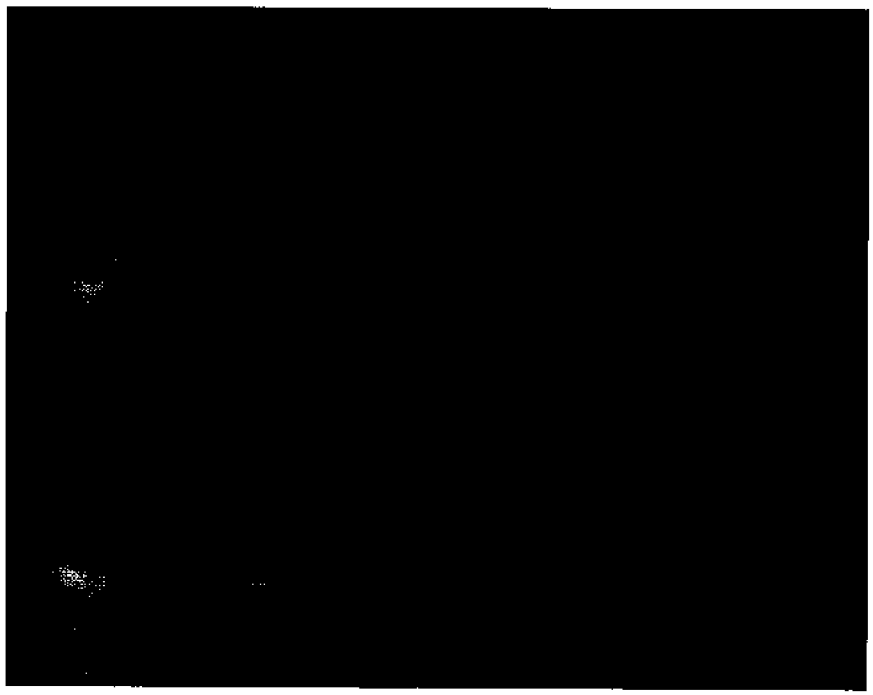
FIG. 62 is an image of a sample taken with a helium ion microscope configured to detect secondary electrons.

In FIG. 62, a secondary electron image of a sample is shown. The sample featured a set of aluminum lines deposited on the surface of an insulating substrate. Scan voltages of maximum amplitude 3 V were introduced on the scanning deflectors to produce a 30 µm field of view on the sample. The He ion beam current was 5 pA and the average ion energy was 26 keV. The ion beam was raster-scanned with a dwell time of 100 µs per pixel.

The sample image shows a series of bright, periodic aluminum lines. In the spaces between these bright lines are a series of darker lines. The middle bright line in the image shows a distinct boundary, beyond which the line is dark. Based on the nature of the sample, the bright lines have a low resistance path to ground, or perhaps a very high capacitance relative to ground, and hence they were not substantially biased due to the action of the He ion beam.

The dark lines were biased positively under the influence of the He ion beam, and hence the secondary electrons produced there returned back to the sample. To determine whether this effect was due to the capacitive or resistive properties of the dark lines, the dark lines were observed over a period of time under the He ion beam. If the effect was capacitive in nature, the lines became increasingly dark over time.

The transition from light to dark for the middle aluminum line may indicate the presence of an electrical disconnect, for example, on the line. The lower, bright portion of the line may not be in full electrical contact with the upper, dark portion of the line.

Figure 63:
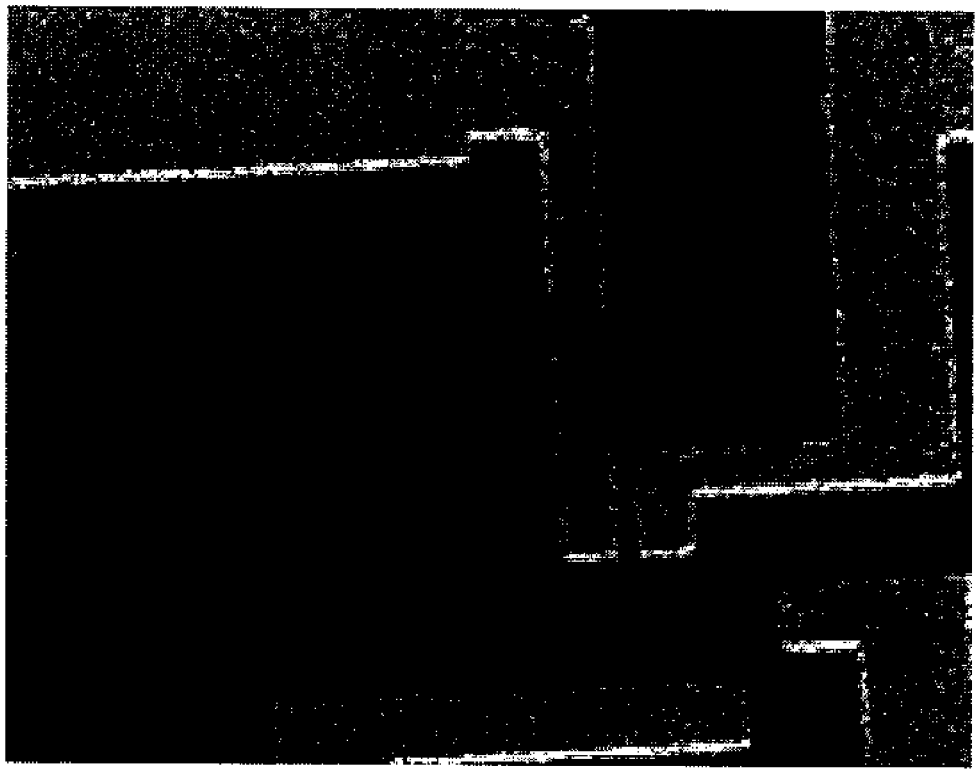
FIG. 63 is an image of a sample taken with a helium ion microscope configured to detect secondary electrons.

FIG. 63 shows an image of another sample recorded using the measurement configuration described above. The sample includes lines and other features formed of copper on a silicon substrate. The smallest features are in the form of letters ("DRAIN"). The positive potential bias on these features increased over the course of image acquisition, as evidenced by the observation that the top of each character appears bright while the bottom of each character appears dark. The raster scan in this image proceeded from top to bottom. As a result, biasing mechanism on the surface features of the sample is primarily capacitive.

10

A tip was prepared following a procedure as described in Example 1, and characterization of geometrical tip properties was performed as described in Example 1. The tip was accepted for use based on the criteria in Example 1.

The tip was sharpened in the FIM using the procedure described in Example 1. The tip was then installed and configured in the He ion microscope. The microscope system was configured as described in Example 1, with changes to the configuration noted below.

The microscope system was configured to measure secondary electrons that left the sample due to the interaction of the sample with the incident He ions. A MCP detector (as described in Example 3) was used to record sample images. The front end of the MCP was biased to +300 V, relative to the common external ground, as was the grid in front of it. In this configuration, the measured signal arose almost entirely from secondary electrons. This was verified by biasing the MCP front end to −300 V, without changing the MCP gain, and observing that the measured signal was diminished to nearly zero.

Scan voltages of maximum amplitude 3 V were introduced on the scanning deflectors to produce a 30 µm field of view on the sample. The He ion beam current was 10 pA and the average ion energy was 22 keV. The ion beam was raster-scanned with a dwell time of 100 µs per pixel.

Figure 64:
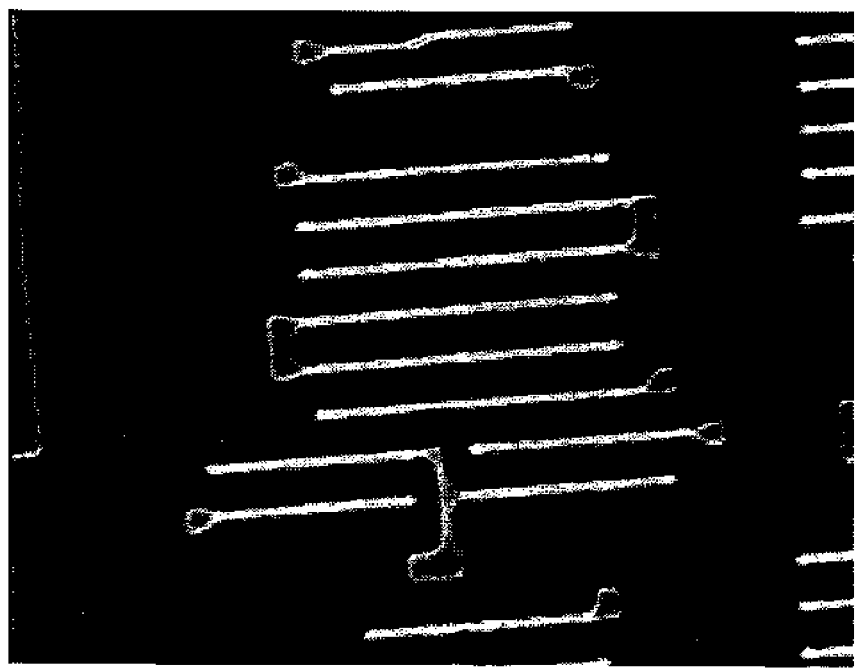
FIG. 64 is an image of a sample taken with a helium ion microscope configured to detect secondary electrons.

A sample that included three distinct layers was imaged. The top most metal layer consisted of patterned lines formed of copper. The next layer consisted of a dielectric material. The bottom layer consisted of another, differently patterned metal layer formed of copper. The image of the sample is shown in FIG. 64. The image clearly shows the topmost metal layer pattern in bright white, superimposed upon grey image features that correspond to the bottom (sub-surface) metal layer. The sub-surface metal layer appears both dimmer and slightly blurred in the image.

The measured signal was the result of secondary electrons generated at the surface of the sample by both scattered He ions and neutral He atoms. This assessment was verified by biasing the MCP and screen negative and noting that almost no signal was detected. Secondary electrons that left the sample due to the interaction of the sample with the incident He ions produced the image of the surface metal layer in FIG. 64. The image of the sub-surface metal layer is produced He ions that have penetrated into the sample and become neutralized. The neutral He atoms scatter from the sub-surface layer, and a fraction of them return to the surface where they produce secondary electrons upon their exit. This accounts for the blurred and dimmed image of the sub-surface features.

11

A tip was prepared following a procedure as described in Example 1, and characterization of geometrical tip properties was performed as described in Example 1. The tip was accepted for use based on the criteria in Example 1.

The tip was sharpened in the FIM using the procedure described in Example 1. The tip was then installed and configured in the He ion microscope. The microscope system was configured as described in Example 1, with changes to the configuration noted below.

The microscope system was configured to measure secondary electrons that left the sample due to the interaction of the sample with the incident He ions. A MCP detector (as described in Example 3) was used to record sample images. The front end of the MCP was biased to +300 V, relative to the common external ground, as was the grid in front of it. In this configuration, the measured signal arose almost entirely from secondary electrons. This was verified by biasing the MCP front end to −300 V, without changing the MCP gain, and observing that the measured signal was diminished to nearly zero.

Scan voltages of maximum amplitude 15 V were introduced on the scanning deflectors to produce a 150 µm field of view on the sample. The He ion beam current was 10 pA and the average ion energy was 21.5 keV. The ion beam was raster-scanned with a dwell time of 100 µs per pixel.

The sample that was imaged consisted of a piece of a tungsten weld. The tungsten had been heated to above its melting point and had subsequently cooled, forming distinct crystallographic domains, with abrupt boundaries between crystal grains. The sample was imaged by measuring secondary electrons that left the sample due to the interaction of the sample with the incident He ions.

Figure 65:
FIG. 65 is an image of a sample taken with a helium ion microscope configured to detect secondary electrons.

An image of the sample is shown in FIG. 65. The image shows distinctly brighter and darker grains. Superimposed on this background are bright image features which span several grains. The bright features correspond to surface topographic relief patterns, which enhance secondary electron production due to the topographic effects disclosed herein. The contrasting image intensities of the various crystal grains were due to the relative orientations of the crystal domains with respect to the incident He ion beam. When the tungsten lattice in a particular grain was oriented so that the He ion beam enters approximately parallel to a low index crystallographic direction, the scattering probability at the surface was low, and so the ion beam penetrated deeply into the grain. As a result, the secondary electron yield at the surface of the material was relatively lower, and the grain appeared darker in the image. Conversely, when the tungsten lattice in a particular grain was oriented so that the He ion beam was incident upon a high index crystallographic direction, the scattering probability at the surface of the grain was high. As a result, the secondary electron yield at the surface of the material was relatively higher, and the grain appeared brighter in the image.

12

A tip was prepared following a procedure as described in Example 1, and characterization of geometrical tip properties was performed as described in Example 1. The tip was accepted for use based on the criteria in Example 1.

The tip was sharpened in the FIM using the procedure described in Example 1. The tip was then installed and configured in the He ion microscope. The microscope system was configured as described in Example 1, with changes to the configuration noted below.

The microscope system was configured to measure He ions and neutral He atoms scattered from a sample in response to incident He ions. A MCP detector (as described in Example 3) was used to record sample images. The front end of the MCP was biased to −100 V, relative to the common external ground, as was the grid in front of it. In this configuration, secondary electrons do not reach the MCP due the negative applied potential bias. The signal measured by the MCP arises from scattered He ions and neutral He atoms that are incident on the front face of the MCP.

Scan voltages of maximum amplitude 15 V were introduced on the scanning deflectors to produce a 150 µm field of view on the sample. The He ion beam current was 10 pA and the average ion energy was 21.5 keV. The ion beam was raster-scanned with a dwell time of 100 µs per pixel.

The imaged sample was the tungsten weld sample that was also examined in Example 11. As before, the tungsten weld included distinct crystallographic domains, with abrupt boundaries between the grains.

Figure 68:
FIG. 68 is an image of a sample taken with a helium ion microscope configured to detect helium ions and neutral helium atoms.

The sample was imaged by detecting the abundance of He atoms and He ions incident on the MCP. An image of the sample obtained using this measurement procedure is shown in FIG. 68. The image shows both bright and dark grains. For a particular crystalline grain, if the tungsten lattice in the grain was oriented so that the He ion beam was incident along a relatively low index crystallographic direction, there was a low probability of He scattering at the surface of the grain. As a result, ions penetrated relatively deeply into the grain before scattering occurred. As a result, the He ions (or He neutral atoms, produced when He ions combine with an electron in the sample) are less likely to leave the sample and be detected by the MCP detector. Grains having these properties appeared dark in the recorded image.

Conversely, if the tungsten lattice in a particular grain was oriented so that the He ion beam was incident along a relatively high index crystallographic direction, there was a relatively high probability of He scattering at the surface of the grain. As a result, penetration of the He ions into the sample before scattering was, on average, relatively shallow. As a result, He ions and/or neutral He atoms were relatively more likely to leave the surface of the sample and be detected by the MCP detector. Grains with high-index crystal orientations with respect to the incident He ion beam therefore appeared brighter in image shown in FIG. 68.

With reference to the image shown in FIG. 65, topographic information in the image of FIG. 68 was significantly reduced because the image was recorded based on scattered He particles, rather than on secondary electrons. In particular, the series of bright lines that appeared on the image in FIG. 65 were largely removed from the image in FIG. 68. The absence of topographic information can make the image in FIG. 68 relatively easier to interpret, especially where the measured intensities in FIG. 68 are used to quantitatively identify the crystallographic properties (such as the relative orientation) of crystalline domains in the sample.

13

A tip was prepared following a procedure as described in Example 1, and characterization of geometrical tip properties was performed as described in Example 1. The tip was accepted for use based on the criteria in Example 1.

The tip was sharpened in the FIM using the procedure described in Example 1. The tip was then installed and configured in the He ion microscope. The microscope system was configured as described in Example 1, with changes to the configuration noted below.

The microscope system was configured to measure He ions and neutral He atoms scattered from a sample in response to incident He ions. A detector—a miniature MCP—was mounted on the shaft of an electrical motor. Copper tape was used to cover the front face of the MCP to restrict measurement of He ions and/or neutral atoms by the MCP. A small circular hole in the copper tape permitted scattered He ions and/or neutral atoms to reach the MCP only if the particles fell within a narrow angular range. In this example, measurement of He ions and/or neutral atoms was restricted to an angular range corresponding to a solid angle of 0.01 steradians. The copper tape and the front of the MCP were biased to −100 V, relative to the common external ground, so that secondary electrons would not enter the MCP detector.

The detector was positioned at a distance of 30 mm from the sample. The motor permitted rotation of the MCP detector with respect to the sample to detect He ions and/or neutral atoms leaving the sample surface at a range of different angles. Typically, for example, the motor permitted rotation of the MCP through approximately 180°.

The sample was a copper ball of diameter of approximately 1 mm. The motor was positioned relative to the sample such that the sample was located along the axis of the motor shaft. The copper ball sample, when exposed to the He ion beam, provided scattered He ions and neutral He atoms at a wide range of angles, due to the shape of the sample surface. That is, by scanning the incident He ion beam across the surface of the sample, a variety of different angles of incidence (e.g., the angle between the He ion beam and a normal to the sample surface) can be realized. For example at the center of the copper ball, the angle of incidence of the He ion beam is 0°. At the edge of the ball (as observed from the perspective of the He ion beam), the angle of incidence is approximately 90°. At a position half-way between the center and the edge of the copper ball, the angle of incidence is approximately 30° from simple trigonometry.

The sample was positioned under the He ion beam, and the detector was positioned with respect to the sample as described above. The He ion beam current was 15 pA, and the average ion energy in the He ion beam was 25 keV. A maximum voltage of 100 V was applied to the scanning deflectors to achieve a 1 mm field of view at the surface of the sample. The distance from the second lens of the microscope system to the sample (e.g., the working distance) was 75 mm. This provided enough open space to allow the MCP detector to rotate with respect to the sample.

The measurements were performed by recording images of the copper ball while the detector was swept through a 180° range of angles in a hemispherical arc with respect to the sample. The He ion beam effectively partitioned the surface of the sample into two sides and, due to the convex surface of the copper ball, scattered He ions and neutral He particles could only be detected from the side on which the detector was positioned. As a result, in FIG. 69A, the intensity profile of the image of the sample appears crescent-shaped, with the bright region on the left corresponding to the position of the detector. The right side of the sample was relatively dark, since scattered He ions and neutral He particles left the surface of the sample in directions such that they could not be measured by the detector.

Successive images of the sample were recorded by incrementing the detector angle between each image. A total of 20 images of the sample were acquired, spanning the scanning range of the detector. Certain images did not provide useful information because the detector was positioned such that it obstructed the incident He ion beam, preventing He ions from being incident on the sample surface. The images shown in FIGS. 69B and 69C correspond to images of the sample recorded with the detector positioned nearly directly above the sample and on the right side of the sample, respectively. In FIG. 69C, a crescent-shaped intensity profile is observed that is analogous to the profile observed in FIG. 69A.

Figure 69A:
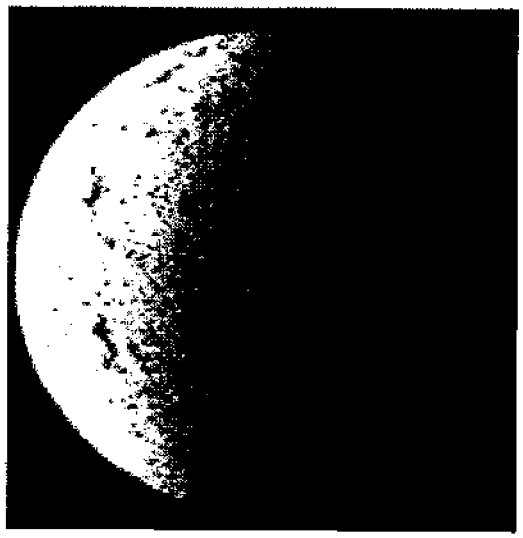
FIGS. 69A-69C are images of a sample taken with a helium ion microscope configured to detect helium ions and neutral helium atoms.
Figure 69B:
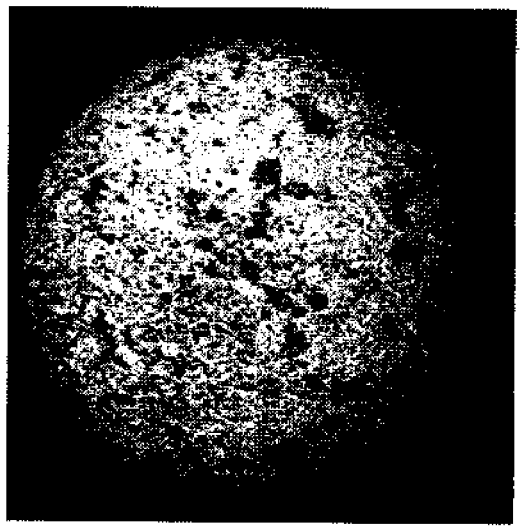
Figure 69C:
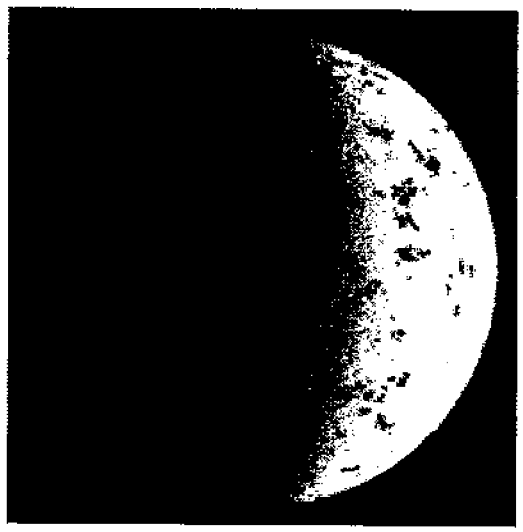

Based on qualitative inspection of the recorded images, it was evident that topographic information about the sample could be determined from images measured with the detector in off-axis positions (e.g., FIGS. 69A and 69C). The information acquired from these measurements could be combined with secondary electron measurements of the sample, for example, to ascertain whether image contrast observed in the secondary electron images was due to the surface topography of the sample, or due to another contrast mechanism such as sample charging or material composition. With the detector in a known position, it was possible, based on the recorded images, to distinguish a bump on the surface of the sample from a depression. The small detector acceptance angle and the known position of the detector for each recorded image could also be used to determine quantitative surface relief (e.g., height) information for the sample by measuring the shadow lengths of surface features in the image and making use of the known angle of the incident He ion beam with respect to the surface features.

Images of the sample also revealed that, depending upon the orientation of the detector with respect to the sample, certain edges of the sample exhibited a bright edge effect, while other edges exhibited a dark edge effect (see FIG. 69A, for example). This information was used in the design of a detector that was configured to reduce the measurement of topographic information from a sample. The detector design balanced the detection angles to provide a nearly uniform edge effect. As a result, images of a sample such as a copper ball would appear uniformly bright, with variations in intensity arising from material differences in the sample.

The image data recorded from the sample was analyzed to determine how the intensity of selected regions of the sample surface changed as the detector was scanned. Variations in intensity were due to the angular distribution of He ions and He neutral atoms that left the sample surface, and this analysis provided information about the distribution of angles, which are sometimes referred to as emission lobes.

Figure 70A:
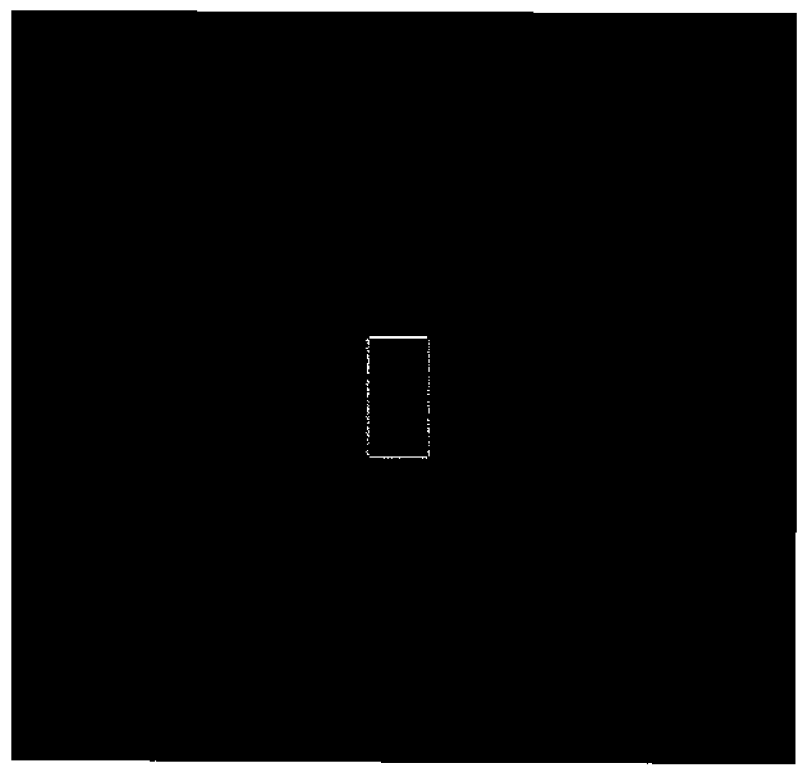
FIG. 70A is an image of a sample taken with a helium ion microscope configured to detect helium ions and neutral helium atoms.

FIG. 70A shows an image of the sample recorded with the detector nearly on-axis with the incident He ion beam; that is, the detector measured scattered He ions and neutral He atoms at an angle of approximately 0°. A region of the sample surface, denoted by the rectangular box, was isolated in a series of images and subjected to further analysis. In the diagram shown in FIG. 70B, the thick horizontal line schematically represents the surface of the sample, and the thin vertical represents the incident He ion beam. The dots represent the average measured intensity of scattered He ions and neutral He atoms at various detector positions. The dots are plotted on a polar scale, where the origin of the polar plot is the point of incidence of the He ion beam on the surface of the sample. The angular position of a given dot corresponds to the angular position of the detector, and the radial distance from the origin to each dot represents the average measured intensity at that particular angular detector position. Individual images of the sample, each corresponding to a different detector position, were analyzed to provide the angular intensity data shown in FIG. 70B. Each dot corresponds to an image recorded at a different detector position.

The polar array of dots forms an emission lobe diagram. The diagram is approximately circular in shape (except for a few missing points where the He ion beam was obstructed by the detector), and corresponds to a cosine distribution about the origin.

Figure 71A:
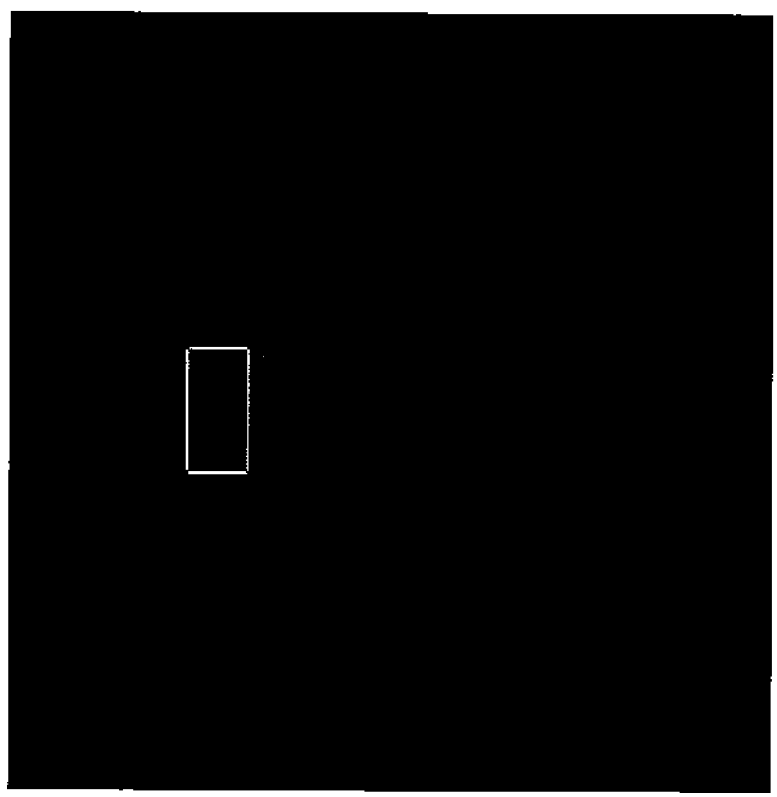
FIG. 71A is an image of a sample taken with a helium ion microscope configured to detect helium ions and neutral helium atoms.

In FIG. 71A, an image of the sample is shown with a superimposed rectangular box denoting a different region of the sample surface that was analyzed using multiple sample images to determine the angular intensity distribution of scattered He ions and neutral atoms from the sample. In this case, the scattering or emission angle was about 40° with respect to the incident He ion beam.

Figure 70B:
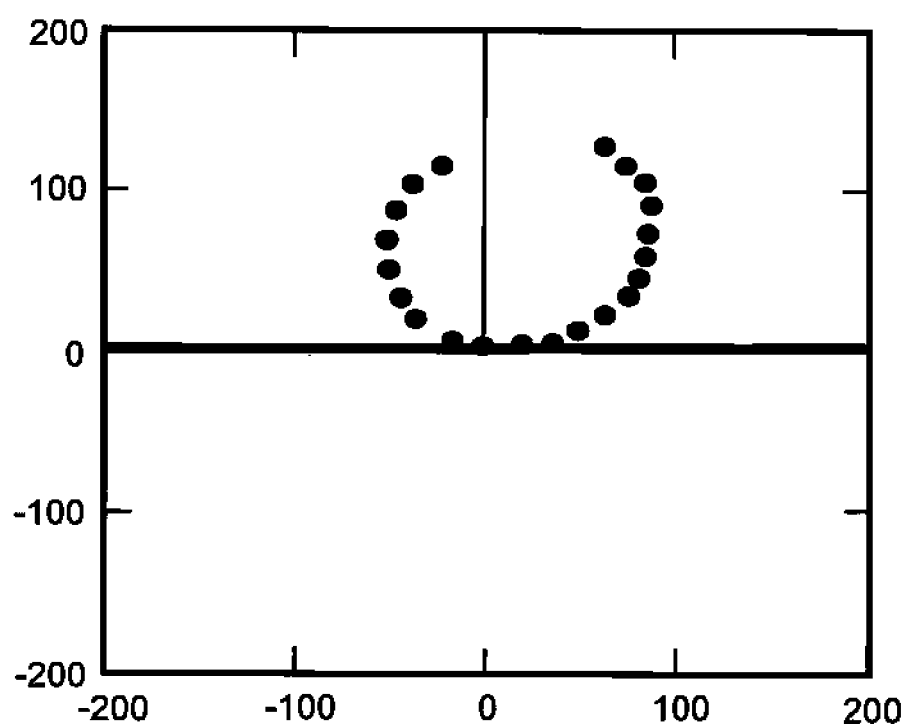
FIG. 70B is a polar plot showing the angular intensity of helium ions and helium atoms leaving the sample for the image of FIG. 70A.
Figure 71B:
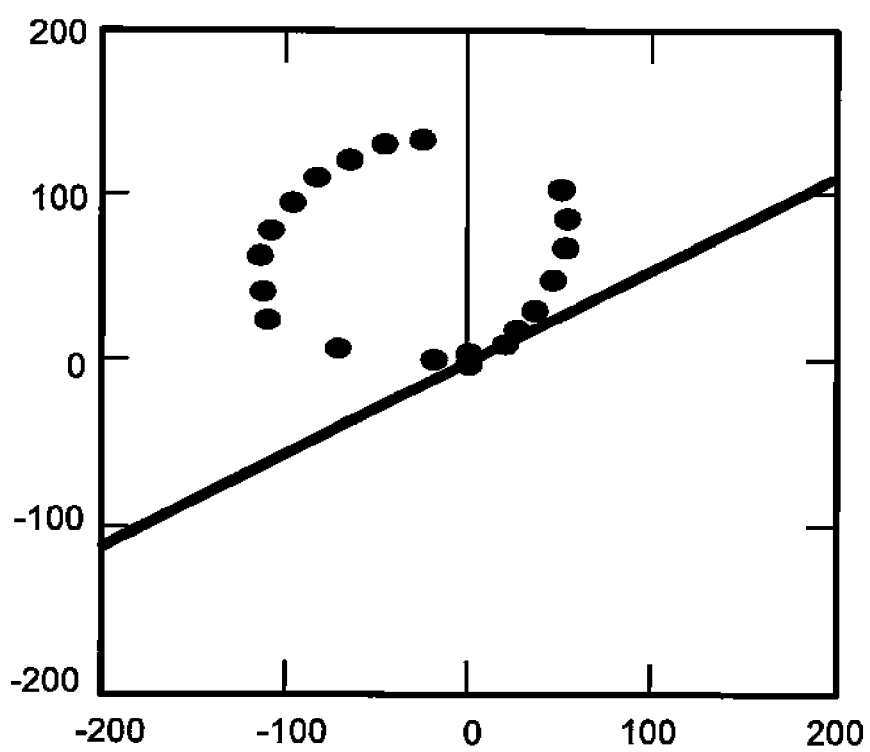
FIG. 71B is a polar plot showing the angular intensity of helium ions and helium atoms leaving the sample for the image of FIG. 71A.

The polar plot of angular emission intensity shown in FIG. 71B was constructed in the manner described in connection with FIG. 70B above. The shape of the lobes at this angle indicated that scattering/emission is preferentially directed away from the incident He ion beam.

This analysis was repeated on a variety of different regions of the sample surface (corresponding to a variety of different angles) to build up a relatively complete picture of the distribution of scattered He ions and neutral He atoms as a function of angle for the copper ball sample.

14

A tip was prepared following a procedure as described in Example 1, and characterization of geometrical tip properties was performed as described in Example 1. The tip was accepted for use based on the criteria in Example 1.

The tip was sharpened in the FIM using the procedure described in Example 1. The tip was then installed and configured in the He ion microscope. The microscope system was configured as described in Example 1, with changes to the configuration noted below.

The microscope system was configured to measure He ions and neutral He atoms scattered from a sample in response to incident He ions. A MCP detector (as described in Example 3) was used to record sample images. The front end of the MCP was biased to −300 V, relative to the common external ground, as was the grid in front of it. In this configuration, secondary electrons do not reach the MCP due the negative applied potential bias. The signal measured by the MCP arises from scattered He ions and neutral He atoms that are incident on the front face of the MCP. From the sample's perspective, the MCP detected He ions and He atoms from within a solid angle of approximately 1.8 steradians. The solid angle was azimuthally symmetric with respect to the incident beam as shown in FIG. 66.

From Example 13, the bright and dark edge effects observed for the copper ball sample provided information regarding the design and configuration of a detector which, when used to image a sample by measuring scattered He ions and/or neutral He atoms, reduced the amount of topographic information in the measured signals, and more accurately reflected differences in material composition rather than differences in local surface topography of the sample. For the MCP detector shown in FIG. 66, a reduction in topographic information in images formed based on measurements of scattered He ions and neutral He atoms was observed if the MCP was positioned at a working distance of approximately 25 mm from the sample.

Samples that included different materials could then be imaged and the materials reliably distinguished visually from one another. A sample that included four different materials—a nickel base layer, a carbon coating, a copper grid, and a gold wire—was imaged using the He ion microscope. The He ion beam current was 1.1 pA and the average He ion energy was 18 keV. Maximum voltages of 4 V were applied to the scanning deflectors to realized a field of view at the sample surface of 40 μm. The total image acquisition time was 90 s.

Figure 72:
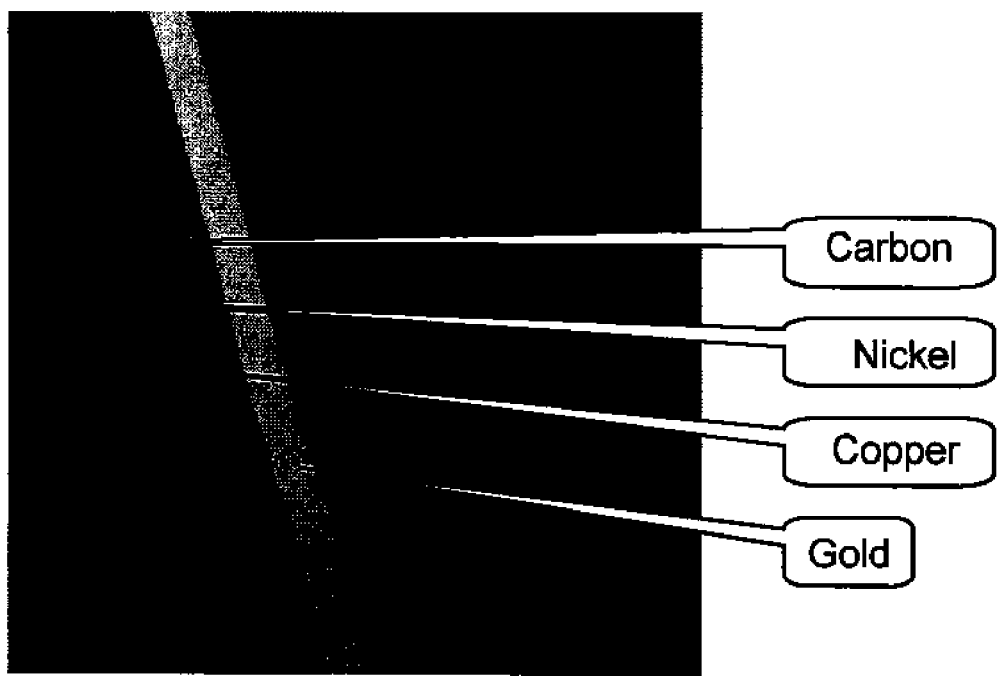
FIG. 72 is an image of a sample taken with a helium ion microscope configured to detect helium ions and neutral helium atoms.

The resulting image is shown in FIG. 72. Different intensities were observed for each of the four different materials in the sample. This is a consequence of the fact that the scattering probability a He ions incident upon a particular material depends upon the atomic number of the material. In FIG. 72, even materials with similar atomic numbers can be distinguished. For example, copper (atomic number 29) is distinguishable visually from nickel (atomic number 28).

Figure 73:
FIG. 73 is an image of a sample taken with a helium ion microscope configured to detect helium ions and neutral helium atoms.

FIG. 73 shows an image of a sample that includes a copper layer underlying a silicon wafer, with an oxide layer overlying the wafer. The image was measured using a He ion microscope system configured for detection of scattered He ions and neutral He atoms as described earlier in this example. The sample includes surface structural features that were produced by directing a laser to be incident on the sample surface. The laser caused an explosive eruption of the underlying copper layer. Visual inspection of the image reveals image contrast (e.g., image intensity variations) that result from the different materials present in the sample. From images such as the image in FIG. 73, the distribution of different materials in a sample can be determined.

15

A tip was prepared following a procedure as described in Example 1, and characterization of geometrical tip properties was performed as described in Example 1. The tip was accepted for use based on the criteria in Example 1.

The tip was sharpened in the FIM using the procedure described in Example 1. The tip was then installed and configured in the He ion microscope. The microscope system was configured as described in Example 1, with changes to the configuration noted below.

The microscope system was configured to measure photons emitted from a sample in response to the incident He ion beam. An image of the sample was constructed from the signal generated by a photomultiplier tube (model R6095, Hamamatsu Photonics K.K., Toyooka, Japan). The photomultiplier tube had an end-on window, a relatively high quantum efficiency, and a broad spectral response from 200 nm to 700 nm. The tube was operated with a signal gain that could be increased up to 1200 V, or to the point where the output signal reached the signal chain's white noise level without excessive saturation. The photomultiplier tube was positioned at a distance of 15 mm from the sample and was oriented to face the sample. In this configuration, the tube subtended a solid angle of about 2 steradians.

A sample of sodium chloride (NaCl) was imaged using the photomultiplier tube detector. For these measurements, the He ion beam current was 10 pA and the average He ion energy was 25 keV. The sample was raster-scanned with a dwell time per pixel of 500 μs. A maximum voltage of 150 V was applied to the scanning deflectors to yield a field of view at the sample surface of 1.35 mm.

Figure 74:
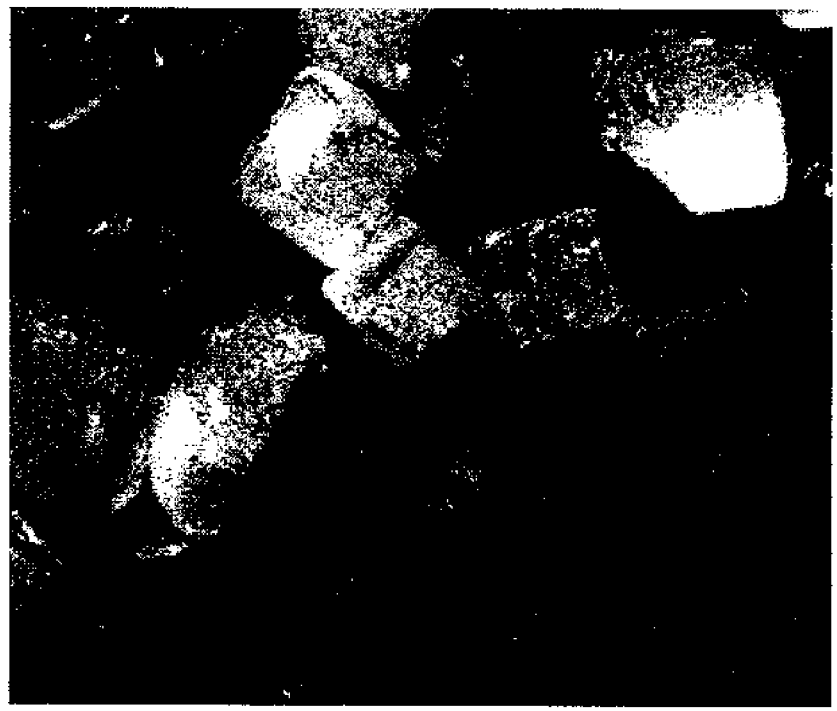
FIG. 74 is an image of a sample taken using a helium ion microscope configured to detect photons.

An image of the sample is shown in FIG. 74. Image contrast (e.g., variations in image intensity) are apparent among different NaCl crystals. Photons can be produced in the sample via two different mechanisms. First, photons can be produced via processes that are analogous to the cathodoluminescence that is observed in SEM images. In this mechanism, atoms of the sample are excited to higher-lying energy states. Photons are emitted during the subsequent de-excitation process. When the He ions from the incident beam return to lower-lying energy states, photons are emitted.

Other samples which have been exposed to the He ion beam and from which emitted photons have been detected include plastics, scintillators, and organic materials.

16

A tip was prepared following a procedure as described in Example 1, and characterization of geometrical tip properties was performed as described in Example 1. The tip was accepted for use based on the criteria in Example 1.

The tip was sharpened in the FIM using the procedure described in Example 1. The tip was then installed and configured in the He ion microscope. The microscope system was configured as described in Example 1, with changes to the configuration noted below.

The tip was biased at +19 kV, relative to the extractor, and He gas was introduced in the vicinity of the tip at a pressure of $2\times10^{-5}$ Torr. A Faraday cup was placed beyond the second lens, and the first lens and alignment deflectors were used to focus the beam so that substantially all of the He ions originating from one of the tip trimer atoms passed through the aperture (diameter 600 μm, positioned 370 mm from the tip), and substantially all of the He ions originating from the other two trimer atoms were blocked by the aperture. After passing through the aperture, the He ion beam was focused by the first lens into the Faraday cup. In this configuration, the astigmatism corrector, the scanning deflectors, and the second lens were off.

The total He ion current originating from the tip atom was measured to be 300 pA using a pico-ammeter (model 487, Keithley Instruments, Cleveland, Ohio) together with the Faraday cup. The Faraday cup was a cylindrical metal cup with a depth-to-diameter ratio of about 6 to 1.

Thereafter, the first lens was turned off. Each of the He ions generated at the tip continued to travel in a straight line, diverging from the tip. The aperture intercepted most of the He ion beam and allowed only a small central portion of it to pass further down the remainder of the ion column. The portion of the He ion beam that passed through the aperture was detected with the Faraday cup, yielding a measured He ion current of 5 pA passing through the aperture. The angular intensity of the He ion beam was then calculated as the He ion beam current passing through the aperture (5 pA) divided by the solid angle of the aperture from the perspective of the tip. The half-angle of the cone formed by the apex of the tip and the aperture was calculated as $\tan^{-1}(0.300/370)=0.046°=8.1\times10^{-4}$ radians. The corresponding solid angle was calculated as $2.1\times10^{-6}$ steradians (sr). Based upon the solid angle, the angular intensity of the He ion beam was determined to be 2.42 μA/sr.

The brightness of the He ion source was determined from the He ion beam angular intensity and the virtual source size. The virtual source size was estimated by examining a FIM image of the tip recorded during sharpening of the tip. From this image, it was evident that individual ionization discs corresponding to the tip trimer atoms were not overlapping. Further, it was known from the crystallography of tungsten that the trimer atoms were separated by approximately 5 Angstroms. Therefore, the actual ionization disks were estimated to have a diameter of about 3 Angstroms.

The virtual source size is generally smaller than the actual ionization area. The virtual source size was determined using the general procedure discussed previously: by back-projecting asymptotic trajectories of 100 He ions once the ions were beyond the electric field region (e.g., the region in the vicinity of the tip and the extractor) of the ion source. The back-projected trajectories moved closer to one another until they passed through a region of space in which they were most closely spaced with respect to one another, and then they diverged again. The circular diameter of the closest spacing of the back-projected trajectories was defined to be the virtual source size.

As an upper bound, we used a value of 3 Angstroms for the diameter of the virtual source. Where the microscope is configured to permit only a portion of the He ion beam originating from a single tip atom to pass through the aperture, the virtual source size can be considerably smaller. The brightness was calculated as the angular intensity divided by the area A of the virtual source size, $A=\pi(D/2)^2$. The brightness of the ion source was $3.4\times10^9$ A/cm$^2$sr.

The reduced brightness was calculated as the brightness divided by the voltage used to extract the beam (e.g., the voltage bias applied to the tip). The tip to extractor voltage was 19 kV, and the reduced brightness was $1.8\times10^9$ A/m$^2$srV.

The etendue is a measure of the product of the He ion beam's virtual source size and its angular divergence (as a solid angle). Using the brightness determined above, the etendue was determined to be $1.5\times10^{-21}$ cm$^2$sr.

The reduced etendue is the etendue multiplied by the He ion beam voltage. The reduced etendue, based on the etendue calculated above, was determined (using the tip bias voltage of +19 kV) to be $2.8\times10^{-17}$ cm$^2$srV.

17

A tip was prepared following a procedure as described in Example 1, and characterization of geometrical tip properties was performed as described in Example 1. The tip was accepted for use based on the criteria in Example 1.

The tip was sharpened in the FIM using the procedure described in Example 1. The tip was then installed and configured in the He ion microscope. The microscope system was configured as described in Example 1, with changes to the configuration noted below.

The microscope system was configured to measure secondary electrons using an ET detector. The detector was positioned at a distance of 10 mm vertically (parallel to the He ion beam) from the sample, displaced 25 mm laterally from the sample, and inclined towards the sample. The ET screen was biased at a potential of +300 V, relative to the common external ground.

The He ion beam current was 1 pA, and the average ion energy in the beam was 22 keV. The He ion beam was raster-scanned across the surface of the sample with a dwell time per pixel of 100 μs. A maximum voltage of 100 mV was applied to the scanning deflectors to yield a field of view of 1000 nm on the surface of the sample.

Figure 75:
FIG. 75 is an image of a sample taken with a helium ion microscope configured to detect secondary electrons.
Figure 76:
FIG. 76 is an expanded view of a portion of the image of FIG. 75.

The sample included gold islands formed on the surface of a carbon substrate, and was obtained from Structure Probe Inc. (West Chester, Pa.). An image of the sample recorded using the above measurement configuration is shown in FIG. 75. A region of the sample image, denoted by the rectangle superimposed on the image in FIG. 75, was selected to examine the quality of edge contrast observed with the He ion microscope. The region designated by a rectangle includes a nearly-vertical gold edge. The region includes 20 rows, each with 57 pixels. An expanded view of the selected region is shown in FIG. 76.

Figure 77:
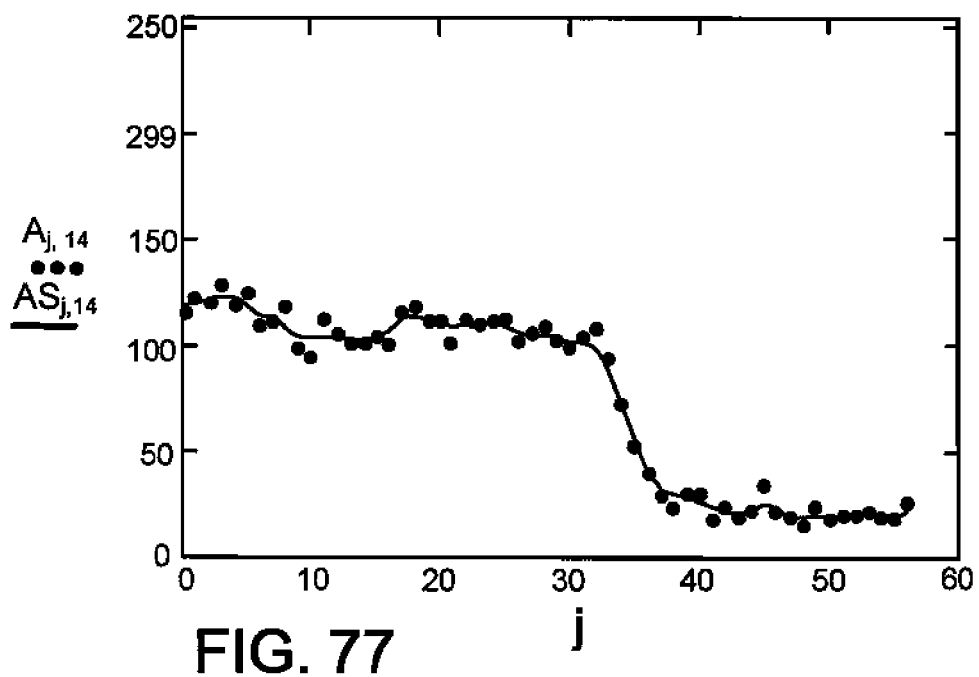
FIG. 77 is a plot of image intensity as a function of pixel position for a line scan through the image of FIG. 76.

Each row of the selected image region was individually analyzed as follows. First, to reduce noise, each row was smoothed with a Gaussian kernel of bandwidth 3 pixels using the MathCAD ksmooth function (PTC Inc., Needham, Mass.). FIG. 77 shows a graph on which pixel intensity values for one particular line (line #14) before smoothing (dots) and after smoothing (curve) are plotted. The vertical axis corresponds to the image intensity, ranging from 0 (black) to 255 (white). The horizontal axis corresponds to the pixel number, ranging from 0 (left edge) to 57 (right edge).

For each intensity line scan in the selected region of the image, the center of the left to right light-to-dark transition was determined by locating the minimum value of the first derivative of the intensity line scan. For edges with a left to right dark-to-light transition, the center of the transition would have been found by determining the location of the maximum value of the first derivative of the intensity line scan.

Each line was then trimmed to contain just 21 pixels. The trimming operation such that the transition point, the 10 pixels preceding the transition point, and the 10 pixels following the transition point were retained in each line. Intensity values for the first five pixels in each trimmed line were averaged together and the average was identified as the 100% value. Intensity values for the final five pixels in each trimmed line were averaged together and the average was identified as the 0% value. The smoothed data from each line scan was then rescaled in terms of the 100% and 0% values. The rescaled data from FIG. 77 is shown in FIG. 78.

Figure 78:
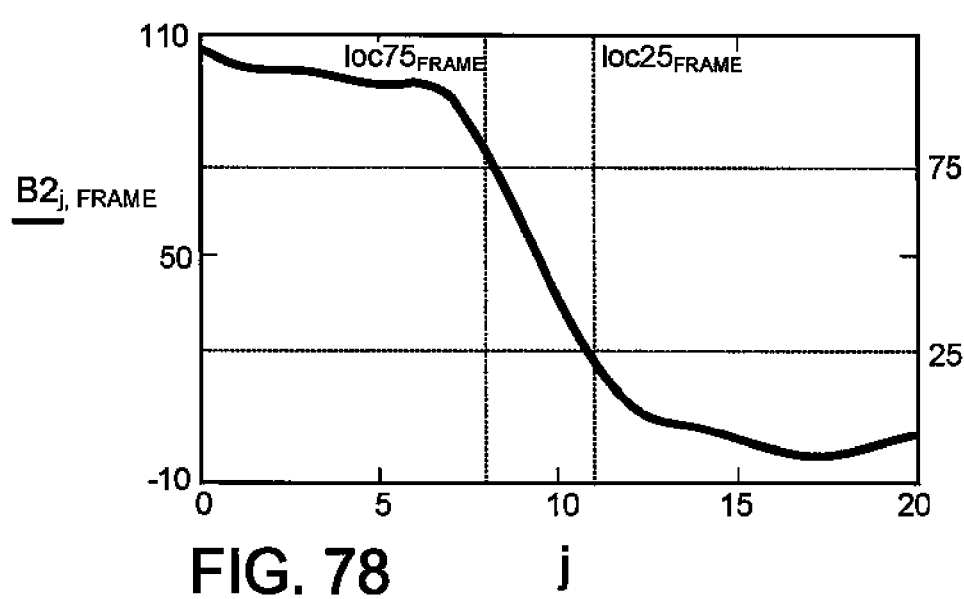
FIG. 78 is a plot of the data shown in FIG. 77 after numerical scaling and smoothing operations.

With reference to FIG. 78, the 75% and 25% values were determined with reference to the 0% and 100% values. The spot size of the He ion beam was subsequently determined as the separation along the horizontal axis between the 25% and 75% values. Based upon the data in FIG. 78, the spot size was determined to be 3.0 pixels. The pixel size was converted to nanometers using the known field of view in the measurement configuration and the number of pixels in the image. For this measurement, the field of view was 641 nm, and there were 656 pixels spanning the field of view. The spot size of the He ion beam was therefore determined to be 2.93 nm. This was repeated for each of the 20 lines in the selected region of the image, and the results were averaged to yield a mean He ion beam spot size of 2.44 nm.

18

A tip was prepared following a procedure as described in Example 1, and characterization of geometrical tip properties was performed as described in Example 1. The tip was accepted for use based on the criteria in Example 1.

The tip was sharpened in the FIM using the procedure described in Example 1. The tip was then installed and configured in the He ion microscope. The microscope system was configured as described in Example 1, with changes to the configuration noted below.

The microscope system was configured to measure scattered He ions and neutral He atoms leaving a sample surface in response to incident He ions. A MCP detector as described in Example 3 was positioned 10 mm from the sample. A potential bias of 0 V relative to the external ground was applied to the MCP grid and front face.

The He ion beam current was 1 pA and the average He ion beam energy was 26 keV. The He ion beam was raster-scanned over the surface of the sample with a dwell time per pixel of 100 µs. A maximum potential of 1.30 V was applied to the scanning deflectors to yield a field of view at the surface of the sample of 13 µm.

The sample, which included a silicon wafer substrate with surface features formed of polysilicon, was known as the Metrocal and was obtained from Metroboost (Santa Clara, Calif.). The sample was oriented so that the He ion beam was incident at a normal angle to the sample surface. The sample was biased to +19.4 kV, relative to the common external ground, so He ions in the incident ion beam arrived at the sample with a landing energy of 6.6 keV. The large electric field between the sample and the MCP detector prevented secondary electrons from reaching the detector. Substantially all of the secondary electrons that left the sample returned to the sample surface under the influence of the electric field. As a result, the MCP detector measured scattered He ions and neutral atoms. Neutral He atoms measured by the detector had a maximum energy of 6.6 keV, while He ions measured by the detector were accelerated up to a maximum energy of 26 keV by the time they reached the MCP.

Figure 79:
FIG. 79 is an image of a sample taken with a helium ion microscope configured to detect helium ions and neutral helium atoms.

FIG. 79 shows an image of the sample recorded using the measurement configuration described above. Various features on the surface of the sample have measured intensities which are relatively uniform, and different from the intensity of the substrate. Visual inspection of the edges of the surface features reveals that there are no apparent bright edge effects (e.g., edge blooming) which can lead to saturation of the signal chain, and can make the precise location of the edge difficult to find. In addition, there is no visual evidence of charging artifacts on the sample surface; such artifacts, if present, would manifest as voltage contrast in the image.

Figure 80:
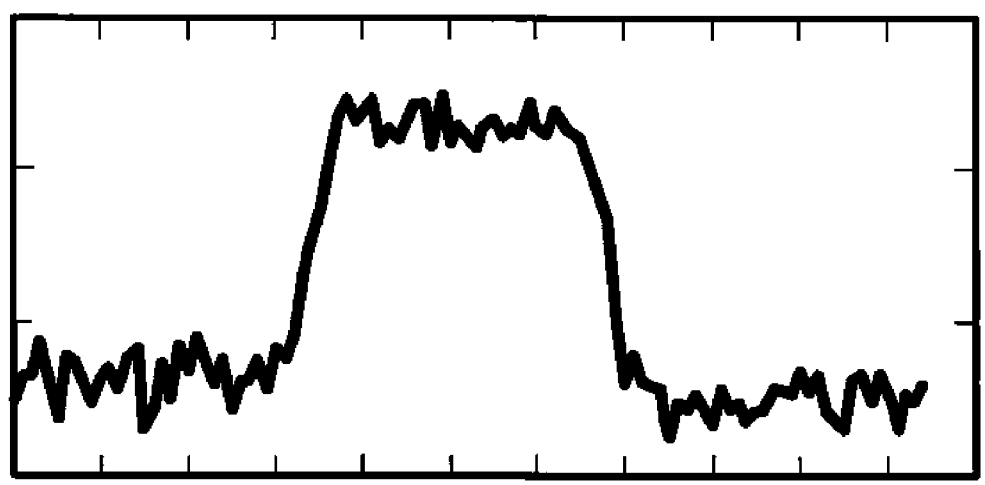
FIG. 80 is a plot of image intensity as a function of pixel position for a line scan through a portion of the image of FIG. 79.
Figure 81:
FIG. 81 is an image of a sample taken with a scanning electron microscope.

A horizontal line scan through one of the sample's surface features is shown in FIG. 80. The horizontal axis of the line scan shows the pixel number, and the vertical axis indicates the measured image intensity at particular pixels. For purposes of comparison, the same sample was imaged in a Schottky Field Emission SEM (AMRAY model 1860) with a beam energy of 3 keV and a beam current of 30 pA, at a magnification of 30,000× (corresponding to a field of view of about 13 um). The resulting image is shown in FIG. 81, and a horizontal line scan through the same feature that was scanned in FIG. 80 is shown in FIG. 82.

Figure 82:
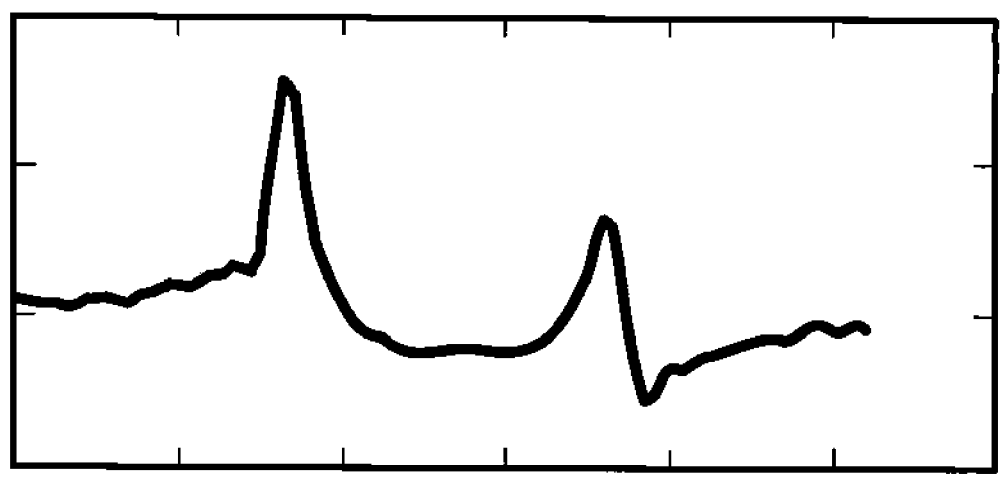
FIG. 82 is a plot of image intensity as a function of pixel position for a line scan through a portion of the image of FIG. 81.

The line scan in FIG. 82 showed significant bright edge effects, and the signal chain at the edges of the imaged surface feature was nearly saturated. In the body of the surface feature, the SEM line scan does not show a relatively uniform steady state intensity level. Instead, the intensity level in the body of the feature is either decreasing or increasing everywhere but in a small region at the center of the feature. Finally, the asymmetry of the SEM line scan indicates that time-dependent charging of the surface feature was occurring during SEM exposure. In comparison, the line scan image of the feature recorded by detecting scattered He ions and neutral He atoms shows considerably reduced edge effects, and no apparent charging artifacts.

Multiple measurements of a particular feature on the surface of the sample could also have been performed. If multiple measurements of a feature were made, it would have been possible to ascertain statistical data about the dimensions of the measured feature. For example, the mean feature width, the standard deviation of the feature width, and/or the mean and standard deviation of the location of the first edge and/or the second edge of the feature could have been measured. Fourier methods could also have been used to analyze the positions of the edges of one or more features to determine the spectrum of spatial wavelengths corresponding to the edge shapes.

19

Measurement of Topographic and Crystalline Information from a Sample

To measure topographic and crystalline information from a sample, the sample is fixed in position on a sample mount in a gas field ion microscope as described herein. The gas field ion microscope is configured to expose a 100 $\mu m^2$ FOV on the surface of the sample to a He ion beam having a beam current of 1 pA, an average ion energy of 20 keV, and a beam spot size on the surface of the sample of 0.1% of the FOV.

To measure crystalline information from the sample, the He ion beam is raster-scanned in discrete steps over the FOV region of the sample surface. A two-dimensional detector is used to capture an image of scattered He ions from the surface of the sample at each step. Each two-dimensional image corresponds to a Kikuchi pattern at a particular position on the surface of the sample. Based on the Kikuchi pattern, the sample's crystal structure, lattice spacing, and crystal orientation at that position can be determined. By measuring Kikuchi patterns at discrete steps throughout the FOV, a complete map of the sample's surface crystal structure is obtained.

To measure topographic information from the sample, a detector is configured to measure a total intensity of secondary electrons from the sample produced in response to the incident He ion beam. The He ion beam is raster-scanned in discrete steps over the entire FOV region of the sample surface, and the total intensity of secondary electrons is measured as a function of the position of the He ion beam on the sample surface. The measured crystalline information is then used to remove contributions to the secondary electron intensity measurements that arise from crystal structure variations in the sample. The corrected total secondary electron intensity values are used to construct a grayscale image of the sample, where the gray level at a particular image pixel is determined by the corrected intensities of secondary electrons at a corresponding He ion beam position on the sample. Topographic information is provided by the image, which shows the surface relief pattern of the sample in the FOV.

20

Measurement of Topographic and Crystalline Information from a Sample

To measure topographic and crystalline information from a sample, the sample is fixed in position on a sample mount in a gas field ion microscope as described herein. The gas field ion microscope is configured as described in Example 19.

To measure crystalline information from the sample, the He ion beam is raster-scanned in discrete steps over the FOV region of the sample surface. A detector is used to measured a total abundance of scattered He ions as a function of the position of the He ion beam on the sample surface. The measured total abundance values are used to construct a grayscale image of the sample, where the gray level at a particular image pixel is determined by the total measured abundance of He ions at a corresponding He ion beam position on the sample. Differently-oriented crystal grains at the surface of the sample have different yields of scattered He ions, and the image shows the differently-oriented crystal grains as variable gray levels. Using the information in the image, crystal grains and grain boundaries can be identified at the sample surface.

To measure topographic information from the sample, the total secondary electron intensity is measured as described in Example 19. The measured crystalline information is then used to remove contributions to the secondary electron intensity measurements that arise from crystal structure variations in the sample. The corrected total secondary electron intensity values are used to construct a grayscale image of the sample, where the gray level at a particular image pixel is determined by the corrected intensities of secondary electrons at a corresponding He ion beam position on the sample. Topographic information is provided by the image, which shows the surface relief pattern of the sample in the FOV.

21

Measurement of Topographic and Crystalline Information from a Sample

To measure topographic and crystalline information from a sample, the sample is fixed in position on a sample mount in a gas field ion microscope as described herein. The gas field ion microscope is configured as described in Example 19.

To measure crystalline information from the sample, the He ion beam is raster-scanned in discrete steps over the FOV region of the sample surface. A detector is used to measured a total abundance of scattered He ions as a function of the position of the He ion beam on the sample surface. The measured total abundance values are used to construct a grayscale image of the sample, where the gray level at a particular image pixel is determined by the total measured abundance of He ions at a corresponding He ion beam position on the sample. Differently-oriented crystal grains at the surface of the sample have different yields of scattered He ions, and the image shows the differently-oriented crystal grains as variable gray levels. Using the information in the image, crystal grains and grain boundaries can be identified at the sample surface. Once the grain boundaries on the surface of the sample have been identified, the He ion beam is scanned from one grain to another on the surface of the sample. At each position of the He ion beam, a two-dimensional detector is used to capture an image of scattered he ions from the surface of the sample. Each two-dimensional image corresponds to a Kikuchi pattern for a particular crystal grain at the surface of the sample. Based on the Kikuchi pattern, the grain's crystal structure, lattice spacing, and crystal orientation can be determined. By measuring a single Kikuchi pattern for each grain rather than at each pixel throughout the FOV, a complete map of the sample's surface crystal structure is obtained in a shorter time.

To measure topographic information from the sample, the total secondary electron intensity is measured as described in Example 19. The measured crystalline information is then used to remove contributions to the secondary electron intensity measurements that arise from crystal structure variations in the sample. The corrected total secondary electron intensity values are used to construct a grayscale image of the sample, where the gray level at a particular image pixel is determined by the corrected intensities of secondary electrons at a corresponding He ion beam position on the sample.

Topographic information is provided by the image, which shows the surface relief pattern of the sample in the FOV.

22

Measurement of Topographic and Crystalline Information from a Sample

To measure topographic and crystalline information from a sample, the sample is fixed in position on a sample mount in a gas field ion microscope as described herein. The gas field ion microscope is configured as described in Example 19.

Crystalline information from the sample is measured as described in Example 19.

To measure topographic information from the sample, a detector is configured to measure a total intensity of secondary electrons from the sample produced in response to the incident He ion beam. The sample is tilted with respect to the He ion beam, so that the He ion beam is incident at a non-normal angle to the surface of the sample. The He ion beam is raster-scanned in discrete steps over the entire FOV region of the sample surface, and the total intensity of secondary electrons is measured as a function of the position of the He ion beam on the sample surface. The measured crystalline information is then used to remove contributions to the secondary electron intensity measurements that arise from crystal structure variations in the sample. The corrected total intensity values are used to construct a grayscale image of the sample, where the gray level at a particular image pixel is determined by the corrected total intensities of secondary electrons at a corresponding He ion beam position on the sample. Topographic information is provided by the image, which shows the surface relief pattern of the sample in the FOV. Tilting the sample with respect to the He ion beam can reveal topographic information that would otherwise remain hidden if the He ion beam was incident on the sample surface only at normal angles.

Optionally, the sample tilt can then be adjusted so that the He ion beam is incident at a different non-normal angle to the surface of the sample, and the He ion beam is raster-scanned is discrete steps over the entire FOV region of the sample surface. The total intensity of secondary electrons is measured as a function of the position of the He ion beam on the sample surface, and the measured crystalline information is used to remove contributions to the secondary electron intensity measurements that arise from crystal structure variations in the sample. The corrected total secondary electron intensity values are used to construct a second grayscale image of the sample corresponding to the second non-normal incidence angle of the He ion beam, where the gray level at a particular image pixel is determined by the corrected total intensities of secondary electrons at a corresponding He ion beam position on the sample. The information from the two images measured at different He ion beam angles of incidence can then be combined and used to determine quantitative three-dimensional topographic information about the surface of the sample.

23

Measurement of Topographic and Crystalline Information from a Sample

To measure topographic and crystalline information from a sample, the sample is fixed in position on a sample mount in a gas field ion microscope as described herein. The gas field ion microscope is configured as described in Example 19.

Crystalline information from the sample is measured as described in Example 20.

To measure topographic information from the sample, the total intensity of secondary electrons from the sample is measured as described in Example 22. The measured crystalline information is used to remove contributions to the secondary electron intensity measurements, at each ion beam angle of incidence, that arise from crystal structure variations in the sample. The corrected total secondary electron intensity values are used to construct grayscale images of the sample as described in Example 22. The information from the two images measured at different He ion beam angles of incidence can then be combined and used to determine quantitative three-dimensional topographic information about the surface of the sample.

24

Measurement of Topographic and Crystalline Information from a Sample

To measure topographic and crystalline information from a sample, the sample is fixed in position on a sample mount in a gas field ion microscope as described herein. The gas field ion microscope is configured as described in Example 192.

Crystalline information from the sample is measured as described in Example 21.

To measure topographic information from the sample, the total intensity of secondary electrons from the sample is measured as described in Example 22. The measured crystalline information is used to remove contributions to the secondary electron intensity measurements, at each ion beam angle of incidence, that arise from crystal structure variations in the sample. The corrected total secondary electron intensity values are used to construct grayscale images of the sample as described in Example 22. The information from the two images measured at different He ion beam angles of incidence can then be combined and used to determine quantitative three-dimensional topographic information about the surface of the sample.

25

Measurement of Topographic and Crystalline Information from a Sample

To measure topographic and crystalline information from a sample, the sample is fixed in position on a sample mount in a gas field ion microscope as described herein. The gas field ion microscope is configured as described in Example 19.

Crystalline information from the sample is measured as described in Example 19.

To measure topographic information from the sample, two or more detectors, each oriented at a different angle and position with respect to the sample, are configured to measure a total intensity of secondary electrons from the sample produced in response to the incident He ion beam. The He ion beam is raster-scanned in discrete steps over the entire FOV region of the sample surface, and the total intensity of secondary electrons is measured by each detector as a function of the position of the He ion beam on the sample surface. The measured crystalline information is used to remove contributions to the secondary electron intensity measurements at each detector that arise from crystal structure variations in the sample. The corrected total intensity values are used to construct a series of grayscale images of the sample, each image corresponding to one of the detectors, where the gray level at a particular pixel in a particular image is determined by the corrected total intensity of secondary electrons at a corresponding He ion beam position on the sample. Information from the images measured by the multiple detectors can then be combined and used to determine quantitative three-dimensional topographic information about the surface of the sample.

26

Measurement of Topographic and Crystalline Information from a Sample

To measure topographic and crystalline information from a sample, the sample is fixed in position on a sample mount in a gas field ion microscope as described herein. The gas field ion microscope is configured as described in Example 19.

Crystalline information from the sample is measured as described in Example 20.

To measure topographic information from the sample, the total intensity of secondary electrons from the sample is measured as described in Example 25. The measured crystalline information is used to remove contributions to the secondary electron intensity measurements, at each detector, that arise from crystal structure variations in the sample. The corrected total secondary electron intensity values are used to construct grayscale images of the sample as described in Example 25. Information from the images measured by the multiple detectors can then be combined and used to determine quantitative three-dimensional topographic information about the surface of the sample.

27

Measurement of Topographic and Crystalline Information from a Sample

To measure topographic and crystalline information from a sample, the sample is fixed in position on a sample mount in a gas field ion microscope as described herein. The gas field ion microscope is configured as described in Example 19.

Crystalline information from the sample is measured as described in Example 21.

To measure topographic information from the sample, the total intensity of secondary electrons from the sample is measured as described in Example 25. The measured crystalline information is used to remove contributions to the secondary electron intensity measurements, at each detector, that arise from crystal structure variations in the sample. The corrected total secondary electron intensity values are used to construct grayscale images of the sample as described in Example 25. Information from the images measured by the multiple detectors can then be combined and used to determine quantitative three-dimensional topographic information about the surface of the sample.

28

Measurement of Topographic and Crystalline Information from a Sample

To measure topographic and crystalline information from a sample, the sample is fixed in position on a sample mount in a gas field ion microscope as described herein. The gas field ion microscope is configured as described in Example 19.

Crystalline information from the sample is measured as described in Example 19.

To measure topographic information from the sample, a detector configured to measure He ions is positioned to detect He ions scattered from the surface of the sample at large scattering angles. The He ion beam is raster-scanned in discrete steps over the entire FOV region of the sample surface, and the total abundance of He ions is measured by the detector as a function of the position of the He ion beam on the sample surface. The total abundance values are used to construct a grayscale image of the sample, where the gray level at a particular image pixel is determined by the total measured abundance of scattered He ions at a corresponding He ion beam position on the sample. Topographic information is provided by the image, which shows the surface relief pattern of the sample in the FOV.

29

Measurement of Topographic and Crystalline Information from a Sample

To measure topographic and crystalline information from a sample, the sample is fixed in position on a sample mount in a gas field ion microscope as described herein. The gas field ion microscope is configured as described in Example 19.

Crystalline information from the sample is measured as described in Example 20.

Topographic information from the sample is measured as described in Example 28.

30

Measurement of Topographic and Crystalline Information from a Sample

To measure topographic and crystalline information from a sample, the sample is fixed in position on a sample mount in a gas field ion microscope as described herein. The gas field ion microscope is configured as described in Example 19.

Crystalline information from the sample is measured as described in Example 31.

Topographic information from the sample is measured as described in Example 28.

31

Measurement of Topographic and Crystalline Information from a Sample

To measure topographic and crystalline information from a sample, the sample is fixed in position on a sample mount in a gas field ion microscope as described herein. The gas field ion microscope is configured as described in Example 19.

Crystalline information from the sample is measured as described in Example 19.

To measure topographic information from the sample, two or more detectors configured to measure He ions are positioned to detect He ions scattered from the surface of the sample at large scattering angles. The He ion beam is raster-scanned in discrete steps over the entire FOV region of the sample surface, and the total abundance of He ions is measured by each of the detectors as a function of the position of the He ion beam on the sample surface. The total abundance values are used to construct grayscale images of the sample corresponding to each of the detectors, where the gray level at a particular image pixel is determined by the total measured abundance of scattered He ions at a corresponding He ion beam position on the sample. Information from the multiple images measured by the detectors can then be combined and used to determine quantitative three-dimensional topographic information about the surface of the sample.

32

Measurement of Topographic and Crystalline Information from a Sample

To measure topographic and crystalline information from a sample, the sample is fixed in position on a sample mount in a gas field ion microscope as described herein. The gas field ion microscope is configured as described in Example 19.

Crystalline information from the sample is measured as described in Example 20.

Topographic information from the sample is measured as described in Example 31.

33

Measurement of Topographic and Crystalline Information from a Sample

To measure topographic and crystalline information from a sample, the sample is fixed in position on a sample mount in a gas field ion microscope as described herein. The gas field ion microscope is configured as described in Example 19.

Crystalline information from the sample is measured as described in Example 21.

Topographic information from the sample is measured as described in Example 31.

34

Measurement of Topographic and Material Information from a Sample

To measure topographic and material information from a sample, the sample is fixed in position on a sample mount in a gas field ion microscope as described herein. The gas field ion microscope is configured as described in Example 19.

To measure material information from the sample, a detector configured to measure He ions is positioned to detect He ions backscattered from the sample. The He ion beam is raster-scanned in discrete steps over the entire FOV region of the sample surface, and the total abundance of backscattered He ions is measured as a function of the position of the He ion beam on the sample surface. The total abundance measurements of backscattered He ions are used to construct a grayscale image of the sample, where the gray level at a particular image pixel is determined by the total measured abundance of backscattered He ions at a corresponding He ion beam position on the sample. Because the He ion scattering cross-sections depends roughly on the square of the atomic number of the scattering atom, the intensities in the image can be used to quantitatively determine the composition of the sample.

To measure topographic information from the sample, a total intensity of secondary electrons is measured as a function of the position of the He ion beam on the sample surface as described in Example 19. The measured material information is then used to remove contributions to the total secondary electron intensity measurements that arise from composition variations in the sample. The corrected total secondary electron intensity values are used to construct a grayscale image of the sample, where the gray level at a particular image pixel is determined by the corrected total intensity values. Topographic information is provided by the image, which shows the surface relief pattern of the sample in the FOV.

35

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from a sample as described in Example 34.

To measure topographic information from the sample, the total intensity of secondary electrons from the sample is measured as described in Example 22. The measured material information is used to remove contributions to the secondary electron intensity measurements, at each ion beam angle of incidence, that arise from composition variations in the sample. The corrected total secondary electron intensity values are used to construct grayscale images of the sample as described in Example 22. The information from the two images measured at different He ion beam angles of incidence can then be combined and used to determine quantitative three-dimensional topographic information about the surface of the sample.

36

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from a sample as described in Example 34.

To measure topographic information from the sample, the total intensity of secondary electrons from the sample is measured as described in Example 25. The measured material information is used to remove contributions to the secondary electron intensity measurements, at each detector, that arise from composition variations in the sample. The corrected total secondary electron intensity values are used to construct grayscale images of the sample as described in Example 25. Information from the images measured by the multiple detectors can then be combined and used to determine quantitative three-dimensional topographic information about the surface of the sample.

37

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 34.

Topographic information from the sample is measured as described in Example 28.

38

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 34.

Topographic information from the sample is measured as described in Example 31.

39

Measurement of Topographic and Material Information from a Sample

To measure topographic and material information from a sample, the sample is fixed in position on a sample mount in a gas field ion microscope as described herein. The gas field ion microscope is configured as described in Example 19.

To measure material information from the sample, a energy- and angle-resolved detector configured to measure He ions is positioned to detect He from the sample. The He ion beam is raster-scanned in discrete steps over the entire FOV region of the sample surface, and the energies and angles of scattered He ions are measured as a function of the position of the He ion beam on the sample surface. From the average angles and energies of the scattered He ions, the mass of the scattering atoms can be determined, and the composition of the sample can be determined.

To measure topographic information from the sample, a total intensity of secondary electrons is measured as a function of the position of the He ion beam on the sample surface as described in Example 19. The measured material information is then used to remove contributions to the total secondary electron intensity measurements that arise from composition variations in the sample. The corrected total secondary electron intensity values are used to construct a grayscale image of the sample, where the gray level at a particular image pixel is determined by the corrected total intensity values. Topographic information is provided by the image, which shows the surface relief pattern of the sample in the FOV.

40

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 39.

To measure topographic information from the sample, the total intensity of secondary electrons from the sample is measured as described in Example 22. The measured material information is used to remove contributions to the secondary electron intensity measurements, at each ion beam angle of incidence, that arise from composition variations in the sample. The corrected total secondary electron intensity values are used to construct grayscale images of the sample as described in Example 22. The information from the two images measured at different He ion beam angles of incidence can then be combined and used to determine quantitative three-dimensional topographic information about the surface of the sample.

41

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 39.

To measure topographic information from the sample, the total intensity of secondary electrons from the sample is measured as described in Example 25. The measured material information is used to remove contributions to the secondary electron intensity measurements, at each detector, that arise from composition variations in the sample. The corrected total secondary electron intensity values are used to construct grayscale images of the sample as described in Example 25. Information from the images measured by the multiple detectors can then be combined and used to determine quantitative three-dimensional topographic information about the surface of the sample.

42

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 39.

Topographic information from the sample is measured as described in Example 28.

43

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 39.

Topographic information from the sample is measured as described in Example 31.

44

Measurement of Topographic and Material Information from a Sample

To measure topographic and material information from a sample, the sample is fixed in position on a sample mount in a gas field ion microscope as described herein. The gas field ion microscope is configured as described in Example 19.

To measure material information, an x-ray detector can be used to detect x-rays emerging from the sample in response to the incident He ion beam. The He ion beam is raster-scanned in discrete steps over the entire FOV region of the sample surface, and the x-ray emission spectrum is measured as a function of the position of the He ion beam on the sample surface. Certain emission lines in the x-ray spectrum are particular to certain types of atoms, and so based on the measured x-ray spectrum, the composition at each step on the surface of the sample is determined.

To measure topographic information from the sample, a total intensity of secondary electrons is measured as a function of the position of the He ion beam on the sample surface as described in Example 19. The measured material information is then used to remove contributions to the total secondary electron intensity measurements that arise from composition variations in the sample. The corrected total secondary electron intensity values are used to construct a grayscale image of the sample, where the gray level at a particular image pixel is determined by the corrected total intensity values. Topographic information is provided by the image, which shows the surface relief pattern of the sample in the FOV.

45

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 44.

To measure topographic information from the sample, the total intensity of secondary electrons from the sample is measured as described in Example 22. The measured material information is used to remove contributions to the secondary electron intensity measurements, at each ion beam angle of incidence, that arise from composition variations in the sample. The corrected total secondary electron intensity values are used to construct grayscale images of the sample as described in Example 22. The information from the two images measured at different He ion beam angles of incidence can then be combined and used to determine quantitative three-dimensional topographic information about the surface of the sample.

46

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 44.

To measure topographic information from the sample, the total intensity of secondary electrons from the sample is measured as described in Example 25. The measured material information is used to remove contributions to the secondary electron intensity measurements, at each detector, that arise from composition variations in the sample. The corrected total secondary electron intensity values are used to construct grayscale images of the sample as described in Example 25. Information from the images measured by the multiple detectors can then be combined and used to determine quantitative three-dimensional topographic information about the surface of the sample.

47

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 44.

Topographic information from the sample is measured as described in Example 28.

48

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 44.

Topographic information from the sample is measured as described in Example 31.

49

Measurement of Topographic and Material Information from a Sample

To measure topographic and material information from a sample, the sample is fixed in position on a sample mount in a gas field ion microscope as described herein. The gas field ion microscope is configured as described in Example 19.

To measure material information, a photon detector can be used to detect photons emerging from the sample in response to the incident He ion beam. The He ion beam is raster-scanned in discrete steps over the entire FOV region of the sample surface, and the photon emission spectrum is measured as a function of the position of the He ion beam on the sample surface. Certain emission lines in the spectrum are particular to certain types of atoms, and so based on the measured spectrum, the composition at each step on the surface of the sample is determined.

To measure topographic information from the sample, a total intensity of secondary electrons is measured as a function of the position of the He ion beam on the sample surface as described in Example 19. The measured material information is then used to remove contributions to the total secondary electron intensity measurements that arise from composition variations in the sample. The corrected total secondary electron intensity values are used to construct a grayscale image of the sample, where the gray level at a particular image pixel is determined by the corrected total intensity values. Topographic information is provided by the image, which shows the surface relief pattern of the sample in the FOV.

50

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 49.

To measure topographic information from the sample, the total intensity of secondary electrons from the sample is measured as described in Example 22. The measured material information is used to remove contributions to the secondary electron intensity measurements, at each ion beam angle of incidence, that arise from composition variations in the sample. The corrected total secondary electron intensity values are used to construct grayscale images of the sample as described in Example 22. The information from the two images measured at different He ion beam angles of incidence can then be combined and used to determine quantitative three-dimensional topographic information about the surface of the sample.

51

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 49.

To measure topographic information from the sample, the total intensity of secondary electrons from the sample is measured as described in Example 25. The measured material information is used to remove contributions to the secondary electron intensity measurements, at each detector, that arise from composition variations in the sample. The corrected total secondary electron intensity values are used to construct grayscale images of the sample as described in Example 25. Information from the images measured by the multiple detectors can then be combined and used to determine quantitative three-dimensional topographic information about the surface of the sample.

52

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 49.

Topographic information from the sample is measured as described in Example 28.

53

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 49.

Topographic information from the sample is measured as described in Example 31.

54

Measurement of Topographic and Material Information from a Sample

To measure topographic and material information from a sample, the sample is fixed in position on a sample mount in a gas field ion microscope as described herein. The gas field ion microscope is configured as described in Example 19.

To measure material information, an Auger electron detector can be used to detect Auger electrons emerging from the sample in response to the incident He ion beam. The He ion beam is raster-scanned in discrete steps over the entire FOV region of the sample surface, and the Auger electron emission spectrum is measured as a function of the position of the He ion beam on the sample surface. Certain emission lines in the spectrum are particular to certain types of atoms, and so based on the measured spectrum, the composition at each step on the surface of the sample is determined.

To measure topographic information from the sample, a total intensity of secondary electrons is measured as a function of the position of the He ion beam on the sample surface as described in Example 19. The measured material information is then used to remove contributions to the total secondary electron intensity measurements that arise from composition variations in the sample. The corrected total secondary electron intensity values are used to construct a grayscale image of the sample, where the gray level at a particular image pixel is determined by the corrected total intensity values. Topographic information is provided by the image, which shows the surface relief pattern of the sample in the FOV.

55

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 54.

To measure topographic information from the sample, the total intensity of secondary electrons from the sample is measured as described in Example 22. The measured material information is used to remove contributions to the secondary electron intensity measurements, at each ion beam angle of incidence, that arise from composition variations in the sample. The corrected total secondary electron intensity values are used to construct grayscale images of the sample as described in Example 22. The information from the two images measured at different He ion beam angles of incidence can then be combined and used to determine quantitative three-dimensional topographic information about the surface of the sample.

56

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 54.

To measure topographic information from the sample, the total intensity of secondary electrons from the sample is measured as described in Example 25. The measured material information is used to remove contributions to the secondary electron intensity measurements, at each detector, that arise from composition variations in the sample. The corrected total secondary electron intensity values are used to construct grayscale images of the sample as described in Example 25. Information from the images measured by the multiple detectors can then be combined and used to determine quantitative three-dimensional topographic information about the surface of the sample.

57

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 54.

Topographic information from the sample is measured as described in Example 28.

58

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 54.

Topographic information from the sample is measured as described in Example 31.

59

Measurement of Topographic and Material Information from a Sample

To measure topographic and material information from a sample, the sample is fixed in position on a sample mount in a gas field ion microscope as described herein. The gas field ion microscope is configured as described in Example 19.

To measure material information, a TOF detector can be used to detect secondary ions and/or atoms emerging from the sample in response to the incident He ion beam. The He ion beam is raster-scanned in discrete steps over the entire FOV region of the sample surface, and the times-of-flight of secondary ions and/or atoms from sample 180 are measured as a function of the position of the He ion beam on the sample surface. Based on the measured times-of-flight of the ions/atoms, and the known voltage of the accelerating electrodes in the TOF instrument, the masses of the detected particles can be calculated and the identities of the particles can be determined.

To measure topographic information from the sample, a total intensity of secondary electrons is measured as a function of the position of the He ion beam on the sample surface as described in Example 19. The measured material information is then used to remove contributions to the total secondary electron intensity measurements that arise from composition variations in the sample. The corrected total secondary electron intensity values are used to construct a grayscale image of the sample, where the gray level at a particular image pixel is determined by the corrected total intensity values. Topographic information is provided by the image, which shows the surface relief pattern of the sample in the FOV.

60

Measurement of Topographic and Material Information from a Sample

To measure topographic and material information from a sample, the sample is fixed in position on a sample mount in a gas field ion microscope as described herein. The gas field ion microscope is configured as described in Example 19

Material information can be measured from the sample as described in Example 59

To measure topographic information from the sample, the total intensity of secondary electrons from the sample is measured as described in Example 22. The measured material information is used to remove contributions to the secondary electron intensity measurements, at each ion beam angle of incidence, that arise from composition variations in the sample. The corrected total secondary electron intensity values are used to construct grayscale images of the sample as described in 22. The information from the two images measured at different He ion beam angles of incidence can then be combined and used to determine quantitative three-dimensional topographic information about the surface of the sample.

61

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 59.

To measure topographic information from the sample, the total intensity of secondary electrons from the sample is measured as described in Example 25. The measured material information is used to remove contributions to the secondary electron intensity measurements, at each detector, that arise from composition variations in the sample. The corrected total secondary electron intensity values are used to construct grayscale images of the sample as described in Example 25. Information from the images measured by the multiple detectors can then be combined and used to determine quantitative three-dimensional topographic information about the surface of the sample.

62

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 59.

Topographic information from the sample is measured as described in Example 28.

63

Measurement of Topographic and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 59.

Topographic information from the sample is measured as described in Example 31.

64

Measurement of Crystalline and Material Information from a Sample

To measure topographic and material information from a sample, the sample is fixed in position on a sample mount in a gas field ion microscope as described herein. The gas field ion microscope is configured as described in Example 192.

Material information can be measured from the sample as described in Example 44.

Crystalline information can be measured from the sample as described in Example 19.

65

Measurement of Crystalline and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 44.

Crystalline information can be measured from the sample as described in Example 20.

66

Measurement of Crystalline and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 44.

Crystalline information can be measured from the sample as described in Example 21.

67

Measurement of Crystalline and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 49.

Crystalline information can be measured from the sample as described in Example 19.

68

Measurement of Crystalline and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 49.

Crystalline information can be measured from the sample as described in Example 20.

69

Measurement of Crystalline and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 49.

Crystalline information can be measured from the sample as described in Example 214.

70

Measurement of Crystalline and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 54.

71

Measurement of Crystalline and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 54.

Crystalline information can be measured from the sample as described in Example 20.

72

Measurement of Crystalline and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 54. Crystalline information can be measured from the sample as described in Example 21.

73

Measurement of Crystalline and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 59.

Crystalline information can be measured from the sample as described in Example 192.

74

Measurement of Crystalline and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 59.

Crystalline information can be measured from the sample as described in Example 20.

75

Measurement of Crystalline and Material Information from a Sample

To measure topographic and material information from a sample, the sample is fixed in position on a sample mount in a gas field ion microscope as described herein. The gas field ion microscope is configured as described in Example 19.

Material information can be measured from the sample as described in Example 59.

Crystalline information can be measured from the sample as described in Example 21.

Other embodiments are in the claims.

What is claimed is:

1. A system, comprising:
a gas field ion source capable of interacting with a gas to generate an ion beam that can interact with a sample to cause scattered ions to leave the sample;
at least one detector configured so that, during use, the at least one detector can detect at least some of the scattered ions; and
an electronic processor electrically connected to the at least one detector so that, during use, the electronic processor can process information based on the detected scattered ions to determine information about the sample.

2. The system of claim 1, wherein the information about the sample is selected from the group consisting of topographical information about a surface of the sample, material constituent information of a surface of the sample, material constituent information about a sub-surface region of the sample, crystalline information about the sample, voltage contrast information about a surface of the sample, voltage contrast information about a sub-surface region of the sample, magnetic information about the sample, and optical information about the sample.

3. The system of claim 1, wherein the electronic processor can process information based on the detected scattered ions to determine information about the energy of the detected scattered ions.

4. The system of claim 3, wherein the information about the energy of the detected scattered ions is an energy distribution of the detected scattered ions.

5. The system of claim 3, wherein the electronic processor can process information based on the detected scattered ions to determine information about angles of trajectories of the detected scattered ions.

6. The system of claim 1, wherein the electronic processor can process information based on the detected scattered ions to determine information about angles of trajectories of the detected scattered ions.

7. The system of claim 6, wherein the information about the angles of the trajectories of the detected scattered ions is a distribution of the angles of the trajectories distribution of the detected scattered ions.

8. The system of claim 1, wherein the at least one detector comprises multiple detectors.

9. The system of claim 1, wherein the at least one detector is configured to provide angularly resolved information about the detected scattered ions.

10. The system of claim 9, wherein the at least one detector comprises multiple detectors that are located at different angles with respect to the sample.

11. The system of claim 9, wherein the at least one detector comprises a hemispherical detector.

12. The system of claim 9, wherein the at least one detector is capable of moving between a first solid angle with respect to the sample and a second solid angle with respect to the sample.

13. The system of claim 1, wherein, for a given scattered ion, the at least one detector is capable of providing a signal based on an energy of the given scattered ion.

14. The system of claim 13, wherein the at least one detector is configured to provide angularly resolved information about the detected scattered ions.

15. The system of claim 1, further comprising a device electrically connected within the system so that, during use, the ion beam is pulsed.

16. The system of claim 15, further comprising a time of flight sub-system configured so that, during use, the time of flight sub-system can measure time of flight information of the scattered ions.

17. The system of claim 1, further comprising a time of flight sub-system configured so that, during use, the time of flight sub-system can measure time of flight information of the scattered ions.

18. The system of claim 1, wherein, during use the ion beam impinges on a first surface of the sample, and at least one of the detectors is located adjacent to a second surface of the sample, the second surface being opposite the first surface.

19. The system of claim 1, wherein the ion beam has a reduced etendue of $1 \times 10^{-16}$ $cm^2 srV$ or less.

20. The system of claim 1, wherein the ion beam has an etendue of $5 \times 10^{-21}$ $cm^2 sr$ or less.

21. The system of claim 1, wherein the ion beam has a reduced brightness at a surface of the sample of $5 \times 10^8$ $A/m^2 srV$ or more.

22. The system of claim 1, wherein the ion beam has a brightness at a surface of the sample of $1 \times 10^9$ $A/cm^2 sr$ or more.

23. The system of claim 1, wherein the ion beam has a spot size with a dimension of 10 nm or less at a surface of the sample.

24. The system of claim 1, wherein the system is a gas field ion microscope.

25. The system of claim 1, wherein the system is a helium ion microscope.

26. The system of claim 1, wherein the system is a scanning ion microscope.

27. The system of claim 1, wherein the system is a scanning helium ion microscope.

28. The system of claim 1, wherein the gas field ion source comprises an electrically conductive tip having a terminal shelf with 20 atoms or less.

29. A method, comprising:
generating an ion beam by interacting a gas with a gas field ion source;
interacting the ion beam with a sample to cause scattered ions to leave the sample;
detecting at least some of the scattered ions; and
determining information about the sample based on the detected scattered ions.

30. A system, comprising:
a gas field ion source capable of interacting with a gas to generate an ion beam that can interact with a sample to cause primary neutral particles to leave the sample;
at least one detector configured so that, during use, the at least one detector can detect at least some of the primary neutral particles; and
an electronic processor electrically connected to the at least one detector so that, during use, the electronic processor can process information based on the detected primary neutral particles to determine information about the sample.

31. A method, comprising:
generating an ion beam by interacting a gas with a gas field ion source;
interacting the ion beam with a sample to cause primary neutral particles to leave the sample;
detecting at least some of the primary neutral particles; and
determining information about the sample based on the detected primary neutral particles.

32. The method of claim 29, wherein the information about the sample is selected from the group consisting of topographical information about a surface of the sample, material constituent information of a surface of the sample, material constituent information about a sub-surface region of the sample, crystalline information about the sample, voltage contrast information about a surface of the sample, voltage contrast information about a sub-surface region of the sample, magnetic information about the sample, and optical information about the sample.

33. The method of claim 29, further comprising determining information about energies of the detected scattered ions.

34. The method of claim 33, wherein the information about the energies of the detected scattered ions is an energy distribution of the detected scattered ions.

35. The method of claim 33, further comprising determining information about angles of trajectories of the detected scattered ions.

36. The method of claim 29, further comprising determining information about angles of trajectories of the detected scattered ions.

37. The method of claim 36, wherein the information about the angles of the trajectories of the detected scattered ions is a distribution of the angles of the trajectories of the detected scattered ions.

38. The method of claim 29, wherein the method includes using multiple detectors.

39. The method of claim 38, wherein the multiple detectors are located at different angles with respect to the sample.

40. The method of claim 29, wherein the method includes using a hemispherical detector.

41. The method of claim 38, further comprising moving one or more detectors from a first solid angle with respect to the sample to a second solid angle with respect to the sample.

42. The method of claim 29, further comprising pulsing the ion beam.

43. The method of claim 42, further comprising a time of flight sub-system configured so that, during use, the time of flight sub-system can measure time of flight information of the detected scattered ions.

44. The method of claim 29, further comprising a time of flight sub-system configured so that, during use, the time of flight sub-system can measure time of flight information of the detected scattered ions.

45. The method of claim 29, wherein, during use the ion beam impinges on a first surface of the sample, and at least one detector is located adjacent to a second surface of the sample, the second surface being opposite the first surface.

46. The method of claim 29, wherein the ion beam has a reduced etendue of $1 \times 10^{-16}$ $cm^2 srV$ or less.

47. The method of claim 29, wherein the ion beam has an etendue of $5 \times 10^{-21}$ $cm^2 sr$ or less.

48. The method of claim 29, wherein the ion beam has a reduced brightness at a surface of the sample of $5 \times 10^8$ $A/m^2 srV$ or more.

49. The method of claim 29, wherein the ion beam has a brightness at a surface of the sample of $1 \times 10^9 A/cm^2 sr$ or more.

50. The method of claim 29, wherein the ion beam has a spot size with a dimension of 10 nm or less at a surface of the sample.

51. The method of claim 29, wherein the method is performed using a gas field ion microscope.

52. The method of claim 29, wherein the method is performed using is a helium ion microscope.

53. The method of claim 29, wherein the method is performed using is a scanning ion microscope.

54. The method of claim 29, wherein the method is performed using is a scanning helium ion microscope.

55. The method of claim 29, wherein the method can distinguish atoms in the sample having atomic numbers that differ by one.

56. The method of claim 29, wherein the method can distinguish atoms in the sample having masses that differ by one atomic mass unit.

57. The system of claim 30, wherein the information about the sample is selected from the group consisting of topographical information about a surface of the sample, material constituent information of a surface of the sample, material constituent information about a sub-surface region of the sample, crystalline information about the sample, voltage contrast information about a surface of the sample, voltage contrast information about a sub-surface region of the sample, magnetic information about the sample, and optical information about the sample.

58. The system of claim 30, wherein the electronic processor can process information based on the detected primary neutral particles to determine information about the energy of the detected primary neutral particles.

59. The system of claim 58, wherein the information about the energy of the detected primary neutral particles is an energy distribution of the detected primary neutral particles.

60. The system of claim 58, wherein the electronic processor can process information based on the detected primary neutral particles to determine information about angles of trajectories of the detected primary neutral particles.

61. The system of claim 30, wherein the electronic processor can process information based on the detected primary neutral particles to determine information about angles of trajectories of the detected primary neutral particles.

62. The system of claim 61, wherein the information about the angles of the trajectories of the detected primary neutral particles is a distribution of the angles of the trajectories of the detected primary neutral particles.

63. The system of claim 30, wherein the at least one detector comprises multiple detectors.

64. The system of claim 30, wherein the at least one detector is configured to provide angularly resolved information about the detected primary neutral particles.

65. The system of claim 64, wherein the at least one detector comprises multiple detectors that are located at different angles with respect to the sample.

66. The system of claim 30, wherein the at least one detector comprises a hemispherical detector.

67. The system of claim 64, wherein the at least one detector is capable of moving between a first solid angle with respect to the sample and a second solid angle with respect to the sample.

68. The system of claim 30, wherein, for a given primary neutral particle, the at least one detector is capable of providing a signal based on an energy of the given primary neutral particle.

69. The system of claim 66, wherein the at least one detector is configured to provide angularly resolved information about the detected primary neutral particle.

70. The system of claim 30, further comprising a device electrically connected within the system so that, during use, the ion beam is pulsed.

71. The system of claim 70, further comprising a time of flight sub-system configured so that, during use, the time of flight sub-system can measure time of flight information of the primary neutral particles.

72. The system of claim 30, further comprising a time of flight sub-system configured so that, during use, the time of flight sub-system can measure time of flight information of the primary neutral particles.

73. The system of claim 30, wherein, during use the ion beam impinges on a first surface of the sample, and at least one of the detectors is located adjacent to a second surface of the sample, the second surface being opposite the first surface.

74. The system of claim 30, wherein, during use:
the gas field ion source interacts with the sample to cause additional particles to leave the sample, the additional particles being selected from the group consisting of electrons and scattered ions;
the at least one detector is configured to detect at least some of the scattered ions; and
the electronic processor can process information based on the detected scattered ions to determine information about the sample.

75. The system of claim 30, wherein the ion beam has a reduced etendue $1 \times 10^{-16}$ cm$^2$srV or less.

76. The system of claim 30, wherein the ion beam has an etendue of $5 \times 10^{-21}$ cm$^2$sr or less.

77. The system of claim 30, wherein the ion beam has a reduced brightness at the surface of a sample of $5 \times 10^8$ A/m$^2$srV or more.

78. The system of claim 30, wherein the ion beam has a brightness at a surface of the sample of $1 \times 10^9$ A/cm$^2$sr or more.

79. The system of claim 30, wherein the ion beam has a spot size with a dimension of 10 nm or less at a surface of the sample.

80. The system of claim 30, wherein the system is a gas field ion microscope.

81. The system of claim 30, wherein the system is a helium ion microscope.

82. The system of claim 30, wherein the system is a scanning ion microscope.

83. The system of claim 30, wherein the system is a scanning helium ion microscope.

84. The system of claim 30, wherein the gas field ion source comprises an electrically conductive tip having a terminal shelf with 20 atoms or less.

85. The method of claim 31, wherein the information about the sample is selected from the group consisting of topographical information about a surface of the sample, material constituent information of a surface of the sample, material constituent information about a sub-surface region of the sample, crystalline information about the sample, voltage contrast information about a surface of the sample, voltage contrast information about a sub-surface region of the sample, magnetic information about the sample, and optical information about the sample.

86. The method of claim 31, further comprising determining information about energies of the detected primary neutral particles.

87. The method of claim 86, wherein the information about the energies of the detected scattered primary neutral particles is an energy distribution of the detected primary neutral particles.

88. The method of claim 86, further comprising determining information about angles of trajectories of the detected primary neutral particles.

89. The method of claim 31, further comprising determining information about angles of trajectories of the detected primary neutral particles.

90. The method of claim 89, wherein the information about the angles of the trajectories of the detected primary neutral particles is a distribution of the angles of the trajectories of the detected primary neutral particles.

91. The method of claim 31, wherein the method includes using multiple detectors.

92. The method of claim 91, wherein the multiple detectors are located at different angles with respect to the sample.

93. The method of claim 91, wherein the at least one detector comprises a hemispherical detector.

94. The method of claim 91, further comprising moving one or more detectors from a first solid angle with respect to the sample to a second solid angle with respect to the sample.

95. The method of claim 31, comprising pulsing the ion beam.

96. The method of claim 95, further comprising a time of flight sub-system configured so that, during use, the time of flight sub-system can measure time of flight information of the detected scattered primary neutral particles.

97. The method of claim 31, further comprising a time of flight sub-system configured so that, during use, the time of flight sub-system can measure time of flight information of the detected scattered primary neutral particles.

98. The method of claim 31, wherein, during use the ion beam impinges on a first surface of the sample, and at least one detector is located adjacent to a second surface of the sample, the second surface being opposite the first surface.

99. The method of claim 31, wherein interacting the ion beam with a sample forms scattered ions, and the method further comprises:

detecting at least some of the scattered ions; and
determining information about the sample based on the detected scattered ions.

100. The method of claim 31, wherein the ion beam has a reduced etendue of $1\times10^{-16}$ cm$^2$srV or less.

101. The method of claim 31, wherein the ion beam has an etendue of $5\times10^{-21}$ cm$^2$sr or less.

102. The method of claim 31, wherein the ion beam has a reduced brightness at a surface of the sample of $5\times10^8$ A/m$^2$srV or more.

103. The method of claim 31, wherein the ion beam has a brightness at a surface of the sample of $1^{109}$ A/cm$^2$sr or more.

104. The method of claim 31, wherein the ion beam has a spot size with a dimension of 10 nm or less at a surface of the sample.

105. The method of claim 31, wherein the method is performed using a gas field ion microscope.

106. The method of claim 31, wherein the method is performed using is a helium ion microscope.

107. The method of claim 31, wherein the method is performed using is a scanning ion microscope.

108. The method of claim 31, wherein the method is performed using is a scanning helium ion microscope.

109. The method of claim 31, wherein the method can distinguish atoms in the sample having atomic numbers that differ by one.

110. The method of claim 31, wherein the method can distinguish atoms in the sample having masses that differ by one atomic mass unit.

\* \* \* \* \*

UNITED STATES PATENT AND TRADEMARK OFFICE
CERTIFICATE OF CORRECTION

PATENT NO.       : 7,557,361 B2
APPLICATION NO. : 11/600874
DATED            : July 7, 2009
INVENTOR(S)      : Billy W. Ward It is certified that error appears in the above-identified patent and that said Letters Patent is hereby corrected as shown below:

Title Pg, Item (56) Ref Cited, Page 3, Column 2, Line 10: Delete "microsope" insert --microscope--.

Title Pg, Item (56) Ref Cited, Page 3, Column 2, Line 13: Delete "Interation" insert --Interaction--.

Title Pg, Item (56) Ref Cited, Page 3, Column 2, Line 14: Delete "Abastract" insert --Abstract--.

Title Pg, Item (56) Ref Cited, Page 3, Column 2, Line 46-47: Delete "Tehcnology" insert --Technology--.

Title Pg, Item (56) Ref Cited, Page 4, Column 1, Line 6-7: Delete "Intruments" insert --Instruments--.

Title Pg, Item (56) Ref Cited, Page 4, Column 1, Line 11: Delete "Intruments" insert --Instruments--.

Title Pg, Item (56) Ref Cited, Page 4, Column 1, Line 27: Delete "Muclear" insert --Nuclear--.

Title Pg, Item (56) Ref Cited, Page 4, Column 2, Line 9: Delete "Interations" insert --Interactions--.

Title Pg, Item (56) Ref Cited, Page 4, Column 2, Line 26: Delete "Feasiblity" insert --Feasibility--.

Column 32, Line 26: Delete "operating-" and insert --operating--.

Column 49, Line 10: Delete "$1 \times 10^{10}$" and insert --$1 \times 10^{10}$--.

Column 49, Line 50: After "measured" insert --.--.

Column 50, Line 28: Delete "micro scope" and insert --microscope--.

CERTIFICATE OF CORRECTION (continued)
U.S. Pat. No. 7,557,361 B2

Column 53, Line 47: Delete "unionized" and insert --un-ionized--.

Column 58, Line 40: Delete "front" and insert --from--.

Column 70, Line 46: Delete "80140*a*" and insert --80140 a--.

Column 83, Lines 1-3: Delete "This is a distinct advantage........for a sample" insert at Col. 82, line 67, after "voids." as a continuation of the same paragraph.

Column 122, Line 25: Delete "Example 192." and insert --Example 19.--.

Column 134, Line 37: After "19" insert --.--.

Column 134, Line 39: After "59" insert --.--.

Column 135, Line 48: Delete "Example 192." and insert --Example 21.--.

Column 136, Line 55: Delete "Example 214." and insert --Example 21.--.

Column 137, Line 43: Delete "Example 192." and insert --Example 19.--.

Column 143, Line 14: Claim 95, after "claim 31," insert --further--.

Column 144, Line 12: Claim 103, delete "$1^{109}$" and insert --$1 \times 10^9$--.

Signed and Sealed this

Twenty-third Day of February, 2010

David J. Kappos
*Director of the United States Patent and Trademark Office*